(12) United States Patent
Qin et al.

(10) Patent No.: US 9,517,988 B2
(45) Date of Patent: Dec. 13, 2016

(54) PHENOL DERIVATIVE AND PREPARATION METHOD AND USE IN MEDICINE THEREOF

(71) Applicant: Sichuan Haisco Pharmaceutical Co., Ltd., Chengdu (CN)

(72) Inventors: Linlin Qin, Chengdu (CN); Fangqiong Li, Chengdu (CN); Shixu Yi, Chengdu (CN); Huadong Luo, Chengdu (CN); Xinfeng Luo, Chengdu (CN); Songlin Wan, Chengdu (CN); Lei Ren, Chengdu (CN); Guoliang Liu, Chengdu (CN); Yonggang Wei, Chengdu (CN); Jianyu Liu, Chengdu (CN); Peng Cho Tang, Chengdu (CN)

(73) Assignee: Sichuan Haisco Pharmaceutical Co., Ltd., Chengdu (CN)

( * ) Notice: Subject to any disclaimer, the term of this patent is extended or adjusted under 35 U.S.C. 154(b) by 0 days.

(21) Appl. No.: 14/936,310

(22) Filed: Nov. 9, 2015

(65) Prior Publication Data

US 2016/0060197 A1    Mar. 3, 2016

Related U.S. Application Data

(63) Continuation of application No. PCT/CN2014/076907, filed on May 6, 2014.

(30) Foreign Application Priority Data

May 9, 2013   (CN) .......................... 2013 1 0169462

(51) Int. Cl.
| | | |
|---|---|---|
| C07C 43/00 | (2006.01) |
| C07C 39/00 | (2006.01) |
| C07D 213/00 | (2006.01) |
| C07F 9/00 | (2006.01) |
| C07C 39/17 | (2006.01) |
| C07C 39/42 | (2006.01) |
| C07C 69/96 | (2006.01) |
| C07C 43/21 | (2006.01) |
| C07C 43/23 | (2006.01) |
| C07C 69/157 | (2006.01) |
| C07C 69/24 | (2006.01) |
| C07C 69/82 | (2006.01) |
| C07D 207/16 | (2006.01) |
| C07F 9/6574 | (2006.01) |
| C07F 9/09 | (2006.01) |
| C07F 9/12 | (2006.01) |
| C07F 9/24 | (2006.01) |
| C07D 213/80 | (2006.01) |
| C07C 271/22 | (2006.01) |
| C07C 271/44 | (2006.01) |
| C07C 229/08 | (2006.01) |
| C07C 229/36 | (2006.01) |
| C07C 37/00 | (2006.01) |
| C07C 37/62 | (2006.01) |
| C07C 41/18 | (2006.01) |

(Continued)

(52) U.S. Cl.
CPC ............... *C07C 39/17* (2013.01); *C07C 37/00* (2013.01); *C07C 37/001* (2013.01); *C07C 37/62* (2013.01); *C07C 39/42* (2013.01); *C07C 41/18* (2013.01); *C07C 43/21* (2013.01); *C07C 43/23* (2013.01); *C07C 67/10* (2013.01); *C07C 68/00* (2013.01); *C07C 69/07* (2013.01); *C07C 69/157* (2013.01); *C07C 69/24* (2013.01); *C07C 69/78* (2013.01); *C07C 69/82* (2013.01); *C07C 69/96* (2013.01); *C07C 227/04* (2013.01); *C07C 229/08* (2013.01); *C07C 229/36* (2013.01); *C07C 269/00* (2013.01); *C07C 271/22* (2013.01); *C07C 271/44* (2013.01); *C07D 207/16* (2013.01); *C07D 213/80* (2013.01); *C07D 213/803* (2013.01); *C07F 9/06* (2013.01); *C07F 9/091* (2013.01); *C07F 9/094* (2013.01); *C07F 9/12* (2013.01); *C07F 9/242* (2013.01); *C07F 9/2458* (2013.01); *C07F 9/65744* (2013.01); *C07C 2101/02* (2013.01); *C07C 2101/04* (2013.01)

(58) Field of Classification Search
CPC ....... C07C 43/21; C07C 43/23; C07C 37/62; C07C 69/78; C07D 213/80; C07F 9/00
USPC ....... 568/644, 731; 562/23; 560/27, 85, 173, 560/255; 514/111, 121, 130, 352, 423, 486, 514/512, 719, 729
See application file for complete search history.

(56) References Cited

FOREIGN PATENT DOCUMENTS

| CN | 101151234 A | 3/2008 |
|---|---|---|
| EP | 1 206 934 A1 | 5/2002 |

(Continued)

OTHER PUBLICATIONS

International Search Report for International Application No. PCT/CN2014/076907, dated Oct. 10 2014, (2p).

(Continued)

*Primary Examiner* — Sikarl Witherspoon
(74) *Attorney, Agent, or Firm* — Brinks Gilson & Lione

(57) ABSTRACT

The present invention relates to a phenol derivative and the preparation method and use in medicine thereof, and particular to a phenol derivative represented by general formula (A) or a stereoisomer, a solvate, a metabolite, a prodrug, a pharmaceutically acceptable salt or a cocrystal thereof, a preparation method thereof, a pharmaceutical composition comprising the same, and use of the compound or composition of the present invention in the field of the central nervous system; wherein the definitions of substituents in general formula (A) are the same as those in the Description.

23 Claims, 2 Drawing Sheets

(51) Int. Cl.
| | |
|---|---|
| C07C 67/10 | (2006.01) |
| C07C 68/00 | (2006.01) |
| C07C 69/07 | (2006.01) |
| C07C 69/78 | (2006.01) |
| C07C 227/04 | (2006.01) |
| C07C 269/00 | (2006.01) |
| C07D 213/803 | (2006.01) |
| C07F 9/06 | (2006.01) |

(56) References Cited

FOREIGN PATENT DOCUMENTS

| WO | WO 03/026632 A2 | 4/2003 |
|---|---|---|
| WO | WO 2006/106906 A1 | 10/2006 |
| WO | WO 2008/008492 A2 | 1/2008 |
| WO | WO 2009140275 A1 | 11/2009 |

OTHER PUBLICATIONS

First Office Action and Search Report to Chinese Patent Application No. 201480000451.3, dated Aug. 5, 2015 and English translation (10p).

Cohen, L.B., "*Clinical Trial: A Dose-Response Study of Fospropofol Disodium for Moderate Sedation During Colonscopy*", Alimentary Pharmacology & Therapeutics, vol. 27, pp. 597-608.

Doenicke, Alfred W., et al., "*Reducing Pain During Propofol Injection: The Role of the Solvent*", Anesth Analg., vol. 82, (1996), pp. 472-474.

Hara, Manami, et al., "*Propofol Activates $GABA_A$ Receptor-Chloride Ionophore Complex in Dissociated Hippocampal Pyramidal Neurons of the Rat*", Anesthesiology, vol. 79:4, Oct. 1993, pp. 781-788.

Klement, W., et al., "*Pain on Injection of Propofol: Effects of Concentration and Diluent*", British Journal of Anaesthesia, vol. 67, (1991), pp. 281-284.

Miller, Bernard, et al., "*Migrations of Cyclopropylmethyl Groups in Thermal and Acid Catalized Reactions of Cyclohexadienones*", Tetrahedron Letters No. 6, (1972), pp. 517-520.

Picard, Pascale, et al., "*Prevention of Pain on Injection With Propofol: A Quantitative Systematic Review*", Anesth Analg., vol. 90, (2000), pp. 963-969.

Tan, C.H., et al., "The Effect of Ketamine Pretreatment on Propofol Injection Pain in 100 Women", Anaesthesia, vol. 53, (1998), pp. 302-305.

Ueki, Ryusuke, et al., "*Emulsion of Flurbiprofen Axetil Reduces Propofol Injection pain due to a Decrease in Free Propofol Concentration*", Journal of Anesthesia vol. 21, (2007), pp. 325-329.

Chinese OA2 and English translation corresponding to Chinese Application No. 201480000451.3, dated Apr. 18, 2016, (5p).

SIPO Search Report to Chinese Application No. 201480000451.3, dated Apr. 18, 2016, and English translation (4p).

RN 1407113-07-08 STN Registry (1p).

PHENOL DERIVATIVE AND PREPARATION METHOD AND USE IN MEDICINE THEREOF

TECHNICAL FIELD

The present invention relates to a phenol derivative represented by general formula (A) or a stereoisomer, a solvate, a metabolite, a prodrug, a pharmaceutically acceptable salt or a cocrystal thereof, also to a preparation method thereof, a pharmaceutical composition thereof, and use of the compound of the present invention in the field of central nervous system.

BACKGROUND ART

The $GABA_A$ receptor is a receptor of the chief inhibitory neurotransmitter in the central nervous system. The $GABA_A$ receptor is composed of a pentamer of transmembrane polypeptide subunits, and 19 different subunits assemble into various $GABA_A$ receptor subtypes. The $GABA_A$ receptor is involved in pathogenesis, diagnosis and treatment of various conditions such as anesthesia, depression, anxiety, epilepsy, memory disorders, and drug dependence, and has accordingly become a pharmacologically and clinically important target for drugs. Propofol and its derivatives represent a marked class of $GABA_A$-targeting compounds.

Propofol can activate many $GABA_A$ receptor subtypes, and is a clinically sophisticated venous anesthetic widely used for induction and maintenance of general anesthesia. Clinical dosage-related propofol can directly activate the $GABA_A$ receptor-chloride channel complex in mammalian neurons, thereby enhancing transportation of $Cl^-$, reducing excitability of the neural network, and in turn inducing general anesthesia (Manami Hara, et al., (1993) Anesthesiology, 79, 781-788). Propofol shows remarkable pharmacokinetic and pharmacodynamic characteristics in that it rapidly takes effect, acts for a short period, and is quickly reversible. Upon intravenous administration, propofol in the blood rapidly enters hyperperfusion sites such as heart, lung and liver, and its high liposolubility allows propofol to easily travel across the blood-brain barrier into the brain to affect general anesthesia.

However, propofol has obvious limitations and disadvantages. It has been reported that approximately 70% of patients on propofol injections feel certain pain or discomfort (Pascale Picard (2000) Anesthesia & Analgesia, 90, 963-969), which is reportedly believed to be injection-induced pain caused by propofol in the aqueous phase of a lipid emulsion (Klement W, et al., 1991, Br J Anaesth 67, 281). Several studies have reported that a decreased concentration of propofol in the aqueous phase, as compared to the propofol content in the aqueous phase of DIPRIVAN, results in significantly less pain on injection (Doenicke A W, et al., 1996, Anesth Analg 82, 472; Ueki R, et al., 2007, J Anesth 21, 325). Although it is also reported that pre-treatment with other drugs or combined administration of drugs may reduce the incidence and severity of pain on propofol injections (C. H. Tan, et al., (1998) Anaesthesia, 53, 302-305), such pain is still unavoidable. It has been demonstrated that propofol can lower the systolic pressure, the diastolic pressure, and the mean arterial pressure, and thus may clinically cause hypotension. Furthermore, respiratory depression is also an unneglectable risk upon use of propofol. These adverse effects have considerably impeded application of propofol in certain clinical cases, such as cardiovascular diseases, brain injury, and chronic hypotension.

Fospropofol is a water-soluble prodrug of propofol, and can be rapidly hydrolyzed by alkaline phosphatase to release propofol, phosphate, and formaldehyde. Although fospropofol relieves pain at sites of intravenous propofol injection, it still poses risks of respiratory depression and adverse haemodynamic effects (Cohen L B (2008) Aliment Pharmacol Ther, 27, 597) because it takes effect in the form of the active compound propofol. In addition, fospropofol may also cause abnormal sensation and itching.

Because of the limitations and disadvantages of propofol and fospropofol, there is a need for developing novel $GAGA_A$-receptor agonist possessing better pharmacokinetic and pharmacodynamic characteristics and fewer side effects. An objective of the present invention is to introduce a new group of propofol derivatives that take effect faster, act for a similar period, and have a greater therapeutic index as compared to propofol, and also reduce the likelihood of pain on injection thanks to their increased liposolubility (A W Doenicke, et al., (1996) Anesth Analg, 82, 472-474).

WO2009140275 describes a propofol analog or a pharmaceutically acceptable salt thereof, useful as an anesthetic, wherein X may be a hydrogen or fluorine atom. The general formulae of the compounds of this invention are shown below:

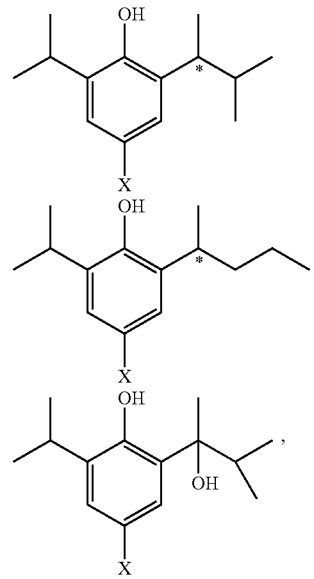

which are structurally very different from the compounds of the present invention.

EP1206934 describes a phenol derivative or a pharmaceutically acceptable salt or prodrug thereof, useful for local anesthesia, anti-arrhythmia and anti-convulsion, wherein, $R^1$, $R^3$, $R^4$, $R^5$ and $R^6$ each are a hydrogen atom, a halogen atom, or $C_{1-7}$ alkyl; $R^2$ is $C_{1-7}$ alkyl or hydroxyl; alternatively, $R^1$ and $R^2$ may optionally form a 5- or 6-membered ring. The general formula of the compound of this invention is shown below:

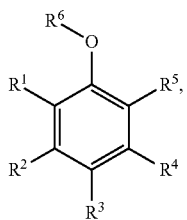

which is structurally very different from the compound of the present invention.

WO03026632 describes a phenol derivative or a pharmaceutically acceptable salt thereof, useful for anesthesia and sedation, wherein $R^1$ and $R^2$ are each independently selected from $C_{1-8}$ alkyl or $C_{1-8}$ cycloalkyl; L is selected from a covalent bond or $C_{1-12}$ hydrocarbylene; and $R^3$ is selected from —C(=O)OR$^a$, wherein $R^a$ is selected from $C_{1-12}$ hydrocarbyl. The general formula of the compound of this invention is shown below:

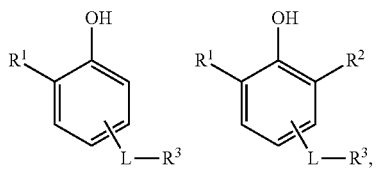

which is structurally very different from the compounds of the present invention. The specific descriptions in WO03026632 are not considered as part of the present invention.

WO2008008492 describes a substituted hydrofluoroalkyl phenol compound and a pharmaceutically acceptable salt or prodrug thereof, useful as an anesthetic, wherein $R^1$ is a substituted or unsubstituted branched $C_{3-6}$ alkyl; $R^2$ is a hydrogen atom, or a substituted or unsubstituted $C_{1-3}$ alkyl; $R^3$ is a $C_{1-3}$ fluoroalkyl. As defined in its specification, alkyl refers to a saturated aliphatic group, including linear, branched and cyclic alkyl groups; a substituted alkyl refers to an alkyl in which one or more hydrogen atoms on a carbon atom have been substituted with substituents, and the substituents include fluorine, chlorine, bromine, iodine, hydroxyl, alkoxy, cyano, amino, mercapto, alkylthio, nitro, and azido. The general formula of the compound of this invention is shown below:

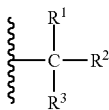

The specific descriptions in WO2008008492 are not considered as part of the present invention.

WO2006106906 describes preparation of a cyclopropyl phenol derivative represented by the general formula below,

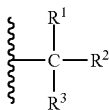

wherein $R^1$, $R^2$, $R^3$, and $R^4$ may each independently be hydrogen, F, Cl, Br, I, optionally substituted $C_{1-6}$ alkyl, etc.; Z is hydrogen, optionally substituted $C_{1-6}$ alkyl, etc.; $Y^1$, $Y^2$ and $Y^3$ are hydrogen atoms. The specific descriptions in WO2006106906 are not considered as part of the present invention.

SUMMARY OF THE INVENTION

The objective of the present invention is to provide a structurally novel GABA$_A$ receptor agonist that has improved drug efficacy and safety and can cause less pain on injection, or any of a stereoisomer, a solvate, a metabolite, a pharmaceutically acceptable salt, a cocrystal or a prodrug thereof, as well as a preparation method thereof, a pharmaceutical composition thereof, and use of the compound of the present invention in the field of the central nervous system, whereby providing more and better choices for medicaments for inducing and maintaining anesthesia in an animal or a human, facilitating sedation and hypnosis, or treating and preventing anxiety, nausea, vomiting, migraine, convulsion, epilepsy, nervous degenerative diseases and central nervous system-associated diseases.

The present invention relates to a compound of general formula (A), (A)

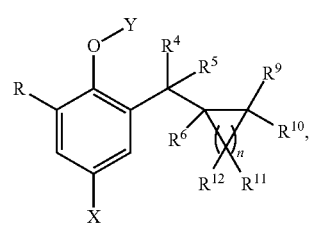

or any of a stereoisomer, a solvate, a metabolite, a prodrug, a pharmaceutically acceptable salt, or a cocrystal thereof; wherein
R is selected from F, Cl, Br, I, —OR$^7$ or

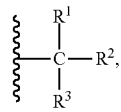

preferably F, Br, or

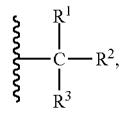

more preferably F or

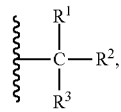

and even more preferably

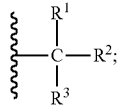

$R^1$, $R^2$ and $R^3$ are each independently selected from H, F, Cl, Br, I, hydroxyl, $C_{1-8}$ alkyl, $C_{1-8}$ alkoxy, a 3- to 8-membered carbocyclic group, or a 3- to 8-membered heterocyclic group, wherein the alkyl, alkoxy, carbocyclic group or heterocyclic group is optionally further substituted with 0 to 5 substituents selected from F, Cl, Br, I, hydroxyl, $C_{1-8}$ alkyl, $C_{1-8}$ alkoxy, a 3- to 8-membered carbocyclic group or a 3- to 8-membered heterocyclic group, the heterocyclic group has 1 to 2 heteroatoms selected from N, O or S, and $R^1$, $R^2$ and $R^3$ are not all H;

Alternatively, any pair of $R^1$ and $R^2$, $R^2$ and $R^3$, or $R^1$ and $R^3$ may form a 3- to 8-membered ring, the 3- to 8-membered ring may have 0 to 2 heteroatoms selected from N, O or S, and the formed 3- to 8-membered ring may optionally be further substituted with 0 to 4 $R^8$s;

$R^4$, $R^5$, $R^9$, $R^{10}$, $R^{11}$ and $R^{12}$ are each independently selected from H, F, Cl, Br, I, hydroxyl, cyano, $C_{1-8}$ alkyl, $C_{1-8}$ alkoxy, a 3- to 8-membered carbocyclic group, or a 3- to 8-membered heterocyclic group, wherein the alkyl, alkoxy, carbocyclic group or heterocyclic group is optionally further substituted with 0 to 5 substituents selected from F, Cl, Br, I, hydroxyl, $C_{1-8}$ alkyl, $C_{1-8}$ alkoxy, a 3- to 8-membered carbocyclic group or a 3- to 8-membered heterocyclic group, the heterocyclic group has 1 to 2 heteroatoms selected from N, O or S, and $R^4$ and $R^5$ are not both H; preferably, $R^9$, $R^{10}$, $R^{11}$ and $R^{12}$ are each independently selected from H or F;

Alternatively, any pair of $R^4$ and $R^5$, $R^9$ and $R^{10}$, or $R^{11}$ and $R^{12}$ may form a 3- to 8-membered ring, the 3- to 8-membered ring may have 0 to 2 heteroatoms selected from N, O or S, and the formed 3- to 8-membered ring may optionally be further substituted with 0 to 4 $R^8$s;

$R^6$ is selected from H, F, Cl, Br, I, hydroxyl or $C_{1-8}$ alkoxy, preferably H, F, Cl, hydroxyl or $C_{1-8}$ alkoxy, more preferably H, hydroxyl or $C_{1-8}$ alkoxy, and even more preferably H or hydroxyl;

$R^7$ is selected from H, $C_{1-8}$ alkyl, a 3- to 8-membered carbocyclic group or a 3- to 8-membered heterocyclic group, wherein the alkyl, carbocyclic group or heterocyclic group is optionally further substituted with 0 to 5 substituents selected from F, Cl, Br, I, hydroxyl, $C_{1-8}$ alkyl, $C_{1-8}$ alkoxy, a 3- to 8-membered carbocyclic group or a 3- to 8-membered heterocyclic group, and the heterocyclic group has 1 to 2 heteroatoms selected from N, O or S;

$R^8$ is selected from F, Cl, Br, I, hydroxyl, carboxyl, amino, a carboxylic ester group, an amide group, $C_{1-8}$ alkyl, $C_{1-8}$ alkoxy, a 3- to 8-membered carbocyclic group or a 3- to 8-membered heterocyclic group, and the heterocyclic group has 1 to 2 heteroatoms selected from N, O or S;

X is selected from H, F or carboxyl, preferably H or F, and more preferably H;

Y is selected from H, $COR^{13}$, PEG, $COOR^{13}$, $CONR^{13}R^{14}$, $COSR^{13}$,

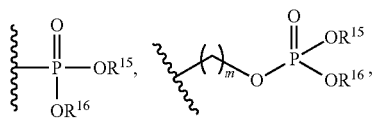

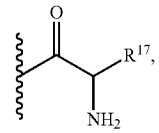

$C_{1-20}$ alkyl, $-(CH_2CH_2O)_q-H$, $-(CR^{ya}R^{yb})_{m1}COOR^{y1}$, $-(CR^{ya}R^{yb})_{m1}-(W_1)_p-C(=O)(W_4R^{y3})$ or $-(CR^{ya}R^{yb})_{m1}-(W_1)_p-P(=O)(W_2R^{y4})(W_3R^{y5})$ or

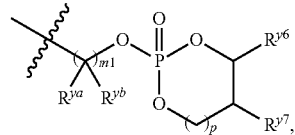

wherein the alkyl is optionally further substituted with 0 to 4 substituents selected from H, F, Cl, Br, I, hydroxyl, amino, cyano, carboxyl, $C_{1-6}$ alkyl, $C_{1-6}$ alkoxy, a $C_{3-8}$ carbocyclic group or a 4- to 8-membered heterocyclic group, and the heterocyclic group has 1 to 2 heteroatoms selected from N, O or S; Y is preferably H, PEG, $COR^{13}$, $CONR^{13}R^{14}$,

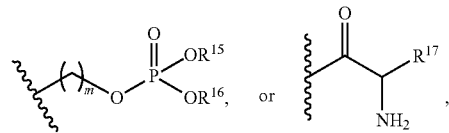

more preferably H, PEG, or

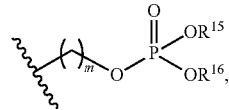

and even more preferably H;

$R^{13}$ and $R^{14}$ are each independently selected from H, $C_{1-6}$ alkyl, a 3- to 8-membered carbocyclic or heterocyclic group, wherein the alkyl, carbocyclic group or heterocyclic group may optionally be further substituted with 0 to 5 substituents selected from F, Cl, Br, I, hydroxyl, $C_{1-6}$ alkyl, $C_{1-6}$ alkoxy, a 3- to 8-membered carbocyclic group or a 3- to 8-membered heterocyclic group, and the heterocyclic group has 1 to 2 heteroatoms selected from N, O or S;

$R^{15}$ and $R^{16}$ are each independently selected from H, an alkali metal ion, an alkali earth metal ion, a protonated amine or a protonated amino acid, wherein the alkali metal ion is selected from $Na^+$, $K^+$ or $Li^+$, the alkali earth metal ion is selected from $Be^{2+}$, $Mg^{2+}$ or $Ca^{2+}$, the amine is selected from trometamol, triethanolamine, ethanolamine, triethylamine or N-methylglucosamine, and the amino acid is selected from arginine or lysine;

alternatively, $R^{15}$ and $R^{16}$ may form a 3- to 8-membered ring, the 3- to 8-membered ring may have 0 to 2 heteroatoms selected from N, O or S, and the formed 3- to 8-membered ring may optionally be further substituted with 0 to 4 $R^8$s;

$R^{17}$ is the side-chain group of an amino acid, wherein the amino acid is selected from lysine, arginine, histidine, proline, 2,3-diaminopropionic acid, 2,4-diaminopropionic acid, alanine, valine, leucine, isoleucine, phenylalanine, tryptophan, methionine, glycine, serine, threonine, cysteine, tyrosine, asparagine, glutamine, aspartic acid, aspartate, or glutamic acid;

$W_1$, $W_2$ and $W_3$ are each independently selected from $NR^{y8}$, O or S;

$W_4$ is selected from $CR^{y9}R^{y10}$, $NR^{y8}$, O, S, or is absent;

$R^{y1}$ is each independently selected from H, $C_{1-6}$ alkyl, a $C_{3-8}$ carbocyclic group or a 4- to 8-membered heterocyclic group, wherein the alkyl, carbocyclic group or heterocyclic group may optionally be further substituted with 0 to 5 substituents selected from H, F, Cl, Br, I, hydroxyl, amino, cyano, carboxyl, $C_{1-6}$ alkyl, $C_{1-6}$ alkoxy, a $C_{3-8}$ carbocyclic group or a 4- to 8-membered heterocyclic group, and the heterocyclic group has 1 to 2 heteroatoms selected from N, O or S;

$R^{y3}$ is selected from H, amino, $C_{1-6}$ alkyl, a $C_{3-8}$ carbocyclic group or a 4- to 8-membered heterocyclic group, —$(CR^{ya}R^{yb})_{m1}$—$NR^{yc}R^{yd}$ or —$(CR^{ya}R^{yb})_{m1}$—$NR^{yc}C(=O)OR^{yd}$, wherein the amino group, alkyl, carbocyclic group or heterocyclic group may optionally be further substituted with 0 to 5 substituents selected from H, F, Cl, Br, I, hydroxyl, amino, cyano, carboxyl, $C_{1-6}$ alkyl, $C_{1-6}$ alkoxy, —$(CH_2)_{m1}$—$OC(=O)$—$C_{1-6}$ alkyl, —$(CH_2)_{m1}$—$C(=O)$O—$C_{1-6}$ alkyl, —$(CH_2)_{m1}$—$C(=O)O(CH_2)_{m1}$—$(C_{3-6}$ carbocyclic group), —$(CH_2)_{m1}$—$C(=O)$—$C_{1-6}$ alkyl, —$(CH_2)_{m1}$—$(C_{3-8}$ carbocyclic group) or —$(CH_2)_{m1}$-(4- to 8-membered heterocyclic group), and the heterocyclic group has 1 to 2 heteroatoms selected from N, O or S;

$R^{y4}$ and $R^{y5}$ are each independently selected from H, an alkali metal ion, an alkali earth metal ion, a protonated amine or a protonated amino acid, $C_{1-6}$ alkyl, —$(CR^{ya}R^{yb})_{m1}$-(3- to 8-membered ring), —$(CR^{ya}R^{yb})_{m1}$—$OC(=O)C_{1-6}$ alkyl, —$(CR^{ya}R^{yb})_{m1}$—$OC(=O)$-(3- to 8-membered ring), —$(CR^{ya}R^{yb})_{m1}$—$C(=O)OC_{1-6}$ alkyl or —$(CR^{ya}R^{yb})_{m1}$—$OC(=O)OC_{1-6}$ alkyl;

$R^{y6}$ and $R^{y7}$ are each independently selected from H, F, Cl, Br, I, hydroxyl, amino, cyano, carboxyl, $C_{1-6}$ alkyl or $C_{1-6}$ alkoxy;

alternatively, $R^{y6}$ and $R^{y7}$ may form a 5- to 8-membered ring together with the atoms to which they are attached, the 5- to 8-membered ring may have 0 to 4 heteroatoms selected from N, O or S, and the 5- to 8-membered ring may optionally be further substituted with 0 to 4 substituents selected from H, F, Cl, Br, I, $C_{1-6}$ alkyl or $C_{1-6}$ alkoxy;

$R^{y8}$s are each independently selected from H or $C_{1-6}$ alkyl;

$R^{y9}$ and $R^{y10}$ are each independently selected from H, $C_{1-6}$ alkyl, a $C_{3-8}$ carbocyclic group or a 4- to 8-membered heterocyclic group, wherein the alkyl, carbocyclic group and heterocyclic group are each optionally further substituted with 0 to 4 substituents selected from H, hydroxyl, amino, mercapto, carboxyl, guanidino, carbamoyl, $C_{1-6}$ alkyl, $C_{1-6}$ alkoxy, a 3- to 8-membered carbocycle or a 3- to 8-membered heterocycle;

$R^{ya}$, $R^{yb}$, $R^{yc}$ and $R^{yd}$ are each independently selected from H or $C_{1-6}$ alkyl;

q is selected from 1 to 200;

m1 is selected from 0, 1, 2 or 3;

p is selected from 0, 1 or 2;

m is selected from 1 or 2;

n is selected from 1, 2 or 3; preferably 1 or 2, and more preferably 1.

A preferred embodiment of the present invention comprises a compound of general formula (A), or any of a stereoisomer, a solvate, a metabolite, a prodrug, a pharmaceutically acceptable salt, or a cocrystal thereof;

wherein
R is selected from F, Cl, Br, I, —$OR^7$ or

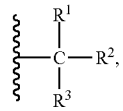

preferably F, Br, or

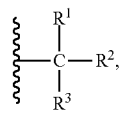

more preferably F or

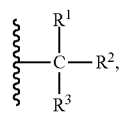

and even more preferably

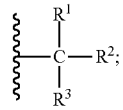

$R^1$, $R^2$ and $R^3$ are each independently selected from H, F, Cl, Br, I, hydroxyl, $C_{1-7}$ alkyl, $C_{1-7}$ alkoxy, a 3- to 6-membered carbocyclic group, or a 3- to 6-membered heterocyclic group, wherein the alkyl, alkoxy, carbocyclic group or heterocyclic group is optionally further substituted with 0 to 5 substituents selected from F, Cl, Br, I, hydroxyl, $C_{1-7}$ alkyl, $C_{1-7}$ alkoxy, a 3- to 6-membered carbocyclic group or a 3- to 6-membered heterocyclic group, the heterocyclic group has 1 to 2 heteroatoms selected from N, O or S, and $R^1$, $R^2$ and $R^3$ are not all H;

alternatively, any pair of $R^1$ and $R^2$, $R^2$ and $R^3$, or $R^1$ and $R^3$ may form a 3- to 6-membered ring, the 3- to 6-membered ring may have 0 to 2 heteroatoms selected from N, O or S, and the formed 3- to 6-membered ring may optionally be further substituted with 0 to 4 $R^8$s;

$R^4$, $R^5$, $R^9$, $R^{10}$, $R^{11}$ and $R^{12}$ are each independently selected from H, F, Cl, Br, I, hydroxyl, $C_{1-7}$ alkyl, $C_{1-7}$ alkoxy, a 3- to 6-membered carbocyclic group, or a 3- to 6-membered heterocyclic group, wherein the alkyl, alkoxy, carbocyclic group or heterocyclic group is optionally further substituted with 0 to 5 substituents selected from F, Cl, Br, I, hydroxyl, $C_{1-7}$ alkyl, $C_{1-7}$ alkoxy, a 3- to 6-membered carbocyclic group or a 3- to 6-membered heterocyclic group, the heterocyclic group has 1 to 2 heteroatoms selected from N, O or S, and $R^4$ and $R^5$ are not both H; preferably, $R^9$, $R^{10}$, $R^{11}$ and $R^{12}$ are each independently selected from H or F;

alternatively, any pair of $R^4$ and $R^5$, $R^9$ and $R^{10}$, or $R^{11}$ and $R^{12}$ may form a 3- to 6-membered ring, the 3- to 6-membered ring may have 0 to 2 heteroatoms selected from N, O or S, and the formed 3- to 6-membered ring may optionally be further substituted with 0 to 4 $R^8$s;

$R^6$ is selected from H, F, Cl, Br, I, hydroxyl or $C_{1-7}$ alkoxy, preferably H, F, Cl, hydroxyl or $C_{1-7}$ alkoxy, more preferably H, hydroxyl or $C_{1-7}$ alkoxy, and even more preferably H or hydroxyl;

R[7] is selected from H, $C_{1-7}$ alkyl, a 3- to 6-membered carbocyclic group or a 3- to 6-membered heterocyclic group, wherein the alkyl, carbocyclic group or heterocyclic group is optionally further substituted with 0 to 5 substituents selected from F, Cl, Br, I, hydroxyl, $C_{1-7}$ alkyl, $C_{1-7}$ alkoxy, a 3- to 6-membered carbocyclic group or a 3- to 6-membered heterocyclic group, and the heterocyclic group has 1 to 2 heteroatoms selected from N, O or S;

R[8] is selected from F, Cl, Br, I, hydroxyl, $C_{1-7}$ alkyl, carboxyl, amino, a carboxylic ester group, an amide group, $C_{1-7}$ alkoxy, a 3- to 6-membered carbocyclic group or a 3- to 6-membered heterocyclic group, and the heterocyclic group has 1 to 2 heteroatoms selected from N, O or S;

Y is selected from H, $COR^{13}$, PEG, $COOR^{13}$, $CONR^{13}R^{14}$, $COSR^{13}$,

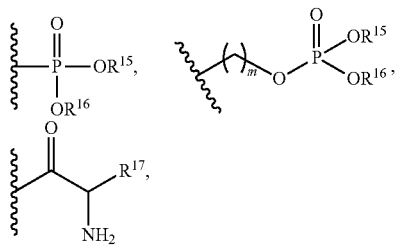

$C_{1-20}$ alkyl, $-(CH_2CH_2O)_q-H$, $-(CR^{ya}R^{yb})_{m1}COOR^{y1}$, $-(CR^{ya}R^{yb})_{m1}-(W_1)_p-C(=O)(W_4R^{y3})$ or $-(CR^{ya}R^{yb})_{m1}-(W_1)_p-P(=O)(W_2R^{y4})(W_3R^{y5})$ or

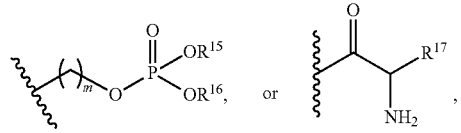

wherein the alkyl is optionally further substituted with 0 to 4 substituents selected from H, F, Cl, Br, I, hydroxyl, amino, cyano, carboxyl, $C_{1-6}$ alkyl, $C_{1-6}$ alkoxy, a $C_{3-8}$ carbocyclic group or a 4- to 8-membered heterocyclic group, and the heterocyclic group has 1 to 2 heteroatoms selected from N, O or S; Y is preferably H, PEG, $COR^{13}$, $CONR^{13}R^{14}$,

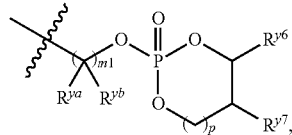

more preferably H, PEG, or

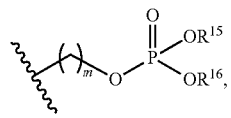

and even more preferably H;

R[13] and R[14] are each independently selected from H or $C_{1-6}$ alkyl;

R[15] and R[16] are each independently selected from H or an alkali metal ion, wherein the alkali metal ion is selected from $Na^+$, $K^+$ or $Li^+$;

R[17] is the side-chain group of an L-amino acid, wherein the L-amino acid is selected from lysine, arginine, histidine, 2,3-diaminopropionic acid, 2,4-diaminopropionic acid, alanine, valine, leucine, isoleucine, phenylalanine, tryptophan, methionine, glycine, serine, threonine, cysteine, tyrosine, asparagine, glutamine, aspartic acid or glutamic acid, and preferably lysine, arginine, or histidine;

X is selected from H, F or carboxyl, preferably H or F, and more preferably H;

m is selected from 1 or 2; and n is selected from 1, 2 or 3; preferably 1 or 2, and more preferably 1.

Another preferred embodiment of the present invention comprises a compound of general formula (A), or any of a stereoisomer, a solvate, a metabolite, a prodrug, a pharmaceutically acceptable salt, or a cocrystal thereof;

wherein

R is selected from F, Cl, Br, I, $-OR^7$ or

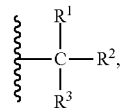

preferably F, Br, or

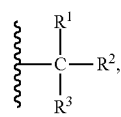

more preferably F or

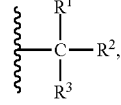

and even more preferably

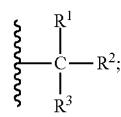

R[1], R[2] and R[3] are each independently selected from H, F, Cl, Br, I, hydroxyl, $C_{1-6}$ alkyl, $C_{1-6}$ alkoxy, a 3- to 5-membered carbocyclic group, or a 3- to 5-membered heterocyclic group, wherein the alkyl, alkoxy, carbocyclic group or heterocyclic group is optionally further substituted with 0 to 5 substituents selected from F, Cl, Br, I, hydroxyl, $C_{1-6}$ alkyl, $C_{1-6}$ alkoxy, a 3- to 5-membered carbocyclic group or a 3- to 5-membered heterocyclic group, the heterocyclic group has 1 to 2 heteroatoms selected from N, O or S, and R[1], R[2] and R[3] are not all H;

alternatively, any pair of R[1] and R[2], R[2] and R[3], or R[1] and R[3] may form a 3- to 5-membered ring, the 3- to 5-membered ring may have 0 to 2 heteroatoms selected from N, O or S, and the formed 3- to 5-membered ring may optionally be further substituted with 0 to 4 R[8]s;

$R^4$, $R^5$, $R^9$, $R^{10}$, $R^{11}$ and $R^{12}$ are each independently selected from H, F, Cl, Br, I, hydroxyl, $C_{1-6}$ alkyl, $C_{1-6}$ alkoxy, a 3- to 5-membered carbocyclic group, or a 3- to 5-membered heterocyclic group, wherein the alkyl, alkoxy, carbocyclic group or heterocyclic group is optionally further substituted with 0 to 5 substituents selected from F, Cl, Br, I, hydroxyl, $C_{1-6}$ alkyl, $C_{1-6}$ alkoxy, a 3- to 5-membered carbocyclic group or a 3- to 5-membered heterocyclic group, the heterocyclic group has 1 to 2 heteroatoms selected from N, O or S, and $R^4$ and $R^5$ are not both H; preferably, $R^9$, $R^{10}$, $R^{11}$ and $R^{12}$ are each independently selected from H or F;

alternatively, any pair of $R^4$ and $R^5$, $R^9$ and $R^{10}$, or $R^{11}$ and $R^{12}$ may form a 3- to 5-membered ring, the 3- to 5-membered ring may have 0 to 2 heteroatoms selected from N, O or S, and the formed 3- to 5-membered ring may optionally be further substituted with 0 to 4 $R^8$s;

$R^6$ is selected from H, hydroxyl or $C_{1-6}$ alkoxy, and preferably H or hydroxyl;

$R^7$ is selected from H, $C_{1-6}$ alkyl, a 3- to 5-membered carbocyclic group or a 3- to 5-membered heterocyclic group, wherein the alkyl, carbocyclic group or heterocyclic group is optionally further substituted with 0 to 5 substituents selected from F, Cl, Br, I, hydroxyl, $C_{1-6}$ alkyl, $C_{1-6}$ alkoxy, a 3- to 5-membered carbocyclic group or a 3- to 5-membered heterocyclic group, and the heterocyclic group has 1 to 2 heteroatoms selected from N, O or S;

$R^8$ is selected from F, Cl, Br, I, hydroxyl, $C_{1-6}$ alkyl, carboxyl, amino, a carboxylic ester group, an amide group, $C_{1-6}$ alkoxy, a 3- to 5-membered carbocyclic group or a 3- to 5-membered heterocyclic group, and the heterocyclic group has 1 to 2 heteroatoms selected from N, O or S;

X is selected from H or F, and preferably H;

Y is selected from H, PEG,

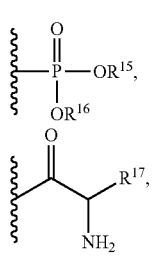, 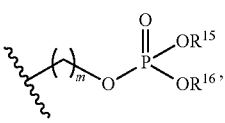

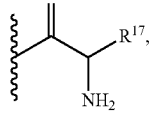

—$(CH_2CH_2O)_q$—H,    —$(CR^{ya}R^{yb})_{m1}$—$(W_1)_p$—C(=O) $(W_4R^{y3})$,    —$(CR^{ya}R^{yb})_{m1}$—$(W_1)_p$—P(=O)$(W_2R^{y4})$ $(W_3R^{y5})$ or

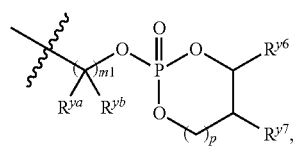

wherein the alkyl is optionally further substituted with 0 to 4 substituents selected from H, F, Cl, Br, I, hydroxyl, amino, cyano, carboxyl, $C_{1-6}$ alkyl, $C_{1-6}$ alkoxy, a $C_{3-8}$ carbocyclic group or a 4- to 8-membered heterocyclic group, and the heterocyclic group has 1 to 2 heteroatoms selected from N, O or S; Y is preferably H, PEG,

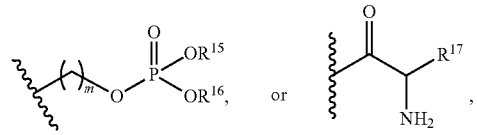

—$(CR^{ya}R^{yb})_{m1}$—$(W^1)_p$—C(=O)$(W_4R^{y3})$,    or
—$(CR^{ya}R^{yb})_{m1}$—$(W_1)_p$—P(=O)$(W_2R^{y4})(W_3R^{y5})$,    and
more preferably H, PEG, or

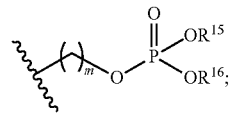

and n is selected from 1, 2 or 3; preferably 1 or 2, and more preferably 1.

Another preferred embodiment of the present invention comprises a compound of general formula (A), or any of a stereoisomer, a solvate, a metabolite, a prodrug, a pharmaceutically acceptable salt, or a cocrystal thereof;
wherein
R is selected from F, Cl, Br, I, —$OR^7$ or

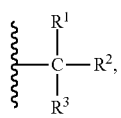

preferably F, Br, or

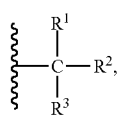

more preferably F or

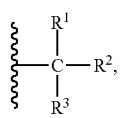

and even more preferably

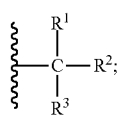

$R^1$, $R^2$ and $R^3$ are each independently selected from H, F, Cl, Br, I, hydroxyl, $C_{1-6}$ alkyl, $C_{1-6}$ alkoxy, a 3- to 5-membered carbocyclic group, or a 3- to 5-membered heterocyclic group, wherein the alkyl, alkoxy, carbocyclic group or heterocyclic group is optionally further substituted with 0 to 5 substituents selected from F, Cl, Br, I, hydroxyl, $C_{1-6}$ alkyl, C$_{1-6}$ alkoxy, a 3- to 5-membered carbocyclic group or a 3- to 5-membered heterocyclic group, the heterocyclic group has 1 to 2 heteroatoms selected from N, O or S, and R$^1$, R$^2$ and R$^3$ are not all H;
alternatively, any pair of R$^1$ and R$^2$, R$^2$ and R$^3$, or R$^1$ and R$^3$ may form a 3- to 5-membered ring, the 3- to 5-membered ring may have 0 to 2 heteroatoms selected from N, O or S, and the formed 3- to 5-membered ring may optionally be further substituted with 0 to 4 R$^8$s;
R$^4$, R$^5$, R$^9$, R$^{10}$, R$^{11}$ and R$^{12}$ are each independently selected from H, F, Cl, Br, I, hydroxyl, C$_{1-6}$ alkyl, C$_{1-6}$ alkoxy, a 3- to 5-membered carbocyclic group, or a 3- to 5-membered heterocyclic group, wherein the alkyl, alkoxy, carbocyclic group or heterocyclic group is optionally further substituted with 0 to 5 substituents selected from F, Cl, Br, I, hydroxyl, C$_{1-6}$ alkyl, C$_{1-6}$ alkoxy, a 3- to 5-membered carbocyclic group or a 3- to 5-membered heterocyclic group, the heterocyclic group has 1 to 2 heteroatoms selected from N, O or S, and R$^4$ and R$^5$ are not both H; preferably, R$^9$, R$^{10}$, R$^{11}$ and R$^{12}$ are each independently selected from H, F, Cl, Br, I, hydroxyl or C$_{1-6}$ alkyl; and more preferably, R$^9$, R$^{10}$, R$^{11}$ and R$^{12}$ are each independently selected from H or F;
alternatively, any pair of R$^4$ and R$^5$, R$^9$ and R$^{10}$, or R$^{11}$ and R$^{12}$ may form a 3- to 5-membered ring, the 3- to 5-membered ring may have 0 to 2 heteroatoms selected from N, O or S, and the formed 3- to 5-membered ring may optionally be further substituted with 0 to 4 R$^8$s; preferably, either pair of R$^9$ and R$^{10}$, or R$^{11}$ and R$^{12}$ may form a 3- to 5-membered ring;
R$^6$ is selected from H or hydroxyl;
R$^7$ is selected from H, C$_{1-6}$ alkyl, a 3- to 5-membered carbocyclic group or a 3- to 5-membered heterocyclic group, wherein the alkyl, carbocyclic group or heterocyclic group is optionally further substituted with 0 to 5 substituents selected from F, Cl, Br, I, hydroxyl, C$_{1-6}$ alkyl, C$_{1-6}$ alkoxy, a 3- to 5-membered carbocyclic group or a 3- to 5-membered heterocyclic group, and the heterocyclic group has 1 to 2 heteroatoms selected from N, O or S;
R$^8$ is selected from F, Cl, Br, I, hydroxyl, C$_{1-6}$ alkyl, carboxyl, amino, a carboxylic ester group, an amide group, C$_{1-6}$ alkoxy, a 3- to 5-membered carbocyclic group or a 3- to 5-membered heterocyclic group, and the heterocyclic group has 1 to 2 heteroatoms selected from N, O or S;
X is selected from H or F;
Y is selected from H; and
n is selected from 1, 2 or 3; preferably 1 or 2, and more preferably 1.

Another preferred embodiment of the present invention is a compound of general formula (A), or a stereoisomer, a solvate, a metabolite, a prodrug, a pharmaceutically acceptable salt, or a cocrystal thereof;
wherein
R is selected from F, Cl, Br, I, OR$^7$ or

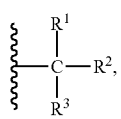

preferably F, Br, or

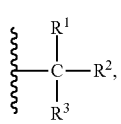

more preferably F or

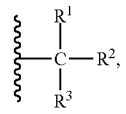

and even more preferably

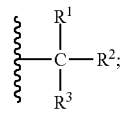

R$^1$, R$^2$ and R$^3$ are each independently selected from H, F, Cl, Br, I, hydroxyl, C$_{1-6}$ alkyl, C$_{1-6}$ alkoxy, a 3- to 5-membered carbocyclic group, or a 3- to 5-membered heterocyclic group, wherein the alkyl, alkoxy, carbocyclic group or heterocyclic group is optionally further substituted with 0 to 5 substituents selected from F, Cl, Br, I, hydroxyl, C$_{1-6}$ alkyl, C$_{1-6}$ alkoxy, a 3- to 5-membered carbocyclic group or a 3- to 5-membered heterocyclic group, the heterocyclic group has 1 to 2 heteroatoms selected from N, O or S, and R$^1$, R$^2$ and R$^3$ are not all H;
alternatively, any pair of R$^1$ and R$^2$, R$^2$ and R$^3$, or R$^1$ and R$^3$ may form a 3- to 5-membered ring, the 3- to 5-membered ring has 0 to 2 heteroatoms selected from N, O or S, and the formed 3- to 5-membered ring is optionally further substituted with 0 to 4 R$^8$s;
R$^4$ and R$^5$ are each independently selected from H, F, Cl, Br, I, hydroxyl, cyano, C$_{1-6}$ alkyl, C$_{1-6}$ alkoxy, a 3- to 5-membered carbocyclic group, or a 3- to 5-membered heterocyclic group, wherein the alkyl, alkoxy, carbocyclic group or heterocyclic group is optionally further substituted with 0 to 5 substituents selected from F, Cl, Br, I, hydroxyl, C$_{1-6}$ alkyl, C$_{1-6}$ alkoxy, a 3- to 5-membered carbocyclic group or a 3- to 5-membered heterocyclic group, the heterocyclic group has 1 to 2 heteroatoms selected from N, O or S, and R$^4$ and R$^5$ are not both H;
alternatively, R$^4$ and R$^5$ may form a 3- to 5-membered ring, the 3- to 5-membered ring may have 0 to 2 heteroatoms selected from N, O or S, and the formed 3- to 5-membered ring may optionally be further substituted with 0 to 4 R$^8$s;
R$^6$ is selected from H, hydroxyl or C$_{1-6}$ alkoxy, and preferably H or hydroxyl;
R$^7$ is selected from H, C$_{1-4}$ alkyl, or a 3- to 5-membered carbocyclic group, wherein the alkyl or carbocyclic group is optionally further substituted with 0 to 5 substituents selected from F, Cl, Br, I, hydroxyl, C$_{1-4}$ alkyl, C$_{1-4}$ alkoxy, or a 3- to 5-membered carbocyclic group;
R$^8$ is selected from F, Cl, Br, hydroxyl, C$_{1-4}$ alkyl, C$_{1-4}$ alkoxy, a 3- to 5-membered carbocyclic group or a 3- to 5-membered heterocyclic group, and the heterocyclic group has 1 to 2 heteroatoms selected from N, O or S;
R$^9$, R$^{10}$, R$^{11}$ and R$^{12}$ are each independently selected from H, F, Cl, Br, I, hydroxyl, C$_{1-6}$ alkyl or C$_{1-6}$ alkoxy;
X is selected from H, F or carboxyl, and preferably H;
Y is selected from H, COR$^{13}$, PEG, COOR$^{13}$, CONR$^{13}$R$^{14}$, COSR$^{13}$,

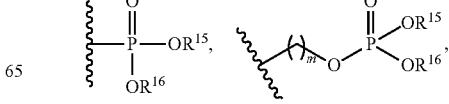

-continued

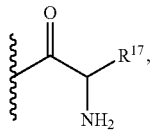

$C_{1-20}$ alkyl, $-(CH_2CH_2O)_q-H$, $-(CR^{ya}R^{yb})_{m1}COOR^{y1}$, $-(CR^{ya}R^{yb})_{m1}-(W_1)_p-C(=O)(W_4R^{y3})$ or $-(CR^{ya}R^{yb})_{m1}-(W_1)_p-P(=O)(W_2R^{y4})(W_3R^{y5})$ or

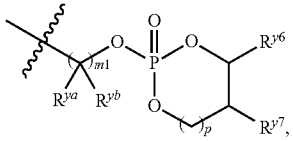

wherein the alkyl is optionally further substituted with 0 to 4 substituents selected from H, F, Cl, Br, I, hydroxyl, amino, cyano, carboxyl, $C_{1-6}$ alkyl, $C_{1-6}$ alkoxy, a $C_{3-8}$ carbocyclic group or a 4- to 8-membered heterocyclic group, and the heterocyclic group has 1 to 2 heteroatoms selected from N, O or S;

$R^{13}$ and $R^{14}$ are each independently selected from H, $C_{1-6}$ alkyl, a 3- to 8-membered carbocyclic or heterocyclic group, wherein the alkyl, carbocyclic group or heterocyclic group may optionally be further substituted with 0 to 5 substituents selected from F, Cl, Br, I, hydroxyl, $C_{1-6}$ alkyl, $C_{1-6}$ alkoxy, a 3- to 8-membered carbocyclic group or a 3- to 8-membered heterocyclic group, and the heterocyclic group has 1 to 2 heteroatoms selected from N, O or S;

$R^{15}$ and $R^{16}$ are each independently selected from H, an alkali metal ion, an alkali earth metal ion, a protonated amine or a protonated amino acid, wherein the alkali metal ion is selected from $Na^+$, $K^+$ or $Li^+$, the alkali earth metal ion is selected from $Be^{2+}$, $Mg^{2+}$ or $Ca^{2+}$, the amine is selected from trometamol, triethanolamine, ethanolamine, triethylamine or N-methylglucosamine, and the amino acid is selected from arginine or lysine;

alternatively, $R^{15}$ and $R^{16}$ may form a 3- to 8-membered ring, the 3- to 8-membered ring may have 0 to 2 heteroatoms selected from N, O or S, and the formed 3- to 8-membered ring may optionally be further substituted with 0 to 4 $R^8$s;

$R^{17}$ is the side-chain group of an amino acid, wherein the amino acid is selected from lysine, arginine, histidine, proline, 2,3-diaminopropionic acid, 2,4-diaminopropionic acid, alanine, valine, leucine, isoleucine, phenylalanine, tryptophan, methionine, glycine, serine, threonine, cysteine, tyrosine, asparagine, glutamine, aspartic acid, aspartate, or glutamic acid;

$W_1$, $W_2$ and $W_3$ are each independently selected from $NR^{y8}$, O or S;

$W_4$ is selected from $CR^{y9}R^{y10}$, $NR^{y8}$, O, S, or is absent;

$R^{y1}$ is each independently selected from H, $C_{1-6}$ alkyl, a $C_{3-8}$ carbocyclic group or a 4- to 8-membered heterocyclic group, wherein the alkyl, carbocyclic group or heterocyclic group may optionally be further substituted with 0 to 5 substituents selected from H, F, Cl, Br, I, hydroxyl, amino, cyano, carboxyl, $C_{1-6}$ alkyl, $C_{1-6}$ alkoxy, a $C_{3-8}$ carbocyclic group or a 4- to 8-membered heterocyclic group, and the heterocyclic group has 1 to 2 heteroatoms selected from N, O or S;

$R^{y3}$ is selected from H, amino, $C_{1-6}$ alkyl, a $C_{3-8}$ carbocyclic group or a 4- to 8-membered heterocyclic group, $-(CR^{ya}R^{yb})_{m1}-NR^{yc}R^{yd}$ or $-(CR^{ya}R^{yb})_{m1}-NR^{yc}C(=O)OR^{yd}$, wherein the amino group, alkyl, carbocyclic group or heterocyclic group may optionally be further substituted with 0 to 5 substituents selected from H, F, Cl, Br, I, hydroxyl, amino, cyano, carboxyl, $C_{1-6}$ alkyl, $C_{1-6}$ alkoxy, $-(CH_2)_{m1}-OC(=O)-C_{1-6}$ alkyl, $-(CH_2)_{m1}-C(=O)O-C_{1-6}$ alkyl, $-(CH_2)_{m1}-C(=O)O(CH_2)_{m1}-(C_{3-6}$ carbocyclic group), $-(CH_2)_{m1}-C(=O)-C_{1-6}$ alkyl, $-(CH_2)_{m1}-(C_{3-8}$ carbocyclic group) or $-(CH_2)_{m1}-(4-$ to 8-membered heterocyclic group), and the heterocyclic group has 1 to 2 heteroatoms selected from N, O or S;

$R^{y4}$ and $R^{y5}$ are each independently selected from H, an alkali metal ion, an alkali earth metal ion, a protonated amine or a protonated amino acid, $C_{1-6}$ alkyl, $-(CR^{ya}R^{yb})_{m1}-(3-$ to 8-membered ring), $-(CR^{ya}R^{yb})_{m1}-OC(=O)C_{1-6}$ alkyl, $-(CR^{ya}R^{yb})_{m1}-OC(=O)-(3-$ to 8-membered ring), $-(CR^{ya}R^{yb})_{m1}-C(=O)OC_{1-6}$ alkyl or $-(CR^{ya}R^{yb})_{m1}-OC(=O)OC_{1-6}$ alkyl;

$R^{y6}$ and $R^{y7}$ are each independently selected from H, F, Cl, Br, I, hydroxyl, amino, cyano, carboxyl, $C_{1-6}$ alkyl or $C_{1-6}$ alkoxy;

alternatively, $R^{y6}$ and $R^{y7}$ may form a 5- to 8-membered ring together with the atoms to which they are attached, the 5- to 8-membered ring may have 0 to 4 heteroatoms selected from N, O or S, and the 5- to 8-membered ring may optionally be further substituted with 0 to 4 substituents selected from H, F, Cl, Br, I, $C_{1-6}$ alkyl or $C_{1-6}$ alkoxy;

$R^{y8}$s are each independently selected from H or $C_{1-6}$ alkyl;

$R^{y9}$ and $R^{y10}$ are each independently selected from H, $C_{1-6}$ alkyl, a $C_{3-8}$ carbocyclic group or a 4- to 8-membered heterocyclic group, wherein the alkyl, carbocyclic group and heterocyclic group are each optionally further substituted with 0 to 4 substituents selected from H, hydroxyl, amino, mercapto, carboxyl, guanidino, carbamoyl, $C_{1-6}$ alkyl, $C_{1-6}$ alkoxy, a 3- to 8-membered carbocycle or a 3- to 8-membered heterocycle;

$R^{ya}$, $R^{yb}$, $R^{yc}$ and $R^{yd}$ are each independently selected from H or $C_{1-6}$ alkyl;

n is selected from 1, 2 or 3;

m is selected from 1 or 2;

q is selected from 1 to 200;

m1 is selected from 0, 1, 2 or 3; and p is selected from 0, 1 or 2.

Another preferred embodiment of the present invention comprises a compound of general formula (A), or any of a stereoisomer, a solvate, a metabolite, a prodrug, a pharmaceutically acceptable salt, or a cocrystal thereof;

wherein

R is selected from F, Cl, Br, I, $-OR^7$ or

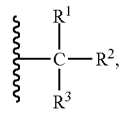

preferably F, Br, or

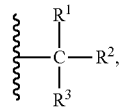

more preferably F or

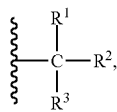

and even more preferably

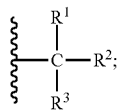

$R^1$, $R^2$ and $R^3$ are each independently selected from H, F, Cl, Br, I, hydroxyl, $C_{1-7}$ alkyl, $C_{1-7}$ alkoxy, a 3- to 6-membered carbocyclic group, or a 3- to 6-membered heterocyclic group, wherein the alkyl, alkoxy, carbocyclic group or heterocyclic group is optionally further substituted with 0 to 5 substituents selected from F, Cl, Br, I, hydroxyl, $C_{1-7}$ alkyl, $C_{1-7}$ alkoxy, a 3- to 6-membered carbocyclic group or a 3- to 6-membered heterocyclic group, the heterocyclic group has 1 to 2 heteroatoms selected from N, O or S, and $R^1$, $R^2$ and $R^3$ are not all H;
alternatively, any pair of $R^1$ and $R^2$, $R^2$ and $R^3$, or $R^1$ and $R^3$ may form a 3- to 6-membered ring, the 3- to 6-membered ring may have 0 to 2 heteroatoms selected from N, O or S, and the formed 3- to 6-membered ring may optionally be further substituted with 0 to 4 $R^8$s;
$R^4$, $R^5$, $R^9$, $R^{10}$, $R^{11}$ and $R^{12}$ are each independently selected from H, F, Cl, Br, I, hydroxyl, $C_{1-7}$ alkyl, $C_{1-7}$ alkoxy, a 3- to 6-membered carbocyclic group, or a 3- to 6-membered heterocyclic group, wherein the alkyl, alkoxy, carbocyclic group or heterocyclic group is optionally further substituted with 0 to 5 substituents selected from F, Cl, Br, I, hydroxyl, $C_{1-7}$ alkyl, $C_{1-7}$ alkoxy, a 3- to 6-membered carbocyclic group or a 3- to 6-membered heterocyclic group, the heterocyclic group has 1 to 2 heteroatoms selected from N, O or S, and $R^4$ and $R^5$ are not both H; preferably, $R^9$, $R^{10}$, $R^{11}$ and $R^{12}$ are each independently selected from H or F;
alternatively, any pair of $R^4$ and $R^5$, $R^9$ and $R^{10}$, or $R^{11}$ and $R^{12}$ may form a 3- to 6-membered ring, the 3- to 6-membered ring may have 0 to 2 heteroatoms selected from N, O or S, and the formed 3- to 6-membered ring may optionally be further substituted with 0 to 4 $R^8$s;
$R^6$ is selected from H, F, Cl, Br, I, hydroxyl or $C_{1-7}$ alkoxy, preferably H, F, Cl, hydroxyl or $C_{1-7}$ alkoxy, more preferably H, hydroxyl or $C_{1-7}$ alkoxy, and even more preferably H or hydroxyl;
$R^7$ is selected from H, $C_{1-7}$ alkyl, a 3- to 6-membered carbocyclic group or a 3- to 6-membered heterocyclic group, wherein the alkyl, carbocyclic group or heterocyclic group is optionally further substituted with 0 to 5 substituents selected from F, Cl, Br, I, hydroxyl, $C_{1-7}$ alkyl, $C_{1-7}$ alkoxy, a 3- to 6-membered carbocyclic group or a 3- to 6-membered heterocyclic group, and the heterocyclic group has 1 to 2 heteroatoms selected from N, O or S;
$R^8$ is selected from F, Cl, Br, I, hydroxyl, $C_{1-7}$ alkyl, carboxyl, amino, a carboxylic ester group, an amide group, $C_{1-7}$ alkoxy, a 3- to 6-membered carbocyclic group or a 3- to 6-membered heterocyclic group, and the heterocyclic group has 1 to 2 heteroatoms selected from N, O or S;

Y is selected from H, PEG, $COR^{13}$, $CONR^{13}R^{14}$,

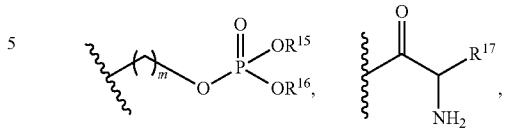

preferably H, PEG, or

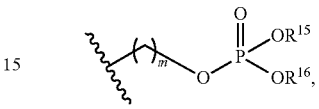

and more preferably H;
$R^{13}$ and $R^{14}$ are each independently selected from H or $C_{1-6}$ alkyl;
$R^{15}$ and $R^{16}$ are each independently selected from H or an alkali metal ion, wherein the alkali metal ion is selected from $Na^+$, $K^+$ or $Li^+$;
$R^{17}$ is the side-chain group of an L-amino acid, wherein the L-amino acid is selected from lysine, arginine, histidine, 2,3-diaminopropionic acid, 2,4-diaminopropionic acid, alanine, valine, leucine, isoleucine, phenylalanine, tryptophan, methionine, glycine, serine, threonine, cysteine, tyrosine, asparagine, glutamine, aspartic acid or glutamic acid, and preferably lysine, arginine, or histidine;
X is selected from H, F or carboxyl, preferably H or F, and more preferably H;
m is selected from 1 or 2; and
n is selected from 1, 2 or 3; preferably 1 or 2, and more preferably 1.
Another preferred embodiment of the present invention comprises a compound of general formula (A), or any of a stereoisomer, a solvate, a metabolite, a prodrug, a pharmaceutically acceptable salt, or a cocrystal thereof;
wherein
R is selected from F, Cl, Br, I, —$OR^7$ or

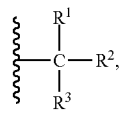

preferably F, Br, or

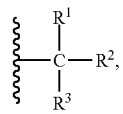

more preferably F or

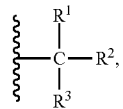

and even more preferably

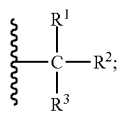

$R^1$, $R^2$ and $R^3$ are each independently selected from H, F, Cl, Br, I, hydroxyl, $C_{1-6}$ alkyl, $C_{1-6}$ alkoxy, a 3- to 5-membered carbocyclic group, or a 3- to 5-membered heterocyclic group, wherein the alkyl, alkoxy, carbocyclic group or heterocyclic group is optionally further substituted with 0 to 5 substituents selected from F, Cl, Br, I, hydroxyl, $C_{1-6}$ alkyl, $C_{1-6}$ alkoxy, a 3- to 5-membered carbocyclic group or a 3- to 5-membered heterocyclic group, the heterocyclic group has 1 to 2 heteroatoms selected from N, O or S, and $R^1$, $R^2$ and $R^3$ are not all H;

alternatively, any pair of $R^1$ and $R^2$, $R^2$ and $R^3$, or $R^1$ and $R^3$ may form a 3- to 5-membered ring, the 3- to 5-membered ring may have 0 to 2 heteroatoms selected from N, O or S, and the formed 3- to 5-membered ring may optionally be further substituted with 0 to 4 $R^8$s;

$R^4$, $R^5$, $R^9$, $R^{10}$, $R^{11}$ and $R^{12}$ are each independently selected from H, F, Cl, Br, I, hydroxyl, $C_{1-6}$ alkyl, $C_{1-6}$ alkoxy, a 3- to 5-membered carbocyclic group, or a 3- to 5-membered heterocyclic group, wherein the alkyl, alkoxy, carbocyclic group or heterocyclic group is optionally further substituted with 0 to 5 substituents selected from F, Cl, Br, I, hydroxyl, $C_{1-6}$ alkyl, $C_{1-6}$ alkoxy, a 3- to 5-membered carbocyclic group or a 3- to 5-membered heterocyclic group, the heterocyclic group has 1 to 2 heteroatoms selected from N, O or S, and $R^4$ and $R^5$ are not both H; preferably, $R^9$, $R^{10}$, $R^{11}$ and $R^{12}$ are each independently selected from H or F;

alternatively, any pair of $R^4$ and $R^5$, $R^9$ and $R^{10}$, or $R^{11}$ and $R^{12}$ may form a 3- to 5-membered ring, the 3- to 5-membered ring may have 0 to 2 heteroatoms selected from N, O or S, and the formed 3- to 5-membered ring may optionally be further substituted with 0 to 4 $R^8$s;

$R^6$ is selected from H, hydroxyl or $C_{1-6}$ alkoxy, and more preferably H or hydroxyl;

$R^7$ is selected from H, $C_{1-6}$ alkyl, a 3- to 5-membered carbocyclic group or a 3- to 5-membered heterocyclic group, wherein the alkyl, carbocyclic group or heterocyclic group is optionally further substituted with 0 to 5 substituents selected from F, Cl, Br, I, hydroxyl, $C_{1-6}$ alkyl, $C_{1-6}$ alkoxy, a 3- to 5-membered carbocyclic group or a 3- to 5-membered heterocyclic group, and the heterocyclic group has 1 to 2 heteroatoms selected from N, O or S;

$R^8$ is selected from F, Cl, Br, I, hydroxyl, $C_{1-6}$ alkyl, carboxyl, amino, a carboxylic ester group, an amide group, $C_{1-6}$ alkoxy, a 3- to 5-membered carbocyclic group or a 3- to 5-membered heterocyclic group, and the heterocyclic group has 1 to 2 heteroatoms selected from N, O or S;

X is selected from H or F, and preferably H;

Y is selected from H; and n is selected from 1, 2 or 3; preferably 1 or 2, and more preferably 1.

Another preferred embodiment of the present invention comprises a compound of general formula (A), or any of a stereoisomer, a solvate, a metabolite, a prodrug, a pharmaceutically acceptable salt, or a cocrystal thereof;

wherein
R is selected from F, Cl, Br, I, —$OR^7$ or

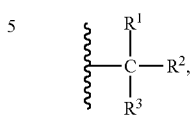

preferably F, Br, or

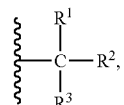

more preferably F or

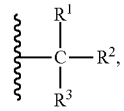

and even more preferably

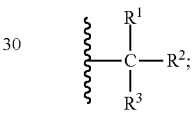

$R^1$, $R^2$ and $R^3$ are each independently selected from H, F, Cl, Br, I, hydroxyl, $C_{1-6}$ alkyl, $C_{1-6}$ alkoxy, a 3- to 5-membered carbocyclic group, or a 3- to 5-membered heterocyclic group, wherein the alkyl, alkoxy, carbocyclic group or heterocyclic group is optionally further substituted with 0 to 5 substituents selected from F, Cl, Br, I, hydroxyl, $C_{1-6}$ alkyl, $C_{1-6}$ alkoxy, a 3- to 5-membered carbocyclic group or a 3- to 5-membered heterocyclic group, the heterocyclic group has 1 to 2 heteroatoms selected from N, O or S, and $R^1$, $R^2$ and $R^3$ are not all H;

alternatively, any pair of $R^1$ and $R^2$, $R^2$ and $R^3$, or $R^1$ and $R^3$ may form a 3- to 5-membered ring, the 3- to 5-membered ring may have 0 to 2 heteroatoms selected from N, O or S, and the formed 3- to 5-membered ring may optionally be further substituted with 0 to 4 $R^8$s;

$R^4$, $R^5$, $R^9$, $R^{10}$, $R^{11}$ and $R^{12}$ are each independently selected from H, F, Cl, Br, I, hydroxyl, $C_{1-6}$ alkyl, $C_{1-6}$ alkoxy, a 3- to 5-membered carbocyclic group, or a 3- to 5-membered heterocyclic group, wherein the alkyl, alkoxy, carbocyclic group or heterocyclic group is optionally further substituted with 0 to 5 substituents selected from F, Cl, Br, I, hydroxyl, $C_{1-6}$ alkyl, $C_{1-6}$ alkoxy, a 3- to 5-membered carbocyclic group or a 3- to 5-membered heterocyclic group, the heterocyclic group has 1 to 2 heteroatoms selected from N, O or S, and $R^4$ and $R^5$ are not both H; preferably, $R^9$, $R^{10}$, $R^{11}$ and $R^{12}$ are each independently selected from H, F, Cl, Br, I, hydroxyl or $C_{1-6}$ alkyl; and more preferably, $R^9$, $R^{10}$, $R^{11}$ and $R^{12}$ are each independently selected from H or F;

alternatively, any pair of $R^4$ and $R^5$, $R^9$ and $R^{10}$, or $R^{11}$ and $R^{12}$ may form a 3- to 5-membered ring, the 3- to 5-membered ring may have 0 to 2 heteroatoms selected from N, O or S, and the formed 3- to 5-membered ring may optionally be further substituted with 0 to 4 $R^8$s; preferably, either pair of $R^9$ and $R^{10}$, or $R^{11}$ and $R^{12}$ may form a 3- to 5-membered ring;

$R^6$ is selected from H or hydroxyl;

$R^7$ is selected from H, $C_{1-6}$ alkyl, a 3- to 5-membered carbocyclic group or a 3- to 5-membered heterocyclic group, wherein the alkyl, carbocyclic group or heterocyclic group is optionally further substituted with 0 to 5 substituents selected from F, Cl, Br, I, hydroxyl, $C_{1-6}$ alkyl, $C_{1-6}$ alkoxy, a 3- to 5-membered carbocyclic group or a 3- to 5-membered heterocyclic group, and the heterocyclic group has 1 to 2 heteroatoms selected from N, O or S;

$R^8$ is selected from F, Cl, Br, I, hydroxyl, $C_{1-6}$ alkyl, carboxyl, amino, a carboxylic ester group, an amide group, $C_{1-6}$ alkoxy, a 3- to 5-membered carbocyclic group or a 3- to 5-membered heterocyclic group, and the heterocyclic group has 1 to 2 heteroatoms selected from N, O or S;

X is selected from H or F;

Y is selected from H; and n is selected from 1, 2 or 3; preferably 1 or 2, and more preferably 1.

Another preferred embodiment of the present invention is a compound of general formula (I):

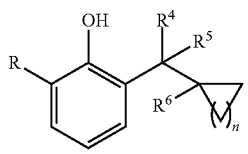

(I)

or any of a stereoisomer, a solvate, a metabolite, a prodrug, a pharmaceutically acceptable salt, or a cocrystal thereof; wherein, R is selected from F, Cl, Br, I, —$OR^7$ or

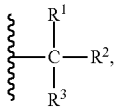

preferably F, Br, —$OR^7$ or

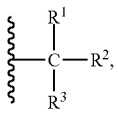

more preferably F, Br or

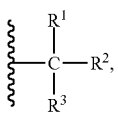

more preferably F or

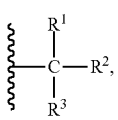

and even more preferably

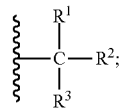

$R^1$, $R^2$ and $R^3$ are each independently selected from H, F, Cl, Br, I, hydroxyl, $C_{1-6}$ alkyl, $C_{1-6}$ alkoxy, a 3- to 5-membered carbocyclic group or a 3- to 5-membered heterocyclic group, preferably H, F, hydroxyl, $C_{1-5}$ alkyl, $C_{1-5}$ alkoxy or a 3- to 5-membered carbocyclic group, more preferably H, F, hydroxyl, $C_{1-4}$ alkyl, $C_{1-4}$ alkoxy or a 3- to 5-membered carbocyclic group, and even more preferably H, $C_{1-3}$ alkyl or a 3- to 4-membered carbocyclic group; wherein the alkyl, alkoxy, carbocyclic group or heterocyclic group is optionally further substituted with 0 to 5 substituents selected from F, Cl, Br, I, hydroxyl, $C_{1-6}$ alkyl, $C_{1-6}$ alkoxy, a 3- to 5-membered carbocyclic group or a 3- to 5-membered heterocyclic group, the heterocyclic group has 1 to 2 heteroatoms selected from N, O or S, and $R^1$, $R^2$ and $R^3$ are not all H;

alternatively, any pair of $R^1$ and $R^2$, $R^2$ and $R^3$, or $R^1$ and $R^3$ may form a 3- to 5-membered ring, the 3- to 5-membered ring may have 0 to 2 heteroatoms selected from N, O or S, and the formed 3- to 5-membered ring may optionally be further substituted with 0 to 4 $R^8$s;

$R^4$ and $R^5$ are each independently selected from H, F, Cl, Br, I, hydroxyl, $C_{1-6}$ alkyl, $C_{1-6}$ alkoxy, a 3- to 5-membered carbocyclic group, or a 3- to 5-membered heterocyclic group, preferably H, F, Cl, Br, hydroxyl, $C_{1-4}$ alkyl or $C_{1-4}$ alkoxy, more preferably H, F, hydroxyl, $C_{1-4}$ alkyl or $C_{1-4}$ alkoxy, and even more preferably H, F or $C_{1-3}$ alkyl; wherein the alkyl, alkoxy, carbocyclic group or heterocyclic group is optionally further substituted with 0 to 5 substituents selected from F, Cl, Br, I, hydroxyl, $C_{1-6}$ alkyl, $C_{1-6}$ alkoxy, a 3- to 5-membered carbocyclic group or a 3- to 5-membered heterocyclic group, the heterocyclic group has 1 to 2 heteroatoms selected from N, O or S, and $R^4$ and $R^5$ are not both H;

alternatively, $R^4$ and $R^5$ may form a 3- to 5-membered ring, the 3- to 5-membered ring may have 0 to 2 heteroatoms selected from N, O or S, and the formed 3- to 5-membered ring may optionally be further substituted with 0 to 4 $R^8$s;

$R^6$ is selected from H, hydroxyl or $C_{1-6}$ alkoxy, preferably H or hydroxyl, and more preferably H;

$R^7$ is selected from H, $C_{1-6}$ alkyl, a 3- to 5-membered carbocyclic group or a 3- to 5-membered heterocyclic group, wherein the alkyl, carbocyclic group or heterocyclic group is optionally further substituted with 0 to 5 substituents selected from F, Cl, Br, I, hydroxyl, $C_{1-6}$ alkyl, $C_{1-6}$ alkoxy, a 3- to 5-membered carbocyclic group or a 3- to 5-membered heterocyclic group, and the heterocyclic group has 1 to 2 heteroatoms selected from N, O or S;

$R^8$ is selected from F, Cl, Br, I, hydroxyl, $C_{1-6}$ alkyl, carboxyl, amino, a carboxylic ester group, an amide group, $C_{1-6}$ alkoxy, a 3- to 5-membered carbocyclic group or a 3- to 5-membered heterocyclic group, and the heterocyclic group has 1 to 2 heteroatoms selected from N, O or S; and n is selected from 1, 2 or 3; preferably 1 or 2, and more preferably 1.

Another preferred embodiment of the present invention comprises a compound of general formula (I) or any of a stereoisomer, a solvate, a metabolite, a prodrug, a pharmaceutically acceptable salt, or a cocrystal thereof;
wherein,
R is selected from F, Cl, Br, I, —OR$^7$ or

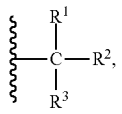

preferably F, Br, —OR$^7$

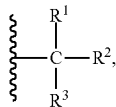

more preferably F, Br or

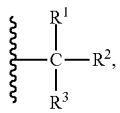

more preferably F or

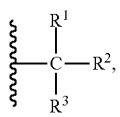

and even more preferably

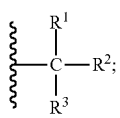

R$^1$, R$^2$ and R$^3$ are each independently selected from H, F, Cl, Br, hydroxyl, C$_{1-6}$ alkyl, C$_{1-6}$ alkoxy, a 3- to 5-membered carbocyclic group or a 3- to 5-membered heterocyclic group, preferably H, F, hydroxyl, C$_{1-4}$ alkyl, C$_{1-4}$ alkoxy or a 3- to 5-membered carbocyclic group, more preferably H, F, hydroxyl, C$_{1-3}$ alkyl, C$_{1-3}$ alkoxy or a 3- to 5-membered carbocyclic group, and even more preferably H, C$_{1-3}$ alkyl or a 3- to 4-membered carbocyclic group; wherein the alkyl, alkoxy, carbocyclic group or heterocyclic group is optionally further substituted with 0 to 5 substituents selected from F, Cl, Br, hydroxyl, C$_{1-6}$ alkyl, C$_{1-6}$ alkoxy, a 3- to 5-membered carbocyclic group or a 3- to 5-membered heterocyclic group, the heterocyclic group has 1 to 2 heteroatoms selected from N, O or S, and R$^1$, R$^2$ and R$^3$ are not all H; alternatively, any pair of R$^1$ and R$^2$, R$^2$ and R$^3$, or R$^1$ and R$^3$ may form a 3- to 5-membered ring, the 3- to 5-membered ring may have 0 to 2 heteroatoms selected from N, O or S, and the formed 3- to 5-membered ring may optionally be further substituted with 0 to 4 R$^8$s;
R$^4$ and R$^5$ are each independently selected from H, F, Cl, Br, hydroxyl, C$_{1-5}$ alkyl, C$_{1-5}$ alkoxy, a 3- to 5-membered carbocyclic group, or a 3- to 5-membered heterocyclic group, preferably H, F, Cl, Br, hydroxyl, C$_{1-4}$ alkyl or C$_{1-4}$ alkoxy, more preferably H, F, hydroxyl, C$_{1-4}$ alkyl or C$_{1-4}$ alkoxy, and even more preferably H, F or C$_{1-3}$ alkyl; wherein the alkyl, alkoxy, carbocyclic group or heterocyclic group is optionally further substituted with 0 to 5 substituents selected from F, Cl, Br, hydroxyl, C$_{1-5}$ alkyl, C$_{1-5}$ alkoxy, a 3- to 5-membered carbocyclic group or a 3- to 5-membered heterocyclic group, the heterocyclic group has 1 to 2 heteroatoms selected from N, O or S, and R$^4$ and R$^5$ are not both H;
alternatively, R$^4$ and R$^5$ may form a 3- to 5-membered ring, the 3- to 5-membered ring may have 0 to 2 heteroatoms selected from N, O or S, and the formed 3- to 5-membered ring may optionally be further substituted with 0 to 4 R$^8$s;
R$^6$ is selected from H or hydroxyl, and preferably H;
R$^7$ is selected from H, C$_{1-5}$ alkyl, a 3- to 5-membered carbocyclic group or a 3- to 5-membered heterocyclic group, wherein the alkyl, carbocyclic group or heterocyclic group is optionally further substituted with 0 to 5 substituents selected from F, Cl, Br, I, hydroxyl, C$_{1-5}$ alkyl, C$_{1-5}$ alkoxy, or a 3- to 5-membered carbocyclic group;
R$^8$ is selected from F, Cl, Br, hydroxyl, C$_{1-5}$ alkyl, C$_{1-5}$ alkoxy, a 3- to 5-membered carbocyclic group or a 3- to 5-membered heterocyclic group, and the heterocyclic group has 1 to 2 heteroatoms selected from N, O or S;
and
n is selected from 1, 2 or 3; preferably 1 or 2, and more preferably 1.

Another preferred embodiment of the present invention comprises a compound of general formula (I) or any of a stereoisomer, a solvate, a metabolite, a prodrug, a pharmaceutically acceptable salt, or a cocrystal thereof;
wherein,
R is selected from F, Cl, Br, —OR$^7$ or

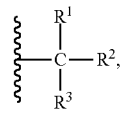

preferably F, B or

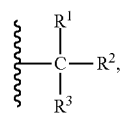

more preferably F or

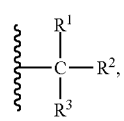

and even more preferably

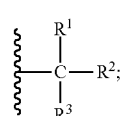

$R^1$, $R^2$ and $R^3$ are each independently selected from H, F, Cl, Br, hydroxyl, $C_{1-6}$ alkyl, $C_{1-6}$ alkoxy, a 3- to 5-membered carbocyclic group or a 3- to 5-membered heterocyclic group, preferably H, F, hydroxyl, $C_{1-4}$ alkyl, $C_{1-4}$ alkoxy or a 3- to 5-membered carbocyclic group, more preferably H, F, hydroxyl, $C_{1-3}$ alkyl, $C_{1-3}$ alkoxy or a 3- to 5-membered carbocyclic group, and even more preferably H, $C_{1-3}$ alkyl or a 3- to 4-membered carbocyclic group; wherein the alkyl, alkoxy, carbocyclic group or heterocyclic group is optionally further substituted with 0 to 5 substituents selected from F, Cl, Br, hydroxyl, $C_{1-6}$ alkyl, $C_{1-6}$ alkoxy, a 3- to 5-membered carbocyclic group or a 3- to 5-membered heterocyclic group, the heterocyclic group has 1 to 2 heteroatoms selected from N, O or S, and $R^1$, $R^2$ and $R^3$ are not all H; alternatively, any pair of $R^1$ and $R^2$, $R^2$ and $R^3$, or $R^1$ and $R^3$ may form a 3- to 5-membered ring, the 3- to 5-membered ring may have 0 to 2 heteroatoms selected from N, O or S, and the formed 3- to 5-membered ring may optionally be further substituted with 0 to 4 $R^8$s;

$R^4$ and $R^5$ are each independently selected from H, F, Cl, Br, hydroxyl, $C_{1-4}$ alkyl, $C_{1-4}$ alkoxy, a 3- to 5-membered carbocyclic group, or a 3- to 5-membered heterocyclic group, preferably H, F, Cl, Br, hydroxyl, $C_{1-4}$ alkyl or $C_{1-4}$ alkoxy, more preferably H, F, hydroxyl, $C_{1-4}$ alkyl or $C_{1-4}$ alkoxy, and even more preferably H, F or $C_{1-3}$ alkyl; wherein the alkyl, alkoxy, carbocyclic group or heterocyclic group is optionally further substituted with 0 to 5 substituents selected from F, Cl, Br, hydroxyl, $C_{1-4}$ alkyl, $C_{1-4}$ alkoxy, a 3- to 5-membered carbocyclic group or a 3- to 5-membered heterocyclic group, the heterocyclic group has 1 to 2 heteroatoms selected from N, O or S, and $R^4$ and $R^5$ are not both H;

alternatively, $R^4$ and $R^5$ may form a 3- to 5-membered ring, the 3- to 5-membered ring may have 0 to 2 heteroatoms selected from N, O or S, and the formed 3- to 5-membered ring may optionally be further substituted with 0 to 4 $R^8$s;

$R^6$ is selected from H or hydroxyl, and preferably H;

$R^7$ is selected from $C_{1-4}$ alkyl or a 3- to 5-membered carbocyclic group, wherein the alkyl or carbocyclic group is optionally further substituted with 0 to 5 substituents selected from F, Cl, Br, I, hydroxyl, $C_{1-4}$ alkyl, $C_{1-4}$ alkoxy, or a 3- to 5-membered carbocyclic group;

$R^8$ is selected from F, Cl, Br, hydroxyl, $C_{1-4}$ alkyl, $C_{1-4}$ alkoxy, a 3- to 5-membered carbocyclic group or a 3- to 5-membered heterocyclic group, and the heterocyclic group has 1 to 2 heteroatoms selected from N, O or S;

and n is selected from 1, 2 or 3; preferably 1 or 2, and more preferably 1.

Another preferred embodiment of the present invention comprises a compound of general formula (I) or any of a stereoisomer, a solvate, a metabolite, a prodrug, a pharmaceutically acceptable salt, or a cocrystal thereof;

wherein,

R is selected from F, Br, —$OR^7$ or

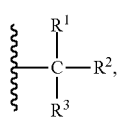

preferably F, Br or

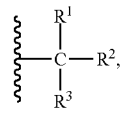

more preferably F or

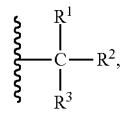

and even more preferably

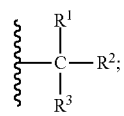

$R^1$, $R^2$ and $R^3$ are each independently selected from H, F, Cl, Br, hydroxyl, $C_{1-5}$ alkyl, $C_{1-5}$ alkoxy, or a 3- to 5-membered carbocyclic group, preferably H, F, hydroxyl, $C_{1-4}$ alkyl, $C_{1-4}$ alkoxy or a 3- to 5-membered carbocyclic group, more preferably H, F, hydroxyl, $C_{1-3}$ alkyl, $C_{1-3}$ alkoxy or a 3- to 5-membered carbocyclic group, and even more preferably H, $C_{1-3}$ alkyl or a 3- to 4-membered carbocyclic group; wherein the alkyl, alkoxy or carbocyclic group is optionally further substituted with 0 to 5 substituents selected from F, Cl, Br, hydroxyl, $C_{1-5}$ alkyl, $C_{1-5}$ alkoxy or a 3- to 5-membered carbocyclic group;

alternatively, any pair of $R^1$ and $R^2$, $R^2$ and $R^3$, or $R^1$ and $R^3$ may form a 3- to 5-membered carbocyclic group, preferably a 3- to 4-membered carbocyclic group, and the carbocyclic group may optionally be further substituted with 0 to 4 $R^8$s;

$R^4$ and $R^5$ are each independently selected from H, F, Cl, Br, hydroxyl, $C_{1-4}$ alkyl or $C_{1-4}$ alkoxy, preferably H, F, hydroxyl, $C_{1-4}$ alkyl or $C_{1-4}$ alkoxy, and more preferably H, F or $C_{1-3}$ alkyl; wherein the alkyl or alkoxy is optionally further substituted with 0 to 5 substituents selected from F, Cl, Br, hydroxyl, $C_{1-4}$ alkyl or $C_{1-4}$ alkoxy, and $R^4$ and $R^5$ are not both H;

alternatively, $R^4$ and $R^5$ may form a 3- to 5-membered carbocyclic group, preferably a 3- to 4-membered carbocyclic group, and the carbocyclic group may optionally be further substituted with 0 to 4 $R^8$s;

$R^6$ is selected from H or hydroxyl;

$R^7$ is selected from $C_{1-4}$ alkyl or a 3- to 4-membered carbocyclic group, wherein the alkyl or carbocyclic group is optionally further substituted with 0 to 5 substituents selected from F, hydroxyl or $C_{1-3}$ alkyl;

$R^8$ is selected from F, Cl, Br, hydroxyl, $C_{1-4}$ alkyl, $C_{1-4}$ alkoxy, or a 3- to 5-membered carbocyclic group;

and n is selected from 1, 2 or 3; preferably 1 or 2, and more preferably 1.

Another preferred embodiment of the present invention comprises a compound of general formula (I) or any of a stereoisomer, a solvate, a metabolite, a prodrug, a pharmaceutically acceptable salt, or a cocrystal thereof;

wherein,
R is selected from F, Br, —OR⁷ or

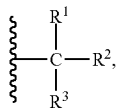

preferably F, Br or

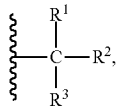

more preferably F or

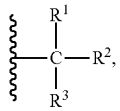

and even more preferably

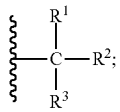

$R^1$, $R^2$ and $R^3$ are each independently selected from H, F, Cl, Br, hydroxyl, $C_{1-5}$ alkyl, $C_{1-5}$ alkoxy or a 3- to 5-membered carbocyclic group, preferably H, F, hydroxyl, $C_{1-4}$ alkyl, $C_{1-4}$ alkoxy or a 3- to 5-membered carbocyclic group, more preferably H, F, hydroxyl, $C_{1-3}$ alkyl, $C_{1-3}$ alkoxy or a 3- to 5-membered carbocyclic group, and even more preferably H, $C_{1-3}$ alkyl or a 3- to 4-membered carbocyclic group; wherein the alkyl, alkoxy or carbocyclic group is optionally further substituted with 0 to 3 substituents selected from F, Cl, Br, hydroxyl, $C_{1-5}$ alkyl, $C_{1-5}$ alkoxy or a 3- to 5-membered carbocyclic group, and $R^1$, $R^2$ and $R^3$ are not all H; wherein more preferably the alkyl, alkoxy or carbocyclic group is optionally further substituted with 0 to 3 substituents selected from F, Cl, Br, hydroxyl, $C_{1-4}$ alkyl, $C_{1-4}$ alkoxy or a 3- to 5-membered carbocyclic group;
alternatively, any pair of $R^1$ and $R^2$, $R^2$ and $R^3$, or $R^1$ and $R^3$ may form a 3- to 5-membered carbocyclic group, preferably a 3- to 4-membered carbocyclic group, and the carbocyclic group may optionally be further substituted with 0 to 4 $R^8$s;
$R^4$ and $R^5$ are each independently selected from H, F, Cl, Br, hydroxyl, $C_{1-4}$ alkyl or $C_{1-4}$ alkoxy, preferably H, F, hydroxyl, $C_{1-4}$ alkyl or $C_{1-4}$ alkoxy, and more preferably H, F or $C_{1-3}$ alkyl; wherein the alkyl or alkoxy is optionally further substituted with 0 to 3 substituents selected from F, Cl, Br, hydroxyl, $C_{1-4}$ alkyl or $C_{1-4}$ alkoxy, and $R^4$ and $R^5$ are not both H;
alternatively, $R^4$ and $R^5$ may form a 3- to 5-membered carbocyclic group, preferably a 3- to 4-membered carbocyclic group, and the carbocyclic group may optionally be further substituted with 0 to 4 $R^8$s;

$R^6$ is selected from H or hydroxyl;
$R^7$ is selected from $C_{1-4}$ alkyl or a 3- to 4-membered carbocyclic group, wherein the alkyl or carbocyclic group is optionally further substituted with 0 to 3 substituents selected from F, hydroxyl or $C_{1-3}$ alkyl;
$R^8$ is selected from F, Cl, Br, hydroxyl, $C_{1-4}$ alkyl or $C_{1-4}$ alkoxy;
and
n is selected from 1 or 2, and preferably 1.

Another preferred embodiment of the present invention comprises a compound of general formula (I) or any of a stereoisomer, a solvate, a metabolite, a prodrug, a pharmaceutically acceptable salt, or a cocrystal thereof;
wherein,
R is selected from F, Br or

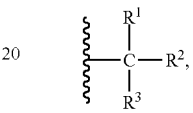

preferably F or

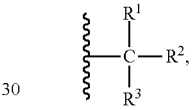

and more preferably

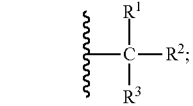

$R^1$, $R^2$ and $R^3$ are each independently selected from H, F, Cl, Br, hydroxyl, $C_{1-4}$ alkyl, $C_{1-4}$ alkoxy or a 3- to 5-membered carbocyclic group, preferably H, F, hydroxyl, $C_{1-4}$ alkyl, $C_{1-4}$ alkoxy or a 3- to 5-membered carbocyclic group, more preferably H, F, hydroxyl, $C_{1-3}$ alkyl, $C_{1-3}$ alkoxy or a 3- to 5-membered carbocyclic group, and even more preferably H, $C_{1-3}$ alkyl or a 3- to 4-membered carbocyclic group; wherein the alkyl, alkoxy or carbocyclic group is optionally further substituted with 0 to 3 substituents selected from F, Cl, Br, hydroxyl, $C_{1-4}$ alkyl, $C_{1-4}$ alkoxy or a 3- to 5-membered carbocyclic group, and $R^1$, $R^2$ and $R^3$ are not all H;
alternatively, any pair of $R^1$ and $R^2$, $R^2$ and $R^3$, or $R^1$ and $R^3$ may form a 3- to 5-membered carbocyclic group, preferably a 3- to 4-membered carbocyclic group, and the carbocyclic group may optionally be further substituted with 0 to 4 $R^8$s;
$R^4$ and $R^5$ are each independently selected from H, F, Cl, Br, hydroxyl, $C_{1-4}$ alkyl or $C_{1-4}$ alkoxy, preferably H, F, hydroxyl, $C_{1-4}$ alkyl or $C_{1-4}$ alkoxy, and more preferably H, F or $C_{1-3}$ alkyl; wherein the alkyl or alkoxy is optionally further substituted with 0 to 3 substituents selected from F, Cl, Br, hydroxyl, $C_{1-4}$ alkyl or $C_{1-4}$ alkoxy, and $R^4$ and $R^5$ are not both H;
alternatively, $R^4$ and $R^5$ may form a 3- to 5-membered carbocyclic group, preferably a 3- to 4-membered carbocyclic group, and the carbocyclic group may optionally be further substituted with 0 to 4 $R^8$s;

$R^6$ is selected from H or hydroxyl, and preferably H;
$R^8$ is selected from F, Cl, Br, hydroxyl, $C_{1-4}$ alkyl or $C_{1-4}$ alkoxy, and preferably F, hydroxyl or $C_{1-3}$ alkyl;
and
n is selected from 1 or 2, and preferably 1.

Another preferred embodiment of the present invention comprises a compound of general formula (I) or any of a stereoisomer, a solvate, a metabolite, a prodrug, a pharmaceutically acceptable salt, or a cocrystal thereof;
wherein,
R is selected from Br or

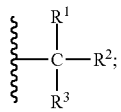

$R^1$, $R^2$ and $R^3$ are each independently selected from H, F, Cl, Br, hydroxyl, $C_{1-4}$ alkyl, $C_{1-4}$ alkoxy or a 3- to 5-membered carbocyclic group, preferably H, F, hydroxyl, $C_{1-4}$ alkyl, $C_{1-4}$ alkoxy or a 3- to 5-membered carbocyclic group, more preferably H, F, hydroxyl, $C_{1-3}$ alkyl, $C_{1-3}$ alkoxy or a 3- to 5-membered carbocyclic group, and even more preferably H, $C_{1-3}$ alkyl or a 3- to 4-membered carbocyclic group; wherein the alkyl, alkoxy or carbocyclic group is optionally further substituted with 0 to 3 substituents selected from F, Cl, Br, hydroxyl, $C_{1-4}$ alkyl, $C_{1-4}$ alkoxy or a 3- to 5-membered carbocyclic group, and $R^1$, $R^2$ and $R^3$ are not all H;
alternatively, any pair of $R^1$ and $R^2$, $R^2$ and $R^3$, or $R^1$ and $R^3$ may form a 3- to 5-membered carbocyclic group, preferably a 3- to 4-membered carbocyclic group, and the carbocyclic group may optionally be further substituted with 0 to 4 $R^8$s;
$R^4$ and $R^5$ are each independently selected from H, F, Cl, Br, hydroxyl, $C_{1-4}$ alkyl or $C_{1-4}$ alkoxy, preferably H, F, hydroxyl, $C_{1-4}$ alkyl or $C_{1-4}$ alkoxy, and more preferably H, F or $C_{1-3}$ alkyl; wherein the alkyl or alkoxy is optionally further substituted with 0 to 3 substituents selected from F, Cl, Br, hydroxyl, $C_{1-4}$ alkyl or $C_{1-4}$ alkoxy, and $R^4$ and $R^5$ are not both H;
alternatively, $R^4$ and $R^5$ may form a 3- to 5-membered carbocyclic group, preferably a 3- to 4-membered carbocyclic group, and the carbocyclic group may optionally be further substituted with 0 to 4 $R^8$s;
$R^6$ is selected from H or hydroxyl, and preferably H;
$R^8$ is selected from F, Cl, Br, hydroxyl, $C_{1-4}$ alkyl or $C_{1-4}$ alkoxy, and preferably F, hydroxyl or $C_{1-3}$ alkyl;
and
n is selected from 1.

Another preferred embodiment of the present invention comprises a compound of general formula (I) or any of a stereoisomer, a solvate, a metabolite, a prodrug, a pharmaceutically acceptable salt, or a cocrystal thereof; wherein, the compound is selected from a compound of general formula (II):

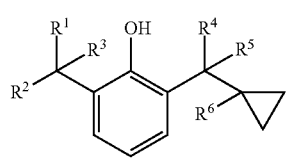

(II)

wherein,
$R^1$, $R^2$ and $R^3$ are each independently selected from H, F, Cl, Br, hydroxyl, $C_{1-4}$ alkyl, $C_{1-4}$ alkoxy or a 3- to 5-membered carbocyclic group, preferably H, F, hydroxyl, $C_{1-4}$ alkyl, $C_{1-4}$ alkoxy or a 3- to 5-membered carbocyclic group, more preferably H, F, hydroxyl, $C_{1-3}$ alkyl, $C_{1-3}$ alkoxy or a 3- to 5-membered carbocyclic group, and even more preferably H, $C_{1-3}$ alkyl or a 3- to 4-membered carbocyclic group; wherein the alkyl, alkoxy or carbocyclic group is optionally further substituted with 0 to 3 substituents selected from F, Cl, Br, hydroxyl, $C_{1-4}$ alkyl, $C_{1-4}$ alkoxy or a 3- to 5-membered carbocyclic group, and $R^1$, $R^2$ and $R^3$ are not all H;
alternatively, any pair of $R^1$ and $R^2$, $R^2$ and $R^3$, or $R^1$ and $R^3$ may form a 3- to 5-membered carbocyclic group, preferably a 3- to 4-membered carbocyclic group, and the carbocyclic group may optionally be further substituted with 0 to 4 $R^8$s;
$R^4$ and $R^5$ are each independently selected from H, F, Cl, Br, hydroxyl, $C_{1-4}$ alkyl or $C_{1-4}$ alkoxy, preferably H, F, hydroxyl, $C_{1-4}$ alkyl or $C_{1-4}$ alkoxy, and more preferably H, F or $C_{1-3}$ alkyl; wherein the alkyl or alkoxy is optionally further substituted with 0 to 3 substituents selected from F, hydroxyl, $C_{1-4}$ alkyl or $C_{1-4}$ alkoxy, and $R^4$ and $R^5$ are not both H;
alternatively, $R^4$ and $R^5$ may form a 3- to 5-membered carbocyclic group, preferably a 3- to 4-membered carbocyclic group, and the carbocyclic group may optionally be further substituted with 0 to 4 $R^8$s;
$R^6$ is selected from H or hydroxyl, and preferably H;
and
$R^8$ is selected from F, hydroxyl, $C_{1-4}$ alkyl or $C_{1-4}$ alkoxy, and preferably F, hydroxyl or $C_{1-3}$ alkyl.

Another preferred embodiment of the present invention comprises a compound of general formula (II) or any of a stereoisomer, a solvate, a metabolite, a prodrug, a pharmaceutically acceptable salt, or a cocrystal thereof;
wherein,
$R^1$, $R^2$ and $R^3$ are each independently selected from H, F, Cl, Br, hydroxyl, $C_{1-4}$ alkyl, $C_{1-4}$ alkoxy or a 3- to 5-membered carbocyclic group, preferably H, F, hydroxyl, $C_{1-3}$ alkyl, $C_{1-3}$ alkoxy or a 3- to 5-membered carbocyclic group, and more preferably H, $C_{1-3}$ alkyl, or a 3- to 4-membered carbocyclic group; wherein the alkyl, alkoxy or carbocyclic group is optionally further substituted with 0 to 3 substituents selected from F or hydroxyl, and $R^1$, $R^2$ and $R^3$ are not all H;
alternatively, any pair of $R^1$ and $R^2$, $R^2$ and $R^3$, or $R^1$ and $R^3$ may form a 3- to 5-membered carbocyclic group, preferably a 3- to 4-membered carbocyclic group, and the carbocyclic group may optionally be further substituted with 0 to 4 substituents selected from F or hydroxyl;
$R^4$ and $R^5$ are each independently selected from H, F, Cl, Br, hydroxyl, $C_{1-4}$ alkyl or $C_{1-4}$ alkoxy, preferably H, F, hydroxyl, $C_{1-4}$ alkyl or $C_{1-4}$ alkoxy, and more preferably H, F or $C_{1-3}$ alkyl; wherein the alkyl or alkoxy is optionally further substituted with 0 to 3 substituents selected from F or hydroxyl, and $R^4$ and $R^5$ are not both H;
alternatively, $R^4$ and $R^5$ may form a 3- to 5-membered carbocyclic group, preferably a 3- to 4-membered carbocyclic group;
and
$R^6$ is selected from H or hydroxyl, and preferably H.

Another preferred embodiment of the present invention comprises a compound of general formula (II) or any of a stereoisomer, a solvate, a metabolite, a prodrug, a pharmaceutically acceptable salt, or a cocrystal thereof;
wherein,
$R^1$, $R^2$ and $R^3$ are each independently selected from H, F, Cl, Br, hydroxyl, $C_{1-4}$ alkyl, $C_{1-4}$ alkoxy or a 3- to 5-membered carbocyclic group, preferably H, F, hydroxyl, $C_{1-3}$ alkyl, $C_{1-3}$ alkoxy or a 3- to 5-membered carbocyclic group, and more preferably H, $C_{1-3}$ alkyl, or a 3- to 4-membered carbocyclic group; wherein the alkyl, alkoxy or carbocyclic group is optionally further substituted with 0 to 3 substituents selected from F or hydroxyl, and $R^1$, $R^2$ and $R^3$ are not all H;
alternatively, any pair of $R^1$ and $R^2$, $R^2$ and $R^3$, or $R^1$ and $R^3$ may form a 3- to 5-membered carbocyclic group, preferably a 3- to 4-membered carbocyclic group, and the carbocyclic group may optionally be further substituted with 0 to 4 substituents selected from F or hydroxyl, more preferably substituted with 0 to 2 substituents selected from F or hydroxyl;
$R^4$ and $R^5$ are each independently selected from H, F, Cl, Br, hydroxyl, $C_{1-4}$ alkyl or $C_{1-4}$ alkoxy, preferably H, F, hydroxyl, $C_{1-4}$ alkyl or $C_{1-4}$ alkoxy, and more preferably H, F or $C_{1-3}$ alkyl; wherein the alkyl or alkoxy is optionally further substituted with 0 to 3 substituents selected from F or hydroxyl, and $R^4$ and $R^5$ are not both H;
alternatively, $R^4$ and $R^5$ may form a 3- to 5-membered carbocyclic group, preferably a 3- to 4-membered carbocyclic group;
and
$R^6$ is selected from H.

Another preferred embodiment of the present invention comprises a compound of general formula (II), or any of a stereoisomer, a solvate, a metabolite, a prodrug, a pharmaceutically acceptable salt, or a cocrystal thereof;
wherein,
$R^1$, $R^2$ and $R^3$ are each independently selected from: H, F, Cl, Br, $CH_2F$, $CHF_2$, $CF_3$, $CH_2CH_2F$, $CHFCH_3$, $CHFCH_2F$, hydroxyl, methyl, ethyl, n-propyl, isopropyl, n-butyl, sec-butyl, t-butyl, hydroxymethyl, hydroxyethyl, methoxy, ethoxy, n-propoxy, isopropoxy, n-butoxy, sec-butoxy, t-butoxy, cyclopropyl or cyclobutyl, where $R^1$, $R^2$ and $R^3$ are not all H; preferably H, F, Br, $CH_2F$, hydroxyl, methyl, ethyl, methoxy, ethoxy, n-propyl, isopropyl, sec-butyl, cyclopropyl, or cyclobutyl, where $R^1$, $R^2$ and $R^3$ are not all H; more preferably H, F, Br, $CH_2F$, hydroxyl, methyl, ethyl, n-propyl, isopropyl, sec-butyl, cyclopropyl, or cyclobutyl; and even more preferably H, F, Br, $CH_2F$, hydroxyl, methyl, ethyl, n-propyl, isopropyl, or cyclopropyl;
alternatively, any pair of $R^1$ and $R^2$, $R^2$ and $R^3$, or $R^1$ and $R^3$ may form cyclopropyl;
$R^4$ and $R^5$ are each independently selected from: H, F, Cl, Br, $CH_2F$, $CHF_2$, $CF_3$, $CH_2CH_2F$, $CHFCH_3$, $CHFCH_2F$, hydroxyl, methyl, ethyl, n-propyl, isopropyl, n-butyl, sec-butyl, t-butyl, hydroxymethyl, hydroxyethyl, methoxy, ethoxy, n-propoxy, isopropoxy, n-butoxy, sec-butoxy or t-butoxy; preferably H, F, Br, $CF_3$, hydroxyl, methyl, ethyl, n-propyl, isopropyl, n-butyl, sec-butyl, t-butyl, hydroxymethyl, hydroxyethyl, methoxy, or ethoxy; more preferably H, F, Br, hydroxyl, methyl, ethyl, n-propyl, isopropyl, methoxy, or ethoxy; even more preferably H, F, hydroxyl, methyl, ethyl, n-propyl, methoxy, or ethoxy; and $R^4$ and $R^5$ are not both H;
alternatively, $R^4$ and $R^5$ may form cyclopropyl;
and
$R^6$ is selected from H.

Another preferred embodiment of the present invention comprises a compound of general formula (II), or any of a stereoisomer, a solvate, a metabolite, a prodrug, a pharmaceutically acceptable salt, or a cocrystal thereof;
wherein,
$R^1$, $R^2$ and $R^3$ are each independently selected from H, F, Br, $CH_2F$, $CHFCH_2F$, hydroxyl, methyl, ethyl, methoxy, ethoxy, n-propyl, isopropyl, sec-butyl, cyclopropyl or cyclobutyl, preferably H, F, $CH_2F$, hydroxyl, methyl, ethyl or cyclopropyl, and $R^1$, $R^2$ and $R^3$ are not all H;
alternatively, any pair of $R^1$ and $R^2$, $R^2$ and $R^3$, or $R^1$ and $R^3$ may form cyclopropyl;
$R^4$ and $R^5$ are each independently selected from H, F, hydroxyl, methyl, ethyl, methoxy or ethoxy, preferably H, hydroxyl, methyl or ethyl, and $R^4$ and $R^5$ are not both H;
and
$R^6$ is selected from H.

Another preferred embodiment of the present invention is a compound of general formula (I) or a stereoisomer, a solvate, a metabolite, a prodrug, a pharmaceutically acceptable salt, or a cocrystal thereof;
wherein,
R is selected from F, Cl, Br, I, —$OR^7$ or

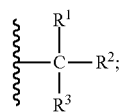

$R^1$, $R^2$ and $R^3$ are each independently selected from H, F, Cl, Br, I, hydroxyl, $C_{1-6}$ alkyl, $C_{1-6}$ alkoxy, a 3- to 5-membered carbocyclic group or a 3- to 5-membered heterocyclic group; wherein the alkyl, alkoxy, carbocyclic group or heterocyclic group is optionally further substituted with 0 to 5 substituents selected from F, Cl, Br, I, hydroxyl, $C_{1-6}$ alkyl, $C_{1-6}$ alkoxy, a 3- to 5-membered carbocyclic group or a 3- to 5-membered heterocyclic group, the heterocyclic group has 1 to 2 heteroatoms selected from N, O or S, and $R^1$, $R^2$ and $R^3$ are not all H;

alternatively, any pair of $R^1$ and $R^2$, $R^2$ and $R^3$, or $R^1$ and $R^3$ may form a 3- to 5-membered ring, the 3- to 5-membered ring has 0 to 2 heteroatoms selected from N, O or S, and the formed 3- to 5-membered ring is optionally further substituted with 0 to 4 $R^8$s;

$R^4$ and $R^5$ are each independently selected from H, F, Cl, Br, I, hydroxyl, cyano, $C_{1-6}$ alkyl, $C_{1-6}$ alkoxy, a 3- to 5-membered carbocyclic group, or a 3- to 5-membered heterocyclic group; wherein the alkyl, alkoxy, carbocyclic group or heterocyclic group is optionally further substituted with 0 to 5 substituents selected from hydroxyl, $C_{1-6}$ alkyl, $C_{1-6}$ alkoxy, a 3- to 5-membered carbocyclic group or a 3- to 5-membered heterocyclic group, the heterocyclic group has 1 to 2 heteroatoms selected from N, O or S, and $R^4$ and $R^5$ are not both H;

alternatively, $R^4$ and $R^5$ may form a 3- to 5-membered ring, the 3- to 5-membered ring may have 0 to 2 heteroatoms selected from N, O or S, and the formed 3- to 5-membered ring may optionally be further substituted with 0 to 4 $R^8$s;

$R^6$ is selected from H or hydroxyl;

$R^7$ is selected from H, $C_{1-4}$ alkyl, or a 3- to 5-membered carbocyclic group, wherein the alkyl or carbocyclic group is optionally further substituted with 0 to 5 substituents selected from F, Cl, Br, I, hydroxyl, $C_{1-4}$ alkyl, $C_{1-4}$ alkoxy, or a 3- to 5-membered carbocyclic group;

$R^8$ is selected from F, Cl, Br, hydroxyl, $C_{1-4}$ alkyl, $C_{1-4}$ alkoxy, a 3- to 5-membered carbocyclic group or a 3- to 5-membered heterocyclic group, and the heterocyclic group has 1 to 2 heteroatoms selected from N, O or S;

and n is selected from 1, 2 or 3.

Another preferred embodiment of the present invention is a compound of general formula (I) or a stereoisomer, a solvate, a metabolite, a prodrug, a pharmaceutically acceptable salt, or a cocrystal thereof;

wherein,

R is selected from F, Br, —$OR^7$ or

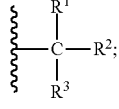

$R^1$, $R^2$ and $R^3$ are each independently selected from H, F, Cl, Br, hydroxyl, $C_{1-5}$ alkyl, $C_{1-5}$ alkoxy, or a 3- to 5-membered carbocyclic group; wherein the alkyl, alkoxy, or carbocyclic group is optionally further substituted with 0 to 3 substituents selected from F, Cl, Br, hydroxyl, $C_{1-4}$ alkyl, $C_{1-4}$ alkoxy, or a 3- to 5-membered carbocyclic group, and $R^1$, $R^2$ and $R^3$ are not all H;

alternatively, any pair of $R^1$ and $R^2$, $R^2$ and $R^3$, or $R^1$ and $R^3$ may form a 3- to 5-membered carbocycle, and the carbocycle may optionally be further substituted with 0 to 4 $R^8$s;

$R^4$ and $R^5$ are each independently selected from H, F, Cl, Br, hydroxyl, cyano, $C_{1-4}$ alkyl, $C_{1-4}$ alkoxy, or a 3- to 5-membered carbocyclic group; wherein the alkyl, alkoxy, or carbocyclic group is optionally further substituted with 0 to 3 substituents selected from hydroxyl, $C_{1-4}$ alkyl, or $C_{1-4}$ alkoxy, and $R^4$ and $R^5$ are not both H;

alternatively, $R^4$ and $R^5$ may form a 3- to 5-membered carbocyclic group, and the carbocyclic group may optionally be further substituted with 0 to 4 $R^8$s;

$R^6$ is selected from H or hydroxyl;

$R^7$ is selected from $C_{1-4}$ alkyl or a 3- to 4-membered carbocyclic group, wherein the alkyl or carbocyclic group may optionally be further substituted with 0 to 3 substituents selected from F, hydroxyl, or $C_{1-3}$ alkyl;

$R^8$ is selected from F, Cl, Br, hydroxyl, $C_{1-4}$ alkyl, or $C_{1-4}$ alkoxy;

and n is selected from 1 or 2.

Another preferred embodiment of the present invention is a compound of general formula (I) or a stereoisomer, a solvate, a metabolite, a prodrug, a pharmaceutically acceptable salt, or a cocrystal thereof;

wherein,

R is selected from Br or

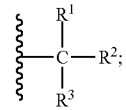

$R^1$, $R^2$ and $R^3$ are each independently selected from H, F, Cl, Br, hydroxyl, $C_{1-4}$ alkyl, $C_{1-4}$ alkoxy, or a 3- to 5-membered carbocyclic group; wherein the alkyl, alkoxy, or carbocyclic group is optionally further substituted with 0 to 3 substituents selected from F, Cl, Br, hydroxyl, $C_{1-4}$ alkyl, $C_{1-4}$ alkoxy, or a 3- to 5-membered carbocyclic group, and $R^1$, $R^2$ and $R^3$ are not all H;

alternatively, any pair of $R^1$ and $R^2$, $R^2$ and $R^3$, or $R^1$ and $R^3$ may form a 3- to 5-membered carbocyclic group, and the carbocyclic group may optionally be further substituted with 0 to 4 $R^8$s;

$R^4$ and $R^5$ are each independently selected from H, F, Cl, Br, hydroxyl, cyano, $C_{1-4}$ alkyl, $C_{1-4}$ alkoxy, or a 3- to 5-membered carbocyclic group; wherein the alkyl, alkoxy, or carbocyclic group is optionally further substituted with 0 to 3 substituents selected from hydroxyl, $C_{1-4}$ alkyl, or $C_{1-4}$ alkoxy, and $R^4$ and $R^5$ are not both H; alternatively, $R^4$ and $R^5$ may form a 3- to 5-membered carbocyclic group, and the carbocyclic group may optionally be further substituted with 0 to 4 $R^8$s;

$R^6$ is selected from H or hydroxyl;

$R^7$ is selected from $C_{1-4}$ alkyl or a 3- to 4-membered carbocyclic group, wherein the alkyl or carbocyclic group may optionally be further substituted with 0 to 3 substituents selected from F, hydroxyl, or $C_{1-3}$ alkyl;

$R^8$ is selected from F, Cl, Br, hydroxyl, $C_{1-4}$ alkyl, or $C_{1-4}$ alkoxy;

and n is selected from 1 or 2.

Another preferred embodiment of the present invention is a compound of general formula (I) or any of a stereoisomer, a solvate, a metabolite, a prodrug, a pharmaceutically acceptable salt, or a cocrystal thereof; wherein, the compound is selected from a compound of general formula (II):

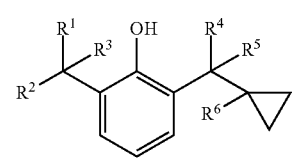

wherein,
R¹, R² and R³ are each independently selected from H, F, Cl, Br, hydroxyl, $C_{1-4}$ alkyl, $C_{1-4}$ alkoxy or a 3- to 5-membered carbocyclic group; wherein the alkyl, alkoxy or carbocyclic group is optionally further substituted with 0 to 3 substituents selected from F, Cl, Br, hydroxyl, $C_{1-4}$ alkyl, $C_{1-4}$ alkoxy or a 3- to 5-membered carbocyclic group, and R¹, R² and R³ are not all H;
alternatively, any pair of R¹ and R², R² and R³, or R¹ and R³ may form a 3- to 5-membered carbocyclic group, preferably a 3-membered carbocyclic group, and the carbocyclic group may optionally be further substituted with 0 to 4 R⁸s;
R⁴ and R⁵ are each independently selected from H, F, Cl, Br, hydroxyl, cyano, $C_{1-4}$ alkyl, $C_{1-4}$ alkoxy, or a 3- to 5-membered carbocyclic group; wherein the alkyl, alkoxy or carbocyclic group is optionally further substituted with 0 to 3 substituents selected from hydroxyl, $C_{1-4}$ alkyl or $C_{1-4}$ alkoxy, and R⁴ and R⁵ are not both H;
alternatively, R⁴ and R⁵ may form a 3- to 5-membered carbocyclic group, and the carbocyclic group may optionally be further substituted with 0 to 4 R⁸s;
R⁶ is selected from H or hydroxyl;
R⁸ is selected from F, Cl, Br, hydroxyl, $C_{1-4}$ alkyl or $C_{1-4}$ alkoxy, and preferably F or hydroxyl;
and
n is selected from 1 or 2.

Another preferred embodiment of the present invention is a compound of general formula (II), or a stereoisomer, a solvate, a metabolite, a prodrug, a pharmaceutically acceptable salt, or a cocrystal thereof;
wherein,
R¹, R² and R³ are each independently selected from H, F, Cl, Br, hydroxyl, $C_{1-4}$ alkyl, $C_{1-4}$ alkoxy or a 3- to 5-membered carbocyclic group; wherein the alkyl, alkoxy or carbocyclic group is optionally further substituted with 0 to 3 substituents selected from F or hydroxyl, and R¹, R² and R³ are not all H;
alternatively, any pair of R¹ and R², R² and R³, or R¹ and R³ may form a 3-membered carbocyclic group, and the carbocyclic group may optionally be further substituted with 0 to 4 substituents selected from F or hydroxyl;
R⁴ and R⁵ are each independently selected from H, F, Cl, Br, hydroxyl, cyano, $C_{1-4}$ alkyl, $C_{1-4}$ alkoxy, or a 3- to 5-membered carbocyclic group; wherein the alkyl, alkoxy or carbocyclic group is optionally further substituted with 0 to 3 hydroxyls, and R⁴ and R⁵ are not both H;
R⁶ is selected from H or hydroxyl;
and
n is selected from 1 or 2.

Another preferred embodiment of the present invention is a compound of general formula (II), or a stereoisomer, a solvate, a metabolite, a prodrug, a pharmaceutically acceptable salt, or a cocrystal thereof;
wherein,
R¹, R² and R³ are each independently selected from H, hydroxyl, $C_{1-4}$ alkyl or a 3- to 5-membered carbocyclic group; wherein the alkyl or carbocyclic group is optionally further substituted with 0 to 3 substituents selected from F or hydroxyl, and R¹, R² and R³ are not all H;
alternatively, any pair of R¹ and R², R² and R³, or R¹ and R³ may form a 3-membered carbocyclic group, and the carbocyclic group may optionally be further substituted with 0 to 4 substituents selected from F or hydroxyl;
R⁴ and R⁵ are each independently selected from H, hydroxyl, cyano, $C_{1-4}$ alkyl or a 3- to 5-membered carbocyclic group; wherein the alkyl or carbocyclic group is optionally further substituted with 0 to 3 hydroxyls, and R⁴ and R⁵ are not both H;
R⁶ is selected from H or hydroxyl;
and
n is selected from 1 or 2.

Another preferred embodiment of the present invention is a compound of general formula (I) or any of a stereoisomer, a solvate, a metabolite, a prodrug, a pharmaceutically acceptable salt, or a cocrystal thereof; wherein, the compound is selected from a compound of general formula (II), wherein,
R¹, R² and R³ are each independently selected from H, hydroxyl, methyl, ethyl or cyclopropyl, and R¹, R² and R³ are not all H;
alternatively, any pair of R¹ and R², R² and R³, or R¹ and R³ may form cyclopropyl;
R⁴ and R⁵ are each independently selected from H, hydroxyl, cyano, methyl, ethyl or cyclopropyl, and R⁴ and R⁵ are not both H;
R⁶ is selected from H or hydroxyl;
and
n is selected from 1 or 2.

Yet another preferred embodiment of the present invention relates to a compound selected from, but not limited to:

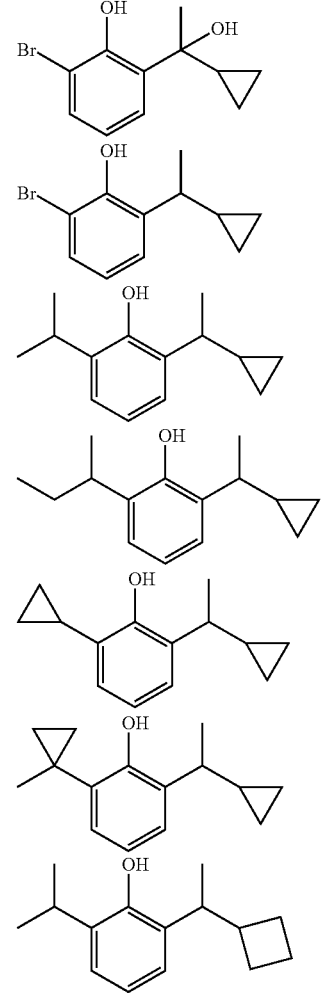

-continued
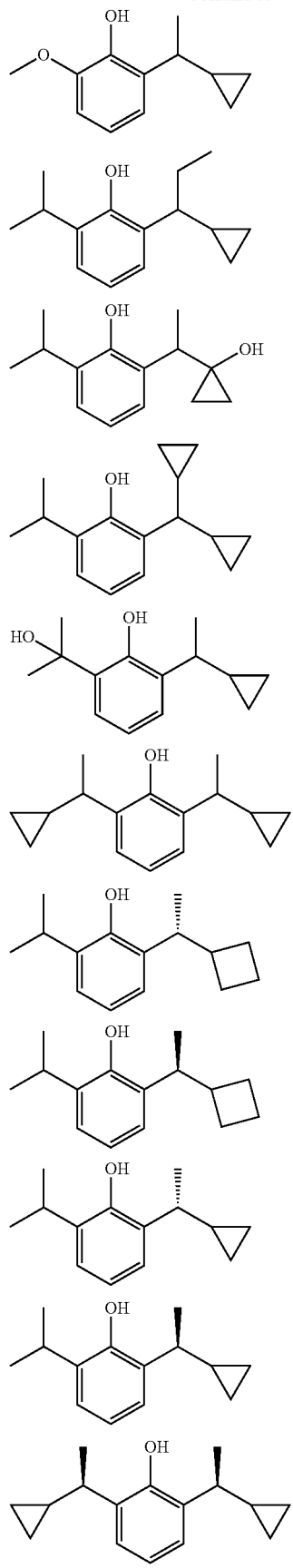
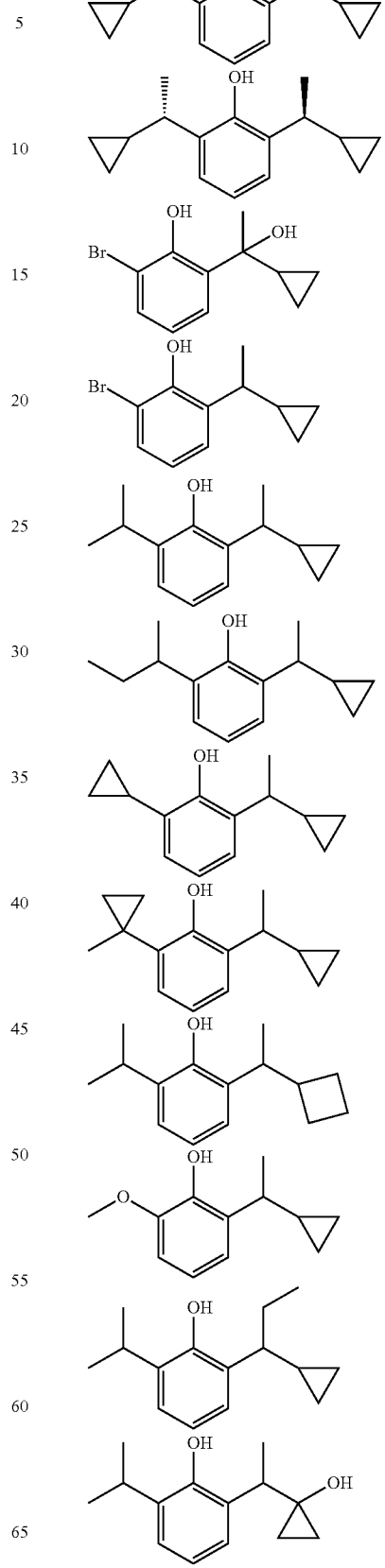

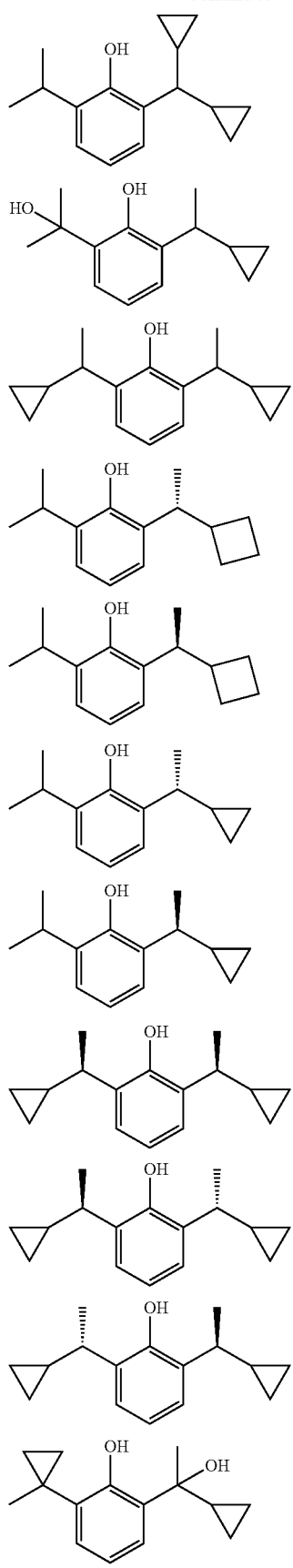
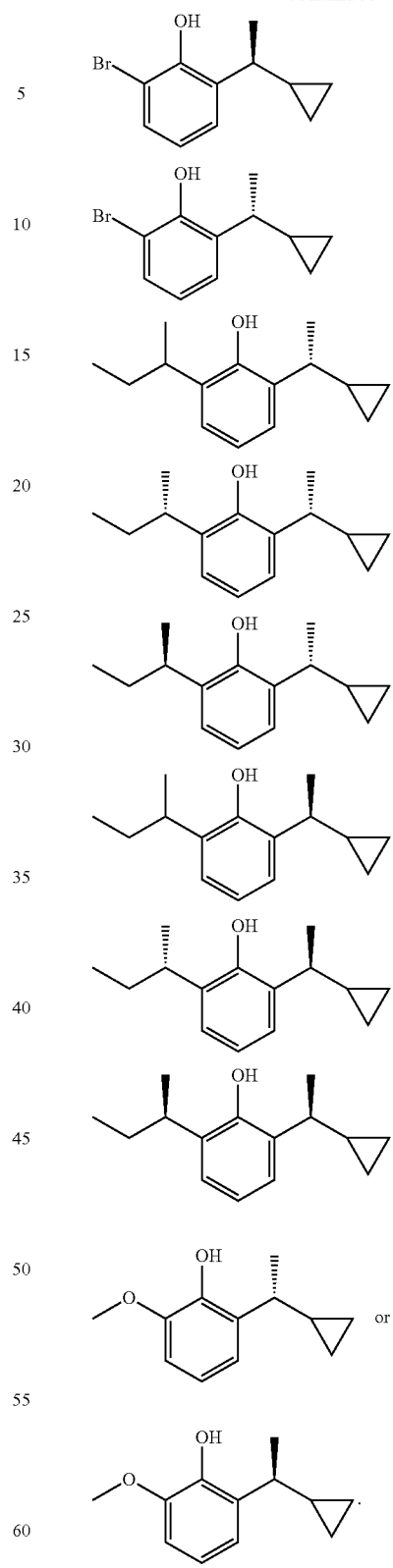
Another preferred embodiment of the present invention is a compound of general formula (A), or a stereoisomer, a solvate, a metabolite, a prodrug, a pharmaceutically acceptable salt, or a cocrystal thereof; wherein $R^9$, $R^{10}$, $R^{11}$ and $R^{12}$ are H;

y is selected from H, PEG,

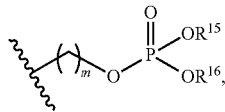

$C_{1-20}$ alkyl, $-(CH_2CH_2O)_q-H$, $-(CR^{ya}R^{yb})_{m1}COOR^{y1}$, $-(CR^{ya}R^{yb})_{m1}-(W_1)_p-C(=O)(W_4R^{y3})$ or $-(CR^{ya}R^{yb})_{m1}-(W_1)_p-P(=O)(W_2R^{y4})(W_3R^{y5})$ or

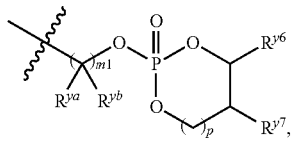

wherein the alkyl is optionally further substituted with 0 to 4 substituents selected from H, F, Cl, Br, I, hydroxyl, amino, cyano, carboxyl, $C_{1-6}$ alkyl, $C_{1-6}$ alkoxy, a $C_{3-8}$ carbocyclic group or a 4- to 8-membered heterocyclic group, and the heterocyclic group has 1 to 2 heteroatoms selected from N, O or S;

$R^{13}$ and $R^{14}$ are each independently selected from H or $C_{1-6}$ alkyl;

$R^{15}$ and $R^{16}$ are each independently selected from H or an alkali metal ion, wherein the alkali metal ion is selected from $Na^+$, $K^+$ or $Li^+$;

$W_1$, $W_2$ and $W_3$ are each independently selected from $NR^{y8}$, O or S;

$W_4$ is selected from $CR^{y9}R^{y10}$, $NR^{y8}$, O, S, or is absent;

$R^{y1}$ is each independently selected from H, $C_{1-6}$ alkyl, a $C_{3-8}$ carbocyclic group or a 4- to 8-membered heterocyclic group, wherein the alkyl, carbocyclic group or heterocyclic group may optionally be further substituted with 0 to 5 substituents selected from H, F, Cl, Br, I, hydroxyl, amino, cyano, carboxyl, $C_{1-6}$ alkyl, $C_{1-6}$ alkoxy, a $C_{3-8}$ carbocyclic group or a 4- to 8-membered heterocyclic group, and the heterocyclic group has 1 to 2 heteroatoms selected from N, O or S;

$R^{y3}$ is selected from H, amino, $C_{1-6}$ alkyl, a $C_{3-8}$ carbocyclic group or a 4- to 8-membered heterocyclic group, $-(CR^{ya}R^{yb})_{m1}-NR^{yc}R^{yd}$ or $-(CR^{ya}R^{yb})_{m1}-NR^{yc}C(=O)OR^{yd}$, wherein the amino group, alkyl, carbocyclic group or heterocyclic group may optionally be further substituted with 0 to 5 substituents selected from H, F, Cl, Br, I, hydroxyl, amino, cyano, carboxyl, $C_{1-6}$ alkyl, $C_{1-6}$ alkoxy, $-(CH_2)_{m1}-OC(=O)-C_{1-6}$ alkyl, $-(CH_2)_{m1}-C(=O)O-C_{1-6}$ alkyl, $-(CH_2)_{m1}-C(=O)O(CH_2)_{m1}-(C_{3-6}$ carbocyclic group), $-(CH_2)_{m1}-C(=O)-C_{1-6}$ alkyl, $-(CH_2)_{m1}-(C_{3-8}$ carbocyclic group) or $-(CH_2)_{m1}-(4-$ to 8-membered heterocyclic group), and the heterocyclic group has 1 to 2 heteroatoms selected from N, O or S;

$R^{y4}$ and $R^{y5}$ are each independently selected from H, an alkali metal ion, an alkali earth metal ion, a protonated amine or a protonated amino acid, $C_{1-6}$ alkyl, $-(CR^{ya}R^{yb})_{m1}-(3-$ to 8-membered ring), $-(CR^{ya}R^{yb})_{m1}-OC(=O)C_{1-6}$ alkyl, $-(CR^{ya}R^{yb})_{m1}-OC(=O)-(3-$ to 8-membered ring), $-(CR^{ya}R^{yb})_{m1}-C(=O)OC_{1-6}$ alkyl or $-(CR^{ya}R^{yb})_{m1}-OC(=O)OC_{1-6}$ alkyl;

$R^{y6}$ and $R^{y7}$ are each independently selected from H, F, Cl, Br, I, hydroxyl, amino, cyano, carboxyl, $C_{1-6}$ alkyl or $C_{1-6}$ alkoxy;

alternatively, $R^{y6}$ and $R^{y7}$ may form a 5- to 8-membered ring together with the atoms to which they are attached, the 5- to 8-membered ring may have 0 to 4 heteroatoms selected from N, O or S, and the 5- to 8-membered ring may optionally be further substituted with 0 to 4 substituents selected from H, F, Cl, Br, I, $C_{1-6}$ alkyl or $C_{1-6}$ alkoxy;

$R^{y8}$s are each independently selected from H or $C_{1-6}$ alkyl;

$R^{y9}$ and $R^{y10}$ are each independently selected from H, $C_{1-6}$ alkyl, a $C_{3-8}$ carbocyclic group or a 4- to 8-membered heterocyclic group, wherein the alkyl, carbocyclic group and heterocyclic group are each optionally further substituted with 0 to 4 substituents selected from H, hydroxyl, amino, mercapto, carboxyl, guanidino, carbamoyl, $C_{1-6}$ alkyl, $C_{1-6}$ alkoxy, a 3- to 8-membered carbocycle or a 3- to 8-membered heterocycle;

$R^{ya}$, $R^{yb}$, $R^{yc}$ and $R^{yd}$ are each independently selected from H or $C_{1-6}$ alkyl;

q is selected from 1 to 200;

m1 is selected from 0, 1, 2 or 3; and p is selected from 0, 1 or 2.

Another preferred embodiment of the present invention is a compound of general formula (A), or a stereoisomer, a solvate, a metabolite, a prodrug, a pharmaceutically acceptable salt, or a cocrystal thereof; wherein Y is selected from $C_{1-10}$ alkyl, $-(CH_2CH_2O)_q-H$, $-(CR^{ya}R^{yb})_{m1}COOR^{y1}$, $-(CR^{ya}R^{yb})_{m1}-(W_1)_p-C(=O)(W_4R^{y3})$ or $-(CR^{ya}R^{yb})_{m1}-(W_1)_p-P(=O)(W_2R^{y4})(W_3R^{y5})$ or

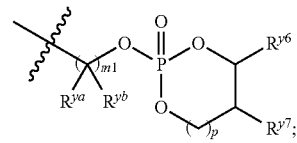

preferably $C_{1-10}$ alkyl, $-(CH_2CH_2O)_q-H$, $-(CR^{ya}R^{yb})_{m1}-(W_1)_p-C(=O)(W_4R^{y3})$ or $-(CR^{ya}R^{yb})_{m1}-(W_1)_p-P(=O)(W_2R^{y4})(W_3R^{y5})$ or

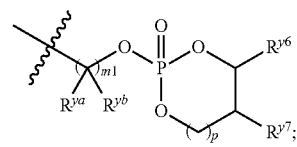

further preferably $C_{1-6}$ alkyl, $-(CH_2CH_2O)_q-H$, $-(CR^{ya}R^{yb})_{m1}-(W_1)_p-C(=O)(W_4R^{y3})$ or $-(CR^{ya}R^{yb})_{m1}-(W_1)_p-P(=O)(W_2R^{y4})(W_3R^{y5})$ or

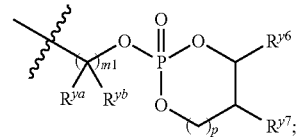

more preferably $C_{1-4}$ alkyl, $-(CR^{ya}R^{yb})_{m1}-(W_1)_p-C(=O)(W_4R^{y3})$ or $-(CR^{ya}R^{yb})_{m1}-(W_1)_p-P(=O)(W_2R^{y4})(W_3R^{y5})$ or

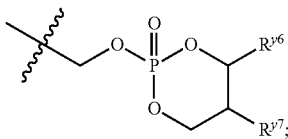

even more preferably methyl, hydroxyethyl, —CH$_2$OC(=O)(R$^{y3}$), —C(=O)(R$^{y3}$), —CH$_2$OC(=O)(W$_4$R$^{y3}$), —C(=O)(W$_4$R$^{y3}$), —CH(CH$_3$)OC(=O)(W$_4$R$^{y3}$), —CH$_2$OP(=O)(W$_2$R$^{y4}$)(W$_3$R$^{y5}$), —P(=O)(W$_2$R$^{y4}$)(W$_3$R$^{y5}$) or

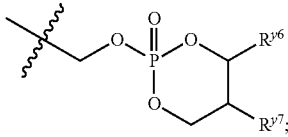

wherein the alkyl is optionally further substituted with 0 to 4 substituents selected from H, F, Cl, Br, I, hydroxyl, amino, cyano, carboxyl, C$_{1-6}$ alkyl, C$_{1-6}$ alkoxy, a C$_3$ carbocyclic group, a C$_4$ carbocyclic group, a C$_5$ carbocyclic group, a C$_6$ carbocyclic group, a C$_7$ carbocyclic group, a C$_8$ carbocyclic group, a 4-membered heterocyclic group, a 5-membered heterocyclic group, a 6-membered heterocyclic group, a 7-membered heterocyclic group, or a 8-membered heterocyclic group; preferably substituted with substituents from H, F, Cl, Br, I, hydroxyl, amino, cyano, carboxyl, C$_{1-6}$ alkyl, a C$_3$ carbocyclic group, a C$_4$ carbocyclic group, a C$_5$ carbocyclic group, or a C$_6$ carbocyclic group; further preferably substituted with substituents from H, F, Cl, Br, I, hydroxyl, amino, cyano, carboxyl, C$_{1-4}$ alkyl, a C$_3$ carbocyclic group, a C$_4$ carbocyclic group, a C$_5$ carbocyclic group, or a C$_6$ carbocyclic group; more preferably substituted with substituents from H, hydroxyl, amino, C$_{1-4}$ alkyl, a C$_5$ carbocyclic group, or a C$_6$ carbocyclic group; even more preferably substituted with substituents from H, methyl, ethyl, propyl, isopropyl or phenyl; and the heterocyclic group has 1 to 2 heteroatoms selected from N, O or S;

q is selected from 1 to 100, preferably from 1 to 10, and more preferably 1, 2, 3, 4 or 5;

m1 is selected from 0, 1, 2 or 3, preferably 0, 1 or 2; and p is selected from 0, 1 or 2, preferably 0 or 1.

Another preferred embodiment of the present invention is a compound of general formula (A), or a stereoisomer, a solvate, a metabolite, a prodrug, a pharmaceutically acceptable salt, or a cocrystal thereof; wherein W$_1$, W$_2$ and W$_3$ are each independently selected from NR$^{y8}$, O or S, preferably NR$^{y8}$ or O;

W$_4$ is selected from CR$^{y9}$R$^{y10}$, NR$^{y8}$, O, S, or is absent; preferably CR$^{y9}$R$^{y10}$, NR$^{y8}$, O or absent;

R$^{y8}$s are each independently selected from H or C$_{1-6}$ alkyl, preferably H or C$_{1-4}$ alkyl, and more preferably H, methyl or ethyl;

R$^{y9}$ and R$^{y10}$ are each independently selected from H, C$_{1-6}$ alkyl, a C$_{3-8}$ carbocyclic group or a 4- to 8-membered heterocyclic group; preferably H, C$_{1-6}$ alkyl, a C$_{3-6}$ carbocyclic group or a 4- to 6-membered heterocyclic group; more preferably H, C$_{1-6}$ alkyl or a 4- to 6-membered heterocyclic group; even more preferably H or C$_{1-4}$ alkyl; and further more preferably H, methyl, isopropyl, sec-butyl, 2-methylpropyl or benzyl;

wherein the alkyl, carbocyclic group and heterocyclic group are each optionally further substituted with 0 to 4 substituents selected from H, hydroxyl, amino, mercapto, carboxyl, guanidino, carbamoyl, C$_{1-6}$ alkyl, C$_{1-6}$ alkoxy, a C$_3$ carbocyclic group, a C$_4$ carbocyclic group, a C$_5$ carbocyclic group, a C$_6$ carbocyclic group, a C$_7$ carbocyclic group, a C$_8$ carbocyclic group, a 4-membered heterocyclic group, a 5-membered heterocyclic group, a 6-membered heterocyclic group, a 7-membered heterocyclic group, or a 8-membered heterocyclic group; preferably substituted with substituents from H, hydroxyl, amino, mercapto, carboxyl, guanidino, carbamoyl, C$_{1-6}$ alkyl, C$_{1-6}$ alkoxy, a C$_3$ carbocyclic group, a C$_4$ carbocyclic group, a C$_5$ carbocyclic group, a C$_6$ carbocyclic group, a 4-membered heterocyclic group, a 5-membered heterocyclic group, or a 6-membered heterocyclic group; further preferably substituted with substituents from H, hydroxyl, amino, mercapto, carboxyl, guanidino, carbamoyl, C$_{1-4}$ alkyl, or a 5- to 6-membered carbocyclic group; more preferably substituted with substituents from H, C$_{1-4}$ alkyl, or a 5- to 6-membered carbocyclic group; and even more preferably substituted with substituents from H, methyl, ethyl, propyl, isopropyl or phenyl.

Another preferred embodiment of the present invention is a compound of general formula (A), or a stereoisomer, a solvate, a metabolite, a prodrug, a pharmaceutically acceptable salt, or a cocrystal thereof; wherein R$^{y1}$ is each independently selected from H, C$_{1-6}$ alkyl, a C$_3$ carbocyclic group, a C$_4$ carbocyclic group, a C$_5$ carbocyclic group, a C$_6$ carbocyclic group, a 4-membered heterocyclic group, a 5-membered heterocyclic group, or a 6-membered heterocyclic group; preferably H, C$_{1-6}$ alkyl, a C$_5$ carbocyclic group, a C$_6$ carbocyclic group, a 5-membered heterocyclic group, or a 6-membered heterocyclic group; further preferably H or C$_{1-6}$ alkyl; more preferable H or C$_{1-4}$ alkyl; and even more preferably H, methyl, ethyl or isopropyl;

wherein the alkyl, carbocyclic group or heterocyclic group may optionally be further substituted with 0 to 5 substituents selected from H, F, Cl, Br, I, hydroxyl, amino, cyano, carboxyl, C$_{1-6}$ alkyl, C$_{1-6}$ alkoxy, a C$_3$ carbocyclic group, a C$_4$ carbocyclic group, a C$_5$ carbocyclic group, a C$_6$ carbocyclic group, a C$_7$ carbocyclic group, a C$_8$ carbocyclic group, a 4-membered heterocyclic group, a 5-membered heterocyclic group, a 6-membered heterocyclic group, a 7-membered heterocyclic group, or a 8-membered heterocyclic group; preferably substituted with substituents from H, F, Cl, Br, I, hydroxyl, amino, cyano, carboxyl, C$_{1-6}$ alkyl, C$_{1-6}$ alkoxy, a C$_5$ carbocyclic group, a C$_6$ carbocyclic group, a 5-membered heterocyclic group, or a 6-membered heterocyclic group; further preferably substituted with substituents from H, F, Cl, Br, I, hydroxyl, amino, cyano, carboxyl, C$_{1-4}$ alkyl, or C$_{1-4}$ alkoxy; more preferably substituted with substituents from H, methyl, ethyl or isopropyl; and the heterocyclic group has 1 to 2 heteroatoms selected from N, O or S.

Another preferred embodiment of the present invention is a compound of general formula (A), or a stereoisomer, a solvate, a metabolite, a prodrug, a pharmaceutically acceptable salt, or a cocrystal thereof; wherein R$^{y3}$ is selected from H, amino, C$_{1-6}$ alkyl, a C$_3$ carbocyclic group, a C$_4$ carbocyclic group, a C$_5$ carbocyclic group, a C$_6$ carbocyclic group, a C$_7$ carbocyclic group, a C$_8$ carbocyclic group, a 4-membered heterocyclic group, a 5-membered heterocyclic group, a 6-membered heterocyclic group, a 7-membered heterocyclic group, or a 8-membered heterocyclic group, —(CR$^{ya}$R$^{yb}$)$_{m1}$—NR$^{yc}$R$^{yd}$ or —(CR$^{ya}$R$^{yb}$)$_{m1}$—NR$^{yc}$C(=O)OR$^{yd}$; preferably H, amino, C$_{1-6}$ alkyl, a C$_3$ carbocyclic group, a C$_4$ carbocyclic group, a $C_5$ carbocyclic group, a $C_6$ carbocyclic group, a 4-membered heterocyclic group, a 5-membered heterocyclic group, a 6-membered heterocyclic group, —$(CR^{ya}R^{yb})_{m1}$—$NR^{yc}R^{yd}$ or —$(CR^{ya}R^{yb})_{m1}$—$NR^{yc}C(=O)OR^{yd}$; further preferably H, amino, $C_{1-4}$ alkyl, a $C_5$ carbocyclic group, a $C_6$ carbocyclic group, a 5-membered heterocyclic group, a 6-membered heterocyclic group, —$(CH_2)_{m1}$—$NR^{yc}CR^{yd}$ or —$(CH_2)_{m1}$—$NR^{yc}C(=O)OR^{yd}$; more preferably amino, aminomethylene, isopropyl, t-butyl, (t-butoxycarbonyl) amino, (t-butoxycarbonyl)aminomethylene, pyrrolylalkyl, phenyl or pyridinyl;
wherein the amino group, alkyl, carbocyclic group or heterocyclic group may optionally be further substituted with 0 to 5 substituents selected from H, F, Cl, Br, I, hydroxyl, amino, cyano, carboxyl, $C_{1-6}$ alkyl, $C_{1-6}$ alkoxy, —$(CH_2)_{m1}$—$OC(=O)$—$C_{1-6}$ alkyl, —$(CH_2)_{m1}$—$C(=O)$O—$C_{1-6}$ alkyl, —$(CH_2)_{m1}$—$C(=O)O(CH_2)_{m1}$—$(C_{3-6}$ carbocyclic group), —$(CH_2)_{m1}$—$C(=O)$—$C_{1-6}$ alkyl, —$(CH_2)_{m1}$—$(C_{3-6}$ carbocyclic group) or —$(CH_2)_{m1}$-(4- to 6-membered heterocyclic group); preferably substituted with substituents from H, —$(CH_2)_{m1}$—$OC(=O)$—$C_{1-4}$ alkyl, —$(CH_2)_{m1}$—$C(=O)O$—$C_{1-4}$ alkyl, —$(CH_2)_{m1}$—$C(=O)O(CH_2)_{m1}$—$(C_{3-6}$ carbocyclic group), —$(CH_2)_{m1}$—$C(=O)$—$C_{1-4}$ alkyl, —$(CH_2)_{m1}$—$(C_{3-6}$ carbocyclic group) or —$(CH_2)_{m1}$-(4- to 6-membered heterocyclic group); further preferably substituted with 0-4 substituents selected from H, —$OC(=O)$—$C_{1-4}$ alkyl, —$C(=O)O$—$C_{1-4}$ alkyl, or —$C(=O)CH_2$—$(C_{5-6}$ carbocyclic group); more preferably substituted with 0-4 substituents selected from t-butoxycarbonyl, acetoxy or benzyloxycarbonyl; and the heterocyclic group has 1 to 2 heteroatoms selected from N, O or S.

Another preferred embodiment of the present invention is a compound of general formula (A), or a stereoisomer, a solvate, a metabolite, a prodrug, a pharmaceutically acceptable salt, or a cocrystal thereof; wherein
$R^{y4}$ and $R^{y5}$ are each independently selected from H, an alkali metal ion, an alkali earth metal ion, a protonated amine or a protonated amino acid, $C_{1-6}$ alkyl, —$(CR^{ya}R^{yb})_{m1}$-(3- to 8-membered ring), —$(CR^{ya}R^{yb})_{m1}$—$OC(=O)C_{1-6}$ alkyl, —$(CR^{ya}R^{yb})_{m1}$—$OC(=O)$-(3- to 8-membered ring), —$(CR^{ya}R^{yb})_{m1}$—$C(=O)OC_{1-6}$ alkyl or —$(CR^{ya}R^{yb})_{m1}$—$OC(=O)OC_{1-6}$ alkyl; preferably H, an alkali metal ion, an alkali earth metal ion, $C_{1-6}$ alkyl, —$(CR^{ya}R^{yb})_{m1}$-(3- to 6-membered ring), —$(CR^{ya}R^{yb})_{m1}$—$OC(=O)C_{1-6}$ alkyl, —$(CR^{ya}R^{yb})_{m1}$—$OC(=O)$-(3- to 6-membered ring), —$(CR^{ya}R^{yb})_{m1}$—$C(=O)OC_{1-6}$ alkyl or —$(CR^{ya}R^{yb})_{m1}$—$OC(=O)OC_{1-6}$ alkyl; further preferably H, an alkali metal ion, $C_{1-4}$ alkyl, —$(CR^{ya}R^{yb})_{m1}$-(3- to 6-membered ring), —$(CR^{ya}R^{yb})_{m1}$—$OC(=O)C_{1-4}$ alkyl, —$(CR^{ya}R^{yb})_{m1}$—$OC(=O)$-(3- to 6-membered ring), —$(CR^{ya}R^{yb})_{m1}$—$C(=O)OC_{1-4}$ alkyl or —$(CR^{ya}R^{yb})_{m1}$—$OC(=O)OC_{1-4}$ alkyl; more preferably H, an alkali metal ion, $C_{1-4}$ alkyl, —$(CR^{ya}R^{yb})_{m1}$-(5- to 6-membered ring), —$(CR^{ya}R^{yb})_{m1}$—$OC(=O)C_{1-4}$ alkyl, —$(CR^{ya}R^{yb})_{m1}$—$C(=O)OC_{1-4}$ alkyl or —$(CR^{ya}R^{yb})_{m1}$—$OC(=O)OC_{1-4}$ alkyl; even more preferably H, Na, K, ethyl, benzyl, —$CH_2OC(=O)C(CH_3)_3$, —$CH(CH_3)OC(=O)CH(CH_3)_2$, —$CH_2OC(=O)CH_2CH_3$, —$CH_2C(=O)OCH_2CH_3$ 或 -$CH_2OC(=O)OCH(CH_3)_2$.

Another preferred embodiment of the present invention is a compound of general formula (A), or a stereoisomer, a solvate, a metabolite, a prodrug, a pharmaceutically acceptable salt, or a cocrystal thereof; wherein
$R^{y6}$ and $R^{y7}$ are each independently selected from H, hydroxyl, amino, cyano, carboxyl, $C_{1-6}$ alkyl or $C_{1-6}$ alkoxy; preferably H, $C_{1-4}$ alkyl or $C_{1-4}$ alkoxy; and further preferably H or $C_{1-4}$ alkyl;
alternatively, $R^{y6}$ and $R^{y7}$, together with the atoms to which they are attached, may form a 5- to 8-membered ring, preferably a 5- to 6-membered ring, more preferably phenyl; the ring may have 1 to 4 heteroatoms selected from N, O or S; and the ring may optionally be further substituted with 0 to 4 substituents selected from H, F, Cl, Br, I, $C_{1-6}$ alkyl or $C_{1-6}$ alkoxy, preferably substituted with 0 to 4 substituents selected from H, $C_{1-4}$ alkyl or $C_{1-4}$ alkoxy.

Another preferred embodiment of the present invention is a compound of general formula (A), or a stereoisomer, a solvate, a metabolite, a prodrug, a pharmaceutically acceptable salt, or a cocrystal thereof; wherein
$R^{y9}$ and $R^{y10}$ are each independently selected from H, $C_{1-6}$ alkyl, a $C_3$ carbocyclic group, a $C_4$ carbocyclic group, a $C_5$ carbocyclic group, a $C_6$ carbocyclic group, a 4-membered heterocyclic group, a 5-membered heterocyclic group, or a 6-membered heterocyclic group; preferably H, $C_{1-6}$ alkyl, a 4-membered heterocyclic group, a 5-membered heterocyclic group, or a 6-membered heterocyclic group; further preferably H or $C_{1-4}$ alkyl; and more preferably H, methyl, isopropyl, sec-butyl, 2-methylpropyl or benzyl;
wherein the alkyl, carbocyclic group and heterocyclic group are each optionally further substituted with 0 to 4 substituents selected from H, hydroxyl, amino, mercapto, carboxyl, guanidino, carbamoyl, $C_{1-6}$ alkyl, $C_{1-6}$ alkoxy, a 3- to 8-membered carbocycle or a 3- to 8-membered heterocycle; preferably substituted with 0 to 4 substituents selected from H, hydroxyl, amino, mercapto, carboxyl, guanidino, carbamoyl, $C_{1-6}$ alkyl, $C_{1-6}$ alkoxy, a 3- to 6-membered carbocycle or a 4- to 6-membered heterocycle; further preferably substituted with 0 to 4 substituents selected from H, hydroxyl, amino, mercapto, carboxyl, guanidino, carbamoyl, $C_{1-4}$ alkyl, or a 5- to 6-membered carbocycle; and more preferably substituted with 0 to 4 substituents selected from H, $C_{1-4}$ alkyl, or a 5- to 6-membered carbocycle.

Another preferred embodiment of the present invention is a compound of general formula (A), or a stereoisomer, a solvate, a metabolite, a prodrug, a pharmaceutically acceptable salt, or a cocrystal thereof; wherein $R^{ya}$, $R^{yb}$, $R^{yc}$ and $R^{yd}$ are each independently selected from H or $C_{1-6}$ alkyl, preferable H or $C_{1-4}$ alkyl, more preferably H, methyl, ethyl, propyl or isopropyl.

Another preferred embodiment of the present invention is a compound of general formula (A), or a stereoisomer, a solvate, a metabolite, a prodrug, a pharmaceutically acceptable salt, or a cocrystal thereof; wherein
R is selected from F, Cl, Br, I, —$OR^7$ or

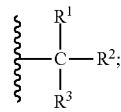

$R^1$, $R^2$ and $R^3$ are each independently selected from H, F, Cl, Br, I, hydroxyl, $C_{1-6}$ alkyl, $C_{1-6}$ alkoxy, a 3- to 5-membered carbocyclic group, or a 3- to 5-membered heterocyclic group, wherein the alkyl, alkoxy, carbocyclic group or heterocyclic group is optionally further substituted with 0 to 5 substituents selected from F, Cl, Br, I, hydroxyl, $C_{1-6}$ alkyl, $C_{1-6}$ alkoxy, a 3- to 5-membered carbocyclic group or a 3- to 5-membered heterocyclic group, the heterocyclic group has 1 to 2 heteroatoms selected from N, O or S, and $R^1$, $R^2$ and $R^3$ are not all H;
alternatively, any pair of $R^1$ and $R^2$, $R^2$ and $R^3$, or $R^1$ and $R^3$ may form a 3- to 5-membered ring, the 3- to 5-membered ring has 0 to 2 heteroatoms selected from N, O or S, and the formed 3- to 5-membered ring is optionally further substituted with 0 to 4 $R^8$s;

$R^4$ and $R^5$ are each independently selected from H, F, Cl, Br, I, hydroxyl, cyano, $C_{1-6}$ alkyl, $C_{1-6}$ alkoxy, a 3- to 5-membered carbocyclic group, or a 3- to 5-membered heterocyclic group, wherein the alkyl, alkoxy, carbocyclic group or heterocyclic group is optionally further substituted with 0 to 5 substituents selected from hydroxyl, $C_{1-6}$ alkyl, $C_{1-6}$ alkoxy, a 3- to 5-membered carbocyclic group or a 3- to 5-membered heterocyclic group, the heterocyclic group has 1 to 2 heteroatoms selected from N, O or S, and $R^4$ and $R^5$ are not both H;

alternatively, $R^4$ and $R^5$ may form a 3- to 5-membered ring, the 3- to 5-membered ring may have 0 to 2 heteroatoms selected from N, O or S, and the formed 3- to 5-membered ring may optionally be further substituted with 0 to 4 $R^8$s;

$R^6$ is selected from H or hydroxyl;

$R^7$ is selected from H, $C_{1-4}$ alkyl, or a 3- to 5-membered carbocyclic group, wherein the alkyl or carbocyclic group is optionally further substituted with 0 to 5 substituents selected from F, Cl, Br, I, hydroxyl, $C_{1-4}$ alkyl, $C_{1-4}$ alkoxy, or a 3- to 5-membered carbocyclic group;

$R^8$ is selected from F, Cl, Br, hydroxyl, $C_{1-4}$ alkyl, $C_{1-4}$ alkoxy, a 3- to 5-membered carbocyclic group or a 3- to 5-membered heterocyclic group, and the heterocyclic group has 1 to 2 heteroatoms selected from N, O or S;

$R^9$, $R^{10}$, $R^{11}$ and $R^{12}$ are H;

X is selected from H, F or carboxyl;

Y is selected from H, PEG,

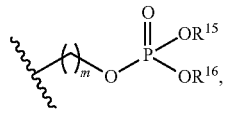

$C_{1-20}$ alkyl, $-(CH_2CH_2O)_q-H$, $-(CR^{ya}R^{yb})_{m1}COOR^{y1}$, $-(CR^{ya}R^{yb})_{m1}-(W_1)_p-C(=O)(W_4R^{y3})$ or $-(CR^{ya}R^{yb})_{m1}-(W_1)_p-P(=O)(W_2R^{y4})(W_3R^{y5})$ or

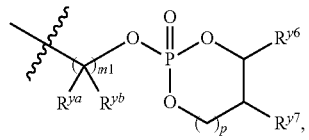

wherein the alkyl is optionally further substituted with 0 to 4 substituents selected from H, F, Cl, Br, I, hydroxyl, amino, cyano, carboxyl, $C_{1-6}$ alkyl, $C_{1-6}$ alkoxy, a $C_{3-8}$ carbocyclic group or a 4- to 8-membered heterocyclic group;

$R^{13}$ and $R^{14}$ are each independently selected from H or $C_{1-6}$ alkyl;

and $R^{15}$ and $R^{16}$ are each independently selected from H or an alkali metal ion, wherein the alkali metal ion is selected from $Na^+$, $K^+$ or $Li^+$.

Another preferred embodiment of the present invention is a compound of general formula (A), or a stereoisomer, a solvate, a metabolite, a prodrug, a pharmaceutically acceptable salt, or a cocrystal thereof; wherein $R^9$, $R^{10}$, $R^{11}$ and $R^{12}$ are H;

R is selected from Br, $-OR^7$ or

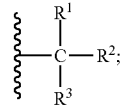

$R^1$, $R^2$ and $R^3$ are each independently selected from H, F, Cl, Br, hydroxyl, $C_{1-5}$ alkyl, $C_{1-5}$ alkoxy, or a 3- to 5-membered carbocyclic group, wherein the alkyl, alkoxy, or carbocyclic group is optionally further substituted with 0 to 3 substituents selected from F, Cl, Br, hydroxyl, $C_{1-4}$ alkyl, $C_{1-4}$ alkoxy, or a 3- to 5-membered carbocyclic group, and $R^1$, $R^2$ and $R^3$ are not all H;

alternatively, any pair of $R^1$ and $R^2$, $R^2$ and $R^3$, or $R^1$ and $R^3$ may form a 3- to 5-membered carbocyclic group, and the carbocyclic group may optionally be further substituted with 0 to 4 $R^8$s;

$R^4$ and $R^5$ are each independently selected from H, F, Cl, Br, hydroxyl, cyano, $C_{1-4}$ alkyl, $C_{1-4}$ alkoxy, or a 3- to 5-membered carbocyclic group, wherein the alkyl, alkoxy, or carbocyclic group is optionally further substituted with 0 to 3 substituents selected from hydroxyl, $C_{1-4}$ alkyl, or $C_{1-4}$ alkoxy, and $R^4$ and $R^5$ are not both H;

alternatively, $R^4$ and $R^5$ may form a 3- to 5-membered carbocyclic group, and the carbocyclic group may optionally be further substituted with 0 to 4 $R^8$s;

$R^6$ is selected from H or hydroxyl;

$R^7$ is selected from H or $C_{1-4}$ alkyl;

$R^8$ is selected from F, Cl, Br, hydroxyl, $C_{1-4}$ alkyl, or $C_{1-4}$ alkoxy;

X is H;

Y is selected from H, PEG,

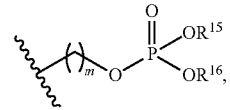

$C_{1-20}$ alkyl, $-(CH_2CH_2O)_q-H$, $-(CR^{ya}R^{yb})_{m1}COOR^{y1}$, $-(CR^{ya}R^{yb})_{m1}-(W_1)_p-C(=O)(W_4R^{y3})$ or $-(CR^{ya}R^{yb})_{m1}-(W_1)_p-P(=O)(W_2R^{y4})(W_3R^{y5})$ or

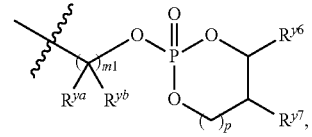

wherein the alkyl is optionally further substituted with 0 to 4 substituents selected from H, F, Cl, Br, I, hydroxyl, amino, cyano, carboxyl, $C_{1-6}$ alkyl, $C_{1-6}$ alkoxy, a $C_{3-8}$ carbocyclic group or a 4- to 8-membered heterocyclic group;

$R^{13}$ and $R^{14}$ are each independently selected from H or $C_{1-6}$ alkyl;

$R^{15}$ and $R^{16}$ are each independently selected from H or an alkali metal ion, wherein the alkali metal ion is selected from $Na^+$, $K^+$ or $Li^+$;

$R^{y1}$ is each independently selected from H, $C_{1-6}$ alkyl, a $C_{3-6}$ carbocyclic group or a 4- to 6-membered heterocyclic group, wherein the alkyl, carbocyclic group or heterocyclic group may optionally be further substituted with 0 to 5 substituents selected from H, F, Cl, Br, I, hydroxyl, amino, cyano, carboxyl, $C_{1-6}$ alkyl, $C_{1-6}$ alkoxy, a $C_{3-8}$ carbocyclic group or a 4- to 8-membered heterocyclic group, and the heterocyclic group has 1 to 2 heteroatoms selected from N, O or S;

$R^{y3}$ is selected from H, amino, $C_{1-6}$ alkyl, a $C_{3-6}$ carbocyclic group or a 4- to 6-membered heterocyclic group, $-(CR^{ya}R^{yb})_{m1}-NR^{yc}R^{yd}$ or $-(CR^{ya}R^{yb})_{m1}-NR^{yc}C(=O)OR^{yd}$, wherein the amino group, alkyl, carbocyclic group or heterocyclic group may optionally be further substituted with 0 to 5 substituents selected from H, F, Cl, Br, I, hydroxyl, amino, cyano, carboxyl, $C_{1-6}$ alkyl, $C_{1-6}$ alkoxy, $-(CH_2)_{m1}-OC(=O)-C_{1-6}$ alkyl, $-(CH_2)_{m1}-C(=O)$ $O-C_{1-6}$ alkyl, $-(CH_2)_{m1}-C(=O)O(CH_2)_{m1}-(C_{3-6}$ carbocyclic group), $-(CH_2)_{m1}-C(=O)-C_{1-6}$ alkyl, $-(CH_2)_{m1}-(C_{3-6}$ carbocyclic group) or $-(CH_2)_{m1}-(4$- to 6-membered heterocyclic group), and the heterocyclic group has 1 to 2 heteroatoms selected from N, O or S;

$R^{y4}$ and $R^{y5}$ are each independently selected from H, an alkali metal ion, an alkali earth metal ion, a protonated amine or a protonated amino acid, $C_{1-6}$ alkyl, $-(CR^{ya}R^{yb})_{m1}$-(3- to 6-membered ring), $-(CR^{ya}R^{yb})_{m1}-OC(=O)C_{1-6}$ alkyl, $-(CR^{ya}R^{yb})_{m1}-OC(=O)$-(3- to 6-membered ring), $-(CR^{ya}R^{yb})_{m1}-C(=O)OC_{1-6}$ alkyl or $-(CR^{ya}R^{yb})_{m1}-OC(=O)OC_{1-6}$ alkyl;

$R^{y9}$ and $R^{y10}$ are each independently selected from H, $C_{1-6}$ alkyl, a $C_{3-6}$ carbocyclic group or a 4- to 6-membered heterocyclic group, wherein the alkyl, carbocyclic group and heterocyclic group are each optionally further substituted with 0 to 4 substituents selected from H, hydroxyl, amino, mercapto, carboxyl, guanidino, carbamoyl, $C_{1-6}$ alkyl, $C_{1-6}$ alkoxy, a 3- to 8-membered carbocycle or a 3- to 8-membered heterocycle.

Another preferred embodiment of the present invention is a compound of general formula (A), or a stereoisomer, a solvate, a metabolite, a prodrug, a pharmaceutically acceptable salt, or a cocrystal thereof; wherein $R^9$, $R^{10}$, $R^{11}$ and $R^{12}$ are H;

R is selected from Br, $-OR^7$ or

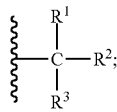

$R^1$, $R^2$ and $R^3$ are each independently selected from H, F, Cl, Br, hydroxyl, $C_{1-4}$ alkyl, $C_{1-4}$ alkoxy, or a 3- to 5-membered carbocyclic group, wherein the alkyl, alkoxy, or carbocyclic group is optionally further substituted with 0 to 3 substituents selected from F, Cl, Br, hydroxyl, $C_{1-4}$ alkyl, $C_{1-4}$ alkoxy, or a 3- to 5-membered carbocyclic group, and $R^1$, $R^2$ and $R^3$ are not all H;

alternatively, any pair of $R^1$ and $R^2$, $R^2$ and $R^3$, or $R^1$ and $R^3$ may form a 3- to 5-membered carbocyclic group, and the carbocyclic group may optionally be further substituted with 0 to 4 $R^8$s;

$R^4$ and $R^5$ are each independently selected from H, F, Cl, Br, hydroxyl, cyano, $C_{1-4}$ alkyl, $C_{1-4}$ alkoxy, or a 3- to 5-membered carbocyclic group, wherein the alkyl, alkoxy, or carbocyclic group is optionally further substituted with 0 to 3 substituents selected from hydroxyl, $C_{1-4}$ alkyl, or $C_{1-4}$ alkoxy, and $R^4$ and $R^5$ are not both H;

alternatively, $R^4$ and $R^5$ may form a 3- to 5-membered carbocyclic group, and the carbocyclic group may optionally be further substituted with 0 to 4 $R^8$s;

$R^6$ is selected from H or hydroxyl;

$R^7$ is selected from H or $C_{1-4}$ alkyl;

$R^8$ is selected from F, Cl, Br, hydroxyl, $C_{1-4}$ alkyl, or $C_{1-4}$ alkoxy;

X is H;

Y is selected from $C_{1-10}$ alkyl, $-(CH_2CH_2O)_q-H$, $-(CR^{ya}R^{yb})_{m1}-(W_1)_p-C(=O)(W_4R^{y3})$ or $-(CR^{ya}R^{yb})_{m1}-(W_1)_p-P(=O)(W_2R^{y4})(W_3R^{y5})$ or

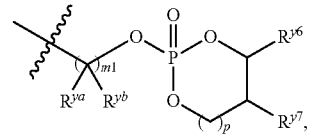

wherein the alkyl is optionally further substituted with 0 to 4 substituents selected from H, F, Cl, Br, I, hydroxyl, amino, cyano, carboxyl, $C_{1-6}$ alkyl, or a $C_{3-6}$ carbocyclic group;

$W_1$, $W_2$ and $W_3$ are each independently selected from $NR^{y8}$, O or S;

$W_4$ is selected from $CR^{y9}R^{y10}$, $NR^{y8}$, O, S, or is absent;

$R^{y3}$ is selected from H, amino, $C_{1-6}$ alkyl, a $C_{3-6}$ carbocyclic group or a 4- to 6-membered heterocyclic group, $-(CR^{ya}R^{yb})_{m1}-NR^{yc}R^{yd}$ or $-(CR^{ya}R^{yb})_{m1}-NR^{yc}C(=O)OR^{yd}$, wherein the amino group, alkyl, carbocyclic group or heterocyclic group may optionally be further substituted with 0 to 5 substituents selected from H, F, Cl, Br, I, hydroxyl, amino, cyano, carboxyl, $C_{1-6}$ alkyl, $C_{1-6}$ alkoxy, $-(CH_2)_{m1}-OC(=O)-C_{1-6}$ alkyl, $-(CH_2)_{m1}-C(=O)$ $O-C_{1-6}$ alkyl, $-(CH_2)_{m1}-C(=O)O(CH_2)_{m1}-(C_{3-6}$ carbocyclic group), $-(CH_2)_{m1}-C(=O)-C_{1-6}$ alkyl, $-(CH_2)_{m1}-(C_{3-6}$ carbocyclic group) or $-(CH_2)_{m1}-(4$- to 6-membered heterocyclic group), and the heterocyclic group has 1 to 2 heteroatoms selected from N, O or S;

$R^{y4}$ and $R^{y5}$ are each independently selected from H, an alkali metal ion, an alkali earth metal ion, a protonated amine or a protonated amino acid, $C_{1-6}$ alkyl, $-(CR^{ya}R^{yb})_{m1}$-(3- to 6-membered ring), $-(CR^{ya}R^{yb})_{m1}-OC(=O)C_{1-6}$ alkyl, $-(CR^{ya}R^{yb})_{m1}-OC(=O)$-(3- to 6-membered ring), $-(CR^{ya}R^{yb})_{m1}-C(=O)OC_{1-6}$ alkyl or $-(CR^{ya}R^{yb})_{m1}-OC(=O)OC_{1-6}$ alkyl;

$R^{y6}$ and $R^{y7}$ are each independently selected from H, F, Cl, Br, I, hydroxyl, amino, cyano, carboxyl, $C_{1-6}$ alkyl or $C_{1-6}$ alkoxy;

alternatively, $R^{y6}$ and $R^{y7}$ may form a 5- to 8-membered ring together with the atoms to which they are attached, the 5- to 8-membered ring may have 0 to 4 heteroatoms selected from N, O or S, and the 5- to 8-membered ring may optionally be further substituted with 0 to 4 substituents selected from H, F, Cl, Br, I, $C_{1-6}$ alkyl or $C_{1-6}$ alkoxy;

$R^{y8}$s are each independently selected from H or $C_{1-6}$ alkyl;

$R^{y9}$ and $R^{y10}$ are each independently selected from H, $C_{1-6}$ alkyl, a $C_{3-6}$ carbocyclic group or a 4- to 6-membered heterocyclic group, wherein the alkyl, carbocyclic group and heterocyclic group are each optionally further substituted with 0 to 4 substituents selected from H, hydroxyl, amino, mercapto, carboxyl, guanidino, carbamoyl, $C_{1-6}$ alkyl, $C_{1-6}$ alkoxy, a 3- to 8-membered carbocycle or a 3- to 8-membered heterocycle;

$R^{ya}$, $R^{yb}$, $R^{yc}$ and $R^{yd}$ are each independently selected from H or $C_{1-6}$ alkyl;

n is selected from 1 to 200;

m1 is selected from 0, 1, 2 or 3; and p is selected from 0, 1 or 2.

Another preferred embodiment of the present invention is a compound of general formula (A), or a stereoisomer, a solvate, a metabolite, a prodrug, a pharmaceutically acceptable salt, or a cocrystal thereof; wherein
$R^9$, $R^{10}$, $R^{11}$ and $R^{12}$ are H;
R is selected from Br, —$OR^7$ or

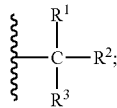

$R^1$, $R^2$ and $R^3$ are each independently selected from H, hydroxyl, methyl, ethyl or cyclopropyl, and $R^1$, $R^2$ and $R^3$ are not all H;
alternatively, any pair of $R^1$ and $R^2$, $R^2$ and $R^3$, or $R^1$ and $R^3$ may form cyclopropyl;
$R^4$ and $R^5$ are each independently selected from H, hydroxyl, cyano, methyl, ethyl or cyclopropyl, and $R^4$ and $R^5$ are not both H;
X is H;
$R^7$ is selected from H, methyl or ethyl;
Y is selected from $C_{1-4}$ alkyl, —$(CR^{ya}R^{yb})_{m1}$—$(W_1)_p$—C(=O)($W_4R^{y3}$) or —$(CR^{ya}R^{yb})_{m1}$—$(W_1)_p$—P(=O)($W_2R^{y4}$)($W_3R^{y5}$) or

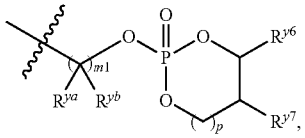

wherein the alkyl is optionally further substituted with 0 to 4 substituents selected from H, F, Cl, Br, I, hydroxyl, amino, cyano, carboxyl, $C_{1-4}$ alkyl, or a $C_{3-6}$ carbocyclic group;
$W_1$, $W_2$ and $W_3$ are each independently selected from $NR^{y8}$, O or S;
$W_4$ is selected from $CR^{y9}R^{y10}$, $NR^{y8}$, O, S, or is absent;
$R^{y3}$ is selected from H, amino, $C_{1-6}$ alkyl, a $C_{3-6}$ carbocyclic group or a 4- to 6-membered heterocyclic group, —$(CR^{ya}R^{yb})_{m1}$—$NR^{yc}R^{yd}$ or —$(CR^{ya}R^{yb})_{m1}$—$NR^{yc}C(=O)OR^{yd}$, wherein the amino group, alkyl, carbocyclic group or heterocyclic group may optionally be further substituted with 0 to 5 substituents selected from —$(CH_2)_{m1}$—OC(=O)—$C_{1-4}$ alkyl, —$(CH_2)_{m1}$—C(=O)O—$C_{1-4}$ alkyl, —$(CH_2)_{m1}$—C(=O)O$(CH_2)_{m1}$—($C_{3-6}$ carbocyclic group), —$(CH_2)_{m1}$—C(=O)—$C_{1-4}$ alkyl, —$(CH_2)_{m1}$—($C_{3-6}$ carbocyclic group) or —$(CH_2)_{m1}$—(4- to 6-membered heterocyclic group), and the heterocyclic group has 1 to 2 heteroatoms selected from N, O or S;
$R^{y4}$ and $R^{y5}$ are each independently selected from H, an alkali metal ion, $C_{1-4}$ alkyl, —$(CR^{ya}R^{yb})_{m1}$-(3- to 6-membered ring), —$(CR^{ya}R^{yb})_{m1}$—OC(=O)$C_{1-4}$ alkyl, —$(CR^{ya}R^{yb})_{m1}$—OC(=O)-(3- to 6-membered ring), —$(CR^{ya}R^{yb})_{m1}$—C(=O)O$C_{1-4}$ alkyl or —$(CR^{ya}R^{yb})_{m1}$—OC(=O)O$C_{1-4}$ alkyl;
$R^{y6}$ and $R^{y7}$ are each independently selected from H, $C_{1-4}$ alkyl or $C_{1-4}$ alkoxy;
alternatively, $R^{y6}$ and $R^{y7}$ may form a 5- to 6-membered ring together with the atoms to which they are attached, and the 5- to 6-membered ring may have 0 to 4 heteroatoms selected from N, O or S;

$R^{y8}$s are each independently selected from H or $C_{1-4}$ alkyl;
$R^{y9}$ and $R^{y10}$ are each independently selected from H, $C_{1-6}$ alkyl or a 4- to 6-membered heterocyclic group, wherein the alkyl and heterocyclic group are each optionally further substituted with 0 to 4 substituents selected from H, hydroxyl, amino, mercapto, carboxyl, guanidino, carbamoyl, $C_{1-6}$ alkyl, $C_{1-6}$ alkoxy, a 3- to 6-membered carbocycle or a 4- to 6-membered heterocycle;
$R^{ya}$, $R^{yb}$, $R^{yc}$ and $R^{yd}$ are each independently selected from H or $C_{1-4}$ alkyl;
q is selected from 1 to 10;
m1 is selected from 0, 1, 2 or 3; and
p is selected from 0, 1 or 2.

Another preferred embodiment of the present invention is a compound of general formula (A), or a stereoisomer, a solvate, a metabolite, a prodrug, a pharmaceutically acceptable salt, or a cocrystal thereof; wherein
$R^9$, $R^{10}$, $R^{11}$ and $R^{12}$ are H;
R is selected from Br, —$OR^7$ or

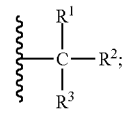

$R^1$, $R^2$ and $R^3$ are each independently selected from H, hydroxyl, methyl, ethyl or cyclopropyl, and $R^1$, $R^2$ and $R^3$ are not all H;
alternatively, any pair of $R^1$ and $R^2$, $R^2$ and $R^3$, or $R^1$ and $R^3$ may form cyclopropyl;
$R^4$ and $R^5$ are each independently selected from H, hydroxyl, cyano, methyl, ethyl or cyclopropyl, and $R^4$ and $R^5$ are not both H;
X is H;
$R^7$ is selected from H, methyl or ethyl;
Y is selected from $C_{1-4}$ alkyl, —$(CR^{ya}R^{yb})_{m1}$—$(W_1)_p$—C(=O)($W_4R^{y3}$) or —$(CR^{ya}R^{yb})_{m1}$—$(W_1)_p$—P(=O)($W_2R^{y4}$)($W_2R^{y5}$) or

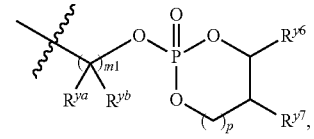

wherein the alkyl is optionally further substituted with 0 to 4 substituents selected from H, hydroxyl, amino, $C_{1-4}$ alkyl, or a $C_{5-6}$ carbocyclic group;
$R^{y3}$ is selected from H, amino, $C_{1-4}$ alkyl, —$(CR^{ya}R^{yb})_{m1}$—$NR^{yc}R^{yd}$, —$(CR^{ya}R^{yb})_{m1}$—$NR^{yc}C(=O)OR^{yd}$, a $C_{3-6}$ carbocyclic group or a 3- to 6-membered heterocyclic group; preferably H, amino, $C_{1-4}$ alkyl, —$(CH_2)_{m1}$—$NR^{yc}R^{yd}$, —$(CH_2)_{m1}$—$NR^{yc}C(=O)OR^{yd}$, a $C_{5-6}$ carbocyclic group or a 5- to 6-membered heterocyclic group; further preferably amino, aminomethylene, isopropyl, t-butyl, (t-butoxycarbonyl)amino, (t-butoxycarbonyl)aminomethylene, pyrrolylalkyl, phenyl or pyridinyl;
wherein the amino group, alkyl, carbocyclic group or heterocyclic group is optionally further substituted with 0 to 4 substituents selected from H, —OC(=O)—$C_{1-4}$ alkyl, —C(=O)O—$C_{1-4}$ alkyl or —C(=O)OCH$_2$—($C_{5-6}$ carbocyclic group), preferably substituted with 0 to 4 substituents selected from t-butoxycarbonyl, acetoxy or benzyloxycarbonyl; and the heterocyclic group has at least 1 to 2 heteroatoms selected from N, O or S;

$R^{y4}$ and $R^{y5}$ are each independently selected from H, an alkali metal ion, $C_{1-4}$ alkyl, $-(CR^{ya}R^{yb})_{m1}$-(5- to 6-membered ring), $-(CR^{ya}R^{yb})_{m1}-OC(=O)C_{1-4}$ alkyl, $-(CR^{ya}R^{yb})_{m1}-C(=O)OC_{1-4}$ alkyl or $-(CR^{ya}R^{yb})_{m1}-OC(=O)OC_{1-4}$ alkyl; preferably H, an alkali metal ion, $C_{1-4}$ alkyl, $-(CH_2)_{m1}$-(5- to 6-membered ring), $-(CH_2)_{m1}-OC(=O)C_{1-4}$ alkyl, $-(CH_2)_{m1}-C(=O)OC_{1-4}$ alkyl or $-(CH_2)_{m1}-OC(=O)OC_{1-4}$ alkyl; and more preferably H, Na$^+$, K$^+$, ethyl, benzyl, $-CH_2OC(=O)C(CH_3)_3$, $-CH(CH_3)OC(=O)CH(CH_3)_2$, $-CH_2OC(=O)CH_2CH_3$, $-CH_2C(=O)OCH_2CH_3$ or $-CH_2OC(=O)OCH(CH_3)_2$;

$R^{y6}$ and $R^{y7}$ are each independently selected from H or $C_{1-4}$ alkyl;

alternatively, $R^{y6}$ and $R^{y7}$ may form a 5- to 6-membered ring together with the atoms to which they are attached, and the 5- to 6-membered ring may have 0 to 4 heteroatoms selected from N, O or S;

$R^{y8}$ is selected from H or $C_{1-4}$ alkyl;

$R^{y9}$ is selected from H or $C_{1-4}$ alkyl;

$R^{y10}$ is selected from H or $C_{1-4}$ alkyl; wherein the alkyl is optionally further substituted with 0 to 4 substituents selected from H, hydroxyl, amino, mercapto, carboxyl, guanidino, carbamoyl, $C_{1-4}$ alkyl, or a 5- to 6-membered carbocycle;

q is selected from 1 to 10;

m1 is selected from 0, 1, 2 or 3; and p is selected from 0, 1 or 2.

Another preferred embodiment of the present invention is a compound of general formula (A), or a stereoisomer, a solvate, a metabolite, a prodrug, a pharmaceutically acceptable salt, or a cocrystal thereof; wherein $R^9$, $R^{10}$, $R^{11}$ and $R^{12}$ are H;

R is selected from Br, $-OR^7$ or

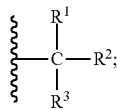

$R^1$, $R^2$ and $R^3$ are each independently selected from H, hydroxyl, methyl, ethyl or cyclopropyl, and $R^1$, $R^2$ and $R^3$ are not all H;

alternatively, any pair of $R^1$ and $R^2$, $R^2$ and $R^3$, or $R^1$ and $R^3$ may form cyclopropyl;

$R^4$ and $R^5$ are each independently selected from H, hydroxyl, cyano, methyl, ethyl or cyclopropyl, and $R^4$ and $R^5$ are not both H;

X is H;

$R^7$ is selected from H, methyl or ethyl;

Y is selected from $C_{1-4}$ alkyl, $-(CR^{ya}R^{yb})_{m1}-(W_1)_p-C(=O)(W_4R^{y3})$ or $-(CR^{ya}R^{yb})_{m1}-(W_1)_p-P(=O)(W_2R^{y4})(W_2R^{y5})$ or

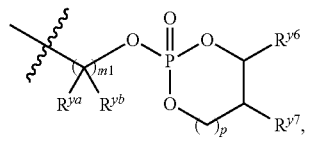

wherein the alkyl is optionally further substituted with 0 to 4 substituents selected from H, hydroxyl, amino, $C_{1-4}$ alkyl, or a $C_{5-6}$ carbocyclic group;

$W_1$, $W_2$ and $W_3$ are each independently selected from NH or O;

$W_4$ is independently selected from $CHR^{y10}$, O, or is absent;

$R^{y3}$ is selected from H, amino, $C_{1-4}$ alkyl, $-(CH_2)_{m1}-NR^{yc}R^{yd}$, $-(CH_2)_{m1}-NR^{yc}C(=O)OR^{yd}$, a $C_{5-6}$ carbocyclic group or a 5- to 6-membered heterocyclic group; preferably amino, aminomethylene, isopropyl, t-butyl, (t-butoxycarbonyl)amino, (t-butoxycarbonyl)aminomethylene, pyrrolylalkyl, phenyl or pyridinyl;

wherein the amino group, alkyl, carbocyclic group or heterocyclic group is optionally further substituted with 0 to 4 substituents selected from H, $-OC(=O)-C_{1-4}$ alkyl, $-C(=O)O-C_{1-4}$ alkyl or $-C(=O)OCH_2-(C_{5-6}$ carbocyclic group), preferably substituted with 0 to 4 substituents selected from t-butoxycarbonyl, acetoxy or benzyloxycarbonyl; and the heterocyclic group has at least 1 to 2 heteroatoms selected from N, O or S;

$R^{y4}$ and $R^{y5}$ are each independently selected from H, an alkali metal ion, $C_{1-4}$ alkyl, $-(CH_2)_{m1}$-(5- to 6-membered ring), $-(CH_2)_{m1}-OC(=O)C_{1-4}$ alkyl, $-(CH_2)_{m1}-C(=O)OC_{1-4}$ alkyl or $-(CH_2)_{m1}-OC(=O)OC_{1-4}$ alkyl; and preferably H, Na$^+$, K$^+$, ethyl, benzyl, $-CH_2OC(=O)C(CH_3)_3$, $-CH(CH_3)OC(=O)CH(CH_3)_2$, $-CH_2OC(=O)CH_2CH_3$, $-CH_2C(=O)OCH_2CH_3$ or $-CH_2OC(=O)OCH(CH_3)_2$;

$R^{y6}$ and $R^{y7}$ are each independently selected from H or $C_{1-4}$ alkyl;

alternatively, $R^{y6}$ and $R^{y7}$, together with the atoms to which they are attached, may form a 5- to 6-membered ring, preferably phenyl, and the 5- to 6-membered ring may have 0 to 4 heteroatoms selected from N, O or S;

$R^{y8}$ is selected from H or $C_{1-4}$ alkyl;

$R^{y9}$ is selected from H or $C_{1-4}$ alkyl;

$R^{y10}$ is selected from H or $C_{1-4}$ alkyl, preferably H, methyl, isopropyl, sec-butyl, 2-methylpropyl or benzyl; wherein the alkyl is optionally further substituted with 0 to 4 substituents selected from H, $C_{1-4}$ alkyl, or a 5- to 6-membered carbocycle;

$R^{ya}$, $R^{yb}$, $R^{yc}$ and $R^{yd}$ are each independently selected from H or $C_{1-4}$ alkyl, preferably H, methyl or ethyl;

q is selected from 1 to 10;

m1 is selected from 0, 1, 2 or 3; and p is selected from 0, 1 or 2.

Another preferred embodiment of the present invention is a compound of general formula (A), or a stereoisomer, a solvate, a metabolite, a prodrug, a pharmaceutically acceptable salt, or a cocrystal thereof; wherein:

the

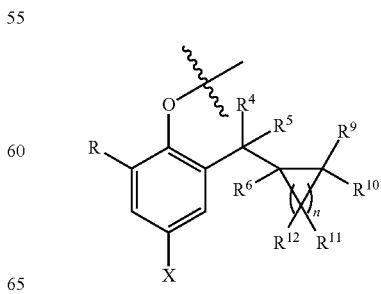

is selected from the structures below:
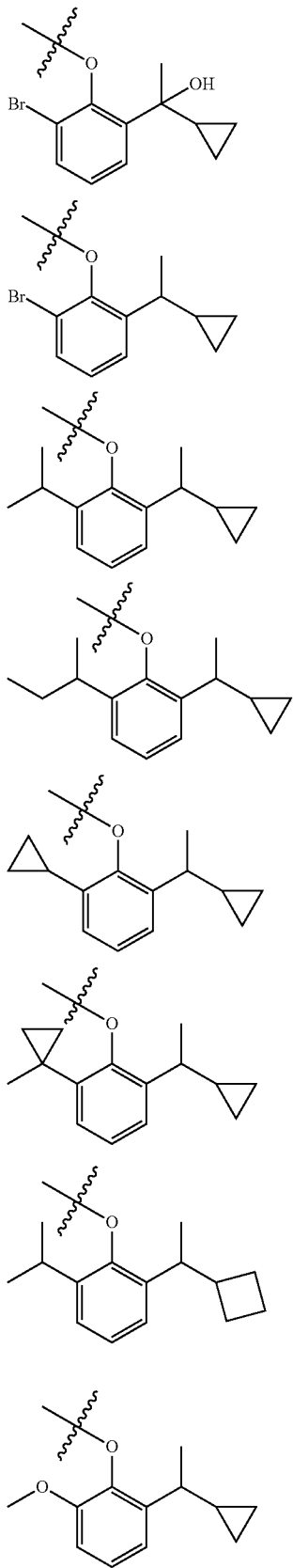
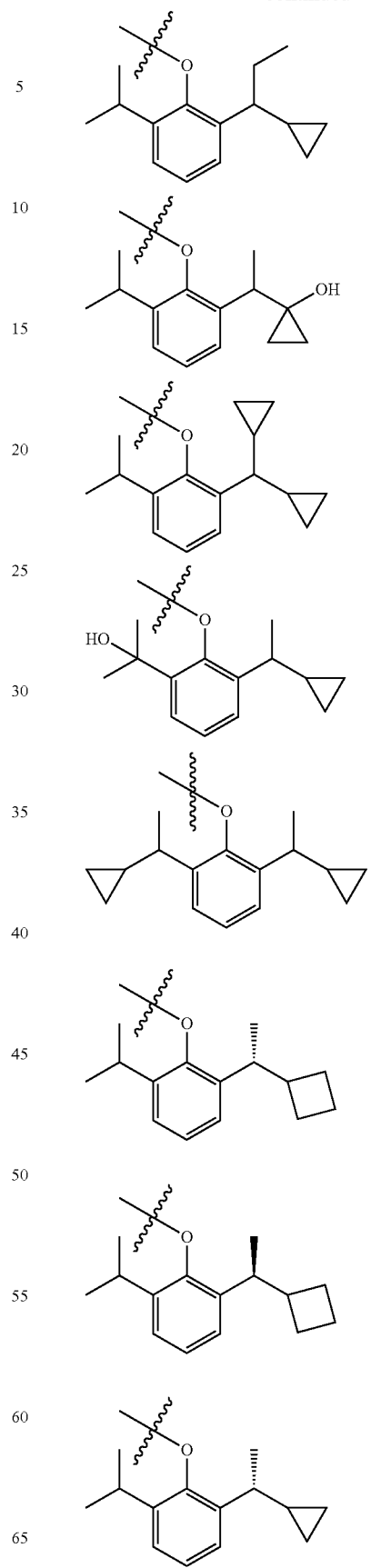

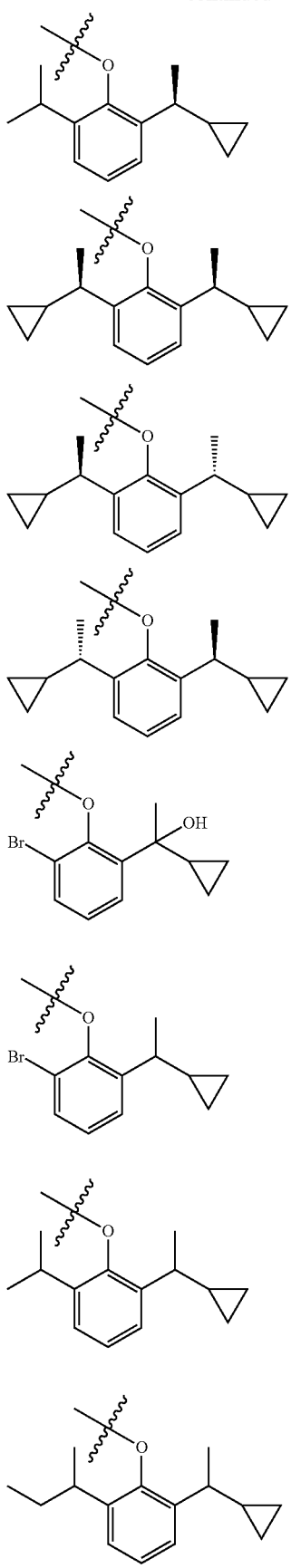
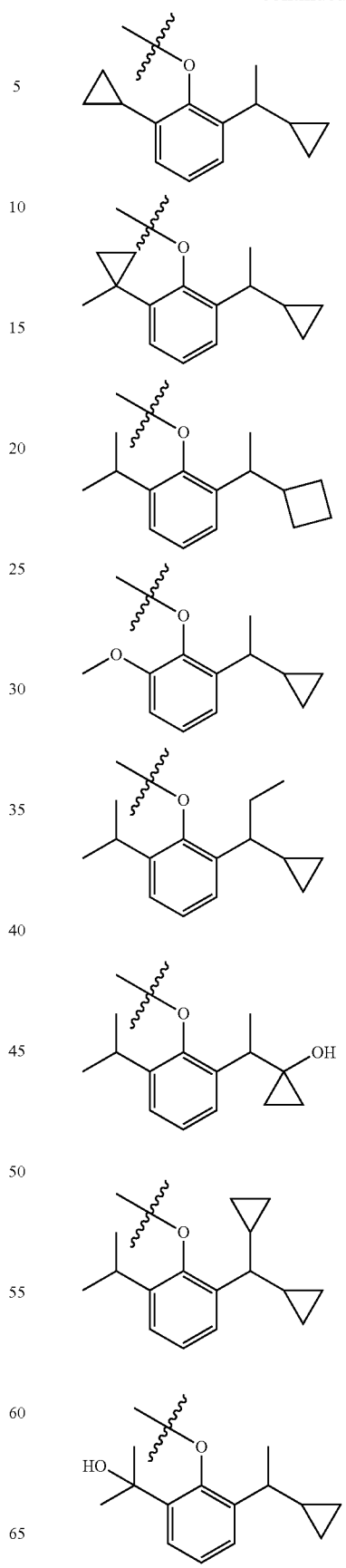

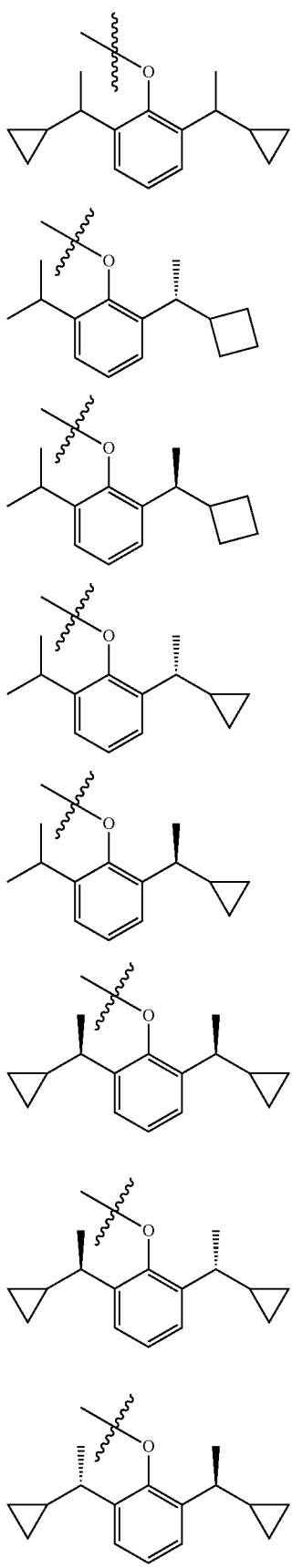
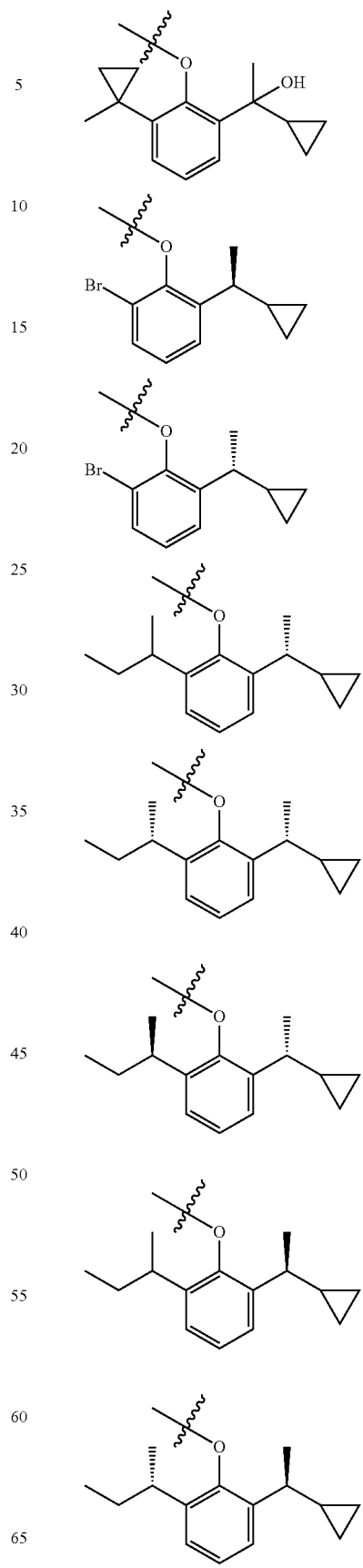

-continued
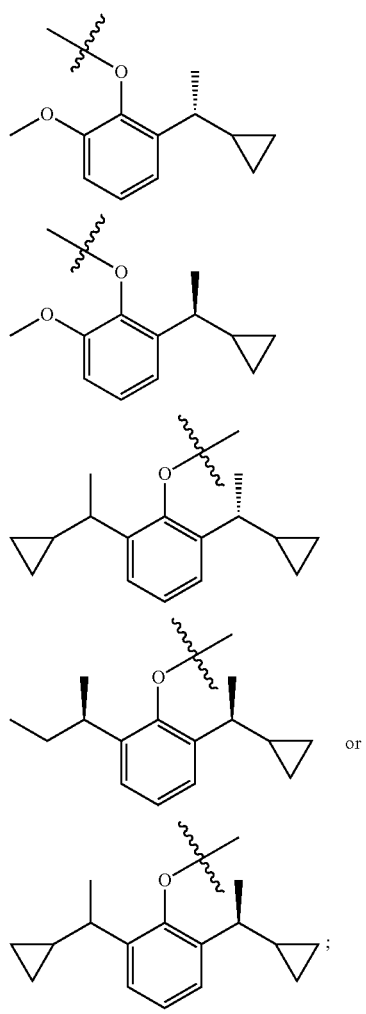
or
preferably
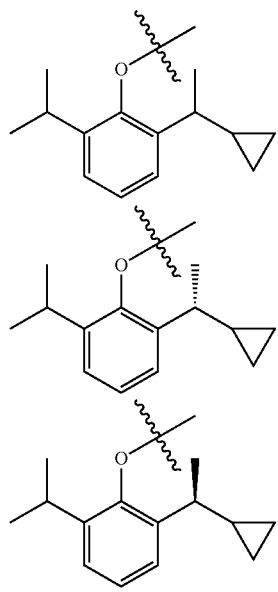
-continued
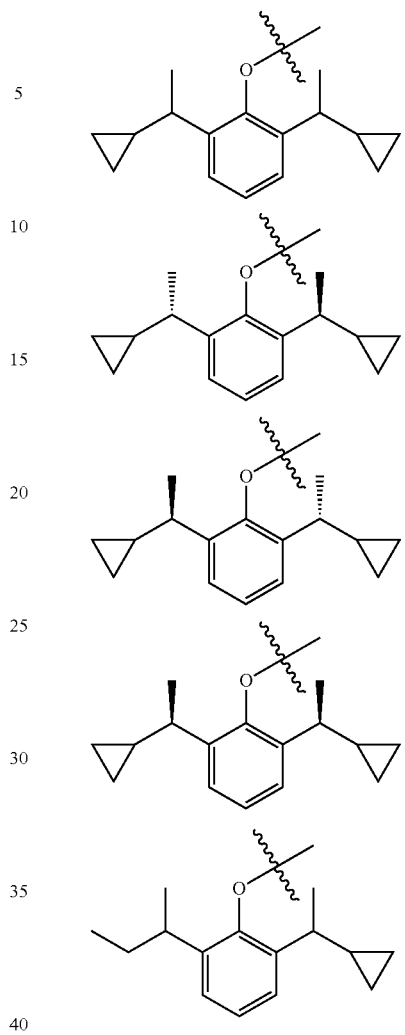
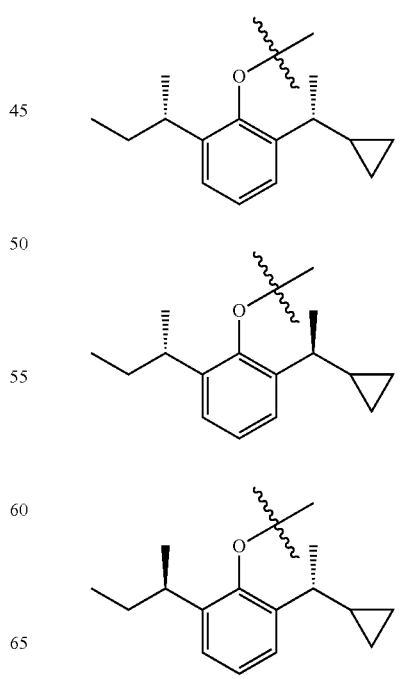

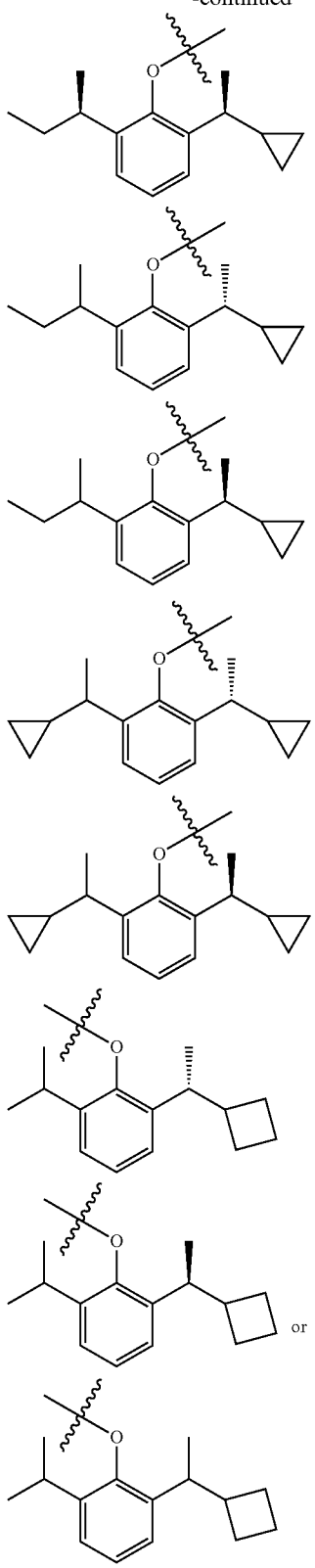

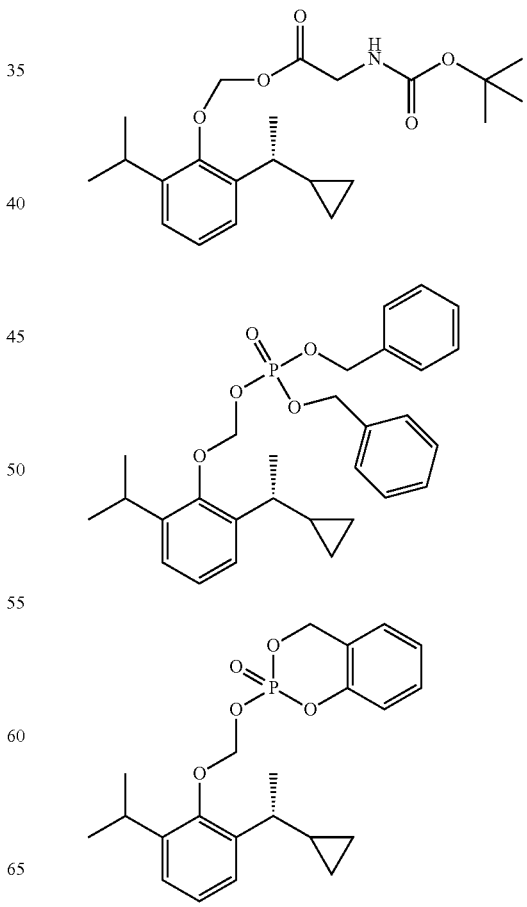

Y is selected from methyl, hydroxyethyl, —CH$_2$OC(=O)(R$^{y3}$), —C(=O)(R$^{y3}$), —CH$_2$OC(=O)(W$_4$R$^{y3}$), —C(=O)(W$_4$R$^{y3}$), —CH(CH$_3$)OC(=O)(W$_4$R$^{y3}$), —CH$_2$OP(=O)(W$_2$R$^{y4}$)(W$_3$R$^{y5}$), —P(=O)(W$_2$R$^{y4}$)(W$_3$R$^{y5}$) or W$_2$ and W$_3$ are each independently selected from NH or O;

W$_4$ is selected from CHR$^{y10}$ or O;

R$^{y3}$ is selected from amino, aminomethylene, isopropyl, t-butyl, (t-butoxycarbonyl)amino, (t-butoxycarbonyl)aminomethylene, pyrrolylalkyl, phenyl or pyridinyl, wherein the amino group, pyrrolylalkyl, phenyl and pyridinyl are optionally further substituted with 0 to 4 substituents selected from t-butoxycarbonyl, acetoxy, or benzyloxycarbonyl;

R$^{y4}$ and R$^{y5}$ are each independently selected from H, Na$^+$, K$^+$, ethyl, benzyl, —CH$_2$OC(=O)C(CH$_3$)$_3$, —CH(CH$_3$)OC(=O)CH(CH$_3$)$_2$, —CH$_2$OC(=O)CH$_2$CH$_3$, —CH$_2$C(=O)OCH$_2$CH$_3$ or —CH$_2$OC(=O)OCH(CH$_3$)$_2$;

R$^{y6}$ and R$^{y7}$ form phenyl together with the atoms to which they are attached;

R$^{y10}$ is selected from H, methyl, isopropyl, sec-butyl, 2-methylpropyl or benzyl.

In a preferred embodiment of the present invention, the prodrug compounds according to the present invention is selected from, but not limited to:

65
-continued
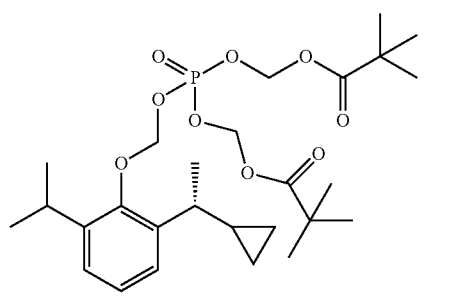
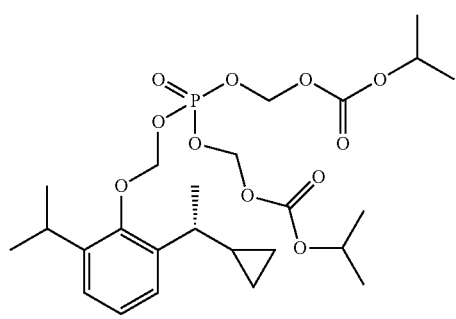
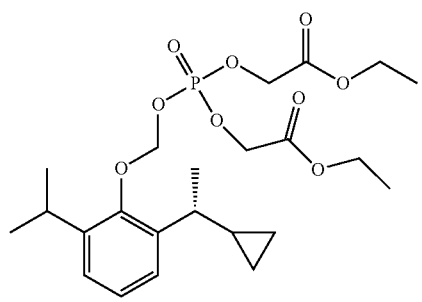
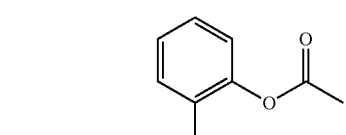
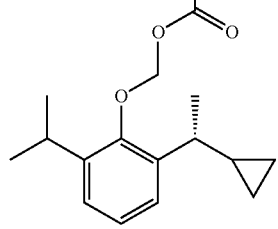
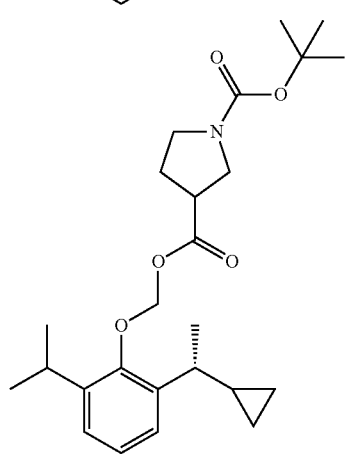
66
-continued
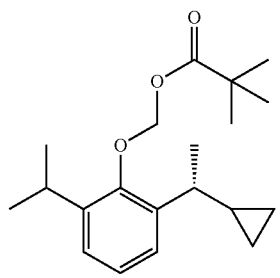
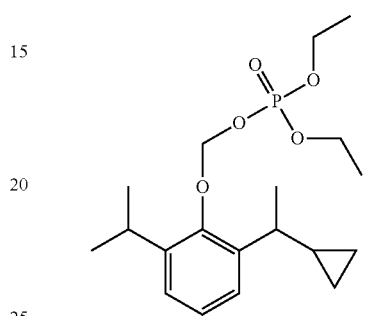
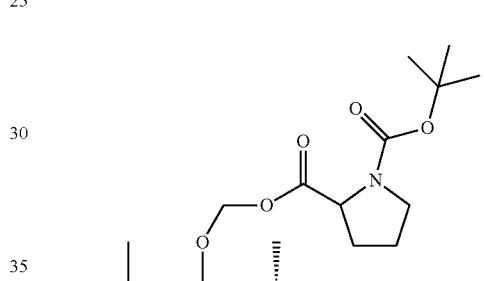
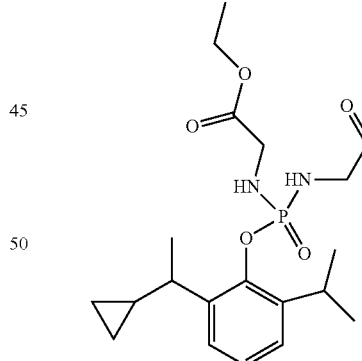
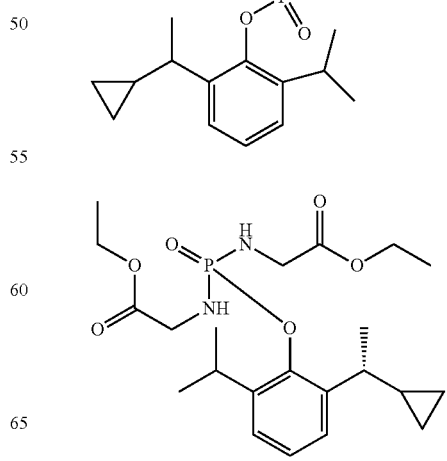

67
-continued
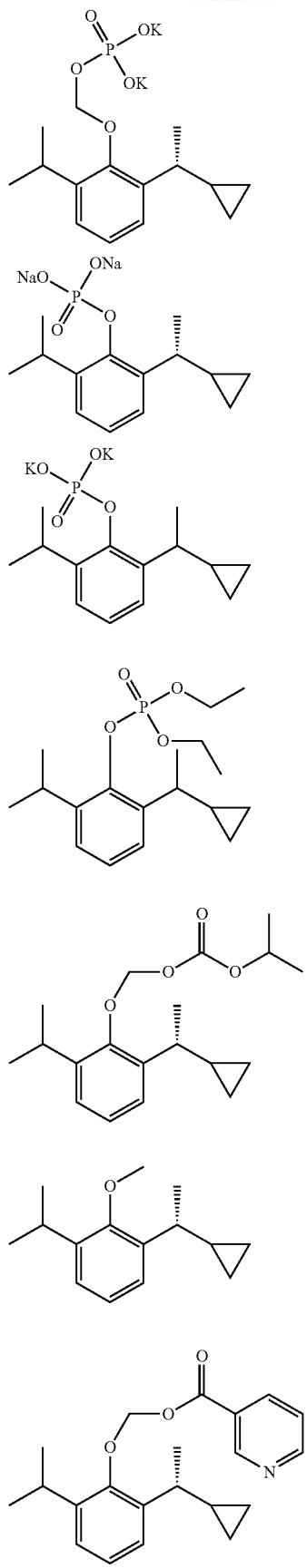
68
-continued
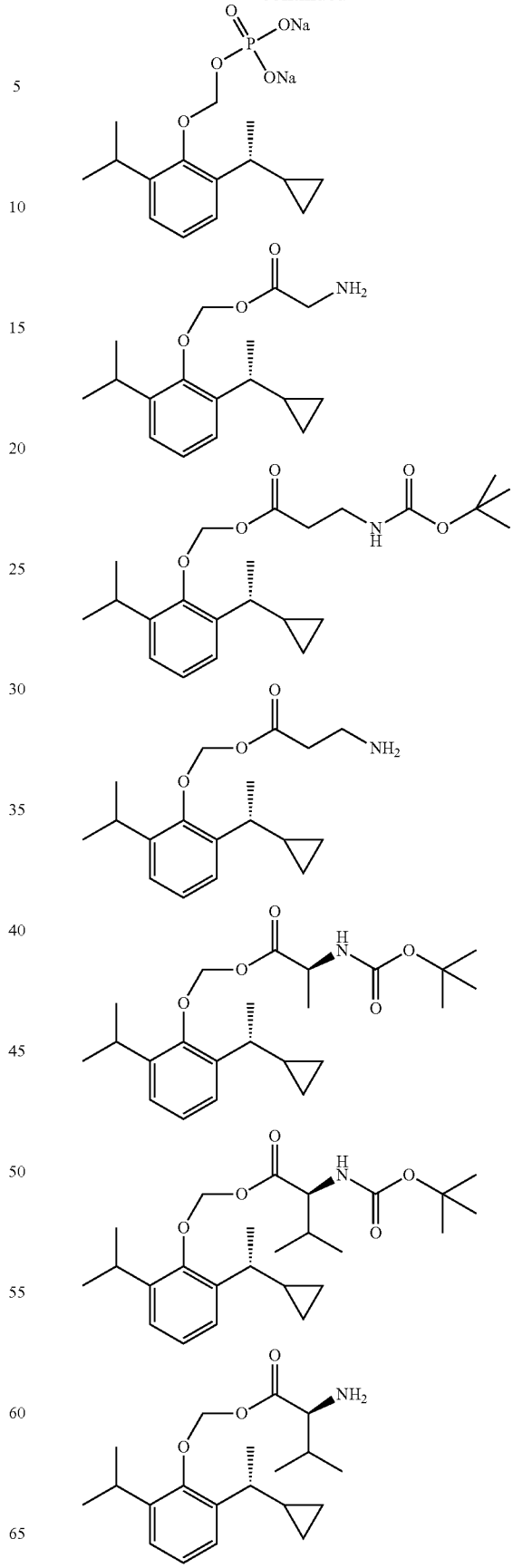

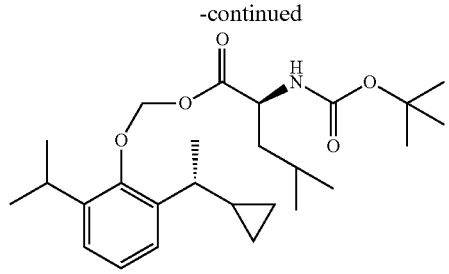
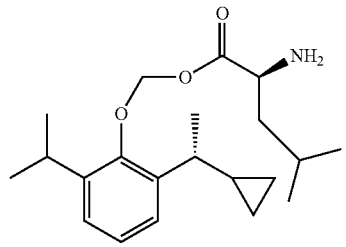
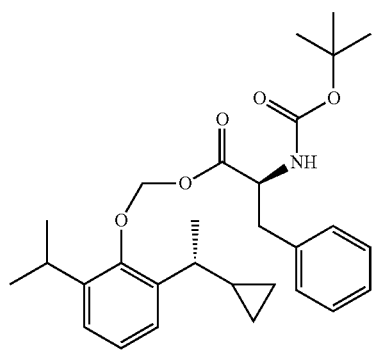
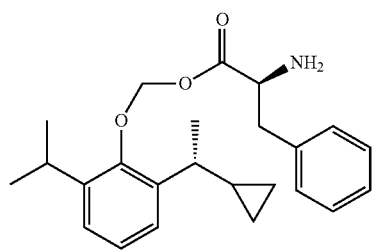
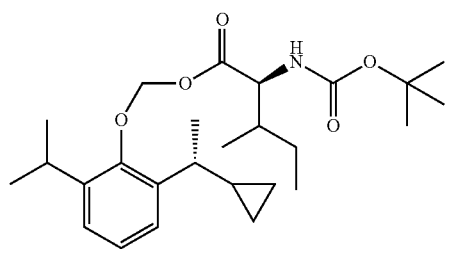
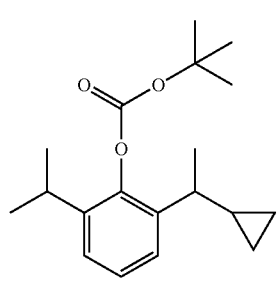
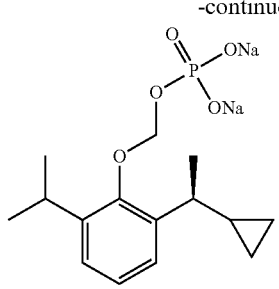
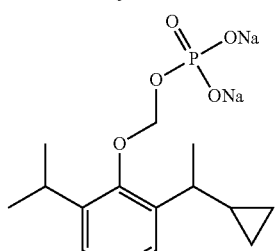
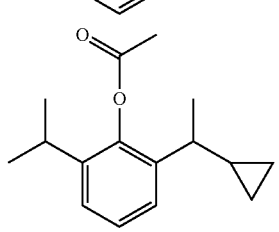

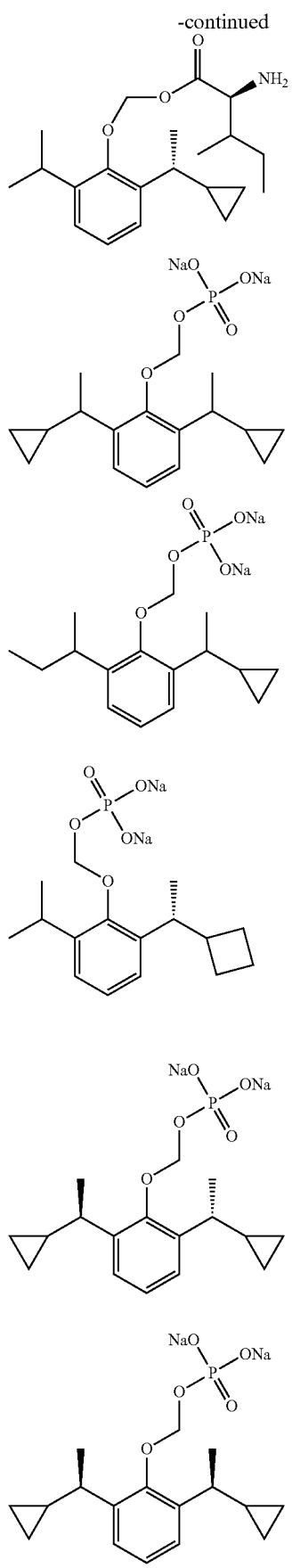

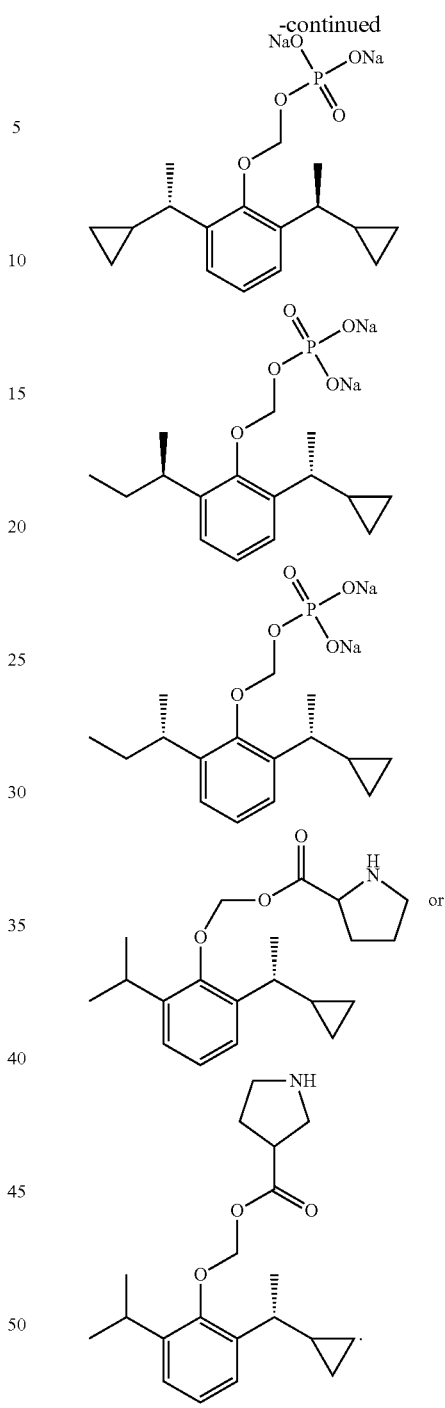

The present invention also relates to pharmaceutically acceptable salts of the compound of general formula (A) or (I), wherein the salts include, but not limited to, an alkali metal salt, an alkali earth metal salt, an ammonium salt, a tetraalkylammonium salt, an ethanolamine salt, a diethanolamine salt, a triethanolamine salt, trimethylamine salt, N-methylglucosamine salt, hydrochloride, sulfate, phosphate, acetate, trifluoroacetate, fumarate, hemifumarate, maleate, malate, citrate, succinate, benzenesulfonate, or p-toluenesulfonate; preferable an ammonium salt, a potassium salt, a sodium salt, a calcium salt, a magnesium salt, hydrochloride, acetate, trifluoroacetate, fumarate, benzenesulfonate, or p-toluenesulfonate.

The present invention relates to a method for preparing the compound of general formula (I) according to the present invention, comprising:

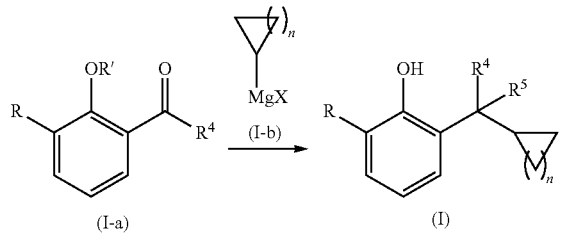

(I-a) (I)

conducting a Grignard reaction between a compound of general formula (I-a) and a compound of general formula (I-b) to afford a compound of general formula (I); wherein preferably conducting the Grignard reaction between a compound of general formula (I-a) and a compound of general formula (I-b) at −4° C. to 35° C., and allowing the reaction to proceed for 2 to 20 h under stirring, to afford a compound of general formula (I);

or conducting a Grignard reaction between a compound of general formula (I-a) and a compound of general formula (I-b), and further removing R' from the product of the reaction to afford a compound of general formula (I); wherein preferably conducting the Grignard reaction between a compound of general formula (I-a) and a compound of general formula (I-b) at −4° C. to 35° C., allowing the reaction to proceed for 2 to 20 h under stirring, and further removing R' from the product of the reaction to afford a compound of general formula (I);

or conducting a Grignard reaction between a compound of general formula (I-a) and a compound of general formula (I-b), and removing hydroxyl from the product of the reaction by a reducing agent, to afford a compound of general formula (I); wherein preferably conducting the Grignard reaction between a compound of general formula (I-a) and a compound of general formula (I-b) at −4° C. to 35° C., allowing the reaction to proceed for 2 to 20 h under stirring, and removing hydroxyl from the product of the reaction by a reducing agent, to afford a compound of general formula (I);

or conducting a Grignard reaction between a compound of general formula (I-a) and a compound of general formula (I-b), removing R' from the product of the reaction, and further removing hydroxyl therefrom by a reducing agent, to afford a compound of general formula (I); wherein preferably conducting the Grignard reaction between a compound of general formula (I-a) and a compound of general formula (I-b) at −4° C. to 35° C., allowing the reaction to proceed for 2 to 20 h under stirring, removing R' from the product of the reaction, and further removing hydroxyl therefrom by a reducing agent, to afford a compound of general formula (I);

wherein R' is selected from H, methyl, ethyl, benzyl, p-methoxybenzyl, triphenylmethyl, trimethylsilyl, or t-butyl (dimethyl)silyl; R, $R^4$, $R^5$ and n have the same definitions as those for the compound of general formula (I); X is selected from F, Cl, Br or I;

or,

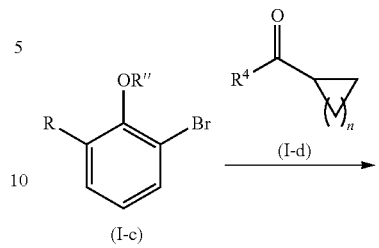

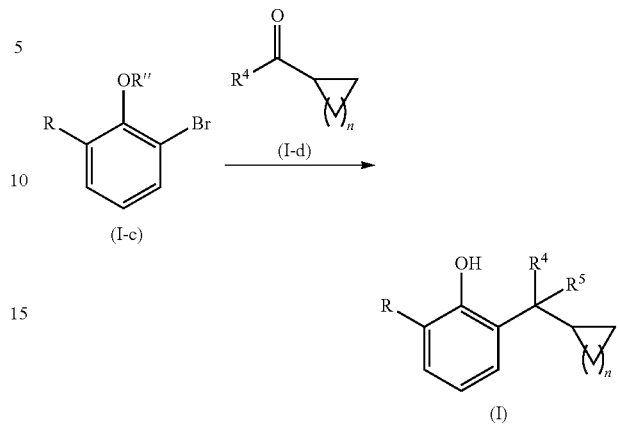

allowing a compound of general formula (I-c) to either undergo a Grignard reaction, or react with a compound of general formula (I-d) under the action of an organolithium reagent, and then removing R" to afford a compound of general formula (I); wherein, preferably, allowing a compound of general formula (I-c) to either undergo a Grignard reaction at −4° C. to 35° C. for 2 to 20 h under stirring, or react with a compound of general formula (I-d) under the action of an organolithium reagent for 30 min to 8 h at −78° C. to −50° C., and then removing R" to afford a compound of general formula (I);

or allowing a compound of general formula (I-c) to either undergo a Grignard reaction, or react with a compound of general formula (I-d) under the action of an organolithium reagent, then removing R" from the product thereof, and further removing hydroxyl therefrom by a reducing agent, to afford a compound of general formula (I); wherein, preferably, allowing a compound of general formula (I-c) to, either undergo a Grignard reaction at −4° C. to 35° C. for 2 to 20 h under stirring, or react with a compound of general formula (I-d) under the action of an organolithium reagent for 30 min to 8 h at −78° C. to −50° C., then removing R" from the product thereof, and further removing hydroxyl therefrom by a reducing agent, to afford a compound of general formula (I);

or allowing a compound of general formula (I-c) to either undergo a Grignard reaction, or react with a compound of general formula (I-d) under the action of an organolithium reagent, further alkylating the product thereof, and then removing R" therefrom to afford a compound of general formula (I); wherein, preferably, allowing a compound of general formula (I-c) to, either undergo a Grignard reaction at −4° C. to 35° C. for 2 to 20 h under stirring, or react with a compound of general formula (I-d) under the action of an organolithium reagent for 30 min to 8 h at −78° C. to −50° C., further alkylating the product thereof, and then removing R" therefrom to afford a compound of general formula (I); wherein R" is selected from, methyl, ethyl, benzyl, p-methoxybenzyl, triphenylmethyl, trimethylsilyl, or t-butyl (dimethyl)silyl; R, $R^4$, $R^5$ and n have the same definitions as those for the compound of general formula (I).

The present invention relates to a method for preparing a prodrug compound of general formula (A) according to the present invention, comprising:

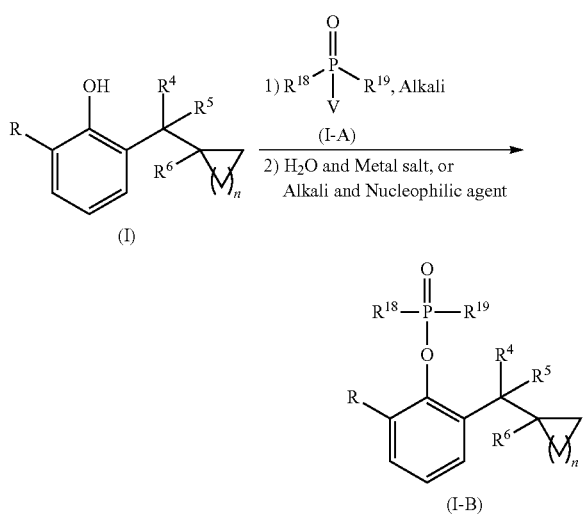

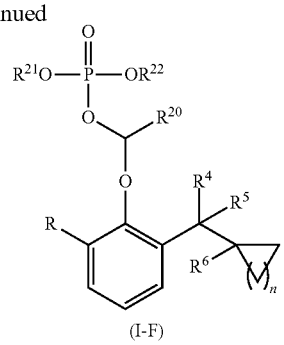

wherein allowing a compound of general formula (I) and a compound of general formula (I-A) to undergo nucleophilic substitution under the action of an alkali to directly afford a compound of general formula (I-B); or allowing a compound of general formula (I) and a compound of general formula (I-A) to undergo nucleophilic substitution under the action of an alkali to afford an intermediate for a compound of general formula (I-B), and subjecting the intermediate to hydrolysis and then to an exchange reaction with a metal salt to afford a compound of general formula (I-B); or allowing a compound of general formula (I) and a compound of general formula (I-A) to undergo nucleophilic substitution under the action of an alkali to afford an intermediate for a compound of general formula (I-B), and allowing the intermediate to further react with a nucleophilic reagent under the action of an alkali to afford a compound of general formula (I-B);

or,

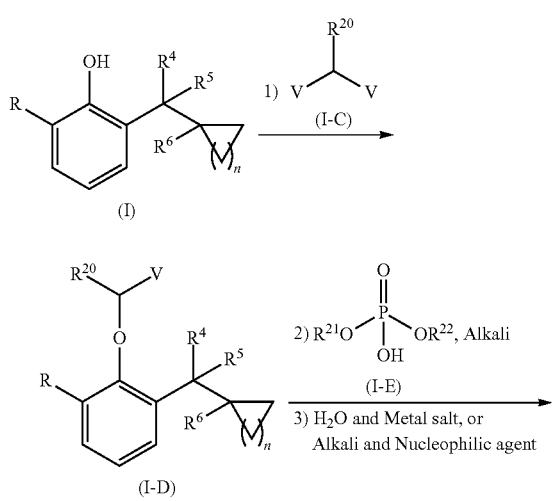

allowing a compound of general formula (I) and a compound of general formula (I-C) to undergo nucleophilic substitution to afford a compound of general formula (I-D); and then allowing the compound of general formula (I-D) and a compound of general formula (I-E) to undergo nucleophilic substitution under the action of an alkali to directly afford a compound of general formula (I-F); or allowing the compound of general formula (I-D) and a compound of general formula (I-E) to undergo nucleophilic substitution under the action of an alkali to afford an intermediate for a compound of general formula (I-F), and subjecting the intermediate to hydrolysis and then to an exchange reaction with a metal salt to afford a compound of general formula (I-F); or allowing the compound of general formula (I-D) and a compound of general formula (I-E) to undergo nucleophilic substitution under the action of an alkali to afford an intermediate for a compound of general formula (I-F), and allowing the intermediate to further react with an electrophilic reagent under the action of an alkali to afford a compound of general formula (I-F);

wherein, $R^{18}$ or $R^{19}$ is each independently selected from F, Cl, Br, I, $C_{1-10}$ alkyl or $C_{1-10}$ alkoxy, preferably F, Cl, Br, I, $C_{1-6}$ alkyl or $C_{1-6}$ alkoxy, and more preferably F, Cl, Br, I, $C_{1-4}$ alkyl or $C_{1-4}$ alkoxy;

$R^{20}$, $R^{21}$ and $R^{22}$ are each independently selected from H, F, Cl, Br, I or $C_{1-10}$ alkyl, preferably H, F, Cl, Br, I or $C_{1-6}$ alkyl, and more preferably H, F, Cl, Br, I or $C_{1-4}$ alkyl;

V is selected from F, Cl, Br, I; and n, R, $R^4$, $R^5$ and $R^6$ have the same definitions as those in general formula (I).

The present invention relates to a pharmaceutical composition, comprising: a compound of general formula (I) or (A), or any of a stereoisomer, a solvate, a metabolite, a pharmaceutically acceptable salt, a cocrystal, or a prodrug thereof; and one or more pharmaceutically acceptable vehicles and/or excipients.

The present invention relates to a usage of a compound of general formula (I) or (A), or any of a stereoisomer, a solvate, a metabolite, a pharmaceutically acceptable salt, a cocrystal, or a prodrug thereof, for the manufacture of a medicament for (i) inducing and maintaining anesthesia in an animal or a human, (ii) facilitating sedation and hypnosis of an animal or a human, or (iii) treating and/or preventing anxiety, depression, insomnia, nausea, vomiting, migraine, schizophrenia, convulsion, and epilepsy; preferably for inducing and maintaining anesthesia in an animal or a human.

DEFINITIONS

Unless otherwise indicated, all terms used throughout the Description and Claims have the following definitions.

All of the carbon, hydrogen, oxygen, sulfur, nitrogen or F, Cl, Br, I involved in the groups and compounds according to the present invention include their isotopes. All of the carbon, hydrogen, oxygen, sulfur, or nitrogen involved in the groups and compounds according to the present invention are optionally further replaced by one or more of their corresponding isotopes, wherein the carbon isotopes include $^{12}$C, $^{13}$C and $^{14}$C, the hydrogen isotopes include protium (H), deuterium (D, also known as heavy hydrogen) and tritium (T, also known as superheavy hydrogen), the oxygen isotopes include $^{16}$O, $^{17}$O and $^{18}$O, the sulfur isotopes include $^{32}$S, $^{33}$S, $^{34}$S and $^{36}$S, the nitrogen isotopes include $^{14}$N and $^{15}$N, the fluorine isotopes include $^{17}$F and $^{19}$F, the chlorine isotopes include $^{35}$Cl and $^{37}$Cl, and the bromine isotopes include $^{79}$Br and $^{81}$Br.

"Alkyl" means a linear or branched saturated aliphatic hydrocarbyl having 1 to 20 carbon atoms, preferably 1 to 8 carbon atoms, more preferably 1 to 6 carbon atoms, and even more preferably 1 to 4 carbon atoms. Non-limiting examples thereof include methyl, ethyl, n-propyl, isopropyl, n-butyl, sec-butyl, t-butyl, n-pentyl, isopentyl, neo-pentyl, n-hexyl, and various branched isomers thereof. The alkyl may optionally be further substituted with 0 to 5 substituents selected from F, Cl, Br, I, =O, hydroxyl, mercapto, —SR$^{18a}$, nitro, cyano, amino, alkylamino, an amide group, alkenyl, alkynyl, $C_{1-6}$ alkyl, $C_{1-6}$ hydroxyalkyl, $C_{1-6}$ alkoxy, a 3- to 8-membered carbocyclic group, a 3- to 8-membered heterocyclic group, (3- to 8-membered carbocyclyl)oxy, (3- to 8-membered heterocyclyl)oxy, carboxyl, or a carboxylic ester group; wherein R$^{18a}$ is selected from $C_{1-6}$ alkyl, a 3- to 8-membered carbocyclic group, or a 3- to 8-membered heterocyclic group. This definition applies to the alkyls used throughout this Description.

"Alkoxy" means —O-alkyl. Non-limiting examples thereof include methoxy, ethoxy, n-propoxy, isopropoxy, n-butoxy, sec-butoxy, t-butoxy, n-pentyloxy, n-hexyloxy, cyclopropoxy, and cyclobutoxy. The alkyl may optionally be further substituted with 0 to 5 substituents selected from F, Cl, Br, I, =O, hydroxyl, mercapto, —SR$^{18a}$, nitro, cyano, amino, alkylamino, an amide group, alkenyl, alkynyl, alkyl, hydroxyalkyl, alkoxy, a carbocyclic group, a heterocyclic group, carbocyclyloxy, heterocyclyloxy, carboxyl, or a carboxylic ester group; wherein R$^{18a}$ is defined as above. This definition applies to the alkoxys used throughout this Description.

"PEG" refers to a polymer containing

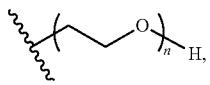

wherein n is an integer of 2 to about 1000, preferably 2 to about 500, more preferably 2 to about 250, more preferably 2 to about 125, even more preferably 2 to about 25.

"Amino" means —NH$_2$.

"Alkylamino" means an amino substituted with one or two alkyls.

"Cyano" means

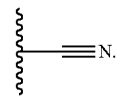 [SMILES: *C#N]

"Nitro" means —NO$_2$.
"Hydroxyl" means —OH.
"Mercapto" means —SH.
"Carboxyl" means —COOH.
"Carbonyl" means —(C=O)—.

A "carboxylic ester group" means —COOR$^{19a}$, wherein R$^{19a}$ is $C_{1-6}$ alkyl.

An "amide group" means —CONR$^{20a}$R$^{21a}$, wherein R$^{20a}$ and R$^{21a}$ are each independently selected from H, alkyl or a carbocyclic group, and R$^{20a}$ and R$^{21a}$ may optionally be further substituted with 0 to 3 substituents selected from F, Cl, Br, I, hydroxyl, mercapto, —SR$^{18a}$, nitro, cyano, amino, alkylamino, an amide group, alkenyl, alkynyl, alkyl, hydroxyalkyl, alkoxy, a carbocyclic group, a heterocyclic group, carbocyclyloxy, heterocyclyloxy, carboxyl, or a carboxylic ester group, wherein R$^{18a}$ is defined as above.

"=O" is a conventional expression used in the art to refer to an oxygen atom linked via a double bond, for example, the double-bonded oxygen atom linked to the carbon atom in carbonyl.

"Hydroxyalkyl" refers to an alkyl substituted with 1, 2 or 3 hydroxyls, wherein the alkyl is preferably $C_{1-4}$ alkyl. Non-limiting examples thereof include hydroxymethyl, 1-hydroxyethyl, 2-hydroxyethyl, 1,2-dihydroxypropyl, 1,3-dihydroxypropyl and 2,3-dihydroxypropyl.

"Alkenyl" means a linear or branched unsaturated aliphatic hydrocarbyl having 1 to 3 carbon-carbon double bonds, and comprising 2 to 20 carbon atoms, preferably 2 to 12 carbon atoms, more preferably 2 to 8 carbon atoms. Non-limiting examples thereof include vinyl, propen-2-yl, buten-2-yl, buten-2-yl, penten-2-yl, penten-4-yl, hexen-2-yl, hexen-3-yl, hepten-2-yl, hepten-3-yl, hepten-4-yl, octen-3-yl, nonen-3-yl, decen-4-yl and hendecen-3-yl. The alkenyl may optionally be further substituted with 0 to 4 substituents selected from F, Cl, Br, I, alkyl, alkoxy, linear alkenyl, linear alkynyl, amino, nitro, cyano, mercapto, an amide group, a carbocyclic group, or a heterocyclic group.

"Alkynyl" means a linear or branched unsaturated aliphatic hydrocarbyl having 1 to 3 carbon-carbon triple bonds, and comprising 2 to 20 carbon atoms, preferably 2 to 12 carbon atoms, more preferably 2 to 8 carbon atoms. Non-limiting examples thereof include ethynyl, propyn-1-yl, propyn-2-yl, butyn-1-yl, butyn-2-yl, butyn-3-yl, 3,3-dimethyl-butyn-2-yl, pentyn-1-yl, pentyn-2-yl, hexyn-1-yl, heptyn-1-yl, heptyn-3-yl, heptyn-4-yl, octyn-3-yl, nonyn-3-yl, decyn-4-yl, hendecyn-3-yl or dodecyn-4-yl. The alkynyl may optionally be further substituted with 0 to 4 substituents selected from F, Cl, Br, I, alkyl, alkoxy, linear alkenyl, linear alkynyl, amino, nitro, cyano, mercapto, an amide group, a carbocyclic group, or a heterocyclic group.

A "carbocyclic group" means a saturated or unsaturated aromatic or non-aromatic ring, and the aromatic or non-aromatic ring may be a 3- to 8-membered monocyclic, a 4- to 12-membered bicyclic or a 10- to 15-membered tricyclic system. The carbocyclic group may have attached bridge rings or spiral rings. Non-limiting examples thereof include cyclopropyl, cyclobutyl, cyclopentyl, cyclohexyl, cycloheptyl, cyclooctyl, cyclodecyl and cyclododecyl, cyclohexenyl,

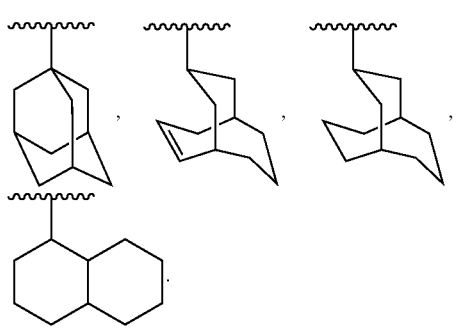

The carbocyclic group may optionally be further substituted with 0 to 8 substituents selected from F, Cl, Br, I, =O, hydroxyl, mercapto, —$SR^{18a}$, nitro, cyano, amino, alkylamino, an amide group, alkenyl, alkynyl, alkyl, hydroxyalkyl, alkoxy, a carbocyclic group, a heterocyclic group, carbocyclyloxy, heterocyclyloxy, carboxyl, or a carboxylic ester group, wherein $R^{18a}$ is defined as above. This definition applies to the carbocyclic groups used throughout this Description.

A "heterocyclic group" means a substituted or unsubstituted, saturated or unsaturated, aromatic or non-aromatic ring, and the aromatic or non-aromatic ring may be a 3- to 8-membered monocyclic, a 4- to 12-membered bicyclic or a 10- to 15-membered tricyclic system, and contains 1 to 3 heteroatoms selected from N, O or S. A 3- to 8-membered heterocyclic group is preferred. The optionally substituted N or S on the ring of a heterocyclic group may be oxidized into various oxidation states. The carbocyclic group may be attached via a heteroatom or a carbon atom, and may have attached bridge rings or spiral rings. Non-limiting examples thereof include epoxyethyl, azacyclopropyl, oxzcyclobutyl, azacyclobutyl, 1,3-dioxolane, 1,4-dioxolane, 1,3-dioxane, azacycloheptyl, pyridinyl, furyl, thiophenyl, pyranyl, N-alkylpyrrolyl, pyrimidinyl, pyrazinyl, pyridazinyl, imidazolyl, piperidinyl, hexahydropyridinyl, morpholinyl, thiomorpholinyl, 1,3-dithia-, dihydrofuryl, dihydropyranyl, dithiacyclopentyl, tetrahydrofuryl, tetrahydropyrrolyl, tetrahydroimidazolyl, tetrahydrothiazolyl, tetrahydropyranyl, benzimidazolyl, benzopyridinyl, pyrrolopyridinyl, benzodihydrofuryl, azabicyclo[3.2.1]octyl, azabicyclo[5.2.0]nonyl, azatricyclo[5.3.1.1]dodecyl, aza-adamantanyl, and oxaspiro [3.3]heptyl. The heterocyclic group may optionally be further substituted with 0 to 5 substituents selected from F, Cl, Br, I, =O, hydroxyl, mercapto, —$SR^{18a}$, nitro, cyano, amino, alkylamino, an amide group, alkenyl, alkynyl, alkyl, hydroxyalkyl, alkoxy, a carbocyclic group, a heterocyclic group, carbocyclyloxy, heterocyclyloxy, carboxyl, or a carboxylic ester group, wherein $R^{18a}$ is defined as above. This definition applies to the heterocyclic groups used throughout this Description.

A "pharmaceutically acceptable salt" or "pharmaceutically acceptable salt thereof" refers to a salt obtained by reaction between a free acid form of the compound of the present invention and a nontoxic inorganic or organic base, or by reaction between a free base form of the compound of the present invention and a nontoxic inorganic or organic acid, wherein the bioavailability and characteristics of the free acid or free base form of the compound of the present invention is retained. Non-limiting examples of the inorganic base include Al, Ca, Li, Mg, K, Na and Zn. Non-limiting examples of the organic base include ammonia, isopropylamine, trimethylamine, diethylamine, triethylamine, tripropylamine, tetramethylamine, diethanolamine, ethanolamine, dimethylethanolamine, 2-dimethylaminoethanol, 2-diethylaminoethanol, dicyclohexylamine, caffeine, procaine, choline, betaine, benethamine penicillin, ethylenediamine, glucosamine, N-methylmethylglucosamine, theobromine, triethanolamine, trometamol, purine, piperazine, piperidine, N-ethylpiperidine and polyamine resin. Non-limiting examples of the inorganic and organic acids include sulfuric acid, phosphoric acid, nitric acid, hydrobromic acid, hydrochloric acid, methanoic acid, acetic acid, propionic acid, benzenesulfonic acid, benzoic acid, phenylacetic acid, salicylic acid, alginic acid, anthranilic acid, camphoric acid, citric acid, vinylsulfonic acid, formic acid, fumaric acid, pyromucic acid, gluconic acid, glucuronic acid, glutamic acid, glycolic acid, hydroxyethylsulfonic acid, lactic acid, maleic acid, malic acid, mandelic acid, mucic acid, dihydroxylnaphthoic acid, pantothenic acid, stearic acid, succinic acid, sulfanilic acid, tartaric acid, p-toluenesulfonic acid, malonic acid, 2-hydroxylpropionic acid, oxalic acid, glycolic acid, glucuronic acid, galacturonic acid, citric acid, lysine, arginine, aspartate, cinnamic acid, p-toluenesulfonic acid, methanesulfonic acid, ethanesulfonic acid and trifluoromethanesulfonic acid.

A "pharmaceutical composition" refers to a mixture formed by one or more compounds according to the present invention or a pharmaceutically acceptable salt or prodrug thereof and additional chemical components, wherein the "additional chemical components" refer to pharmaceutically acceptable carriers, excipients and/or one or more other therapeutic agents.

"Carrier" means a material that does not cause significant stimulation to an organism and does not eliminate the biological activity and characteristics of a given compound.

"Excipient" means an inert substance added into a pharmaceutical composition to facilitate administration of a compound. Non-limiting examples thereof include calcium carbonate, calcium phosphate, sugar, starch, cellulose derivatives (including microcrystalline cellulose), gelatin, vegetable oils, polyethylene glycols, diluent, a granulating agent, lubricant, binder and disintegrant.

A "prodrug" means a compound that can be converted upon in vivo metabolism into the biologically active compound of the present invention. A prodrug of the present invention is prepared by modification of the phenol group of the compound of the present invention. Such a modification can be removed in vivo or by conventional operations, so as to afford the parent compound. When a prodrug of the present invention is administered to a mammalian individual, it is cleaved to expose a free hydroxyl.

A "cocrystal" refers to a crystal formed by an active pharmaceutical ingredient (API) and a cocrystal former (CCF) combined via hydrogen bonds or other non-covalent bonds, wherein both API and CCF in their pure form are solid at room temperature and these components are present in a fixed stoichiometric ratio therebetween. A cocrystal is a multi-component crystal, including both a binary cocrystal formed by two neutral solids and a multiple cocrystal formed by a neutral solid and a salt or solvate. Non-limiting examples thereof include alanine, valine, leucine, isoleucine, proline, phenylalanine, tryptophan, methionine, glycine, serine, threonine, cysteine, tyrosine, asparagine, glutamine, lysine, arginine, histidine, aspartic acid, aspartate, or glutamic acid, pyroglutamic acid, sulfuric acid, phosphoric acid, nitric acid, hydrobromic acid, hydrochloric acid, methanoic acid, acetic acid, propionic acid, benzenesulfonic acid, benzoic acid, phenylacetic acid, salicylic acid, alginic acid, anthranilic acid, camphoric acid, citric acid, vinylsulfonic acid, formic acid, fumaric acid, pyromucic acid, gluconic acid, glucuronic acid, glutamic acid, glycolic acid, hydroxyethylsulfonic acid, lactic acid, maleic acid, malic acid, mandelic acid, mucic acid, dihydroxylnaphthoic acid, pantothenic acid, stearic acid, succinic acid, sulfanilic acid, tartaric acid, p-toluenesulfonic acid, malonic acid, 2-hydroxylpropionic acid, oxalic acid, glycolic acid, glucuronic acid, galacturonic acid, citric acid, cinnamic acid, p-toluenesulfonic acid, methanesulfonic acid, ethanesulfonic acid or trifluoromethanesulfonic acid, ammonia, isopropylamine, trimethylamine, diethylamine, triethylamine, tripropylamine, diethanolamine, ethanolamine, dimethylethanolamine, 2-dimethylaminoethanol, 2-diethylaminoethanol, dicyclohexylamine, caffeine, procaine, choline, betaine, benethamine penicillin, ethylenediamine, glucosamine, methylglucosamine, theobromine, triethanolamine, trometamol, purine, piperazine, piperidine, and N-ethylpiperidine.

"Animals" include mammals, for example a human, companion animals, zoo animals and domestic animals, preferably a human, horse or dog.

A "stereoisomer" refers to an isomer of a molecule having its atoms in a different spatial arrangement, including cis-trans-isomer, enantiomer, and conformer.

The term "optional" or "optionally" means the event or situation modified by this term may but does not certainly happen, including both the case where the event or situation happens and the case not. For example, "a heterocyclic group optionally substituted with alkyl" means that the alkyl may be present but is not necessarily present, including both the case where the heterocyclic group is substituted with alkyl and the case where the heterocyclic group is not substituted with alkyl.

$ED_{50}$ (median effective dose): dose required to cause 50% of mice to lose their righting reflex in a test.

$ED_{95}$ (95% effective dose): dose required to cause 95% of mice to lose their righting reflex in a test.

$LD_{50}$ (median lethal dose): dose required to cause 50% of mice to die in a test.

$LD_5$ (5% lethal dose): dose required to cause 5% of mice to die in a test.

Anesthesia induction time and anesthesia maintenance time: time recording was started from drug administration, and general symptoms and changes in administration sites and respiration of animals were closely observed. If a normal animal was able to immediately turn its body to normal upright position after being pushed over or made lying on its back, such a reflex was determined as the righting reflex. Otherwise, loss of the righting reflex and the time of loss were recorded, and a reflex recovery time was recorded when the animal restored the righting reflex. The period from finishing of drug administration until loss of the righting reflex was recorded as the anesthesia induction time, and the period from loss of the righting reflex until recovery of the righting reflex was recorded as the anesthesia maintenance time.

TI (therapeutic index, i.e. $LD_{50}/ED_{50}$), SI (safety index, i.e. $LD_5/ED_{95}$).

MTD (maximum tolerated dose): the maximum dose able to cause 100% to loss the righting index without death.

Synthesis Methods for the Compound of the Present Invention

In order to carry out the present invention, the following technical solution is adopted in the present invention:

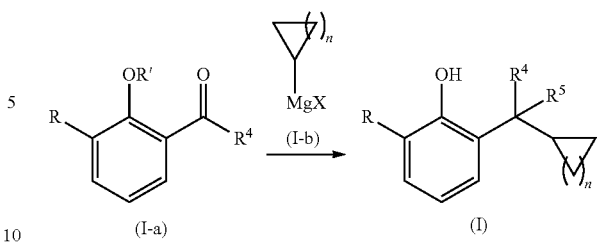

conducting a Grignard reaction between a compound of general formula (I-a) and a compound of general formula (I-b) in a solvent of tetrahydrofuran, toluene, ethyl ether, or methyl t-butyl ether at −4° C. to 35° C. under $N_2$ protection, and allowing the reaction to proceed for 2 to 20 h under stirring, to afford a compound of general formula (I);

or conducting a Grignard reaction between a compound of general formula (I-a) and a compound of general formula (I-b) in a solvent of tetrahydrofuran, toluene, ethyl ether, or methyl t-butyl ether at −4° C. to 35° C. under $N_2$ protection, allowing the reaction to proceed for 2 to 20 h under stirring, and further removing the protecting group (R') for the phenolic hydroxyl to afford a compound of general formula (I), wherein the de-protecting agent is selected from Pd/C, palladium hydroxide, Raney Ni, trifluoroacetic acid, hydrochloric acid, tetrabutylammonium fluoride, aluminum trifluoride, aluminum trichloride or boron trifluoride;

or conducting a Grignard reaction between a compound of general formula (I-a) and a compound of general formula (I-b) in a solvent of tetrahydrofuran, toluene, ethyl ether, or methyl t-butyl ether at −4° C. to 35° C. under $N_2$ protection, allowing the reaction to proceed for 2 to 20 h under stirring, and removing hydroxyl from the product of the reaction under a reducing condition, to afford a compound of general formula (I);

or conducting a Grignard reaction between a compound of general formula (I-a) and a compound of general formula (I-b) in a solvent of tetrahydrofuran, toluene, ethyl ether, or methyl t-butyl ether at −4° C. to 35° C. under $N_2$ protection, allowing the reaction to proceed for 2 to 20 h under stirring, removing the protecting group (R') for the phenolic hydroxyl, and further removing hydroxyl therefrom under a reducing condition, to afford a compound of general formula (I), wherein the reducing condition is selected from triethylsilane/trifluoroacetic acid, Pd/C, trimethylsilane chloride/sodium iodide, or carbon disulfide/sodium hydride;

X is selected from F, Cl, Br or I; R, $R^4$, $R^5$ and n have the same definitions as those for the compound of general formula (I); and R' is defined as above;

or,

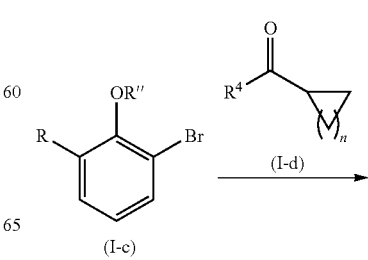

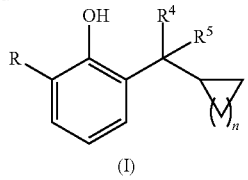

(I)

allowing a compound of general formula (I-c) to react with Mg in a solvent of tetrahydrofuran, toluene, ethyl ether, or methyl t-butyl ether at −4° C. to 35° C. under $N_2$ protection to produce a Grignard reagent, allowing the Grignard reagent and a compound of general formula (I-d) to undergo a Grignard reaction for 2 to 20 h under stirring, and then removing the protecting group (R″) for the phenolic hydroxyl to afford a compound of general formula (I), wherein the de-protecting agent is as described above;
or
allowing a compound of general formula (I-c) to react with a compound of general formula (I-d) for 30 min to 8 h under the action of an organolithium reagent in a solvent of tetrahydrofuran, toluene, ethyl ether, or methyl t-butyl ether at −78° C. to −50° C. under $N_2$ protection, and then removing the protecting group (R″) for the phenolic hydroxyl to afford a compound of general formula (I), wherein the organolithium reagent is selected from n-butyllithium, t-butyllithium, phenyllithium; diisopropylaminolithium or lithium hexamethyldisilylamide, and the de-protecting agent is as described above;
or
allowing a compound of general formula (I-c) to react with a compound of general formula (I-d) for 30 min to 8 h under the action of an organolithium reagent in a solvent of tetrahydrofuran, toluene, ethyl ether, or methyl t-butyl ether at −78° C. to −50° C. under $N_2$ protection, then removing the protecting group (R″) for the phenolic hydroxyl, and further removing hydroxyl therefrom under a reducing condition, to afford a compound of general formula (I); wherein the reducing condition includes triethylsilane/trifluoroacetic acid, Pd/C, trimethylsilane chloride/sodium iodide, or carbon disulfide/sodium hydride, and the organolithium reagent, the reducing agent, and the de-protecting agent are as described above;
or
allowing a compound of general formula (I-c) and a compound of general formula (I-d) to undergo a Grignard reaction for 2 to 20 h under stirring in a solvent of tetrahydrofuran, toluene, ethyl ether, or methyl t-butyl ether at −4° C. to 35° C. under $N_2$ protection, then to react with an alkylating agent, and further removing the protecting group (R″) for the phenolic hydroxyl to afford a compound of general formula (I); wherein the de-protecting agent is as described above;
or
allowing a compound of general formula (I-c) to react with a compound of general formula (I-d) for 30 min to 8 h under the action of an organolithium reagent at −78° C. to −50° C., allowing the product thereof to further react with an alkylating agent in the presence of sodium hydride or potassium t-butoxide, and then removing the protecting group (R″) for the phenolic hydroxyl therefrom to afford a compound of general formula (I); wherein the alkylating agent is selected from iodomethane, methyl p-toluenesulfonate, dimethyl sulfate, bromoethane, ethyl p-toluenesulfonate or diethyl sulfate, and the organolithium reagent, the reducing agent, and the de-protecting agent are as described above;

wherein R, $R^4$, $R^5$ and n have the same definitions as those for the compound of general formula (I); and R″ is defined as above.

The present invention relates to a method for preparing a prodrug compound of general formula (A) according to the present invention, comprising:

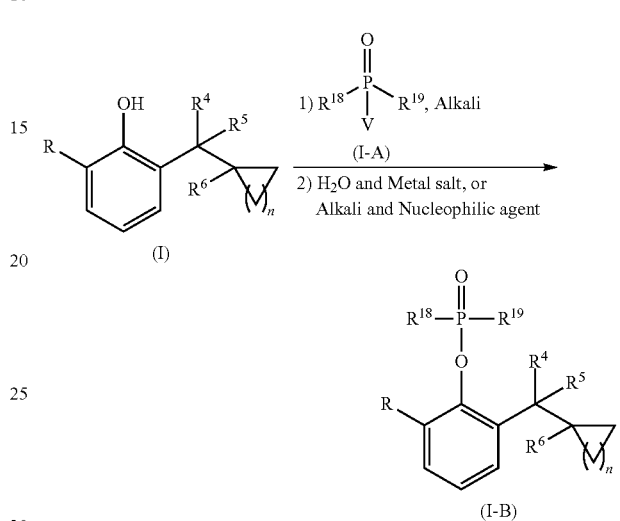

wherein, $R^{18}$ or $R^{19}$ is each independently selected from F, Cl, Br, I, $C_{1-10}$ alkyl or $C_{1-10}$ alkoxy; V is selected from F, Cl, Br, I; and n, R, $R^4$, $R^5$ and $R^6$ have the same definitions as those in general formula (I);

allowing a compound of general formula (I) and a compound of general formula (I-A) to undergo nucleophilic substitution under the action of an alkali to directly afford a compound of general formula (I-B); or allowing a compound of general formula (I) and a compound of general formula (I-A) to undergo nucleophilic substitution under the action of an alkali to afford an intermediate for a compound of general formula (I-B), and subjecting the intermediate to hydrolysis and then to an exchange reaction with a metal salt to afford a compound of general formula (I-B); or allowing a compound of general formula (I) and a compound of general formula (I-A) to undergo nucleophilic substitution under the action of an alkali to afford an intermediate for a compound of general formula (I-B), and allowing the intermediate to further react with a nucleophilic reagent under the action of an alkali to afford a compound of general formula (I-B);

in step 1) above, (I-b) is a halophosphoryl-based compound, wherein $R^{18}$ or $R^{19}$ is selected from F, Cl, Br, I, $C_{1-10}$ alkyl or $C_{1-10}$ alkoxy; the alkali includes inorganic or organic alkali, preferably triethylamine, diisopropylethylamine or sodium hydride; the reaction temperature selected is −80° C. to 150° C.; and the reaction duration is 5 min to 2 days;

in step 2) above, the metal salt is an organic or inorganic salt of metal, preferably an alkali metal salt or alkali earth metal salt; the alkali includes inorganic or organic alkali, preferably triethylamine, diisopropylethylamine or sodium hydride; the reaction temperature selected is −80° C. to 150° C.; and the reaction duration is 5 min to 2 days;

or,

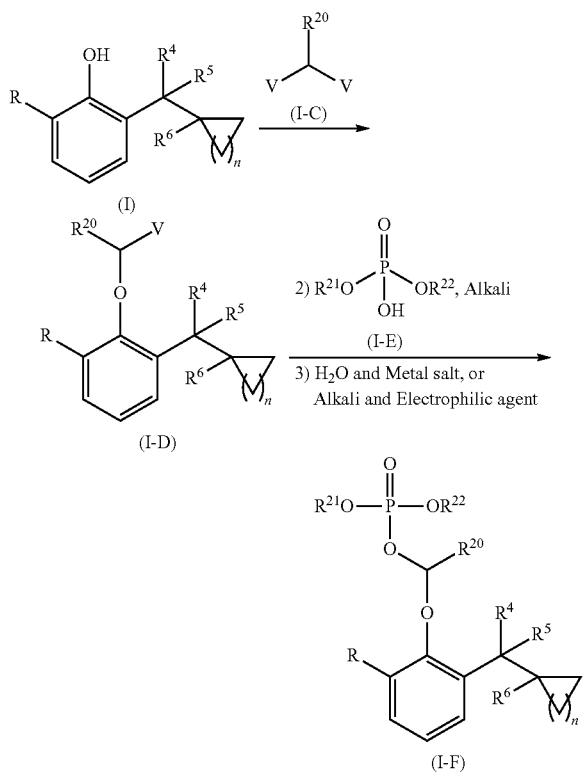

wherein, $R^{20}$, $R^{21}$ and $R^{22}$ are each independently selected from H, F, Cl, Br, I or $C_{1-10}$ alkyl; V is selected from F, Cl, Br, I; and n, R, $R^4$, $R^5$ and $R^6$ have the same definitions as those in general formula (I);

allowing a compound of general formula (I) and a compound of general formula (I-C) to undergo nucleophilic substitution to afford a compound of general formula (I-D); and then allowing the compound of general formula (I-D) and a compound of general formula (I-E) to undergo nucleophilic substitution under the action of an alkali to directly afford a compound of general formula (I-F); or allowing the compound of general formula (I-D) and a compound of general formula (I-E) to undergo nucleophilic substitution under the action of an alkali to afford an intermediate for a compound of general formula (I-F), and subjecting the intermediate to hydrolysis and then to an exchange reaction with a metal salt to afford a compound of general formula (I-F); or allowing the compound of general formula (I-D) and a compound of general formula (I-E) to undergo nucleophilic substitution under the action of an alkali to afford an intermediate for a compound of general formula (I-F), and allowing the intermediate to further react with an electrophilic reagent under the action of an alkali to afford a compound of general formula (I-F);

in step 1) above, (I-C) is preferably a compound double-substituted with a halogen, V is preferable F, Cl, Br, or I; the preferred reaction temperature is 0° C. to 150° C.; and the preferred reaction duration is 0.5 to 12 h;

in step 2) above, (I-E) is a phosphate-based compound, wherein $R^{21}$ and $R^{22}$ are preferably H, F, Cl, Br, I or $C_{1-10}$ alkyl; the alkali includes inorganic or organic alkali, preferably triethylamine, diisopropylethylamine or sodium hydride; the reaction temperature selected is −50° C. to 150° C.; and the reaction duration is 5 min to 2 days; in step 3) above, the metal salt is an organic or inorganic salt of metal, preferably an alkali metal salt or alkali earth metal salt; the alkali includes inorganic or organic alkali, preferably triethylamine, diisopropylethylamine or sodium hydride; the reaction temperature selected is −80° C. to 150° C.; and the reaction duration is 5 min to 2 days.

DETAILED EMBODIMENTS

Figure 1:
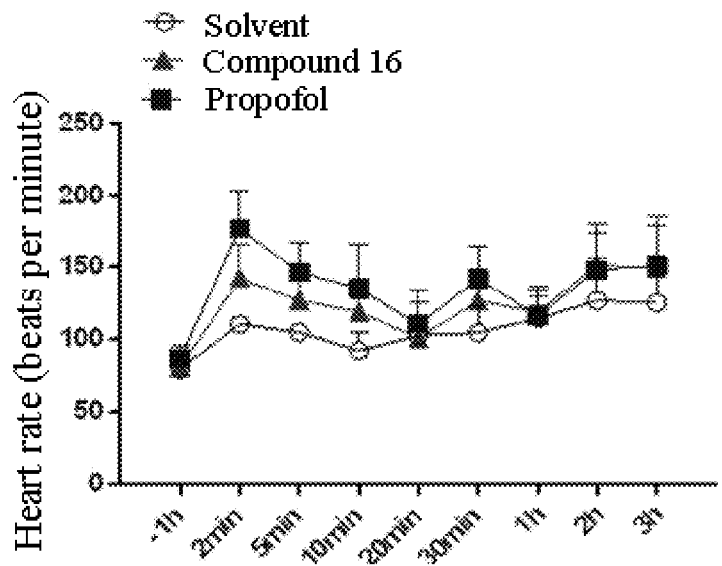
FIG. 1 is a schematic representation of the effects of intravenous administration of a emulsion for injection of test Compound 16 and propofol on the heart rate (bpm) of conscious Beagle dogs ($\overline{X}\pm SD$, n=4)

The technical solutions of the present invention will be described below in detail in conjunction with the Drawings and Examples. However, the scope of protection of the present invention includes but not limited to this.

Structures of compounds were determined by nuclear magnetic resonance (NMR) and/or mass spectrometry (MS). NMR shifts ($\delta$) are shown in the unit of $10^{-6}$ (ppm). For NMR measurement, NMR spectrometers (Bruker Avance III 400 and Bruker Avance 300) were used, deuterium-substituted dimethyl sulfoxide (DMSO-$d_6$), deuterium-substituted chloroform (CDCl$_3$) and deuterium-substituted methanol (CD$_3$OD) were used as solvents, and tetramethylsilane (TMS) was used as the internal standard.

For MS measurement, Agilent 6120B(ESI) and Agilent 6120B(APCI) were used.

For HPLC measurement, an Agilent 1260DA high pressure liquid phase chromatographer (Zorbax SB-C18 100× 4.6 mm, 3.5 μM) was used.

For the silica gel plate for thin-layer chromatography (TLC), HSGF254 (Yantai Yellow sea) or GF254 (Qingdao) silica gel plate was used. The silica gel plate for TLC had the specification of 0.15 mm to 0.20 mm, while TLC separation and purification used a specification of 0.4 mm to 0.5 mm.

For column chromatography, generally employed was a 200 to 300-mesh silica gel from Yantai Yellow sea silica gels as a carrier.

Known starting materials in connection with the present invention can be synthesized following or using methods known in the art, or can be purchased from companies such as Titansci, Energy Chemical, Demochem (Shanghai), Kelong Chemical (Chengdu), Accela ChemBio, and J&K Scientific.

A $N_2$ atmosphere means that the reaction vessel is connected to a $N_2$ balloon of about 1 L in volume.

A $H_2$ atmosphere means that the reaction vessel is connected to a $H_2$ balloon of about 1 L in volume.

Hydrogenation reactions generally involve a vacuuming and $H_2$-charging operation repeating 3 times.

In the Example, unless particularly specified, reactions were carried out under a $N_2$ atmosphere.

In the Example, unless particularly specified, solutions refer to aqueous solutions.

In the Example, unless particularly specified, reaction temperatures are room temperature, most suitable room temperature as a reaction temperature is 20° C. to 30° C.

Me: methyl;
Et: ethyl;
Bn: benzyl;
Bz, benzoyl;
DMSO: dimethyl sulfoxide;
Saline: physiological saline;
Soluto HS15: polyethylene glycol stearic acid 15;
RT: retention time of a peak.

Intermediate 1

2-(1-cyclopropyl-1-hydroxyethyl)phenol (1b)

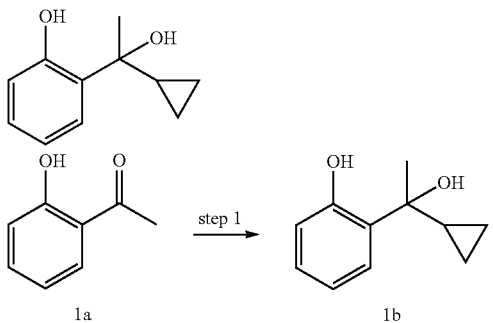

Under nitrogen atmosphere, tetrahydrofuran (200 mL) was stirred in 2-hydroxy acetophenone (1a) (15.00 g, 0.11 mol, Energy), added with a solution of cyclopropyl magnesium bromide in tetrahydrofuran (440 mL, 0.44 mol, 1M) dropwise slowly, stirred at room temperature for 3 h and quenched with a saturated aqueous ammonium chloride solution (50 mL) under ice-water bath. The mixture was extracted with dichloromethane (125 mL×2). The organic layers were combined, washed with saturated brine (100 mL×3), dried over anhydrous sodium sulfate, filtered and concentrated under vacuum. The residue was purified by silica gel column chromatography (hexane/ethyl acetate (v/v)=50:1) to obtain 2-(1-cyclopropyl-1-hydroxyethyl)phenol (1b) as a brown oil (18.10 g, yield: 92%).

MS m/z (ESI): 177.1 [M−1].

$^1$H NMR (400 MHz, CDCl$_3$): δ9.10 (s, 1H), 7.22-7.14 (m, 2H), 6.91-6.80 (m, 2H), 1.50 (s, 3H), 1.36-1.45 (m, 1H), 0.36-0.68 (m, 4H).

Example 1

2-bromo-6-(1-cyclopropyl-1-hydroxyethyl)phenol (Compound 1)

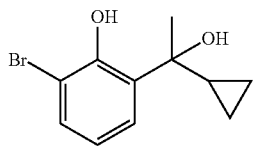

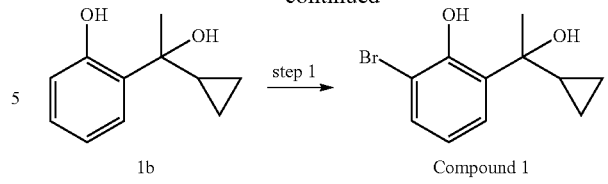

Step 1:
2-bromo-6-(1-cyclopropyl-1-hydroxyethyl)phenol (Compound 1)

2-(1-cyclopropyl-1-hydroxyethyl)phenol (1b) (12.72 g, 71.37 mmol, Intermediate 1), dichloromethane (125 mL) and diisopropylamine (0.73 g, 7.14 mmol) were added into reaction flask accordingly, cooled with ice-water bath, N-Bromosuccinimide (12.70 g, 71.37 mmol) was added and the mixture was stirred for 15 h under ice-water bath. The reaction mixture was washed with saturated brine (100 mL×3). The organic layer was dried over anhydrous sodium sulfate, filtered and concentrated under vacuum. The residue was purified by silica gel column chromatography (hexane/ethyl acetate (v/v)=50:1) to obtain 2-bromo-6-(1-cyclopropyl-1-hydroxyethyl)phenol (Compound 1) as a white solid (7.52 g, yield 41%, HPLC: 98.26%).

MS m/z (ESI): 254.9 [M−1], 257.9[M+1].

$^1$H NMR (400 MHz, CDCl$_3$): δ9.53 (s, 1H), 7.43 (dd, 1H), 7.20 (dd, 1H), 6.72 (t, 1H), 1.48 (s, 3H), 1.41-1.38 (m, 1H), 0.67 (m, 2H), 0.54-0.42 (m, 2H).

Example 2

2-bromo-6-(1-cyclopropylethyl)phenol (Compound 2)

Step 1: 2-bromo-6-(1-cyclopropylethyl)phenol (Compound 2)

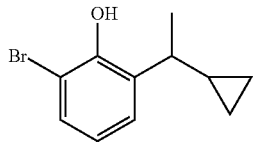

Under nitrogen atmosphere, 2-bromo-6-(1-cyclopropyl-1-hydroxyethyl)phenol (Compound 1) (0.25 g, 0.97 mmol), dichloromethane (200 mL) and triethylsilane (0.57 g, 4.86 mmol) were added into reaction flask in sequence. The mixture was cooled under ice-water bath. And trifluoroacetic acid (1.11 g, 9.72 mmol) was added dropwise. Then the mixture was stirred at room temperature for 15 h. The reaction mixture was washed with a saturated solution of sodium bicarbonate (30 mL×1), and saturated brine (30 mL×3). The organic layer was dried over anhydrous sodium sulfate, filtered and concentrated under vacuum. The residue was purified by silica gel column chromatography (hexane/ethyl acetate (v/v)=50:1) to give 2-bromo-6-(1-cyclopropylethyl)phenol (Compound 2) as a colorless oil (0.16 g, yield 69%, HPLC: 96.89%).

MS m/z (ESI): 240.9 [M−1], 241.9 [M+1].

$^1$H NMR (400 MHz, CDCl$_3$): δ 7.29 (dd, 1H), 7.25 (dd, 1H), 6.79 (t, 1H), 5.58 (s, 1H), 2.48-2.40 (m, 1H), 1.29 (d, 3H), 1.07-0.98 (m, 1H), 0.61-0.43 (m, 2H), 0.26-0.16 (m, 2H).

Example 3

2-(1-cyclopropylethyl)-6-isopropylphenol (Compound 3)

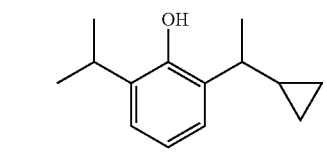

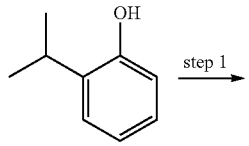

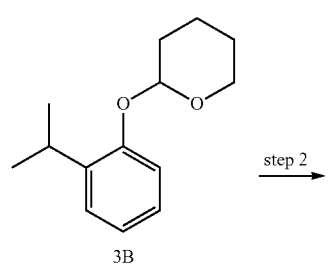

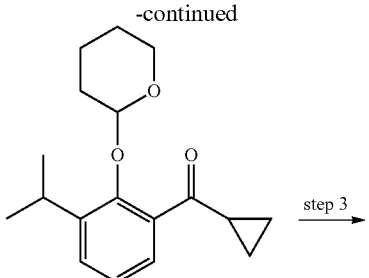

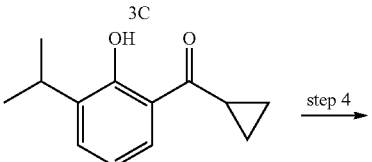

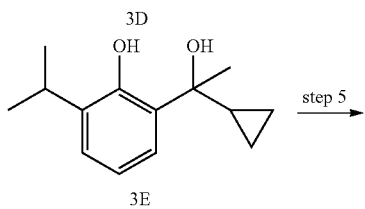

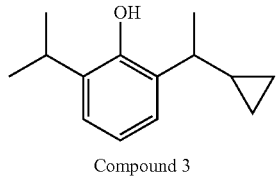

Compound 3

Step 1: 2-(2-isopropylphenoxy)tetrahydropyran (3B)

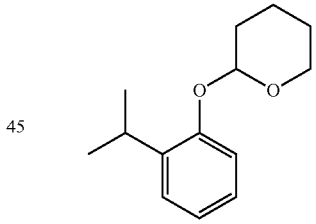

2-isopropylphenol (3A) (10.00 g, 73.40 mmol), 3,4-2H-dihydropyran and dichloromethane (50 mL) were added into reaction flask. After the mixture was stirred thoroughly, pyridinium p-toluenesulfonate (1.86 g, 7.40 mmol) was added, followed by an additional stirring at room temperature for 20 h. The reaction mixture was added with water (30 mL), extracted with dichloromethane (30 mL×3). The organic layers were combined, washed with brine (30 mL×3), dried over anhydrous sodium sulfate, filtered and concentrated under vacuum. The residue was purified by silica gel column chromatography (petroleum ether/ethyl acetate (v/v)=500:1) to obtain 2-(2-isopropylphenoxy)tetrahydropyran (3B) as a colorless oil (13.4 g, yield: 82.71%, HPLC: 99.15%).

$^1$HNMR (400 MHz, CDCl$_3$): δ7.25-7.20 (m, 1H), δ7.15-7.09 (m, 2H), δ6.97-6.93 (m, 1H), δ5.44-5.42 (m, 1H),

δ3.94-3.88 (m, 1H), δ3.65-3.62 (m, 1H), δ3.39-3.22 (m, 1H), δ1.90-1.86 (m, 1H), δ1.73-1.67 (m, 2H), δ1.60-1.54 (m, 3H), δ1.25 (2d, 6H).

Step 2: cyclopropyl-(3-isopropyl-2-tetrahydropyran-2-yloxy-phenyl)methanone (3C)

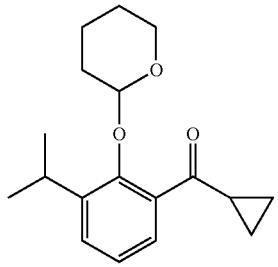 [SMILES: CC(C)c1cccc(C(=O)C2CC2)c1OC1CCCCO1]

Under nitrogen atmosphere, 2-(2-isopropylphenoxy)tetrahydropyran (3B) (10.00 g, 45.40 mmol) and dry tetrahydrofuran (30 mL) were added into reaction flask. The mixture was cooled to −20° C. with dry ice bath. 2.5M N-butyllithium (20.00 mL, 50.00 mmol) was added, followed by a stirring at room temperature for 1 h. N-methoxy-N-methyl cyproterone amide (7.00 g, 54.20 mmol) was added at −20° C. with dry ice bath, the mixture was stirred at room temperature for 2 h. The reaction mixture was quenched with a saturated aqueous solution of ammonium chloride (30 mL) under ice-water bath, extracted with ethyl acetate (30 mL×3). The organic layers were combined, washed with brine (30 mL×3), dried over anhydrous sodium sulfate, filtered and concentrated in vacuo to obtain cyclopropyl-(3-isopropyl-2-tetrahydropyran-2-yloxy-phenyl) methanone (3C) as a red liquid (17.4 g, crude product, HPLC: 68.00%), which was submitted to the next step without further purification.

Step 3: cyclopropyl-(2-hydroxy-3-isopropyl-phenyl)methanone (3D)

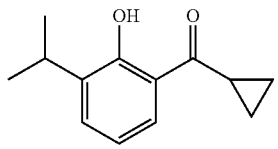

Cyclopropyl-(3-isopropyl-2-tetrahydropyran-2-yloxy-phenyl)methanone (3C) (17.4 g crude product) and methanol (50 ml) were added into reaction flask. The mixture was cooled to 0° C. under ice bath and a solution of hydrochloric acid (2M, 35 mL, 70.00 mmol) was added, followed by a stirring at room temperature for half an hour. The reaction mixture was treated with a saturated aqueous of sodium bicarbonate until pH=6, concentrated in vacuo, extracted with ethyl acetate (50 mL×3). The organic layers were combined, washed with brine (50 mL×3), dried over anhydrous sodium sulfate, filtered and the filtrate was concentrated in vacuo. The residue was purified by silica gel column chromatography (petroleum ether/ethyl acetate (v/v)=300:1) to afford cyclopropyl-(2-hydroxy-3-isopropyl-phenyl)methanone (3D) as a colorless liquid (7.23 g, the total yield of two steps: 78.26%, HPLC: 96.29%).

MS m/z (ESI): 205.1 (M−1).
¹HNMR (400 MHz, DMSO-$_{d6}$): δ12.98 (s, 1H), δ8.08 (dd, 1H), δ7.51 (dd, 1H), δ6.98 (t, 1H), δ3.34-3.26 (m, 1H), δ3.04-3.01 (m, 1H), δ1.19-1.12 (m, 10H).

Step 4: 2-(1-cyclopropyl-1-hydroxy-ethyl)-6-isopropyl-phenol (3E)

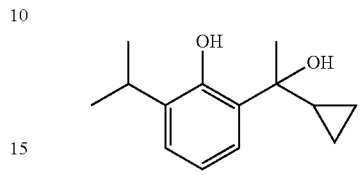

Cyclopropyl-(2-hydroxy-3-isopropyl-phenyl)methanone (3D) (10 g, 48.80 mmol) and dry toluene (50 mL) were added into reaction flask, under nitrogen atmosphere, the mixture was cooled to −30° C. under dry ice bath, a solution of methylmagnesium bromide in hexane (3M, 49.00 mL, 146.30 mmol) was added, followed by a stirring for 2 h at room temperature. The reaction was quenched with a saturated aqueous solution of ammonium chloride (100 mL), extracted with ethyl acetate (100 mL×3). The organic layers were combined, washed with saturated brine (100 mL×3), dried over anhydrous sodium sulfate, filtered and the filtrate was concentrated in vacuo. The residue was purified by column chromatography (petroleum ether/ethyl acetate (v/v)=50:1) to obtain 2-(1-cyclopropyl-1-hydroxy-ethyl)-6-isopropyl-phenol (3E) as a yellow liquid (10.2 g, yield: 95.17%, HPLC: 97.96%).

MS m/z (ESI): 219.1 (M−1).
¹HNMR (400 MHz, CDCl₃): δ7.32 (dd, 1H), δ7.24 (dd, 1H), δ7.13 (t, 1H), δ4.64 (s, 1H), δ3.43-3.36 (m, 1H), δ1.56 (s, 3H), δ1.37-1.31 (m, 1H), δ1.27 (d, 6H), δ0.54-0.39 (m, 4H).

Step 5: 2-(1-cyclopropylethyl)-6-isopropylphenol (Compound 3)

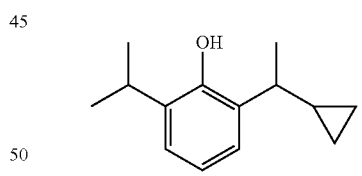

2-(1-cyclopropyl-1-hydroxy-ethyl)-6-isopropyl-phenol (3E) (3 g, 13.80 mmol), triethylsilane (6.42 g, 55.21 mmol) and dichloromethane (25 mL) were added into reaction flask, the mixture was cooled to 30° C. with dry ice bath, trifluoroacetic acid (12.59 g, 110.40 mmol) was added slowly, followed by a stirring for 2 h with temperature below 0° C. The mixture was extracted with dichloromethane (100 mL×3).

The organic layers were combined, washed with brine (100 mL×3), dried over anhydrous sodium sulfate, filtered and concentrated in vacuo. The residue was purified by silica gel column chromatography (petroleum ether/ethyl acetate (v/v)=100:1) to afford 2-(1-cyclopropylethyl)-6-isopropyl-phenol (Compound 3) as a colorless liquid (2.02 g, yield: 71.63%, HPLC: 98.58%).

MS m/z (ESI): 203.1 (M−1).

¹HNMR (400 MHz, CDCl₃): δ 7.13 (dd, 1H), δ 7.08 (dd, 1H), δ4.93 (s, 1H), δ 3.20-3.13 (m, 1H), δ 2.53-2.46 (m, 1H), δ 1.29 (d, 3H), δ 1.26 (d, 6H), δ 1.07-1.05 (m, 1H), δ 0.58-0.45 (m, 2H), δ 0.24-0.16 (m, 2H).

Example 4

2-sec-butyl-6-(1-cyclopropylethyl)phenol
(Compound 4)

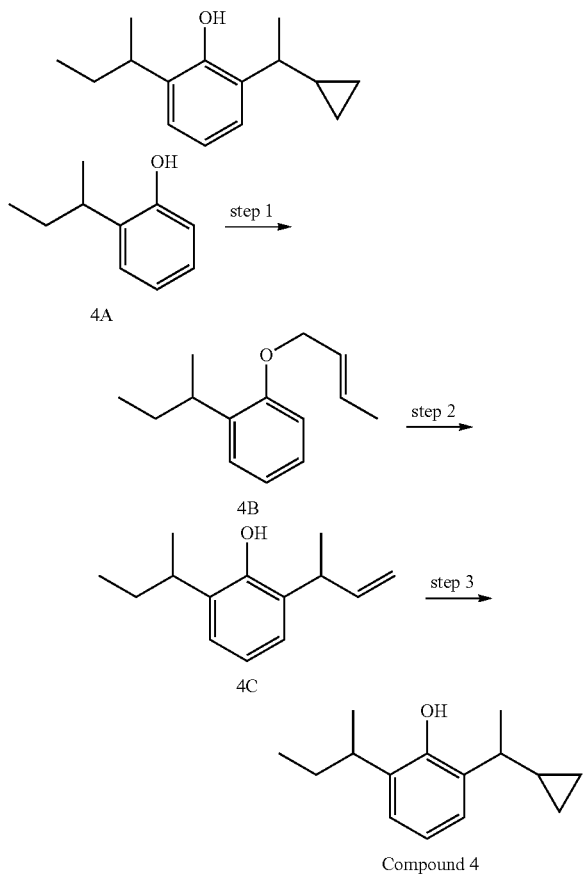

Step 1: 1-(but-2-enyloxy)-2-sec-butylbenzene (4B)

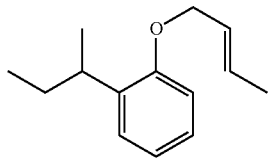

2-sec-butylphenol (4A) (20.00 g, 0.13 mol), anhydrous diethyl ether (100 mL), crotonyl alcohol (14.42 g, 0.20 mol) and triphenyl phosphine (52.46 g, 0.20 mol) were added into reaction flask in sequence, diisopropyl azodicarboxylate (40.44 g, 0.20 mol) was added dropwise slowly under ice bath, and then the mixture was stirred at room temperature overnight. The reaction mixture was filtered and concentrated in vacuo. The residue was purified by silica gel column chromatography (hexane/ethyl acetate (v/v)=300:1) to obtain 1-(but-2-enyloxy)-2-sec-butylbenzene (4B) as a light yellow oil (20.40 g, yield: 76.8%).

MS m/z (ESI): 205.1 [M+1].

¹H NMR (300 MHz, CDCl₃): δ 7.16 (dd, 1H), 7.11 (dd, 1H), 6.94-6.90 (m, 1H), 6.84 (d, 1H), 5.90-5.69 (m, 2H), 4.44 (t, 2H), 3.15-3.00 (m, 1H), 1.75 (dd, 3H), 1.68-1.50 (m, 2H), 1.17 (d, 3H), 0.85 (t, 3H).

Step 2: 2-(but-3-en-2-yl)-6-sec-butylphenol (4C)

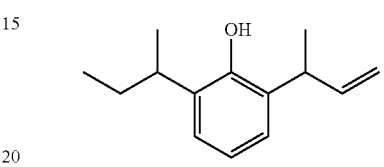

To the reaction flask, 1-(but-2-enyloxy)-2-sec-butylbenzene (4B) (10.00 g, 0.05 mol) was added, stirred at 200° C. for 4 h. The reaction mixture was purified by column chromatography (hexane) to afford 2-(but-3-en-2-yl)-6-sec-butylphenol (4C) as a light yellow oil (1.74 g, yield 17.4%, HPLC: 96.50%).

MS m/z (ESI): 203.1 [M−1].

¹H NMR (400 MHz, CDCl₃): δ7.06 (dd, 1H), 6.99 (dd, 1H), 6.89 (t, 1H), 6.14-6.02 (m, 1H), 5.30-5.16 (m, 3H), 3.70-3.57 (m, 1H), 3.05-2.92 (m, 1H), 1.72-1.50 (m, 2H), 1.42 (d, 3H), 1.22 (d, 3H), 0.87 (t, 3H).

Step 3: 2-sec-butyl-6-(1-cyclopropylethyl)phenol
(Compound 4)

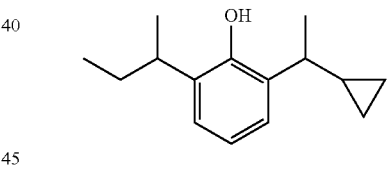

Under nitrogen atmosphere, dichloromethane (10 mL) was added into reaction flask, diethylzinc (1.21 g, 9.80 mmol) and trifluoroacetic acid (1.12 g, 9.80 mmol) were slowly added dropwise under ice bath, the mixture was stirred for 30 minutes. Methylene iodide (2.63 g, 9.80 mmol) was added with ice bath and stirred for 30 min. Added 2-(but-3-en-2-yl)-6-sec-butylphenol (4C) (1.00 g, 4.90 mmol), stirred for 4 h at room temperature. The reaction mixture was quenched with a solution of hydrochloric acid (1M, 30 mL), extracted with dichloromethane (30 mL×2), and the organic layers were combined, washed with brine (30 mL×3). dried over anhydrous sodium sulfate, filtered and concentrated in vacuo. The residue was purified by silica gel column chromatography (hexane) to obtain 2-sec-butyl-6-(1-cyclopropylethyl)phenol (Compound 4) as a light yellow oil (0.60 g, yield: 56.6%, HPLC: 96.87%).

MS m/z (ESI): 217.1 [M−1].

¹H NMR (400 MHz, CDCl₃): δ7.14-7.08 (m, 1H), 7.02 (dd, 1H), 6.89 (t, 1H), 2.97-2.84 (m, 1H), 2.57-2.44 (m, 1H), 1.74-1.51 (m, 2H), 1.30 (d, 3H), 1.24 (d, 3H), 1.10-1.00 (m, 1H), 0.89 (t, 3H), 0.62-0.40 (m, 2H), 0.27-0.10 (m, 2H).

Example 5

2-cyclopropyl-6-(1-cyclopropylethyl)phenol (Compound 5)

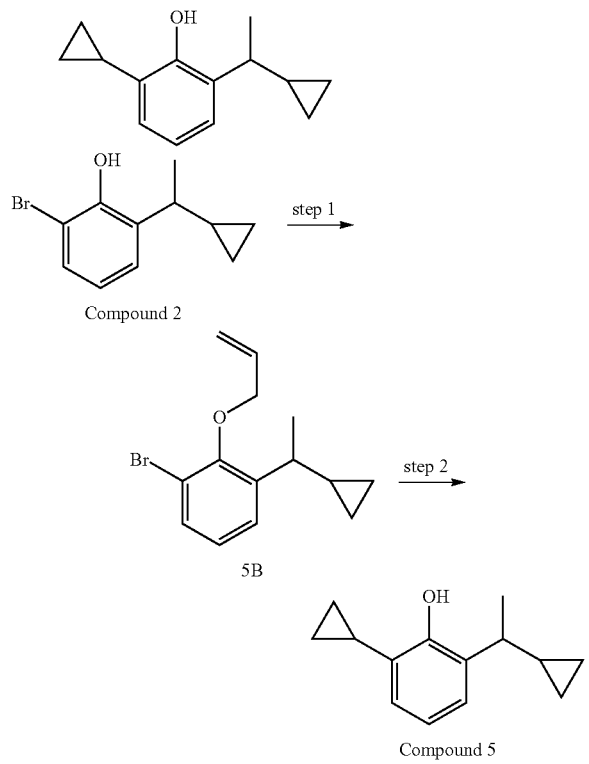

Step 1: 2-(allyloxy)-1-bromo-3-(1-cyclopropylethyl)benzene (5B)

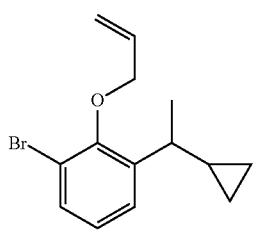 [SMILES: C=CCOc1c(Br)cccc1C(C)C1CC1]

2-bromo-6-(1-cyclopropylethyl)phenol (Compound 2) (10.00 g, 41.47 mmol), potassium carbonate (11.46 g, 82.94 mmol) and acetonitrile (100 mL) were added into reaction flask accordingly, the mixture was heated to 40° C. and stirred for 30 minutes. Allyl bromide (34.20 g, 300 mmol) was added and stirred at 40° C. for 20 h. The reaction mixture was cooled to room temperature and filtered, the filtrate was concentrated in vacuo. The residue was purified by silica gel column chromatography (petroleum ether) to afford 2-(allyloxy)-1-bromo-3-(1-cyclopropylethyl)benzene (5B) as a colorless oil (10.50 g, yield: 90.0%).

$^1$H NMR (300 MHz, CDCl$_3$): δ 7.41 (dd, 1H), 7.33 (dd, 1H), 7.00 (t, 1H), 6.15-6.07 (m, 1H), 5.46-5.27 (m, 2H), 4.45-4.41 (m, 2H), 2.52-2.44 (m, 1H), 1.29 (d, 3H), 1.01-0.95 (m, 1H), 0.59-0.38 (m, 2H), 0.25-0.12 (m, 2H).

Step 2: 2-cyclopropyl-6-(1-cyclopropylethyl)phenol (Compound 5)

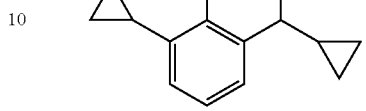

2-(allyloxy)-1-bromo-3-(1-cyclopropylethyl)benzene (5B) (10.00 g, 35.81 mmol) and anhydrous diethyl ether (200 mL) were added into reaction flask under nitrogen atmosphere. The mixture was stirred thoroughly. N-butyllithium (30 mL, 2.5M) was added slowly under a temperature of −75° C. with dry ice bath, and stirred at −75° C. for 1 h. N,N,N',N'-tetramethylethylenediamine (9.57 g, 82.37 mmol) was added slowly and stirred at room temperature for 10 h. The reaction was stopped with a saturated solution of ammonium chloride (100 mL). The reaction mixture was extracted with ethyl acetate (200 mL×2), washed with brine (200 mL×2), dried over anhydrous sodium sulfate, and filtered. The filtrate was concentrated in vacuo. The residue was purified by silica gel column chromatography (petroleum ether) to obtain 2-cyclopropyl-6-(1-cyclopropylethyl)phenol (Compound 5) as a yellow oil (480 mg, yield: 6.6%, HPLC: 99%).

MS m/z (ESI): 201.1 [M−1].

$^1$H NMR (300 MHz, CDCl$_3$): δ 7.19 (dd, 1H), 6.98 (dd, 1H), 6.84 (t, 1H), 5.60 (s, 1H), 2.51-2.43 (m, 1H), 1.77-1.74 (m, 1H), 1.31 (d, 3H), 1.12-0.98 (m, 1H), 0.98-0.95 (m, 2H), 0.67-0.63 (m, 2H), 0.63-0.39 (m, 2H), 0.24-0.16 (m, 2H).

Example 6

2-(1-cyclopropylethyl)-6-(1-methylcyclopropyl)phenol (Compound 6)

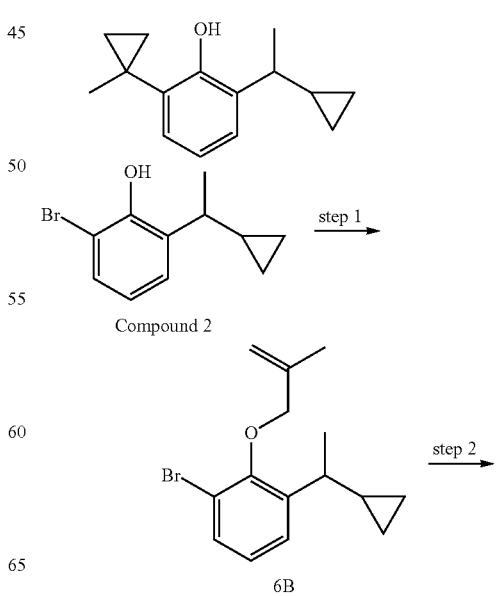

-continued

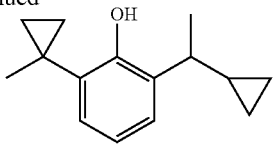

Compound 6

Step 1: 1-bromo-3-(1-cyclopropylethyl)-2-((2-methylallyl)oxy)benzene (6B)

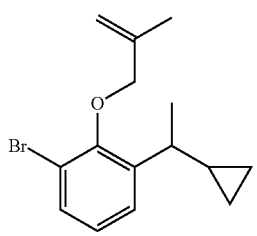 [SMILES: C=C(C)COc1c(Br)cccc1C(C)C1CC1]

2-bromo-6-(1-cyclopropylethyl)phenol (Compound 2) (10.00 g, 41.47 mmol), potassium carbonate (11.46 g, 82.94 mmol) and acetonitrile (100 mL) were added into reaction flask in sequence. The mixture was heated to 40° C. and stirred for 30 minutes and 3-bromo-2-methylpropene (34.20 g, 300 mmol) was added and the mixture stirred at 40° C. for 20 h. The reaction mixture was cooled to room temperature and filtered. The filtrate was concentrated in vacuo. The residue was purified by silica gel column chromatography (petroleum ether) to provide 1-bromo-3-(1-cyclopropylethyl)-2-((2-methylallyl)oxy)benzene (6B) as a colorless oil (10.50 g, yield: 90.0%).

$^1$H NMR (300 MHz, CDCl$_3$): δ 7.39 (dd, 1H), 7.31 (dd, 1H), 6.98 (t, 1H), 5.14-4.98 (m, 2H), 4.27 (s, 2H), 2.50-2.41 (m, 1H), 1.88 (s, 3H), 1.28 (d, 3H), 0.96-0.94 (m, 1H), 0.59-0.36 (m, 2H), 0.22-0.12 (m, 2H).

Step 2: 2-(1-cyclopropylethyl)-6-(1-methylcyclopropyl)phenol (Compound 6)

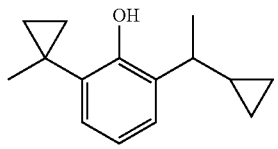 [SMILES: CC(c1cccc(C2(C)CC2)c1O)C1CC1]

Under nitrogen atmosphere, 1-bromo-3-(1-cyclopropylethyl)-2-((2-methylallyl)oxy)benzene (6B) (10.57 g, 35.81 mmol) and anhydrous diethyl ether (200 mL) were added into reaction flask. The mixture was stirred well and cooled to −75° C. with dry ice bath. N-butyllithium (30 mL, 2.5M) was added slowly into the mixture, followed by 1 h stirring at −75° C. N,N-tetramethylethylenediamine (9.57 g, 82.37 mmol) was added slowly. The mixture was recovered to room temperature after addition and stirred at room temperature for 10 h. The reaction mixture was quenched with a saturated solution of ammonium chloride (100 mL), and extracted with ethyl acetate (200 mL×2), washed with brine (200 mL×2), dried over anhydrous sodium sulfate, filtered and concentrated in vacuo. The residue was purified by silica gel column chromatography (petroleum ether) to provide 2-(1-cyclopropylethyl)-6-(1-methylcyclopropyl)phenol (Compound 6) as a yellow oil (600 mg, yield: 8.0%, HPLC: 97%).

MS m/z (ESI): 215.1 [M−1].

$^1$H NMR (300 MHz, CDCl$_3$): δ 7.22 (dd, 1H), 7.10 (dd, 1H), 6.86 (t, 1H), 5.76 (s, 1H), 2.54-2.46 (m, 1H), 1.35-1.05 (m, 6H), 0.83-0.81 (m, 1H), 0.57-0.54 (m, 4H), 0.42-0.39 (m, 2H), 0.23-0.18 (m, 2H).

Example 7

2-(1-cyclobutylethyl)-6-isopropylphenol (Compound 7)

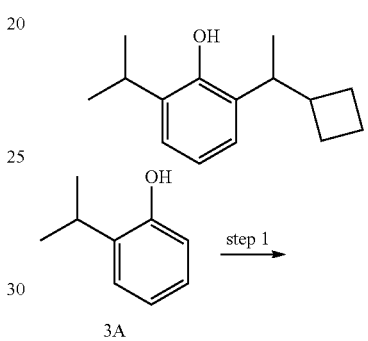

3A

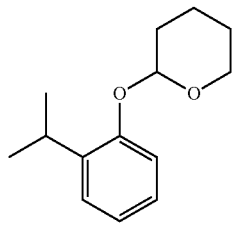 [SMILES: CC(C)c1ccccc1OC1CCCCO1]

7B

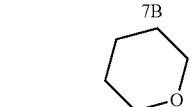

step 2

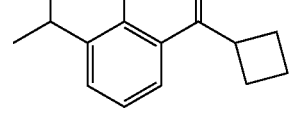

7C

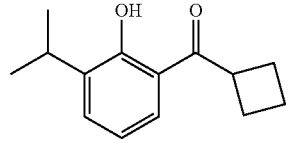

7D

7E

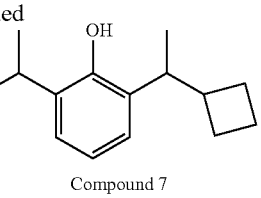

Compound 7

Step 1: 2-(2-isopropylphenoxy)tetrahydropyran (7B)

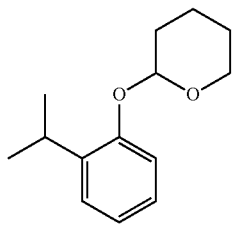

2-isopropylphenol (3A) (1.5 Kg, 11.01 mol) and dichloromethane (6 L) were added into reaction flask, the mixture was stirred well and added with pyridinium toluene-4-sulphonate (276.78 g, 1.10 mol). 2H-3,4-dihydropyran (1.39 Kg, 16.52 mol) was added dropwise under ice water bath, and then the mixture was stirred at room temperature overnight. The reaction mixture was washed with water (2 L×3), a solution of sodium hydroxide (2 L×4), water (2 L×2), brine (2 L×2), dried over anhydrous sodium sulfate, filtered and concentrated in vacuo to obtain 2-(2-isopropylphenoxy)tetrahydropyran (7B) (crude product), which was used in the next step without further purification.

Step 2: cyclobutyl(3-isopropyl-2-((tetrahydro-2H-pyran-2-yl)oxy)phenyl)methanone (7C)

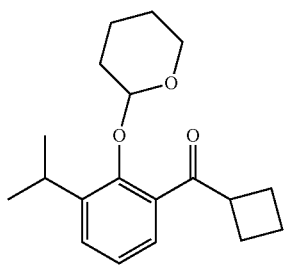 [SMILES: CC(C)c1cccc(C(=O)C2CCC2)c1OC1CCCCO1]

Under nitrogen atmosphere, 2-(2-isopropylphenoxy)tetrahydropyran (7B) (33.00 g, crude product) and tetrahydrofuran (150 mL) were added into reaction flask, cooled to −35° C. with dry ice bath, added N-butyllithium (72 mL, 2.5 M) dropwise slowly, and stirred at room temperature for 2 h. N-Methoxy-N-Methylcyclobutanecarboxamide (30.00 g, 210.00 mmol) was added slowly at −35° C., stirred at room temperature for 4 h. Under ice water bath, the reaction was quenched with a solution of saturated ammonium chloride, extracted with ethyl acetate (150 mL×2), washed with brine (200 mL×2), dried over anhydrous sodium sulfate, filtered and concentrated in vacuo to get cyclobutyl(3-isopropyl-2-((tetrahydro-2H-pyran-2-yl)oxy)phenyl) methanone (7C) as a red oil (crude product), which was used in the next step without further purification.

Step 3: cyclobutyl(2-hydroxy-3-isopropylphenyl)methanone (7D)

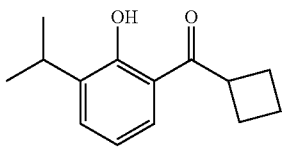 [SMILES: CC(C)c1cccc(C(=O)C2CCC2)c1O]

Under ice water bath, cyclobutyl(3-isopropyl-2-((tetrahydro-2H-pyran-2-yl)oxy)phenyl) methanone (7C) (50.00 g, crude product) was dissolved in a solution of hydrochloric acid in methanol (1M, 120 mL) and stirred for 30 minutes. The reaction mixture was treated with a saturated aqueous of sodium bicarbonate (50 mL) until pH=6~7, concentrated in vacuo. The residue was extracted with ethyl acetate (120 mL×2), washed with saturated brine (100 mL×2), dried over anhydrous sodium sulfate, filtered and concentrated in vacuo. The residue was purified by silica gel column chromatography (petroleum ether) to provide cyclobutyl(2-hydroxy-3-isopropylphenyl)methanone (7D) as a yellow oil (15.00 g, yield: 45.9%).

MS m/z (ESI): 217.1 [M−1].

$^1$H NMR (300 MHz, CDCl3): δ 12.84 (s, 1H), 7.45 (dd, 1H), 7.39 (dd, 1H), 6.83 (t, 1H), 4.09-4.00 (m, 1H), 3.42-3.36 (m, 1H), 2.51-2.42 (m, 2H), 2.34-2.26 (m, 2H), 2.15-2.03 (m, 1H), 1.96-1.87 (m, 1H), 1.24 (d, 6H).

Step 4: 2-(1-cyclobutyl-1-hydroxyethyl)-6-isopropylphenol (7E)

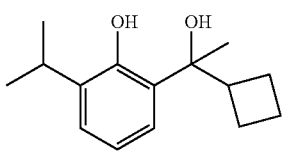 [SMILES: CC(C)c1cccc(C(C)(O)C2CCC2)c1O]

Under nitrogen atmosphere, cyclobutyl(2-hydroxy-3-isopropylphenyl)methanone (7D) (12.00 g, 54.97 mmol) and tetrahydrofuran (36 mL) were added into reaction flask, added methylmagnesium bromide (46 mL, 3M) with ice bath, stirred at room temperature for 4 h and quenched with a saturated aqueous of ammonium chloride solution (50 mL). The reaction mixture was extracted with ethyl acetate (120 mL×2), washed with saturated brine (100 mL×2), dried over anhydrous sodium sulfate, filtered and concentrated under vacuum. The residue was purified by silica gel column chromatography (petroleum ether/ethyl acetate (v/v)=50/1) to get 2-(1-cyclobutyl-1-hydroxyethyl)-6-isopropylphenol (7E) as a white solid (11.20 g, yield: 86.8%).

MS m/z (ESI): 233.2 [M−1].

$^1$H NMR (300 MHz, CDCl$_3$): δ 7.11 (dd, 1H), 6.84 (dd, 1H), 6.77 (t, 1H), 3.40-3.33 (m, 1H), 2.99-2.91 (m, 1H), 1.99-1.89 (m, 6H), 1.70-1.63 (m, 1H), 1.53 (s, 3H), 1.23 (d, 6H).

Step 5: 2-(1-cyclobutylethyl)-6-isopropylphenol (Compound 7)

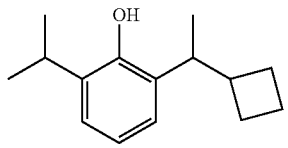 [SMILES: CC(C)c1cccc(C(C)C2CCC2)c1O]

2-(1-cyclobutyl-1-hydroxyethyl)-6-isopropylphenol (7E) (10.40 g, 44.40 mmol) and dichloromethane (100 mL) were added into reaction flask, added with triethylsilane (10.30 g, 88.80 mmol), stirred for 10 minutes. Cooled to −35° C. with dry ice bath, trifluoroacetic acid (40.50 g, 355.20 mmol) was added slowly and stirred for 40 minutes, treated with a saturated aqueous solution of sodium bicarbonate until pH to 7. The organic layer was combined, added tetrabutylammonium fluoride (11.60 g, 44.40 mmol), stirred at room temperature for 2 h. The reaction mixture was washed with brine, dried over anhydrous sodium sulfate, filtered and concentrated under vacuum. The residue was purified by silica gel column chromatography (petroleum ether) to provide 2-(1-cyclobutylethyl)-6-isopropylphenol (Compound 7) as a light yellow liquid (8.20 g, yield: 84.5%, HPLC: 98%).

MS m/z (ESI): 217.2 [M−1].

$^{1}$H NMR (300 MHz, CDCl$_3$): δ 7.03 (dd, 1H), 6.94 (dd, 1H), 6.86 (t, 1H), 4.74 (s, 1H), 3.18-3.11 (m, 1H), 2.97-2.89 (m, 1H), 2.57-2.52 (m, 1H), 2.16-2.13 (m, 1H), 1.82-1.75 (m, 4H), 1.70-1.49 (m, 1H), 1.26 (d, 6H), 1.14 (d, 3H).

Example 8

2-(1-cyclopropylethyl)-6-methoxy-phenol (Compound 8)

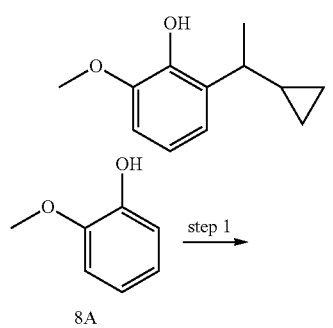

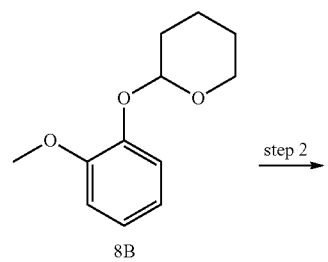

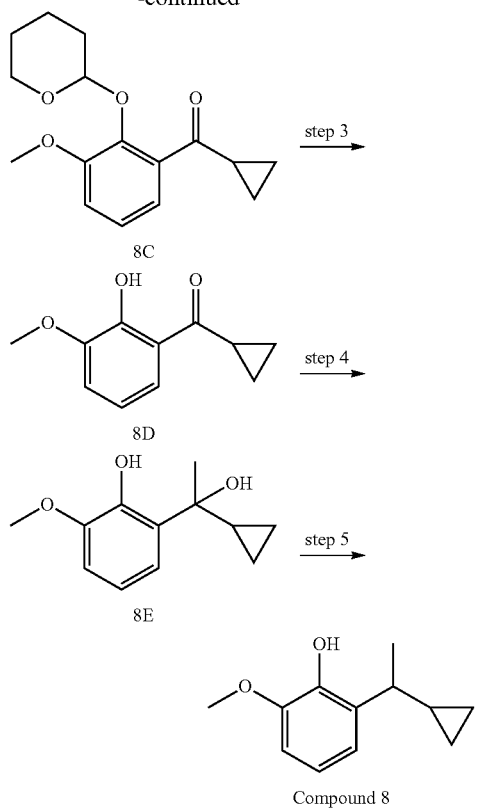

Step 1: 2-(2-methoxyphenoxy)tetrahydropyran (8B)

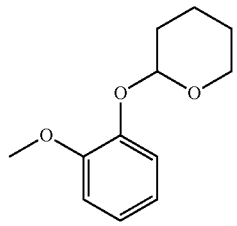

4-bromo-2-methoxyphenol (8A) (200 g, 1.6 mol, JINZHI Chemical Co.), pyridinium toluene-4-sulphonate (40.4 g, 0.16 mol, Chemlin) and dichloromethane (1.6 L) were added into reaction flask accordingly. At room temperature, dihydropyran (203.3 g, 2.4 mol, DEMO Medical Tech) was added slowly into the reaction mixture and stirred for 6 h. The reaction mixture was washed with a solution of sodium hydroxide (1M, 1 L×3), water (1 L×2), and a saturated sodium chloride solution (1 L×1), the organic layer was combined, dried over anhydrous sodium sulfate and concentrated under vacuum to get 2-(2-methoxyphenoxy)tetrahydropyran (8B) as a red liquid (280 g, yield: 84.4%, HPLC: 98.65%).

MS m/z (ESI): 209. (M+1).

$^{1}$HNMR (CDCl$_3$, 400 MHz) δ: 1.59-1.86 (m, 4H), 1.87-3.00 (m, 3H), 3.03-3.61 (m, 1H), 3.85 (s, 3H), 5.37 (t, 1H), 6.86-6.99 (m, 3H), 7.12-7.14 (m, 1H).

Step 2: cyclopropyl-(3-methoxy-2-tetrahydropyran-2-yloxy-phenyl)methanone (8C)

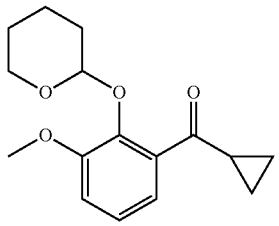 [SMILES: COc1cccc(C(=O)C2CC2)c1OC1CCCCO1]

To the reaction flask, 2-(2-methoxyphenoxy)tetrahydropyran (8B) (200 g, 0.96 mol) and tetrahydrofuran (1000 ml) were added under nitrogen atmosphere, cooled to −20° C. with dry ice-acetone bath, added n-Butyllithium (460 mL, 1.15 mol, 2.5M, Energy Chemical) dropwise slowly, stirred at −10° C. for 2 h. N-methyl-N-methoxyacetamide (186 g, 1.44 mol) was added and stirred at room temperature overnight. The reaction mixture was quenched with a saturated ammonium chloride solution (1000 mL), the organic phase was collected, washed with water (1000 mL×2), brine (1000 mL×2), dried over anhydrous sodium sulfate and concentrated under vacuum to obtain cyclopropyl-(3-methoxy-2-tetrahydropyran-2-yloxy-phenyl)methanone (8C) as a red liquid (280 g, crude product), which was submitted to the next step without further purification.

Step 3: cyclopropyl-(2-hydroxy-3-methoxy-phenyl)methanone (8D)

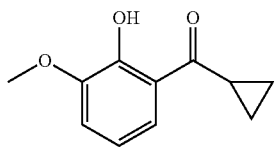

Cyclopropyl-(3-methoxy-2-tetrahydropyran-2-yloxy-phenyl)methanone (8C) (280 g, 1.01 mol) was added into reaction flask, a solution of hydrochloric acid in methanol (1M, 560 mL) was added under ice bath, stirred for 30 minutes. Sodium carbonate was added to adjust pH to about 7. Water was added (200 mL), the aqueous layer was extracted with ethyl acetate (100 mL×3), washed with saturated aqueous solution of sodium chloride (200 mL×2). The organic phase were combined, dried over anhydrous sodium sulfate, concentrated to generate cyclopropyl-(2-hydroxy-3-methoxy-phenyl)methanone (8D) (190 g, yield: 98.4%) as a red liquid.

MS m/z (ESI): 191.0 [M−1].

$^1$HNMR (DMSO-$_{d6}$, 400 MHz) δ: 1.1-1.14 (m, 4H), 2.95-3.01 (m, 1H), 3.81 (s, 3H), 6.91 (t, 1H), 7.24 (d, 1H), 7.67 (d, 1H), 12.22 (s, 1H).

Step 4: 2-(1-cyclopropyl-1-hydroxy-ethyl)-6-methoxy-phenol (8E)

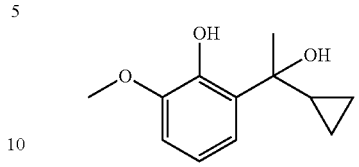

To the reaction flask, cyclopropyl-(2-hydroxy-3-methoxy-phenyl)methanone (8D) (190 g, 988.5 mmol) and tetrahydrofuran (1 L) were added under nitrogen atmosphere, cooled to −10° C. with dry ice-ethanol bath, added methylmagnesium bromide (823 mL, 2.47 mol) slowly, stirred for 4 h at room temperature. The reaction mixture was quenched with a saturated solution of ammonium chloride (300 mL), the organic layer was washed with water (300 mL×2), and brine (300 mL×2), dried over anhydrous sodium sulfate, concentrated under reduced pressure. The residue was purified by silica gel column chromatography (petroleum ether/ethyl acetate (v/v)=20:1) to afford 2-(1-cyclopropyl-1-hydroxy-ethyl)-6-methoxy-phenol (8E) as a yellow solid (65 g, yield: 31.7%).

MS m/z (ESI): 207.1 (M−1).

$^1$HNMR (DMSO-$_{d6}$, 400 MHz) δ: 0.19-0.41 (m, 4H), 1.40-1.47 (m, 1H), 1.49 (s, 3H), 3.74 (s, 3H). 5.63 (s, 1H), 6.69 (d, 1H), 6.80 (d, 1H), 6.87 (t, 1H), 9.40 (s, 1H).

Step 5: 2-(1-cyclopropylethyl)-6-methoxy-phenol (Compound 8)

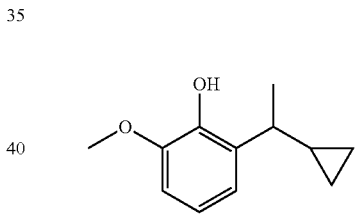

To the reaction flask, 2-(1-cyclopropyl-1-hydroxy-ethyl)-6-methoxy-phenol (8E) (64 g, 307.3 mmol) and tetrahydrofuran (1000 ml) were added. Triethylsilane (72 g, 614.7 mmol, Energy Chemical) was added slowly at −30° C. under dry ice-ethanol bath, stirred for 10 minutes, added with trifluoroacetic acid (280 g, 2.46 mol, AstaTech) slowly, stirred for 20 minutes and then stopped reaction. The pH of reaction mixture was adjusted to about 7 with a saturated solution of sodium bicarbonate. The organic layer was separated, followed by addition of tetrabutylammonium fluoride (40 g, 150 mmol, DEMO medical Tech) and 2 h stirring. The organic layer was washed with water (150 mL×2) and brine (150 mL×2). The combined organic layers were dried over anhydrous sodium sulfate, evaporated under reduced pressure. The residue was purified by silica gel column chromatography (petroleum ether/ethyl acetate (v/v)=100:1) to obtain 2-(1-cyclopropylethyl)-6-methoxy-phenol (Compound 8) as a yellow liquid (38 g, yield: 64.6%, HPLC: 93%).

MS m/z (ESI): 193 (M+1).

$^1$HNMR (CDCl$_3$, 400 MHz) δ: 0.15-1.54 (m, 4H), 1.03-1.05 (m, 1H), 1.31 (dd, 3H), 2.4-2.47 (m, 1H), 3.87 (s, 3H), 5.68 (s, 1H), 6.71 (d, 1H), 6.80 (t, 1H), 6.91 (d, 1H).

Example 9

2-(1-cyclopropylpropyl)-6-isopropyl-phenol (Compound 9)

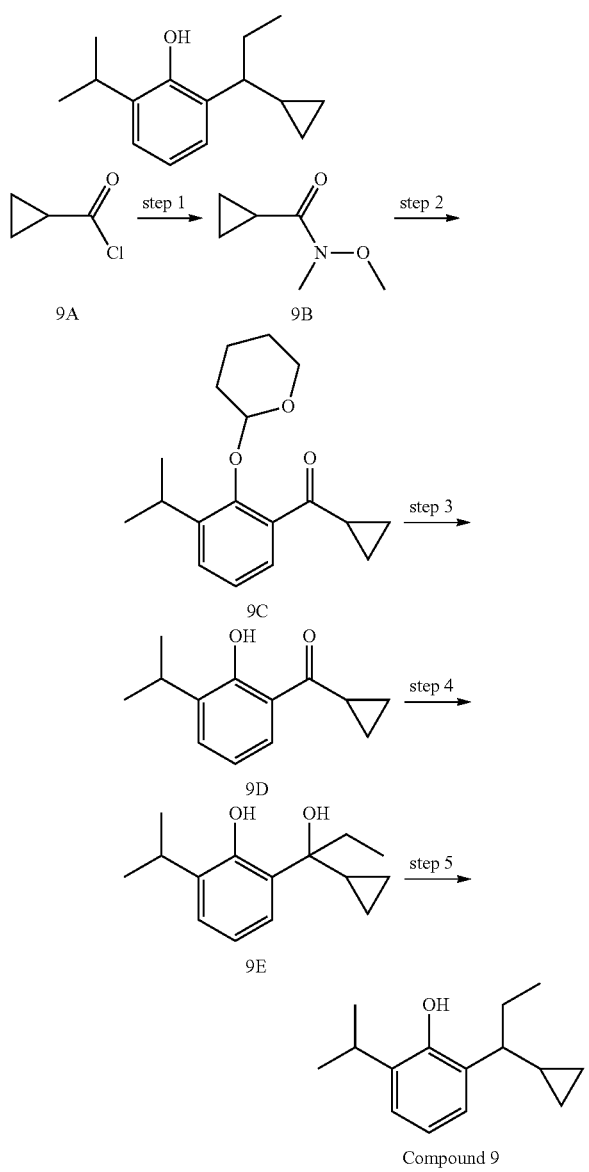

Step 1: N-methoxy-N-methyl-cyclopropanecarboxamide (9B)

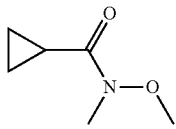

N,O-dimethylhydroxylamine hydrochloride (615.86 g, 6.31 mol) and dichloromethane (6 L) were added into reaction flask, followed by the addition of triethylamine (1.34 Kg, 13.20 mol) dropwise at 10° C. under dry ice bath. Upon completion of the addition, the mixture was stirred for 30 minutes. After the addition of cyclopropanecarboxylic acid chloride (9A) (600 g, 5.74 mol) at 0° C., the reaction was stirred for 2 h at room temperature. The reaction mixture was washed with 1M hydrochloric acid (2 L×3), a solution of sodium hydroxide (0.5 M, 1 L×1), water (1 L×2), brine (1 L×2) successively. The combined organic layers were dried over anhydrous sodium sulfate, filtered and concentrated to afford N-methoxy-N-methyl-cyclopropanecarboxamide (9B) as a colorless oil (1.25 Kg, crude product).

Step 2: cyclopropyl-(3-isopropyl-2-tetrahydropyran-2-yloxy-phenyl)methanone (9C)

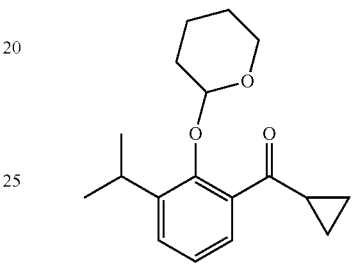

2-(2-isopropylphenoxy)tetrahydropyran (7B) (1 Kg, 4.54 mol) and tetrahydrofuran (5 L) were added into reaction flask under nitrogen atmosphere. Then n-Butyllithium (2.18 L, 5.45 mol) was added dropwise slowly at −20° C. under dry ice-water bath. Upon completion of the addition, the solution was warmed up to room temperature and then stirred for 2 h. N-methoxy-N-methyl-cyclopropanecarboxamide (9B) (821 g, 6.36 mol) was added to the reaction mixture dropwise slowly at −20° C., and then stirred at room temperature overnight. A saturated aqueous solution of ammonium chloride (5 L) was added, stirred for 30 minutes. The reaction was extracted with ethyl acetate (5 L×2), washed with brine (5 L×2), dried over anhydrous sodium sulfate, filtered and concentrated under reduced pressure to afford cyclopropyl-(3-isopropyl-2-tetrahydropyran-2-yloxy-phenyl)methanone (9C) (1.4 Kg, crude product), which was used in the next step.

Step 3: cyclopropyl-(2-hydroxy-3-isopropyl-phenyl)methanone (9D)

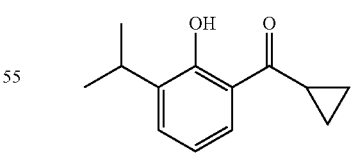

Cyclopropyl-(3-isopropyl-2-tetrahydropyran-2-yloxy-phenyl)methanone (9C) (1.5 Kg, 5.2 mol) was added into reaction flask, cooled to −20° C. under dry ice bath, a solution of hydrochloric acid (180 mL) of methanol (2 L) was added dropwise slowly, stirred for 2 h at room temperature, added water (1 L) and stirred sufficiently. After standing and separation, the water phase was extracted with ethyl acetate (1.5 L×2). The combined organic extracts were washed with saturated brine (2 L×2), dried over anhydrous sodium sulfate, concentrated under reduced pressure to afford cyclopropyl-(2-hydroxy-3-isopropyl-phenyl)methanone (9D) (1.15 Kg, crude product), which was used in the next step without further purification.

Step 4: 2-(1-cyclopropyl-1-hydroxy-propyl)-6-isopropyl-phenol (9E)

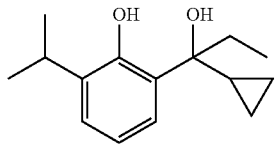 [SMILES: CCC(O)(c1cccc(C(C)C)c1O)C1CC1]

Cyclopropyl-(2-hydroxy-3-isopropyl-phenyl)methanone (9D) (5.0 g, 24.48 mmol) and tetrahydrofuran (25 mL) were added into reaction flask in sequence, ethyl magnesium bromide (3M, 20 mL, 61.20 mmol) was added dropwise slowly under an ice-water bath, stirred for 2 h at room temperature. The reaction mixture was quenched with saturated ammonium chloride solution (30 mL) and extracted with ethyl acetate (30 mL×2), washed with saturated brine (20 mL×1), dried over anhydrous sodium sulfate, filtered and concentrated under reduced pressure. The residue was purified by silica gel column chromatography (hexane/ethyl acetate (v/v)=100:1→10:1) to obtain 2-(1-cyclopropyl-1-hydroxy-propyl)-6-isopropyl-phenol (9E) (4.5 g, yield: 79%) as a colorless oil.

$^1$H NMR (400 MHz, CDCl$_3$): δ 9.43 (brs, 1H), 7.10 (dd, 1H), 6.96 (dd, 1H), 6.78 (t, 1H), 3.30-3.37 (m, 1H), 1.80-2.04 (m, 2H), 1.36-1.45 (m, 1H), 1.21-1.26 (m, 6H), 0.93 (t, 3H), 0.50-0.58 (m, 1H), 0.47-0.50 (m, 2H), 0.26-0.27 (m, 1H).

Step 5: 2-(1-cyclopropylpropyl)-6-isopropyl-phenol (Compound 9)

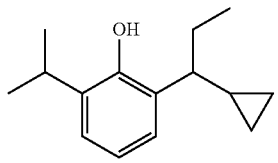 [SMILES: CCC(c1cccc(C(C)C)c1O)C1CC1]

2-(1-cyclopropyl-1-hydroxy-propyl)-6-isopropyl-phenol (9E) (3.0 g, 12.80 mmol), triethylsilane (3.0 g, 25.60 mmol) and dichloromethane (15 mL) were added into reaction flask, trifluoroacetic acid (7.6 mL, 102.42 mmol) was added dropwise under dry ice-ethanol bath, stirred for 1 h at −30° C. Dichloromethane (30 mL) was added. The mixture was washed with water (20 mL×1), saturated sodium bicarbonate solution (20 mL×1) and saturated brine (20 mL×1). To the combined organic phases were added a solution of tetrabutylammonium fluoride of tetrahydrofuran (1M, 12 mL, 12.03 mmol) and the formed mixture was stirred for 1 h at room temperature, and then followed the addition of dichloromethane (20 mL), washed with water (15 mL×2), brine (15 mL×1), dried over anhydrous sodium sulfate, filtered and concentrated. The residue was purified by silica gel column chromatography (hexane/ethyl acetate (v/v)=100:1) to afford 2-(1-cyclopropylpropyl)-6-isopropyl-phenol (Compound 9) as a colorless oil (1.0 g, yield: 32%, HPLC: 99.3%).

$^1$H NMR (400 MHz, CDCl$_3$): δ 7.03-7.07 (m, 2H), 6.89 (t, 1H), 4.50 (s, 1H), 3.11-3.18 (m, 1H), 2.20-2.25 (m, 1H), 1.75-1.77 (m, 2H), 1.26 (d, 6H), 1.05-1.07 (m, 1H), 0.89 (t, 3H), 0.55-0.62 (m, 1H), 0.36-0.42 (m, 1H), 0.19-0.25 (m, 1H), 0.04-0.10 (m, 1H).

Example 11

2-(dicyclopropylmethyl)-6-isopropyl-phenol (Compound 11)

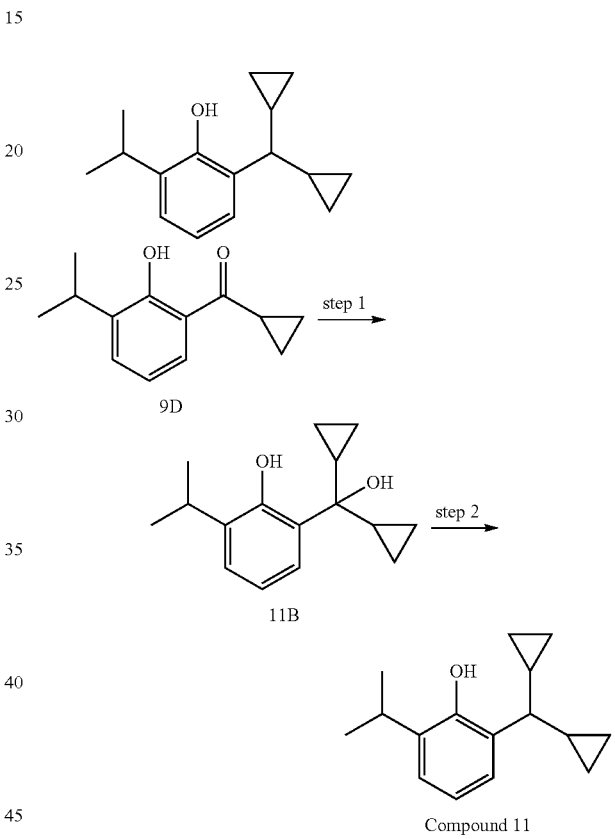

Step 1:2-[dicyclopropyl(hydroxy)methyl]-6-isopropyl-phenol (11B)

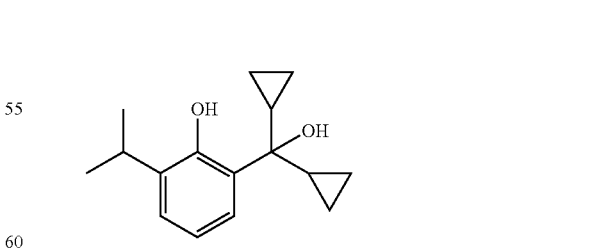

Cyclopropyl-(2-hydroxy-3-isopropyl-phenyl)methanone (9D) (10 g, 48.9 mmol) and tetrahydrofuran (40 mL) were added into reaction flask, a solution of cyclopropyl magnesium bromide (122 mL, 122.4 mmol) was added dropwise under dry ice-ethanol bath. Upon completion of the addition, the mixture was stirred for 2 h while maintaining the inner temperature at 0° C. The reaction was quenched with saturated ammonium chloride solution (200 mL), stirred for 10 minutes and then stood, the organic phase was washed with saturated brine (200 mL×1), dried over anhydrous sodium sulfate, filtered and concentrated under reduced pressure. The residue was purified by silica gel column chromatography (petroleum ether/ethyl acetate (v/v)=30:1) to obtain 2-[dicyclopropyl(hydroxy)methyl]-6-isopropyl-phenol (11B) (4 g, yield: 31%, HPLC: 79.29%) as a white solid.

$^1$H NMR (400 MHz, CDCl$_3$): δ 9.45 (s, 1H), 7.19 (dd, 1H), 7.11 (dd, 1H), 6.78 (t, 1H), 3.32-3.35 (m, 1H), 1.21-1.26 (m, 8H), 0.61-0.64 (m, 4H), 0.39-0.40 (m, 4H).

Step 2: [2-(dicyclopropylmethyl)-6-isopropyl-phenoxy]-triethyl-silane (Compound 11)

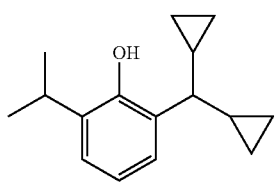 [SMILES: CC(C)c1cccc(C(C2CC2)C2CC2)c1O]

2-[dicyclopropyl(hydroxy)methyl]-6-isopropyl-phenol (11B) (2.0 g, 8.12 mmol) and dichloromethane (10 mL) was added into reaction flask, triethylsilane (1.9 g, 16.24 mmol) was added, and added dropwise slowly with trifluoroacetic acid (3.7 g, 32.47 mmol) under dry ice-ethanol bath. Upon completion of the addition, the mixture was stirred for 3 h while maintaining the temperature at −10° C. The reaction mixture was washed with water (10 mL×1), and saturated sodium bicarbonate solution (10 mL×1) in sequence. The combined organic extracts were dried over anhydrous sodium sulfate for 30 minutes, filtered. The filtrate was transferred to a reaction flask, added with tetrabutylammonium fluoride (1.3 g, 4.06 mmol) was added into filtrate and stirred at room temperature for 2 h. The reaction mixture was washed with water (10 mL×1), dried over anhydrous sodium sulfate, filtered and concentrated under reduced pressure. The residue was purified by silica gel column chromatography (petroleum ether/ethyl acetate (v/v)=50:1) to obtain [2-(dicyclopropylmethyl)-6-isopropyl-phenoxy]-triethyl-silane (Compound 11) (0.2 g, yield: 11%, HPLC: 95.40%).

MS m/z (ESI): 229.1[M−1].

$^1$H NMR (400 MHz, CDCl$_3$): δ7.06-7.10 (m, 2H), 6.88 (t, 1H), 5.10 (brs, 1H), 3.17-3.21 (m, 1H), 2.06 (t, 1H), 1.26 (d, 6H), 1.11-1.15 (m, 2H), 0.55-0.62 (m, 2H), 0.39-0.46 (m, 2H), 0.28-0.34 (m, 2H), 0.12-0.18 (m, 2H).

Example 12

2-(1-cyclopropylethyl)-6-(1-hydroxy-1-methyl-ethyl)phenol (Compound 12)

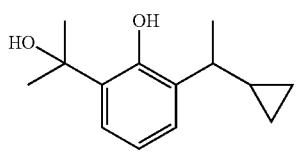 [SMILES: CC(c1cccc(C(C)(C)O)c1O)C1CC1]

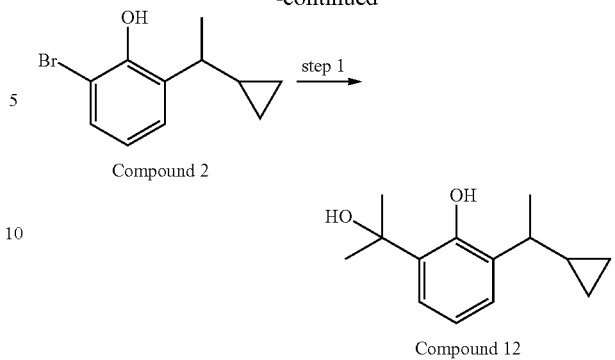

Step 1: 2-(1-cyclopropylethyl)-6-(1-hydroxy-1-methyl-ethyl)phenol (Compound 12)

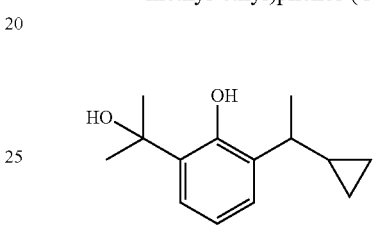

2-bromo-6-(1-cyclopropylethyl)phenol (Compound 2) (5.6 g, 23.2 mmol) was added into reaction flask, under nitrogen atmosphere, N-butyllithium (2.5 M, in n-hexane, 23.2 mL, 58.1 mmol) was added dropwise into reaction flask at −10° C. under dry ice-ethanol bath. After addition, the reaction mixture was stirred at −10° C. for 1 h and then added dropwise with acetone (5.4 g, 92.9 mmol). After completion of addition, the reaction mixture was stirred overnight at room temperature, added with saturated ammonium chloride solution (30 mL) and concentrated under reduced pressure to remove tetrahydrofuran, extracted with ethyl acetate (100 mL×3), washed with saturated brine (100 mL×1), dried over anhydrous sodium sulfate, filtered and concentrated under reduced pressure. The residue was purified by silica gel column chromatography (petroleum ether/ethyl acetate (v/v)=50:1→30:1) to obtain 2-(1-cyclopropylethyl)-6-(1-hydroxy-1-methyl-ethyl)phenol (Compound 12) as a light yellow liquid (3.30 g, yield: 65%, HPLC: 96.08%).

MS m/z (ESI): 219.1[M−1].

$^1$H NMR (400 MHz, CDCl$_3$): δ0.16-0.22 (m, 2H), 0.37-0.40 (m, 1H), 0.51-0.57 (m, 1H), 1.00-1.05 (m, 1H), 1.29 (d, 3H), 1.68 (s, 6H), 2.49-2.57 (m, 1H), 6.81 (t, 1H), 6.95 (dd, 1H), 7.24-7.26 (m, 1H), 9.0 (s, 1H).

Example 13

2,6-bis(1-cyclopropylethyl)phenol (Compound 13)

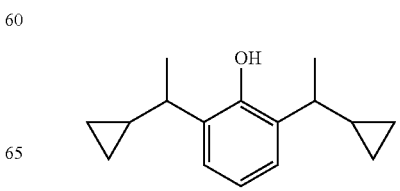

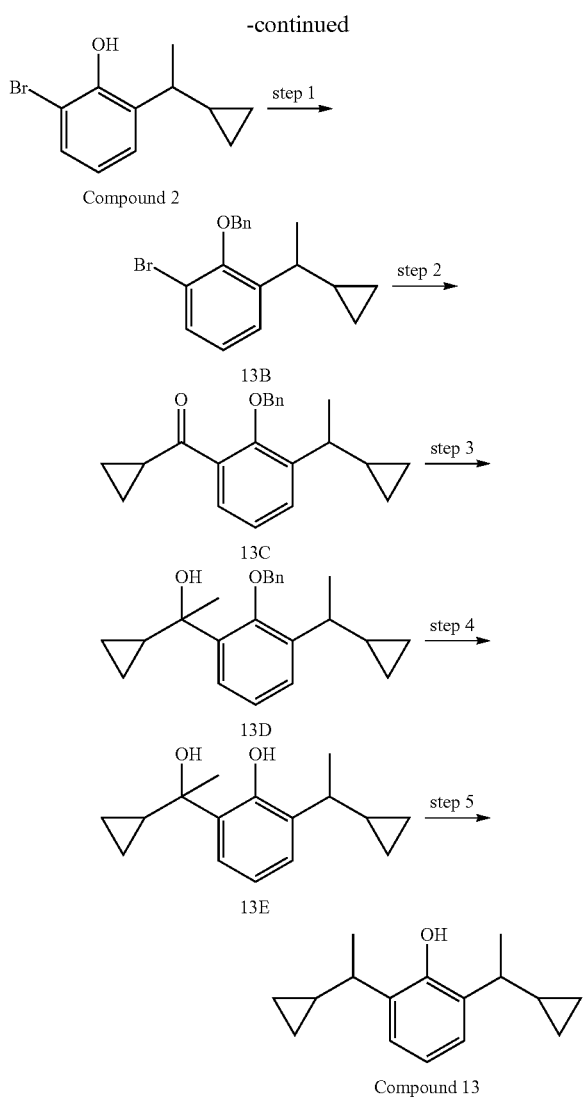

Step 1:
2-benzyloxy-1-bromo-3-(1-cyclopropylethyl)benzene (13B)

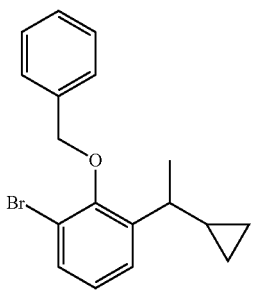 [SMILES: CC(c1cccc(Br)c1OCc1ccccc1)C1CC1]

2-bromo-6-(1-cyclopropylethyl)phenol (Compound 2) (100 g, 414.72 mmol) and acetone (500 mL) were added into reaction flask, potassium carbonate (57.32 g, 414.72 mmol) and benzyl bromide (57.75 g, 456.20 mmol) were added after thorough stirring. The reaction mixture was refluxed for 12 h, filtered and concentrated under reduced pressure. The residue was purified by silica gel column chromatography (petroleum ether/ethyl acetate (v/v)=100:1) to obtain 2-benzyloxy-1-bromo-3-(1-cyclopropylethyl)benzene (13B) (crude product, 128 g, yield: 92.2%), which was submitted to the next step without further purification.

$^1$H NMR (400 MHz, CDCl$_3$): δ 7.44-7.34 (m, 7H) 7.03-6.99 (t, 1H), 4.95-4.85 (m, 2H), 2.49-2.41 (m, 1H), 1.24 (d, 3H), 0.95-0.90 (m, 1H), 0.54-0.51 (m, 1H), 0.35-0.32 (m, 1H), 0.17-0.07 (m, 2H).

Step 2: [2-benzyloxy-3-(1-cyclopropylethyl)phenyl]-cyclopropyl-methanone (13C)

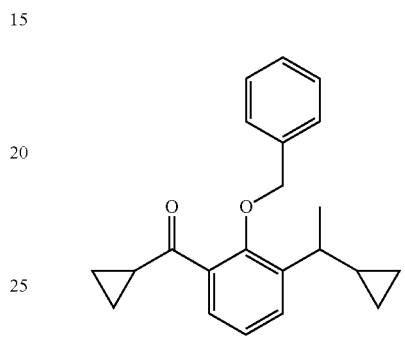

Under nitrogen atmosphere, 2-benzyloxy-1-bromo-3-(1-cyclopropylethyl)benzene (13B) (128 g, 386.42 mmol, crude product) and tetrahydrofuran (500 mL) were added into reaction flask, n-butyllithium (37.13 g, 579.63 mmol) was added dropwise slowly at −78° C. under dry ice-acetone bath and stirred for 1 h at −78° C. N-methoxy-N-methyl cyproterone amide (74.86 g, 579.63 mmol, Asta Tech) was added and stirred for 4 h at −78° C. The reaction was quenched with saturated ammonium chloride solution (200 mL), extracted with ethyl acetate (500 mL×4). The combined organic extracts were washed with saturated brine (200 mL×2), dried over anhydrous sodium sulfate, filtered and concentrated under reduced pressure to obtain [2-benzyloxy-3-(1-cyclopropylethyl)phenyl]-cyclopropyl-methanone (13C) as a yellow oil (144 g, crude product), which was submitted to the next step without further purification.

Step 3: 1-[2-benzyloxy-3-(1-cyclopropylethyl)phenyl]-1-cyclopropyl-ethanol (13D)

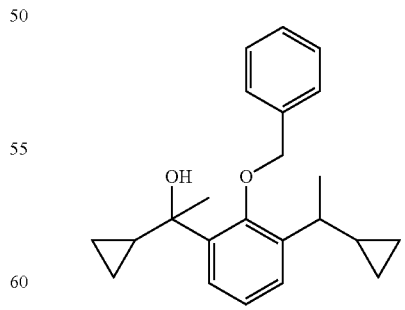

Under nitrogen atmosphere, [2-benzyloxy-3-(1-cyclopropylethyl)phenyl]-cyclopropyl-methanone (13C) (crude product, 144 g, 449.4 mmol) and tetrahydrofuran (500 mL) were added into reaction flask. Then methylmagnesium bromide (69.66 g, 584.22 mmol) was added to the previous solution under an ice-water bath. After completion of addition, the reaction mixture was stirred for 3 h at room temperature. The reaction mixture was quenched with saturated ammonium chloride solution (200 mL), extracted with ethyl acetate (500 mL×3). The combined organic extracts were washed with saturated brine (100 mL×3), dried over anhydrous sodium sulfate, filtered and concentrated under reduced pressure. The residue was purified by silica gel column chromatography (petroleum ether/ethyl acetate (v/v)=10:1) to obtain 2-(1-cyclopropylethyl)-6-(1-hydroxy-1-methyl-ethyl)phenol (13D) (80 g, yield: 57%, HPLC: 95.7%) as a yellow oil.

$^1$H NMR (400 MHz, CDCl$_3$): δ 7.43-7.13 (m, 8H), 4.99-4.89 (m, 2H), 4.6 (d, 1H), 2.53-2.49 (m, 1H), 1.59-1.56 (m, 3H), 1.36-1.24 (m, 3H), 0.95-0.96 (m, 1H), 0.35-0.18 (m, 8H).

Step 4: 2-(1-cyclopropylethyl)-6-(1-cyclopropyl-1-hydroxy-ethyl)phenol (13E)

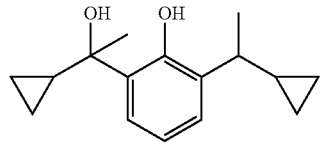 [SMILES: CC(c1cccc(C(C)(O)C2CC2)c1O)C1CC1]

2-(1-cyclopropylethyl)-6-(1-hydroxy-1-methyl-ethyl) phenol (13D) (80 g, 237 mmol), ethanol (200 mL) and Pd/C (4 g, 10% Pd (w/w)) were added into reaction flask. The flask was degassed and back-filled with nitrogen for three times, and then charged with hydrogen for three times. The reaction mixture was heated to 50° C. and stirred for 12 h. The solution was filtered and the filtrate was concentrated under reduced pressure. The residue was purified by silica gel column chromatography (petroleum ether/ethyl acetate (v/v)=50:1) to obtain 2-(1-cyclopropylethyl)-6-(1-cyclopropyl-1-hydroxy-ethyl)phenol (13E) as a colorless oil (3.6 g, yield: 71.43%, HPLC: 97.8%).

MS m/z (ESI): 245[M−1].

$^1$H NMR (400 MHz, DMSO-d$_6$): δ 10.24 (d, 1H), 7.15-7.12 (m, 1H), 7.02-7.00 (dd, 1H), 6.72 (t, 1H), 6.50 (d, 1H), 2.43-2.27 (m, 1H), 1.46 (s, 3H), 1.28-1.19 (m, 1H), 1.19 (d, 3H), 1.03-1.01 (m, 1H), 0.37-0.05 (m, 8H).

Step 5: 2,6-bis(1-cyclopropylethyl)phenol (Compound 13)

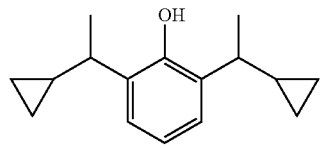 [SMILES: CC(c1cccc(C(C)C2CC2)c1O)C1CC1]

2-(1-cyclopropylethyl)-6-(1-cyclopropyl-1-hydroxy-ethyl)phenol (13E) (120 g, 407.12 mmol) and dichloromethane (500 mL) were added into reaction flask, triethylsilane (113.28 g, 974.24 mmol) was added dropwise at 0° C. and stirred for 15 minutes. Trifluoroacetic acid (222.17 g, 1.95 mol) was added dropwise in portions in an ice-water bath. After addition, the reaction was warmed up to room temperature and stirred for 2 h, added with water (500 mL) and stirred for 5 minutes, stood and stratified. The organic layer was washed with saturated sodium bicarbonate solution (500 mL×3), added with tetrabutylammonium fluoride (127.16 g, 487.12 mmol) and stirred for another 12 h at room temperature. The resulting mixture was added with water (300 mL) and then settled. The organic phase was washed with water (100 mL×3), saturated brine (100 mL×2), dried over anhydrous sodium sulfate, filtered and concentrated under reduced pressure. The residue was purified by silica gel column chromatography (hexane) to afford 2,6-bis(1-cyclopropylethyl)phenol (Compound 13) as a yellow oil (70 g, yield: 62.5%, HPLC: 96.78%).

$^1$H NMR (400 MHz, CDCl$_3$): δ 7.15 (t, 2H), 6.91 (t, 1H), 4.85 (s, 1H), 2.54-2.19 (m, 2H), 1.31 (d, 6H), 1.08-1.04 (m, 2H), 0.53-0.43 (m, 4H), 0.21-0.17 (m, 4H).

Example 14

2-[(1R)-1-cyclobutylethyl]-6-isopropyl-phenol (Compound 14)

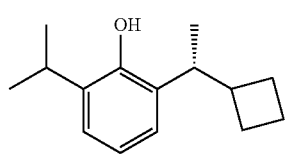

Example 15

2-[(1S)-1-cyclobutylethyl]-6-isopropyl-phenol (Compound 15)

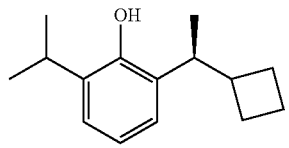 [SMILES: CC(C)c1cccc([C@@H](C)C2CCC2)c1O]

2-(1-cyclobutylethyl)-6-isopropylphenol (Compound 7, 800 mg) was separated to obtain compound 14 and compound 15. Preparation Condition: Instrument: Agilent 1260/LH-Y-J0371(4-1); Columns: CHIRALPAK AD-H (4.6 mm×250 mmL, 5 μM) Number: AD-H-44B; Mobile phase: hexane; flow: 1.0 mL/min, back pressure: 100 bar, column temperature 35° C., wave length 210 nm. Two optical isomers were obtained, peak 1 (retention time: 12.93 min, 340 mg, light yellow liquid, ee, 99%), peak 2 (retention time: 15.55 min, 360 mg, light yellow liquid, ee, 99%) by preparative Chiral-HPLC. (Compound 7 was a racemic mixture, which had only one chiral center. Therefore, only two optical isomers, compound 14 and compound 15, were obtained after separation. The following described compounds (except compound 13) are all related with only two existed optical isomers. No more repeated explanations will be stated here after.

Peak 1: MS m/z (ESI): 217.1[M−1].

$^1$H NMR (400 MHz, CDCl3): δ 7.05 (dd, 1H), 6.96 (dd, 1H), 6.88 (t, 1H), 4.78 (s, 1H), 3.22-3.12 (m, 1H), 2.99-2.92

(m, 1H), 2.63-2.53 (m, 1H), 2.19-2.13 (m, 1H), 1.93-1.73 (m, 4H), 1.65-1.56 (m, 1H), 1.28 (d, 6H), 1.16 (d, 3H).

Peak 2: MS m/z (ESI): 217.1[M−1].

¹HNMR (400 MHz, CDCl3): δ 7.05 (dd, 1H), δ 6.96 (dd, 1H), 6.88 (t, 1H), 4.75 (s, 1H), 3.20-3.12 (m, 1H), 2.99-2.91 (m, 1H), 2.59-2.57 (m, 1H), 2.17-2.16 (m, 1H), 1.88-1.81 (m, 4H), 1.65-1.56 (m, 1H), 1.28 (d, 6H), 1.16 (d, 3H).

Example 16

2-[(1R)-1-cyclopropylethyl]-6-isopropyl-phenol (Compound 16)

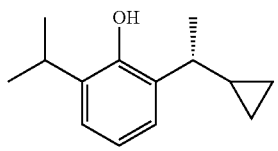

Example 17

2-[(1S)-1-cyclopropylethyl]-6-isopropyl-phenol (Compound 17)

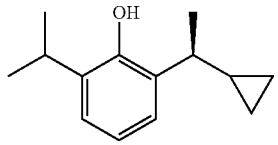

Preparation of Compound 16 and Compound 17:

2-(1-cyclopropylethyl)-6-isopropylphenol (Compound 3) (600 mg) was separated. Preparation Condition: Instrument: Agilent 1260/CH-Y-J0404; Columns: CHIRALPAK OJ-H (4.6 mm×250 mm, 5 µM) Number: OJ-H-27; mobile phase A: isopropanol, B: hexane, flow: 1.0 mL/min, back pressure: 100 bar, column temperature 35° C., wave length 210 nm.

After separation, two optical isomers were obtained: peak 1 (retention time: 10.72 min, 280 mg, light yellow liquid, ee, 99%), peak 2 (retention time: 13.58 min, 280 mg, light yellow liquid, ee, 99%).

Peak 1: MS m/z (ESI): 203.1 (M−1).

¹HNMR (400 MHz, CDCl₃): δ 7.14 (dd, 1H), δ 7.08 (dd, 1H), 6.91 (t, 1H), 4.93 (s, 1H), 3.22-3.14 (m, 1H), 2.55-2.48 (m, 1H), 1.33 (d, 6H), 1.28 (d, 3H), 1.10-1.05 (m, 1H), 0.60-0.58 (m, 1H), 0.49-0.46 (m, 1H), 0.25-0.18 (m, 2H).

Peak 2: MS m/z (ESI): 203.1 (M−1).

¹HNMR (400 MHz, CDCl₃): δ 7.14 (dd, 1H), δ 7.08 (dd, 1H), 6.93 (t, 1H), 4.93 (s, 1H), 3.22-3.15 (m, 1H), 2.55-2.48 (m, 1H), 1.32 (d, 6H), 1.28 (d, 3H), 1.10-1.04 (m, 1H), 0.60-0.58 (m, 1H), 0.49-0.46 (m, 1H), 0.25-0.18 (m, 2H).

Example 18

2,6-bis[(1R)-1-cyclopropylethyl]phenol (Compound 18)

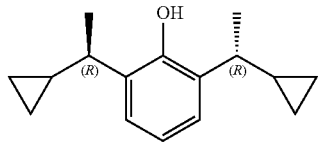

Example 19

2-[(1S)-1-cyclopropylethyl]-6-[(1R)-1-cyclopropyl-ethyl]phenol (Compound 19)

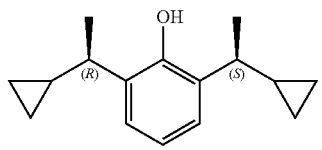

Example 20

2,6-bis[(1S)-1-cyclopropylethyl]phenol (Compound 20)

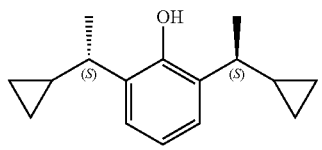

Preparation of Compound 18, Compound 19 and Compound 20:

2,6-bis(1-cyclopropylethyl)phenol (Compound 13) (4.8 g, 14.2 mmol) was separated by chrial HPLC method (conditions: Chiral column CHIRALPAK OZ-H. mobile phase: hexane/isopropanol (v/v)=100:0, flow rate 1.0 mL/min, UV=214 nm, column temperature 35° C.) to collect three fractions which were 15.7 min, 16.8 min and 21.3 min respectively, concentrated under reduced pressure to get peak1 (white solid, 710 mg, yield: 59.1%, HPLC: 96.89%, Chrial-HPLC: 97.92%), peak2 (yellow oil, 1.3 g, yield: 54.16%, HPLC: 97.50%, Chrial-HPLC: 99.33%), peak3 (white solid, 720 mg, yield: 60%, HPLC: 95.55%, Chrial-HPLC: 98.48%).

Compound 13 has two chiral centers, so three optical isomers were obtained after separation, which were compound 18, compound 19 and compound 20 respectively.

Peak 1: MS m/z (ESI): 229.2 [M−1],

¹HNMR: (400 MHz, CDCl₃): δ 7.13 (d, 2H), 6.90 (t, 1H), 5.06 (s, 1H), 2.52-2.48 (m, 2H), 1.29 (d, 6H), 1.06-1.02 (m, 2H), 0.55-0.42 (m, 4H), 0.22-0.16 (m, 4H).

Peak 2: MS m/z (ESI): 229[M−1].

¹H NMR (400 MHz, CDCl₃): δ 7.13 (d, 2H), 6.89 (t, 1H), 5.04 (s, 1H), 2.54-2.47 (m, 2H), 1.30 (d, 6H), 1.06-1.03 (m, 2H), 0.53-0.42 (m, 4H), 0.20-0.15 (m, 4H).

Peak 3: MS m/z (ESI): 229.2 [M−1].

¹HNMR: (400 MHz, CDCl₃): δ 7.13 (d, 2H), 6.89 (t, 1H), 5.05 (s, 1H), 2.53-2.46 (m, 2H), 1.29 (d, 6H), 1.05-1.01 (m, 2H), 0.56-0.42 (m, 4H), 0.20-0.14 (m, 4H).

Example 21

2-(1-cyclopropyl-1-hydroxy-ethyl)-6-(1-methylcyclopropyl)phenol (Compound 21)

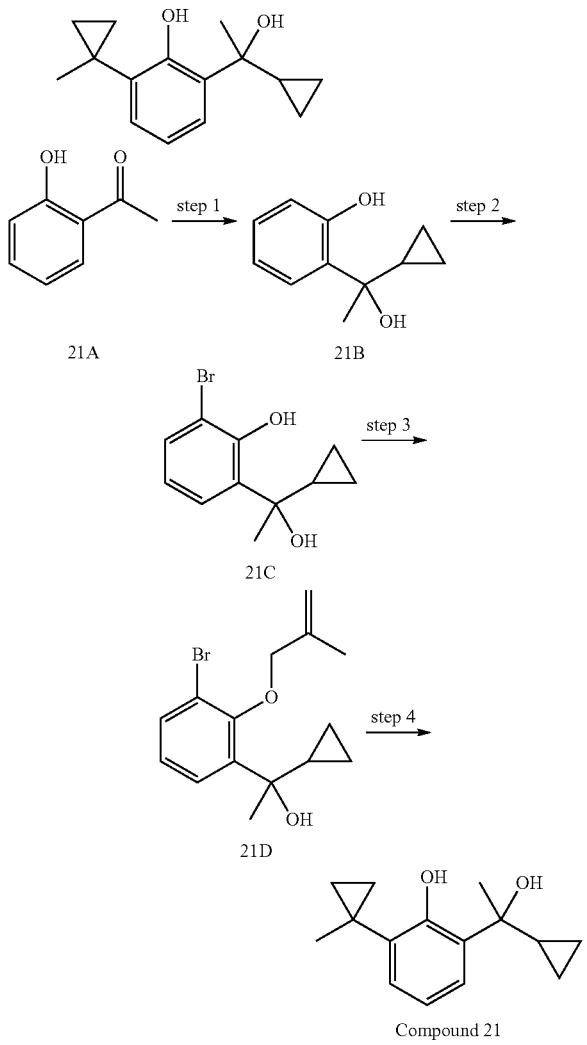

Step 1: 2-(1-cyclopropyl-1-hydroxy-ethyl)phenol (21B)

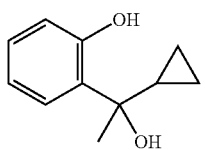

Under nitrogen atmosphere, magnesium (2.68 g, 110.17 mmol) and small amounts of iodine were added into reaction flask. Cyclobutyl bromide (10.66 g, 88.14 mmol) in dry tetrahydrofuran (20 mL) was injected slowly into the flask with maintaining slightly boiling. Upon completion of the addition, the reaction mixture was stirred at room temperature for 2 h, added with 2-hydroxyacetophenone (21A) (3.00 g, 22.03 mmol) and then stirred at 30° C. for another 4 h. The reaction was quenched with a saturated aqueous solution of ammonium chloride solution (30 mL), extracted with ethyl acetate (50 mL×3). The combined organic phases were washed with saturated brine (50 mL×3), dried over anhydrous sodium sulfate, filtered and concentrated under reduced pressure. The residue was purified by silica gel column chromatography (petroleum ether/ethyl acetate (v/v)=10:1) to obtain 2-(1-cyclopropyl-1-hydroxy-ethyl)phenol (21B) as a light yellow liquid (3.0 g, yield: 76.3%).

MS m/z (ESI): 177.1 (M−1).

¹HNMR (400 MHz, CDCl₃): 7.26-7.14 (m, 2H), 6.91-6.80 (m, 2H), 4.78 (s, 1H), 1.41 (s, 3H), 1.39-1.36 (m, 1H), 0.68-0.36 (m, 4H).

Step 2: 2-bromo-6-(1-cyclopropyl-1-hydroxy-ethyl)phenol (21C)

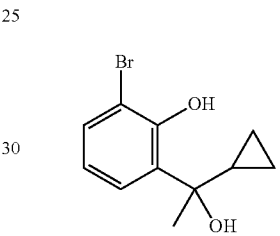

2-(1-cyclopropyl-1-hydroxy-ethyl)phenol (21B) (7.98 g, 44.77 mmol), diisopropylamine (0.45 g, 4.48 mmol) and dichloromethane (60 mL) were added into reaction flask, N-bromosuccinimide (7.96 g, 44.77 mmol) was added in portions at 0° C. under ice-water bath, and stirred at 0° C. for 5 h. The reaction mixture was quenched with a solution of sodium bisulfite (50 mL), extracted with dichloromethane (50 mL×3). The combined organic layers were washed with saturated brine (50 mL×3), dried over anhydrous sodium sulfate, filtered and concentrated under reduced pressure. The residue was purified by silica gel column chromatography (petroleum ether/ethyl acetate (v/v)=50:1) to obtain 2-bromo-6-(1-cyclopropyl-1-hydroxy-ethyl)phenol (21C) as a white solid (2.6 g, yield: 22.6%).

MS m/z (ESI): 225.1 (M−1).

Step 3: 1-[3-bromo-2-(2-methylallyloxy)phenyl]-1-cyclopropyl-ethanol (21D)

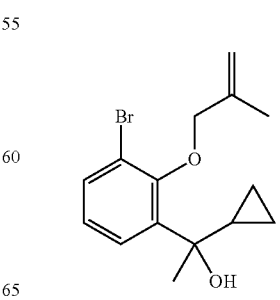

2-bromo-6-(1-cyclopropyl-1-hydroxy-ethyl)phenol (21C) (0.50 g, 1.94 mmol), potassium carbonate (0.54 g, 3.88 mmol) and acetonitrile (30 mL) were added into reaction flask, and stirred at room temperature for 1 h. 3-bromo-2-methylpropene (0.29 g, 2.13 mmol) was added and stirred at 50° C. for overnight. The reaction mixture was cooled to room temperature, filtered and concentrated. Water was added into the residue, and the mixture was extracted with ethyl acetate (30 mL×3), the combined organic phase was washed with saturated brine (50 mL×3), dried over anhydrous sodium sulfate, filtered and concentrated under reduced pressure. The residue was purified by silica gel column chromatography (petroleum ether/ethyl acetate (v/v)=40:1) to afford 1-[3-bromo-2-(2-methylallyloxy)phenyl]-1-cyclopropyl-ethanol as a light yellow liquid (21D) (0.45 g, yield: 75.0%).

MS m/z (ESI): 295.1 (M−17+1).

$^1$HNMR (400 MHz, CDCl$_3$): δ 7.49-7.45 (m, 2H), δ 6.98 (t, 1H), 5.21 (s, 1H), 5.04 (s, 1H), 4.62-4.63 (m, 2H), 3.90 (s, 1H), 1.89 (s, 3H), 1.54 (s, 3H), 1.41-1.26 (m, 1H), 0.59-0.36 (m, 4H).

Step 4: 2-(1-cyclopropyl-1-hydroxy-ethyl)-6-(1-methylcyclopropyl)phenol (Compound 21)

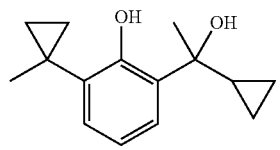 [SMILES: CC1(c2cccc(C(C)(O)C3CC3)c2O)CC1]

Under nitrogen atmosphere, 1-[3-bromo-2-(2-methylallyloxy)phenyl]-1-cyclopropyl-ethanol (21D) (0.40 g, 1.29 mmol) and dry tetrahydrofuran (20 mL) were added into reaction flask, a solution of n-butyllithium in tetrahydrofuran (1.5 mL, 3.86 mmol) was added dropwise at −70° C. under dry ice bath, and then stirred for 1 h at −70° C. N,N,N',N'-Tetramethylethylenediamine was added at −70° C. Upon completion of the addition, the mixture was slowly warmed up to room temperature and stirred for 4 h. The reaction mixture was quenched with a saturated aqueous solution of ammonium chloride solution (30 mL), extracted with ethyl acetate (30 mL×3). The combined organic extracts were washed with saturated brine (50 mL×3), dried over anhydrous sodium sulfate, filtered and concentrated under reduced pressure. The residue was purified by silica gel column chromatography (hexane/ethyl acetate (v/v)=100:1) to obtain 2-(1-cyclopropyl-1-hydroxy-ethyl)-6-(1-methylcyclopropyl)phenol (Compound 21) as a light yellow liquid (0.19 g, yield: 66.0%, HPLC: 99.5%).

MS m/z (ESI): 231.1 (M−1).

$^1$HNMR (400 MHz, CDCl$_3$): δ 7.49 (dd, 1H), δ 7.20 (dd, 1H), δ 7.00 (t, 1H), 6.14 (s, 1H), 3.69 (s, 1H), 1.69 (s, 3H), 1.57 (s, 3H), 1.44-1.25 (m, 3H), 0.88-0.85 (m, 3H), 0.50-0.43 (m, 4H).

Example 22

S-2-bromo-6-(1-cyclopropylethyl)phenol (Compound 22)

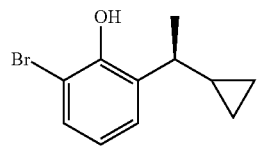

Example 23

R-2-bromo-6-(1-cyclopropylethyl)phenol (Compound 23)

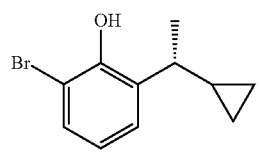

Preparation of Compound 22 and Compound 23:

2-bromo-6-(1-cyclopropylethyl)phenol (Compound 2) (600 mg) was separated Under preparation condition: Agilent 1260/LH-Y-J0371(4-1); CHIRALPAK AD-H (4.6 mm×250 mmL, 5 μM) Number: AD-H-44B; mobile phase hexane, flow 1.0 mL/min, back pressure: 100 bar, column temperature 35° C., wave length 210 nm.

After separation, two optical isomers were obtained, peak 1 (retention time: 5.57 min, 230 mg, light yellow liquid, ee, 99%), peak 2 (retention time: 5.83 min, 200 mg, light yellow liquid, ee, 99%).

Peak 1: MS m/z (ESI): 240.9 [M−1], 241.9[M+1].

$^1$H NMR (400 MHz, CDCl$_3$): δ 7.29 (dd, 1H, Ar—H), 7.25 (dd, 1H, Ar—H), 6.79 (t, 1H, Ar—H), 5.58 (s, 1H, OH), 2.48-2.40 (m, 1H, CH), 1.29 (d, 3H, CH3), 1.07-0.98 (m, 1H, CH), 0.61-0.43 (m, 2H, CH2), 0.26-0.16 (m, 2H, CH2).

Peak 2: MS m/z (ESI): 240.9 [M−1], 241.9 [M+1].

$^1$H NMR (400 MHz, CDCl$_3$): δ 7.29 (dd, 1H, Ar—H), 7.25 (dd, 1H, Ar—H), 6.79 (t, 1H, Ar—H), 5.58 (s, 1H, OH), 2.48-2.40 (m, 1H, CH), 1.29 (d, 3H, CH$_3$), 1.07-0.98 (m, 1H, CH), 0.61-0.43 (m, 2H, CH$_2$), 0.26-0.16 (m, 2H, CH$_2$).

Example 24

2-sec-butyl-6-((R)-1-cyclopropylethyl)phenol (Compound 24)

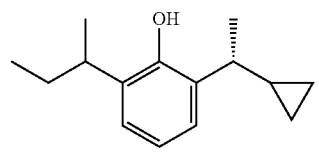

-continued

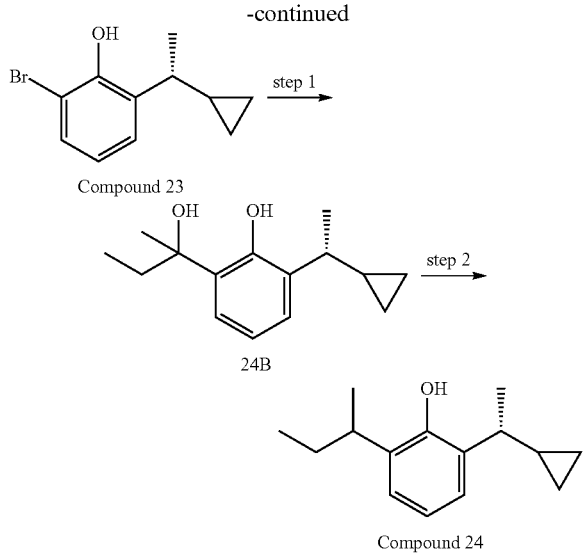

Step 1: 2-[(1R)-1-cyclopropylethyl]-6-(1-hydroxy-1-methyl-propyl)phenol (24B)

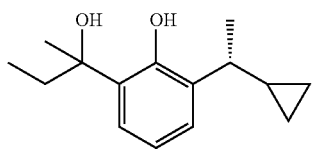 [SMILES: CCC(C)(O)c1cccc([C@H](C)C2CC2)c1O]

2-bromo-6-((1R)-1-cyclopropylethyl)phenol (Compound 23)(10.0 g, 0.04 mol) was added into dry tetrahydrofuran (50 mL), a solution of n-butyllithium in hexane (50 mL, 0.12 mol, 2.5M) was added into the mixture under nitrogen atmosphere, and stirred for 40 minutes below 0° C. Butanone (4.5 g, 0.06 mol) was added dropwise and stirred for 30 minutes at −10° C. and then warmed up to room temperature and stirred overnight. The reaction was quenched with water (20 mL) at 0-5° C., stood and separated. The aqueous phase was extracted with ethyl acetate (40 mL×2). The combined organic phases were washed with saturated brine (50 mL×1), dried over anhydrous sodium sulfate for 10 minutes, concentrated under reduced pressure. The residue was purified by silica gel column chromatography (petroleum ether/ethyl acetate (v/v)=100:1→50:1) to obtain 2-[(1R)-1-cyclopropylethyl]-6-(1-hydroxy-1-methyl-propyl)phenol (24B) as a light yellow liquid (6.8 g, yield: 70%).

Step 2: 2-[(1R)-1-cyclopropylethyl]-6-sec-butyl-phenol (Compound 24)

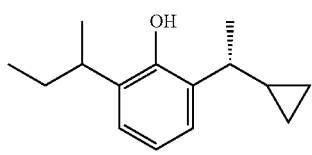 [SMILES: CCC(C)c1cccc([C@H](C)C2CC2)c1O]

A solution of 2-[(1R)-1-cyclopropylethyl]-6-(1-hydroxy-1-methyl-propyl)phenol (24B) (6.0 g, 0.026 mol) was added into dichloromethane (30 mL), triethylsilane (6.0 g, 0.05 mol) was added into the mixture under nitrogen atmosphere. Trifluoroacetic acid (11.7 g, 0.1 mol) was added dropwise below −30° C. After addition, the reaction was stirred for 3 h below 5° C. The reaction mixture was quenched with water (30 mL), stood and separated. The aqueous phase was extracted with dichloromethane (30 mL×2). Tetrabutylammonium fluoride trihydrate (4 g, 0.013 mol) was added to the combined organic extracts, and stirred at room temperature for 30 minutes, then water (20 mL) was added, stirred for 3 minutes, stood and separated. The aqueous layer was extracted with dichloromethane (20 mL×3), The combined organic extracts were washed with saturated brine (30 mL×1), dried over anhydrous sodium sulfate for 10 min, concentrated under reduced pressure. The residue was purified by silica gel column chromatography (eluant: petroleum ether/ethyl acetate=100:1-50:1) to obtain 2-[(1R)-1-cyclopropylethyl]-6-sec-butyl-phenol (Compound 24) as a light yellow liquid (2.8 g, yield: 50%, HPLC: 97.43%).

$^1$H NMR (400 MHz, CDCl$_3$): δ 7.11 (dt, 1H), 7.01 (dd, 1H), 6.88 (t, 1H), 4.88 (br, 1H), 2.91-2.89 (m, 1H), 2.52-2.50 (m, 1H), 1.67-1.57 (m, 2H), 1.30 (d, 3H), 1.24 (d, 3H), 1.06-1.04 (m, 1H), 0.89 (t, 3H), 0.58-0.53 (m, 1H), 0.48-0.44 (m, 1H), 0.21-0.17 (m, 2H).

MS m/z (ESI): 217.3 [M−1].

Example 25

2-[(1R)-1-cyclopropylethyl]-6-[(1S)-1-methylpropyl]phenol (Compound 25)

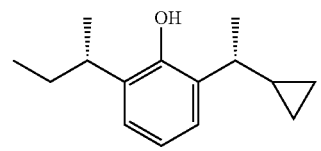

Example 26

2-[(1R)-1-cyclopropylethyl]-6-[(1R)-1-methylpropyl]phenol (Compound 26)

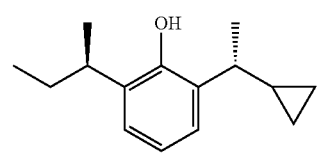 [SMILES: CC[C@@H](C)c1cccc([C@H](C)C2CC2)c1O]

Preparation of Compound 25 and Compound 26.

2-sec-butyl-6-((R)-1-cyclopropylethyl)phenol (Compound 24) (1 g) was separated under preparation condition: Instrument: Gilson GX-281/CH-Y-C0630. Column: CHIRALPAK OJ-H (4.6 mm×150 mmL, 5 μM); Mobile phase: hexane/isopropanol (v/v=100/0); Flow rate 1 mL/min, back pressure: 100 bar, column temperature 35° C., wave length 210 nm.

Two optical isomers were obtained by chiral separation: peak 1 (0.35 g, retention time: 4.977 min, light yellow oil, ee, 99%), peak 2 (0.32 g, retention time: 5.280 min, light yellow liquid, ee, 98%).

Example 27

2-sec-butyl-6-((S)-1-cyclopropylethyl)phenol (Compound 27)

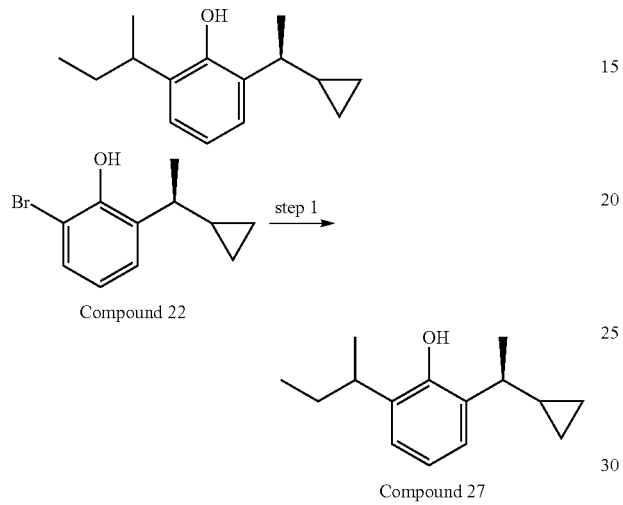

Under nitrogen atmosphere, S-2-bromo-6-(1-cyclopropylethyl)phenol (Compound 22) (30.0 g, 0.12 mol) was dissolved in dry tetrahydrofuran (300 mL), a solution of n-butyllithium (2.5 M in hexane, 0.36 mol) was added dropwise into the mixture. The mixture was stirred for 1.5 hours below 0° C., butanone (55.7 mL, 0.62 mol) was added dropwise into the mixture and the mixture was stirred for 30 minutes at −10° C. and warmed naturally up to room temperature and stirred overnight. The reaction was quenched with water (70 mL) at 0-5° C., stood and separated. The aqueous phase was extracted with ethyl acetate (100 mL×2). The combined layers were washed with saturated brine (50 mL×1), dried over anhydrous sodium sulfate for 10 minutes, concentrated under reduced pressure. The residue was purified by silica gel column chromatography (eluant: petroleum ether/ethyl acetate=100:1~50:1) to obtain crude product (35.5 g).

A solution of crude product (33.0 g) from the previous step in dichloromethane (165 mL) was added with triethylsilane (32.75 g, 0.24 mol) under nitrogen atmosphere, and trifluoroacetic acid (64.23 g, 0.48 mol) was added dropwise into the mixture below −30° C. After addition, the reaction was stirred below 5° C. for 2 hours. The reaction mixture was quenched with water (200 mL), stood and separated. The aqueous phase was extracted with dichloromethane (100 mL×2). The combined organic extracts were added with tetrabutylammonium fluoride trihydrate (100 g, 0.28 mol) and stirred at room temperature for 30 minutes, then water (500 mL) was added, stirred for 3 minutes, stood and separated. The aqueous layer was extracted with dichloromethane (100 mL×3). The combined organic extracts were washed with saturated brine (200 mL×1), dried over anhydrous sodium sulfate for 10 minutes, and concentrated under reduced pressure. The residue was purified by silica gel column chromatography (eluant: petroleum ether/ethyl acetate=100:1-50:1) to afford 2-sec-butyl-6-((S)-1-cyclopropylethyl)phenol (Compound 27) as a light yellow liquid (10.1 g, total yield of the two step: 37%).

$^1$H NMR (400 MHz, CDCl$_3$) δ7.09-7.12 (m, 1H), 7.00-7.02 (m, 1H), 6.89 (t, 1H), 4.88 (s, 1H), 2.87-2.93 (m, 1H), 2.46-2.56 (m, 1H), 1.55-1.69 (m, 2H), 1.29 (d, 3H), 1.24 (d, 3H), 1.02-1.08 (m, 1H), 0.89 (t, 3H), 0.53-0.58 (m, 1H), 0.43-0.49 (m, 1H), 0.16-0.23 (m, 2H).

MS M/Z (ESI): 217.3 (M−1).

Example 28

2-[(1S)-1-cyclopropylethyl]-6-[(1S)-1-methylpropyl]phenol (Compound 28)

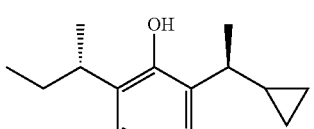

Example 29

2-[(1S)-1-cyclopropylethyl]-6-[(1R)-1-methylpropyl]phenol (Compound 29)

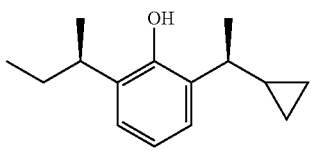 [SMILES: CC[C@@H](C)c1cccc([C@@H](C)C2CC2)c1O]

Preparation of Compound 28 and Compound 29.

2-sec-butyl-6-((S)-1-cyclopropylethyl)phenol (Compound 27) (500 mg) was separated under preparation condition: Agilent 1260/LH-Y-J0371(4-1), column: CHIRALCEL OJHS (0.46 cm I.D×15 cm L, 5 μM) Number: AD-H-44B, mobile phase: hexane/isopropanol=100/1 (v/v), flow rate: 1.0 mL/min, back pressure: 100 bar, column temperature: 35° C., wave length: 214 nm.

Two optical isomers were obtained: peak 1 (retention time: 3.61 min, 190 mg, light yellow liquid, ee, 99%), peak 2 (retention time: 4.21 min, 200 mg, light yellow liquid, ee, 99%).

Peak 1: $^1$H NMR (400 MHz, CDCl$_3$) δ7.09-7.12 (m, 1H), 7.00-7.02 (m, 1H), 6.89 (t, 1H), 4.88 (s, 1H), 2.87-2.93 (m, 1H), 2.46-2.56 (m, 1H), 1.55-1.69 (m, 2H), 1.29 (d, 3H), 1.24 (d, 3H), 1.02-1.08 (m, 1H), 0.89 (t, 3H), 0.53-0.58 (m, 1H), 0.43-0.49 (m, 1H), 0.16-0.23 (m, 2H).

MS M/Z (ESI): 217.3 (M−1).

Peak 2: $^1$H NMR (400 MHz, CDCl$_3$) δ7.09-7.12 (m, 1H), 7.00-7.02 (m, 1H), 6.89 (t, 1H), 4.88 (s, 1H), 2.87-2.93 (m, 1H), 2.46-2.56 (m, 1H), 1.55-1.69 (m, 2H), 1.29 (d, 3H), 1.24 (d, 3H), 1.02-1.08 (m, 1H), 0.89 (t, 3H), 0.53-0.58 (m, 1H), 0.43-0.49 (m, 1H), 0.16-0.23 (m, 2H).
MS M/Z (ESI): 217.3 (M−1).

Example 30

2-[(1R)-1-cyclopropylethyl]-6-methoxy-phenol (Compound 30)

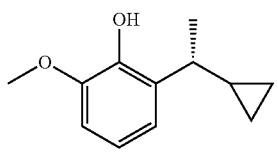

MS m/z (ESI): 191.1 [M−1].
¹HNMR (400 MHz, CDCl₃): δ 0.14 (m, 2H), 0.33 (m, 1H), 0.50 (m, 1H), 0.99 (m, 1H), 1.30 (d, 1H), 3.88 (s, 3H), 6.11 (dd, 1H), 6.80 (t, 1H), 6.9 (d, 1H).

Example 31

2-[(1R)-1-cyclopropylethyl]-6-methoxy-phenol (Compound 31)

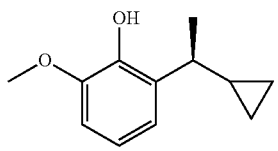

Compound 30 and Compound 31 were prepared as described for example 22.

Example 32

[2-[(1R)-1-cyclopropylethyl]-6-isopropyl-phenoxy]methyl2-(tertbutoxycarbonylamino)acetate (Compound 32)

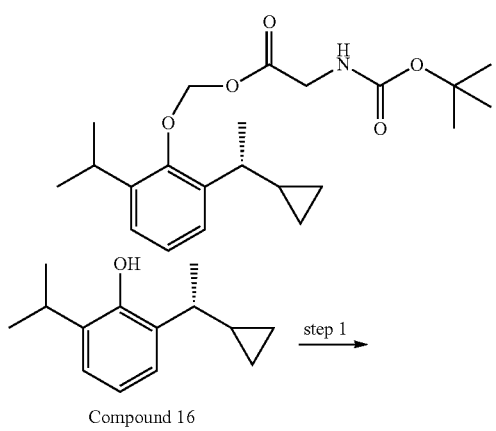

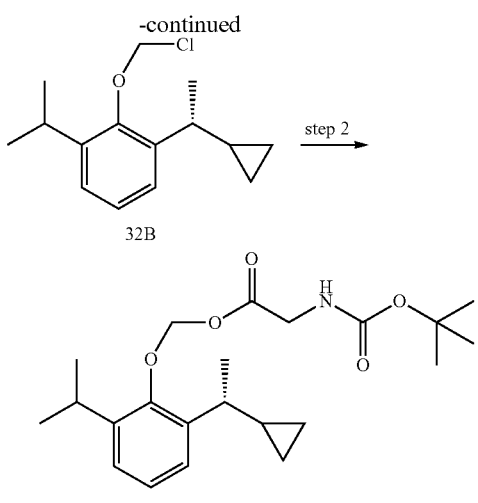

Step 1: 2-(chloromethoxy)-1-[(1R)-1-cyclopropyl-ethyl]-3-isopropyl-benzene (32B)

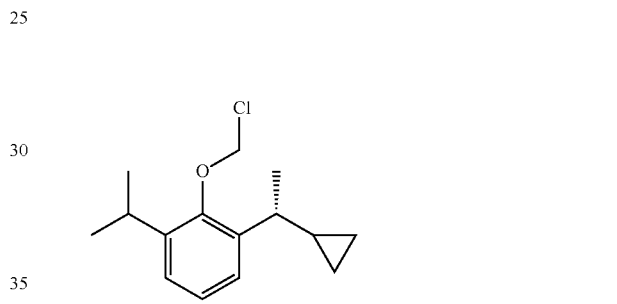

2-[(1R)-1-cyclopropylethyl]-6-isopropyl-phenol (Compound 16) (20.0 g, 0.098 mol), sodium hydroxide (7.84 g, 0.196 mol) and tetrahydrofuran (100 mL) were added into reaction flask, and the mixture was refluxed for 30 minutes, then bromochloromethane (380 g, 2.94 mol) was added into the mixture and the mixture was stirred at 70° C. for 2 h, filtered, the filtrate was concentrated under reduced pressure. The residue was purified by column chromatography (petroleum ether) to obtain crude product (32B) as colourless liquid, which was submitted to the next step without further purification.
¹H NMR (400 MHz, CDCl₃): δ 7.26-7.24 (m, 1H), 7.21-7.14 (m, 2H), 5.70 (s, 2H), 3.34-3.28 (m, 1H), 2.59-2.52 (m, 1H), 1.28 (d, 3H), 1.23 (dd, 6H), 0.95-0.93 (m, 1H), 0.56-0.54 (m, 1H), 0.35-0.33 (m, 1H), 0.24-0.15 (m, 2H).

Step 2: [2-[(1R)-1-cyclopropylethyl]-6-isopropyl-phenoxy]methyl2-(tertbutoxycarbonylamino)acetate (Compound 32)

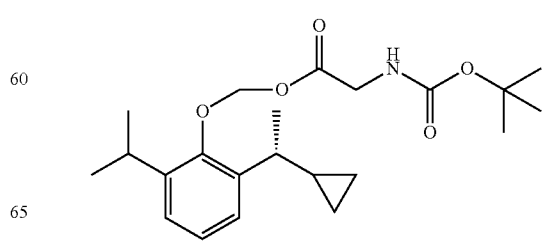

2-(chloromethoxy)-1-[(1R)-1-cyclopropylethyl]-3-isopropyl-benzene (32B) (0.253 g, 1 mmol), bis-boc-aminooxyacetic acid (0.385 g, 2.2 mmol), triethylamine (0.3 mL, 2.2 mmol) and acetonitrile (5 mL) were added into reaction flask accordingly and then were stirred at 60° C. for 2 h. The reaction mixture was concentrated under reduced pressure. The residue was purified by silica gel column chromatography (petroleum ether/ethyl acetate (v/v)=80:1) to afford 2-sec-butyl-6-((S)-1-cyclopropylethyl)phenol (Compound 32) as colourless liquid (0.36 g, yield: 92.3%).

$^1$H NMR (400 MHz, CDCl$_3$): δ 7.24-7.12 (m, 3H), 5.57 (q, 2H), 4.99 (s, 1H), 3.96 (d, 2H), 3.30-3.24 (m, 1H), 2.47-2.43 (m, 1H), 1.45 (s, 9H), 1.28-1.21 (m, 9H), 0.90-0.88 (m, 1H), 0.55-0.50 (m, 1H), 0.36-0.33 (m, 1H), 0.24-0.21 (m, 1H), 0.16-0.13 (m, 1H).

Example 33 dibenzyl [2-[(1R)-1-cyclopropylethyl]-6-isopropyl-phenoxy]methyl phosphate (Compound 33)

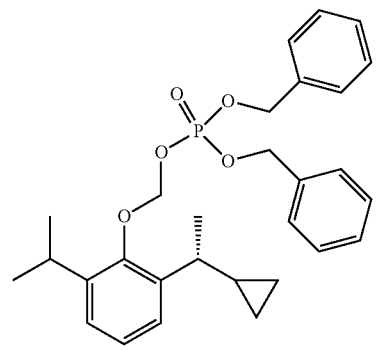

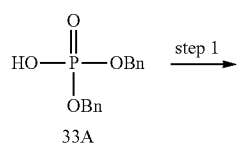
33A

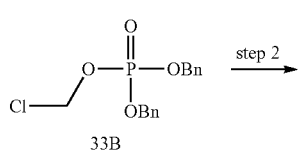
33B

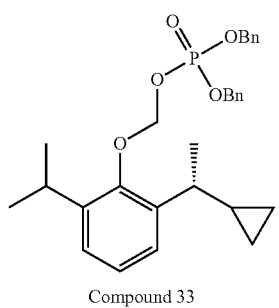
Compound 33

Step 1: Dibenzyl Chloromethyl Phosphate (33B)

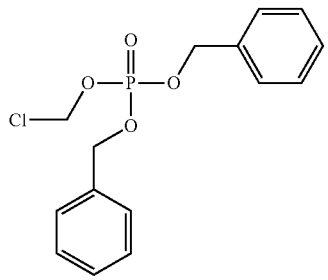 [SMILES: O=P(OCCl)(OCc1ccccc1)OCc1ccccc1]

Dibenzyl phosphate (33A) (5.0 g, 0.018 mol) was dissolved into a mixture of dichloromethane (50 mL) and water (50 mL), then, tetrabutylammonium sulphate (1.22 g, 0.0036 mol) and sodium bicarbonate (6.0 g, 0.072 mol) was added under ice-water bath, followed by adding chloromethanesulfonyl chloride (2.97 g, 1.9 mL), and the mixture was stirred overnight at room temperature, stood and separated, and extracted with dichloromethane (50 mL). The combined organic extracts were washed with saturated brine (100 mL×2), dried over anhydrous sodium sulfate, concentrated under reduced pressure. The residue was purified by silica gel column chromatography (petroleum ether/ethyl acetate (v/v)=5:1→3:1, gradient elution) to afford dibenzyl chloromethyl phosphate (33B) as a colorless liquid (4.35 g, yield: 74.1%).

$^1$H NMR (400 MHz, CDCl$_3$): δ 7.36-7.26 (m, 10H), 5.63 (d, 2H), 5.10 (d, 4H).

Step 2: Dibenzyl [2-[(1R)-1-cyclopropylethyl]-6-isopropyl-phenoxy]methyl phosphate (Compound 33)

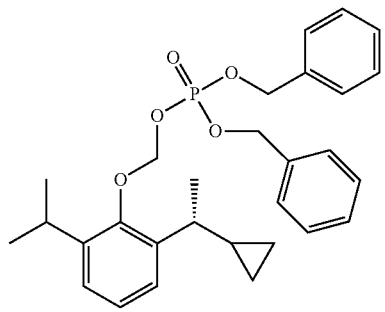 [SMILES: CC(C)c1cccc([C@H](C)C2CC2)c1OCOP(=O)(OCc1ccccc1)OCc1ccccc1]

2-[(1R)-1-cyclopropylethyl]-6-isopropyl-phenol (Compound 16) (1.0 g, 4.9 mmol) was dissolved in dichloromethane (5 mL), tetrabutylammonium bromide (0.32 g, 0.98 mmol) and aqueous solution of sodium hydroxide (0.98 g in 5 mL water, 24.5 mmol) were added into the mixture, followed by a thorough stirring. Then a solution of dibenzyl chloromethyl phosphate (33B) (1.75 g, 5.4 mmol) in dichloromethane (5 mL) was added, and the mixture was stirred at room temperature for 8 h. Dichloromethane (30 mL) was added into the reaction mixture, and the mixture was washed with water (30 mL×2), dried over anhydrous sodium sulfate, filtered and the filtrate was concentrated. The residue was purified by silica gel column chromatography (petroleum ether/ethyl acetate (v/v)=40:1) to obtain dibenzyl [2-[(1R)-

1-cyclopropylethyl]-6-isopropyl-phenoxy]methyl phosphate (Compound 33) as an anhydrous colorless liquid (1.07 g, yield: 45%).

$^1$H NMR (400 MHz, CDCl$_3$): δ 7.33-7.11 (m, 13H), 5.36 (q, 2H), 5.05-4.94 (m, 4H), 3.34-3.27 (m, 1H), 2.55-2.48 (m, 1H), 1.23 (d, 3H), 1.18 (d, 6H), 0.94-0.88 (m, 1H), 0.51-0.48 (m, 1H), 0.32-0.29 (m, 1H), 0.20-0.12 (m, 2H).

Example 34

[2-[(1R)-1-cyclopropylethyl]-6-isopropyl-phenoxy]methyl 2,2-dimethylpropanoate (Compound 34)

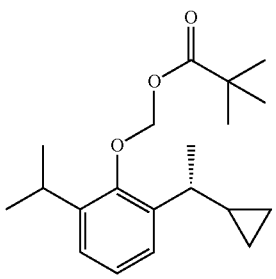

Compound 16 step 1

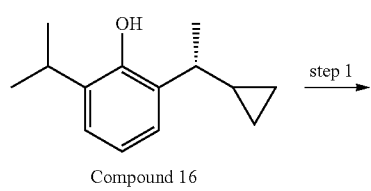

Compound 34

2-[(1R)-1-cyclopropylethyl]-6-isopropyl-phenol (Compound 16) (1.0 g, 4.9 mmol) was dissolved in dichloromethane (5 mL), and then tetrabutylammonium bromide (0.32 g, 0.98 mmol) and anhydrous solution of sodium hydroxide (0.98 g in 5 mL water, 24.5 mmol) were added, after mixing thoroughly, a solution of chloromethyl pivalate (0.74 g, 4.9 mmol, DEMO chem) in dichloromethane (5 mL) was added. The reaction mixture was stirred at room temperature overnight, and dichloromethane (30 mL) was added, the resulting mixture was washed with water (30 mL×2). The combined organic layers were dried over anhydrous sodium sulfate, concentrated and filtered. The concentrated filtrate was purified by silica gel column chromatography (petroleum ether) to afford [2-[(1R)-1-cyclopropylethyl]-6-isopropyl-phenoxy]methyl2,2-dimethylpropanoate (Compound 34) as a colorless liquid (0.78 g, yield: 50%).

$^1$H NMR (400 MHz, CDCl$_3$): δ 7.26-7.13 (m, 3H), 5.52 (dd, 2H), 3.41-3.34 (m, 1H), 2.59-2.51 (m, 1H), 1.24-1.19 (m, 18H), 0.96-0.93 (m, 1H), 0.55-0.53 (m, 1H), 0.25-0.23 (m, 1H), 0.20-0.18 (m, 2H).

Example 35

[[2-[(1R)-1-cyclopropylethyl]-6-isopropyl-phenoxy]methoxy-(2,2-dimethylpropanoyloxymethoxy)phosphoryl]oxymethyl 2,2-dimethylpropanoate (Compound 35)

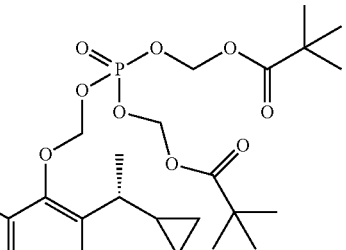

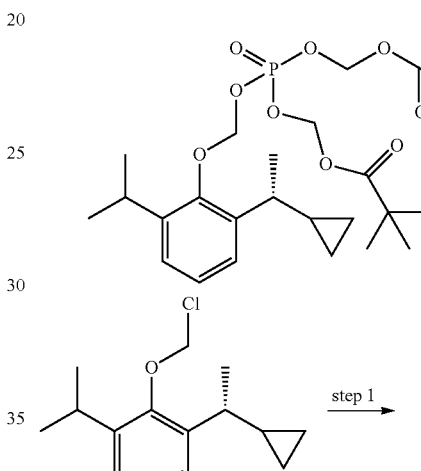

32B step 1

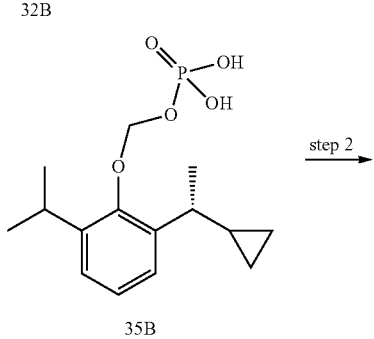

35B step 2

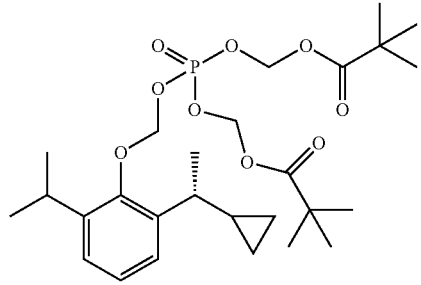

Compound 35

Step 1: [2-[(1R)-1-cyclopropylethyl]-6-isopropyl-phenoxy]methyl dihydrogen phosphate (35B)

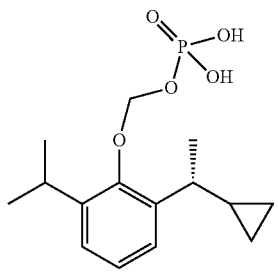 [SMILES: CC(C)c1cccc([C@H](C)C2CC2)c1OCOP(=O)(O)O]

Acetonitrile (100 mL), triethylamine (20.2 g, 0.2 mol) and phosphorous acid (15.68 g, 0.16 mol) were added into reaction flask accordingly, and then were stirred at 60° C. for 30 minutes, then a solution of 2-(chloromethoxy)-1-[(1R)-1-cyclopropylethyl]-3-isopropyl-benzene (32B) (5.0 g, 0.02 mol) in acetonitrile (15 mL) was added, the mixture was stirred at 70° C. for another 1 h. The reaction mixture was filtered and concentrated under reduced pressure. The residue was dissolved in water (100 mL), and the pH of the mixture was adjusted with 3M hydrochloric acid to 2, and then was extracted with toluene (100 mL×3). The organic phases were combined and then washed with saturated brines (100 mL×2), and then dried over anhydrous sodium sulfate, filtered, and the filtrate was concentrated to obtain [2-[(1R)-1-cyclopropylethyl]-6-isopropyl-phenoxy]methyl dihydrogen phosphate (35B) as a light yellow liquid (3.0 g, yield 47.7%).

Step 2: [[2-[(1R)-1-cyclopropylethyl]-6-isopropyl-phenoxy]methoxy-(2,2-dimethylpropanoyloxymethoxy)phosphoryl]oxymethyl 2,2-dimethylpropanoate (Compound 35)

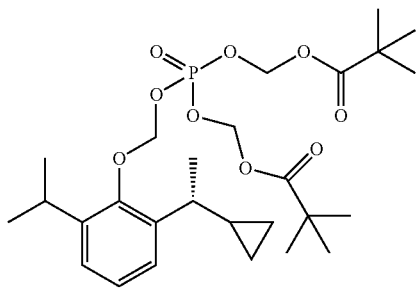 [SMILES: CC(C)c1cccc([C@H](C)C2CC2)c1OCOP(=O)(OCOC(=O)C(C)(C)C)OCOC(=O)C(C)(C)C]

[2-[(1R)-1-cyclopropylethyl]-6-isopropyl-phenoxy]methyl dihydrogen phosphate (35B) (0.442 g, 1.41 mmol) was dissolved in acetonitrile (3 mL), and then iodomethyl pivalate (0.74 g, 4.9 mmol, demo chem) and triethylamine (0.7 g) were added in sequence, the mixture was stirred at room temperature over night, and concentrated. The residue was dissolved in ethyl acetate (10 mL), washed with water (30 mL×2), saturated brine (10 mL×2). The organic layer was dried over anhydrous sodium sulfate, concentrated under reduced pressure. The residue was purified by silica gel column chromatography (petroleum ether/ethyl acetate (v/v)=60:1→10:1, gradient elution) to give [[2-[(1R)-1-cyclopropylethyl]-6-isopropyl-phenoxy]methoxy-(2,2-dimethylpropanoyloxymethoxy)phosphoryl]oxymethyl 2,2-dimethylpropanoate (Compound 35) as a yellow liquid (68 mg, yield: 10%).

$^1$H NMR (400 MHz, CDCl$_3$): δ 7.25-7.12 (m, 3H), 5.62 (q, 4H), 5.45 (d, 2H), 3.32-3.25 (m, 1H), 2.50-2.46 (m, 1H), 1.26-1.19 (m, 27H), 0.94-0.90 (m, 1H), 0.54-0.51 (m, 1H), 0.33-0.31 (m, 1H), 0.24-0.22 (m, 1H), 0.16-0.13 (m, 1H).

Example 36

[[2-[(1R)-1-cyclopropylethyl]-6-isopropyl-phenoxy]methoxy-(isopropoxycarbonyloxymethoxy)phosphoryl]oxymethyl isopropyl carbonate (Compound 36)

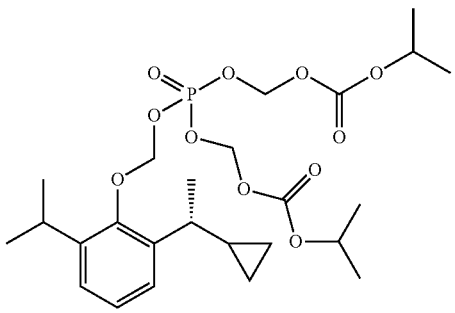

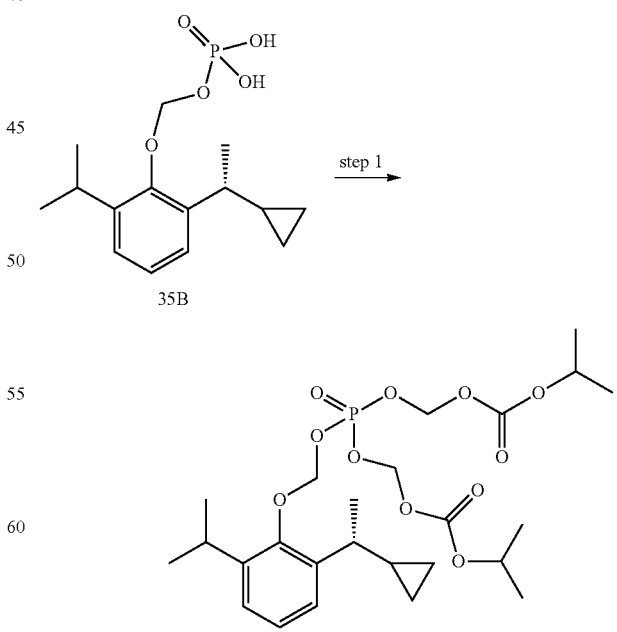

Compound 36

Step 1: [[2-[(1R)-1-cyclopropylethyl]-6-isopropyl-phenoxy]methoxy-(isopropoxycarbonyloxymethoxy)phosphoryl]oxymethyl isopropyl carbonate (Compound 36)

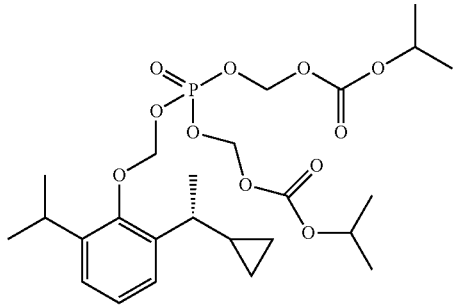 [SMILES: CC(C)OC(=O)OCOP(=O)(OCOC(=O)OC(C)C)OCOc1c(C(C)C)cccc1[C@H](C)C1CC1]

[2-[(1R)-1-cyclopropylethyl]-6-isopropyl-phenoxy]methyl dihydrogen phosphate (35B) (0.8 g, 2.55 mmol) was dissolved in tetrahydrofuran (4 mL), chloromethyl isopropyl carbonate (1.95 g, 12.75 mmol) and triethylamine (1.29 g, 12.75 mmol) were added successively. The reaction mixture was stirred at 60° C. for 3 h, concentrated under reduced pressure. The residue was dissolved by ethyl acetate (30 mL), and washed with water (30 mL×2). The organic phase was dried by anhydrous sodium sulfate, then was filtered and the filtrate was concentrated in reduce pressure. The residue was purified by silica gel column chromatography (petroleum ether/ethyl acetate (v/v)=20:1→5:1) to obtain [[2-[(1R)-1-cyclopropylethyl]-6-isopropyl-phenoxy]methoxy-(isopropoxycarbonyloxymethoxy)phosphoryl]oxymethyl isopropyl carbonate (Compound 36) as a colorless liquid (189 mg, yield: 13.6%).

$^1$H NMR (400 MHz, CDCl$_3$): δ 7.24-7.12 (m, 3H), 5.62 (q, 4H), 5.47 (d, 2H), 4.94-4.88 (m, 2H), 3.32-3.25 (m, 1H), 2.50-2.46 (m, 1H), 1.31-1.20 (m, 21H), 0.94-0.86 (m, 1H), 0.54-0.51 (m, 1H), 0.34-0.31 (m, 1H), 0.27-0.23 (m, 1H), 0.17-0.13 (m, 1H).

Example 37 ethyl2-[[2-[(1R)-1-cyclopropylethyl]-6-isopropyl-phenoxy]methoxy-(2-ethoxy-2-oxoethoxy)phosphoryl]oxyacetate (Compound 37)

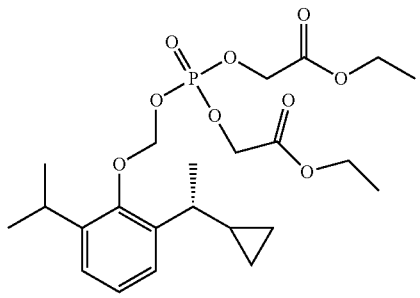

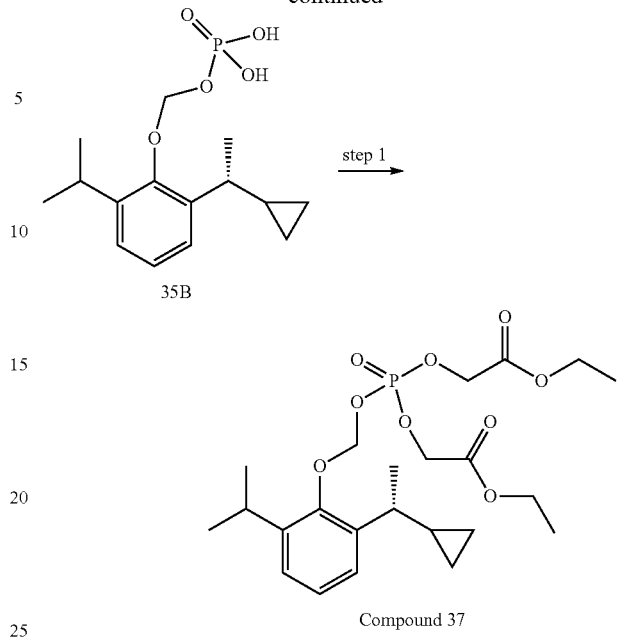

Compound 37

Step 1: ethyl2-[[2-[(1R)-1-cyclopropylethyl]-6-isopropyl-phenoxy]methoxy-(2-ethoxy-2-oxoethoxy)phosphoryl]oxyacetate (Compound 37)

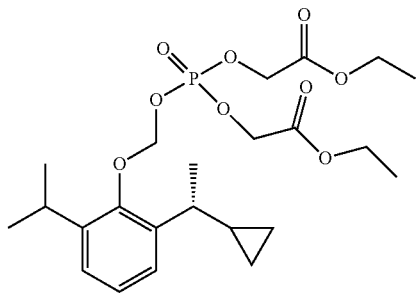 [SMILES: CCOC(=O)COP(=O)(OCOc1c(C(C)C)cccc1[C@H](C)C1CC1)OCC(=O)OCC]

[2-[(1R)-1-cyclopropylethyl]-6-isopropyl-phenoxy]methyl dihydrogen phosphate (35B) (0.8 g, 2.55 mmol) was dissolved in tetrahydrofuran (4 mL), ethyl bromoacetate (2.12 g, 12.75 mmol) and triethylamine (1.29 g, 12.75 mmol) were added successively, and stirred at 60° C. for 3 h, concentrated. The residue was dissolved by ethyl acetate (30 mL), and washed by water (30 mL×2). The organic phase was dried by anhydrous sodium sulfate, then was filtered and the filtrate was concentrated in reduce pressure. The residue was purified by silica gel column chromatography (petroleum ether/ethyl acetate (v/v)=30:1→20:1) to obtain ethyl2-[[2-[(1R)-1-cyclopropylethyl]-6-isopropyl-phenoxy]methoxy-(2-ethoxy-2-oxo ethoxy)phosphoryl]oxyacetate (Compound 37) as colorless liquid (252 mg, yield: 20.3%).

$^1$H NMR (400 MHz, CDCl$_3$): δ 7.25-7.12 (m, 3H), 5.54 (d, 2H), 4.63-4.48 (m, 4H), 4.24-4.21 (m, 4H), 3.35-3.28 (m, 1H), 2.54-2.50 (m, 1H), 1.28-1.21 (m, 15H), 0.94-0.88 (m, 1H), 0.54-0.51 (m, 1H), 0.34-0.32 (m, 1H), 0.26-0.22 (m, 1H) 0.17-0.16 (m, 1H).

Example 38

[2-[(1R)-1-cyclopropylethyl]-6-isopropyl-phenoxy]methyl 2-acetoxybenzoate (Compound 38)

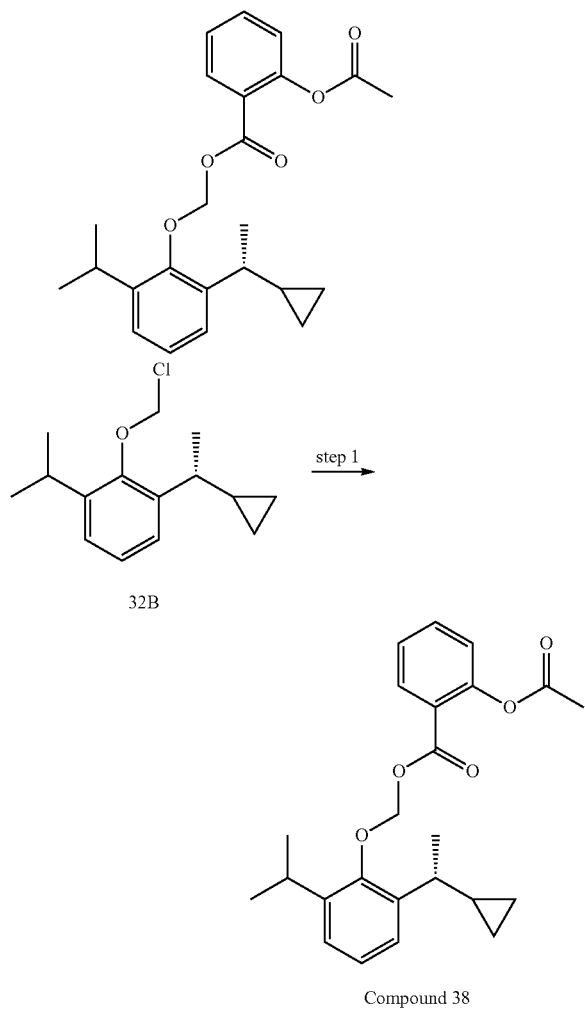

Step 1: [2-[(1R)-1-cyclopropylethyl]-6-isopropyl-phenoxy]methyl 2-acetoxybenzoate (Compound 38)

2-(chloromethoxy)-1-[(1R)-1-cyclopropylethyl]-3-isopropyl-benzene (32B) (253 mg, 1 mmol) and acetonitrile (5 mL) was added into the reaction flask, then, 2-(acetyloxy) benzoic acid (0.4 g, 2.2 mmol) and triethylamine (0.223 g, 2.2 mmol) were added in sequence. The reaction mixture was heated to 60° C. and stirred overnight under nitrogen atmosphere, filtered, and the filtrate was concentrated. The residue was purified by silica gel column chromatography (petroleum ether/ethyl acetate (v/v)=40:1) to afford [2-[(1R)-1-cyclopropylethyl]-6-isopropyl-phenoxy]methyl 2-acetoxybenzoate (Compound 38) as yellow liquid (0.356 g, yield: 90%).

$^1$H NMR (400 MHz, CDCl$_3$): δ 7.87 (d, 1H), 7.44 (t, 1H), 7.15 (t, 1H), 7.07 (d, 1H), 7.04-6.98 (m, 3H), 5.56 (s, 2H), 3.22-3.15 (m, 1H), 2.40-2.33 (m, 1H), 2.17 (s, 3H), 1.10-1.05 (m, 9H), 0.78-0.75 (m, 1H), 0.35-0.33 (m, 1H), 0.19-0.15 (m, 1H), 0.03-0.01 (m, 2H).

Example 39

O1-tert-butyl O2-[[2-[(1R)-1-cyclopropylethyl]-6-isopropyl-phenoxy]methyl]pyrrolidine-1,3-dicarboxylate (Compound 39)

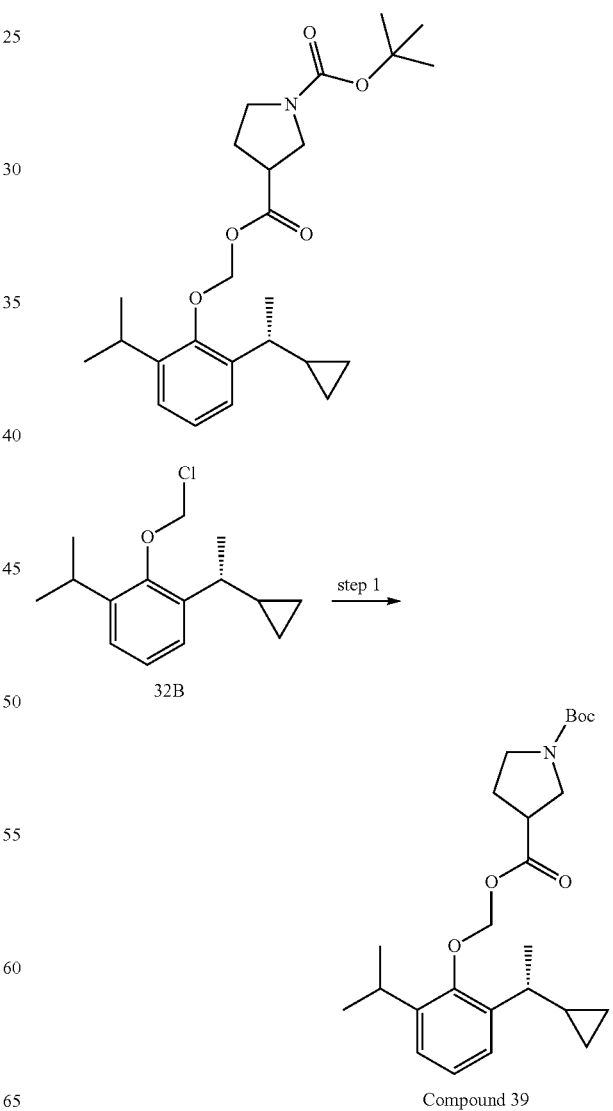

137

Step 1: O1-tert-butyl O2-[[2-[(1R)-1-cyclopropyl-ethyl]-6-isopropyl-phenoxy]methyl]pyrrolidine-1,3-dicarboxylate (Compound 39)

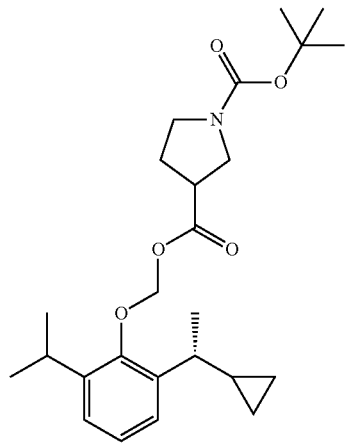 [SMILES: CC(C)c1cccc([C@H](C)C2CC2)c1OCOC(=O)C1CCN(C(=O)OC(C)(C)C)C1]

2-(chloromethoxy)-1-[(1R)-1-cyclopropylethyl]-3-isopropyl-benzene (32B) (0.253 g, 1 mmol) was dissolved in acetonitrile (5 mL), 1-boc-pyrrolidine-3-carboxylic acid (0.474 g, 2.2 mmol) and triethylamine (0.223 g, 2.2 mmol) were added. The reaction mixture was stirred at 60° C. for 3 h under nitrogen atmosphere, filtered and the filtrate was concentrated. The residue was purified by silica gel column chromatography (petroleum ether/ethyl acetate (v/v)=40:1) to obtain O1-tert-butylO2-[[2-[(1R)-1-cyclopropylethyl]-6-isopropyl-phenoxy]methyl]pyrrolidine-1,3-dicarboxylate (Compound 39) as a yellow liquid (0.345 g, yield: 80%).

$^1$H NMR (400 MHz, CDCl$_3$): δ 7.24-7.12 (m, 3H), 5.56-5.53 (m, 2H), 3.64-3.61 (m, 1H), 3.53-3.52 (m, 2H), 3.38-3.26 (m, 2H), 3.09-3.05 (m, 1H), 2.48-2.46 (m, 1H), 2.17-2.11 (m, 2H), 1.46 (s, 9H), 1.25-1.21 (m, 9H), 0.94-0.90 (m, 1H), 0.36-0.33 (m, 1H), 0.22-0.20 (m, 1H), 0.17-0.14 (m, 2H).

Example 40

2-[[2-[(R)-1-cyclopropylethyl]-6-isopropylphenoxy]methyl]-4H-benzod[1,3,2]dioxa phosphinine 2-oxide (Compound 40)

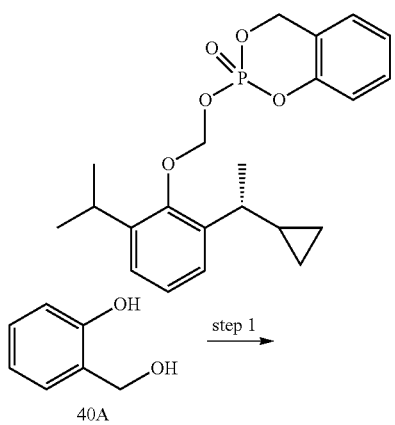

138

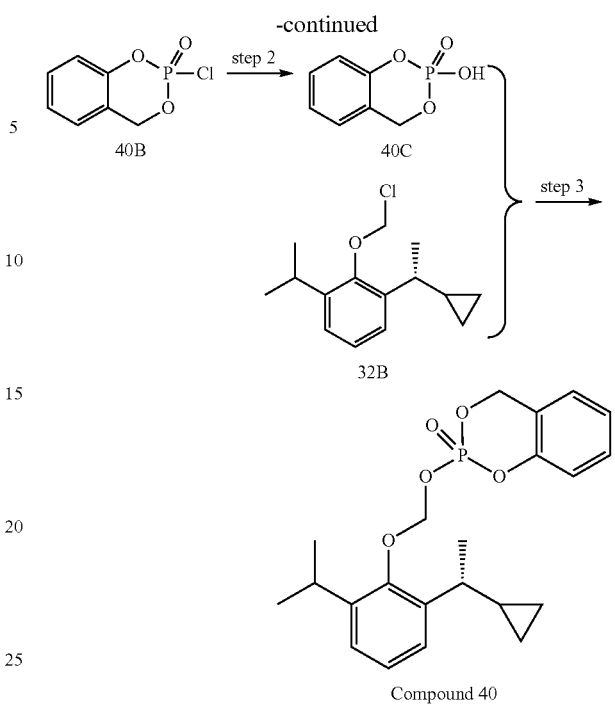

Compound 40

Step 1: 2-chloro-4H-benzo[d][1,3,2]dioxaphosphinine 2-oxide (40B)

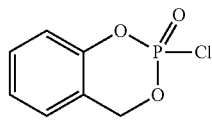 [SMILES: O=P1(Cl)OCc2ccccc2O1]

Phosphorous oxychloride (13.59 g, 88.61 mmol), tetrahydrofuran (100 mL) and triethylamine (17.12 g, 169.17 mmol) were added into the reaction flask in sequence and was cooled down to −70° C. under ice bath, saligenin (40A) (10.0 g, 80.56 mmol) was added under nitrogen atmosphere while maintaining the temperature below −50° C. Upon completion of the addition, the reaction mixture was stirred for 1 h at −50° C. for 1 h and slowly warmed to room temperature over 4 h, filtered and concentrated to obtain 2-chloro-4H-benzo[d][1,3,2]dioxaphosphinine 2-oxide (40B) as a dark brown liquid (18.00 g, crude product), which was submitted to the next step without further purification.

Step 2: 2-hydroxy-4H-benzo[d][1,3,2]dioxaphosphinine 2-oxide (40C)

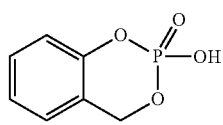 [SMILES: O=P1(O)OCc2ccccc2O1]

2-chloro-4H-benzo[d][1,3,2]dioxaphosphinine 2-oxide (40B) (2.04 g, 10.00 mmol) and water (10 mL) were added into the reaction flask in sequence, the mixture was stirred for 2 h at room temperature. The reaction mixture was washed with ethyl acetate (40 mL×3) until the organic layer was colorless. The aqueous layer was collected and concentrated to provide 2-hydroxy-4H-benzo[d][1,3,2]dioxaphosphinine 2-oxide (40C) as a white solid (1.0 g, yield: 54.5%, crude product), which was submitted to the next step without further purification.

MS m/z (ESI): 185.0 [M−1].

¹HNMR (400 MHz, D₂O): δ 7.62 (t, 1H), δ 7.47 (d, 2H), δ 7.43-7.40 (m, 1H) δ 7.30 (d, 1H), δ 5.55 (d, 2H).

Step 3: 2-[[2-[(R)-1-cyclopropylethyl]-6-isopropyl-phenoxy]methoxy]-4Hbenzo[d][1,3,2]dioxaphosphinine 2-oxide (Compound 40)

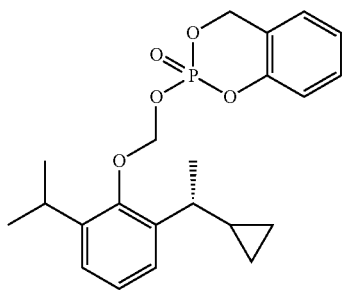 [SMILES: CC(C)c1cccc([C@H](C)C2CC2)c1OCOP1(=O)OCc2ccccc2O1]

2-hydroxy-4H-benzo[d][1,3,2]dioxaphosphinine 2-oxide (40C) (0.2 g, 1.10 mmol), triethylamine (0.9 g, 8.80 mmol) and acetonitrile (20 mL) were added into the reaction flask, the mixture was stirred at 50° C. for 0.5 h, and 2-(chloromethoxy)-1-[(1R)-1-cyclopropylethyl]-3-isopropyl-benzene (32B) (1.00 g, 3.96 mmol) was added, and heated at 70° C. for 20 h. The resulting mixture was concentrated and dissolved in water (30 mL), then was extracted with ethyl acetate (30 mL×3), washed with saturated brine (30 mL×3). The combined organic extracts were dried over anhydrous sodium sulfate, filtered and evaporated under vacuum. The residue was purified by silica gel column chromatography (petroleum ether/ethyl acetate (v/v)=7:1) to obtain 2-[[2-[(R)-1-cyclopropylethyl]-6-isopropylphenoxy]methoxy]-4Hbenzo[d][1,3,2]dioxaphosphinine 2-oxide (Compound 40) as a light yellow liquid (0.34 g, yield: 27.6%, HPLC: 93.0%).

¹HNMR (400 MHz, CDCl₃): δ 7.31 (t, 1H), δ 7.21-7.02 (m, 6H), δ 5.63-5.59 (m, 1H), δ 5.51 (dd, 1H), δ 5.35-5.28 (m, 2H), δ 3.26-3.17 (m, 1H), δ 2.47-2.39 (m, 1H), δ 1.18 (dd, 3H), δ 1.14-1.10 (m, 6H), δ 0.95-0.85 (m, 1H), δ 0.52-0.46 (m, 1H), δ 0.32-0.26 (m, 1H), δ 0.12-0.06 (m, 2H).

Example 41

[2-(1-cyclopropylethyl)-6-isopropyl-phenoxy]methyl diethyl phosphate (Compound 41)

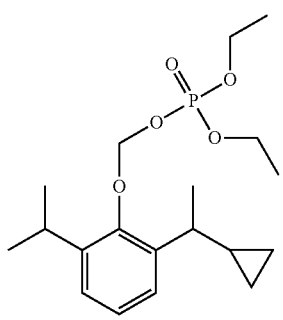

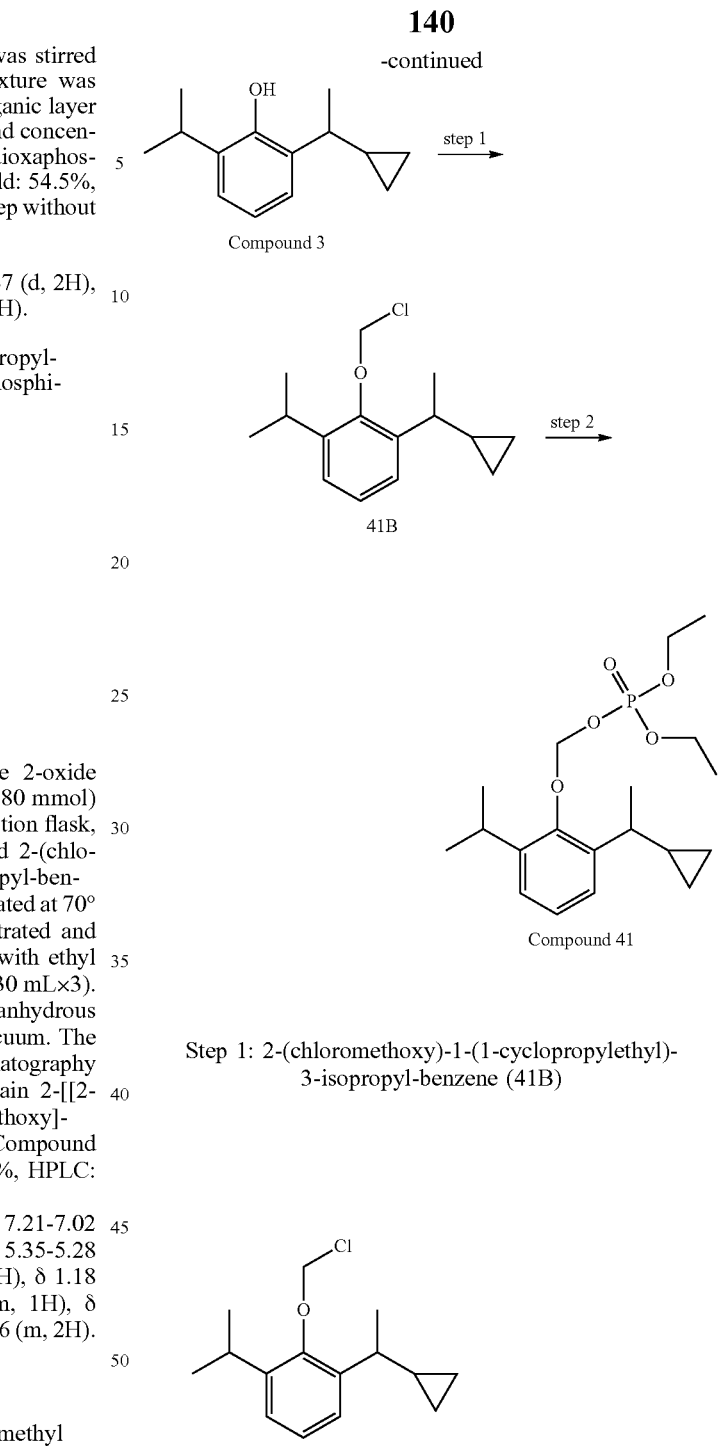

Step 1: 2-(chloromethoxy)-1-(1-cyclopropylethyl)-3-isopropyl-benzene (41B)

2-(1-cyclopropylethyl)-6-isopropylphenol (Compound 3) (10.00 g, 48.95 mmol), tetrahydrofuran (50 mL) and sodium hydroxide (3.92 g, 97.89 mmol) were added into the reaction flask in sequence, the mixture was stirred at 60° C. for 0.5 h under nitrogen atmosphere, and then bromochloromethane (189.98 g, 1470.00 mmol) was added. After being stirred for 3 h at 70° C., the resulting mixture was filtered and concentrated. The residue was purified by silica gel column chromatography (petroleum ether) to afford 2-(chloromethoxy)-1-(1-cyclopropylethyl)-3-isopropyl-benzene (41B) as a colorless oil (10.0 g, crude product, yield: 78.7%).

Step 2:
[2-(1-cyclopropylethyl)-6-isopropyl-phenoxy]methyl diethyl phosphate (Compound 41)

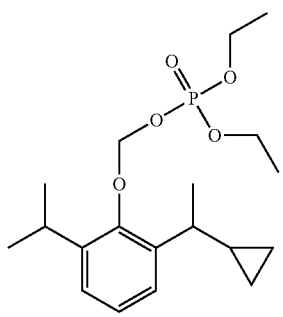 [SMILES: CCOP(=O)(OCC)OCOc1c(C(C)C)cccc1C(C)C1CC1]

Phosphate (1.22 g, 7.91 mmol), triethylamine (0.84 g, 8.30 mmol) and acetonitrile (20 mL) were added into the reaction flask, the mixture was stirred at 60° C. for 0.5 h, and 2-(chloromethoxy)-1-(1-cyclopropylethyl)-3-isopropyl-benzene (41B) (1.00 g, 3.96 mmol) was added. The reaction was stirred at 70° C. for 12 h, concentrated. The residue was added in water (30 mL), extracted with tert-Butyl methyl ether (30 mL×3), the combined organic extracts were washed with saturated brine (30 mL×3), dried over anhydrous sodium sulfate, filtered and evaporated under vacuum. The residue was purified by silica gel column chromatography (petroleum ether/ethyl acetate (v/v)=4:1) to obtain [2-(1-cyclopropylethyl)-6-isopropyl-phenoxy]methyl diethyl phosphate (Compound 41) as a light yellow liquid (0.4 g, yield: 27.4%, HPLC: 95.6%).

¹HNMR (400 MHz, CDCl₃): δ 7.25-7.22 (m, 1H), δ 7.18-7.12 (m, 2H), δ 5.42-5.37 (m, 2H), δ 4.13-4.03 (m, 4H), δ 3.37-3.30 (m, 1H), δ 2.58-2.50 (m, 1H), δ 1.33-1.29 (m, 6H), δ 1.27 (d, 3H), δ 1.22 (dd, 6H), δ 1.00-0.91 (m, 1H), δ 0.58-0.51 (m, 1H), δ 0.37-0.32 (m, 1H), δ 0.26-0.12 (m, 2H).

Example 42

O1-tert-butyl O2-[[2-[(1R)-1-cyclopropylethyl]-6-isopropyl-phenoxy]methyl]pyrrolidine-1,2-dicarboxylate (Compound 42)

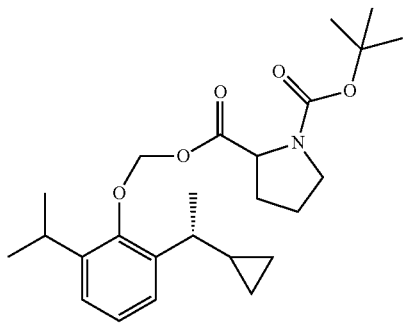

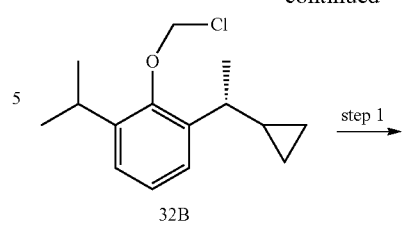

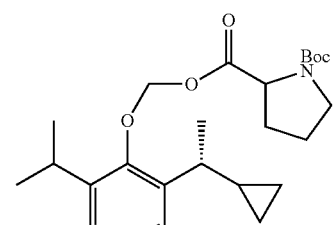

Step 1: O1-tert-butylO2-[[2-[(1R)-1-cyclopropyl-ethyl]-6-isopropyl-phenoxy]methyl]pyrrolidine-1,2-dicarboxylate (Compound 42)

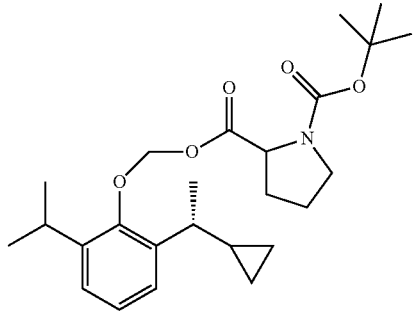 [SMILES: CC(C)c1cccc([C@H](C)C2CC2)c1OCOC(=O)C1CCCN1C(=O)OC(C)(C)C]

2-(chloromethoxy)-1-[(1R)-1-cyclopropylethyl]-3-isopropyl-benzene (32B) (0.253 g, 1 mmol) was dissolved in acetonitrile (5 mL), 1-(tert-butoxycarbonyl)pyrrolidine-2-carboxylic acid (0.474 g, 2.2 mmol) and triethylsilane (0.223 g, 2.2 mmol) were added. The mixture was stirred at 60° C. for 3 h under nitrogen atmosphere. The resulting mixture was filtered and concentrated. The residue was purified by silica gel column chromatography (petroleum ether/ethyl acetate (v/v)=40:1) to afford O1-tert-butylO2-[[2-[(1R)-1-cyclopropylethyl]-6-isopropyl-phenoxy]methyl]pyrrolidine-1,2-dicarboxylate (Compound 42) as a yellow liquid (0.333 g, yield: 77%).

¹H NMR (400 MHz, CDCl₃): δ 7.24-7.14 (m, 3H), 5.73-5.37 (m, 2H), 4.32-4.21 (m, 1H), 3.56-3.31 (m, 3H), 2.55-2.50 (m, 1H), 2.25-2.15 (m, 1H), 2.10-1.80 (m, 3H), 1.46 (s, 3H), 1.27 (s, 6H), 1.26-1.20 (m, 9H), 0.94-0.90 (m, 1H), 0.56-0.54 (m, 1H), 0.23-0.20 (m, 1H), 0.18-0.16 (m, 1H), 0.15-0.13 (m, 1H).

Example 43

Ethyl2-[[[2-(1-cyclopropylethyl)-6-isopropyl-phenoxy]-[(2-ethoxy-2-oxoethyl)amino]phosphoryl]amino]acetate (Compound 43)

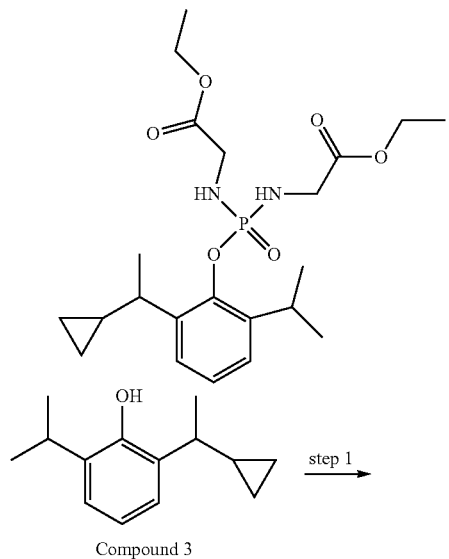

Step 1: ethyl2-[[[2-(1-cyclopropylethyl)-6-isopropyl-phenoxy]-[(2-ethoxy-2-oxo-ethyl)amino]phosphoryl]amino]acetate (Compound 43)

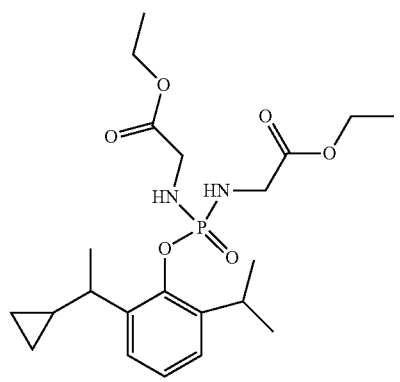 [SMILES: CCOC(=O)CNP(=O)(NCC(=O)OCC)Oc1c(C(C)C)cccc1C(C)C1CC1]

Phosphorous oxychloride (3.3 g, 21.54 mmol), dichloromethane (100 mL) and triethylsilane (9.91 g, 97.89 mmol) were added into the reaction flask in sequence, the mixture was cooled to 0° C. under nitrogen atmosphere, and 2-(1-cyclopropylethyl)-6-isopropylphenol (Compound 3) (4.0 g, 19.58 mmol) was added below 10° C. After addition, the reaction mixture was warmed up to room temperature and stirred for 1 h, then glycine ethyl ester hydrochloride (8.20 g, 58.73 mmol) was added and the mixture was stirred for 20 h. The resulting mixture was filtered and concentrated. The residue was purified by silica gel column chromatography (petroleum ether/ethyl acetate (v/v)=3:1) to obtain ethyl2-[[[2-(1-cyclopropylethyl)-6-isopropyl-phenoxy]-[(2-ethoxy-2-oxo-ethyl)amino]phosphoryl]amino]acetate (Compound 43) as a colorless thick liquid (1.51 g, yield: 17%, HPLC: 87.86%).

$^1$HNMR (400 MHz, CDCl$_3$): δ 7.26-7.23 (m, 1H), δ 7.16-7.12 (m, 2H), δ 4.23-4.18 (m, 4H), δ 3.85-3.81 (m, 2H), δ 3.74-3.67 (m, 2H), δ 3.46-3.37 (m, 3H), δ 2.74-2.67 (m, 1H), δ 1.29-1.22 (m, 15H), δ 1.00-0.92 (m, 1H), δ 0.58-0.51 (m, 1H), δ 0.40-0.33 (m, 1H), δ 0.28-0.15 (m, 2H).

MS m/z (ESI): 455.4 [M+1].

Example 44 ethyl2-[[[2-[(1R)-1-cyclopropylethyl]-6-isopropyl-phenoxy]-[(2-ethoxy-2-oxoethyl)amino]phosphoryl]amino]acetate (Compound 44)

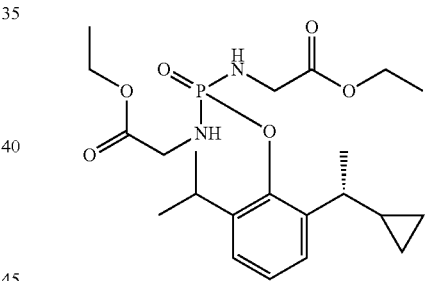

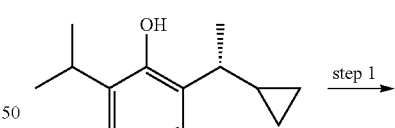

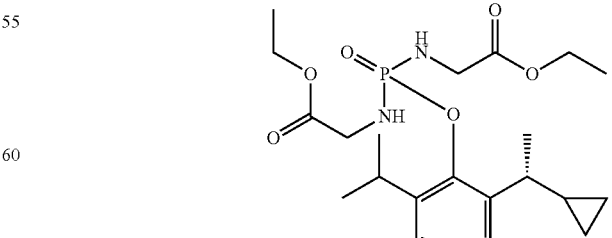

Step 1: ethyl2-[[[2-[(1R)-1-cyclopropylethyl]-6-isopropyl-phenoxy]-[(2-ethoxy-2-oxoethyl)amino]phosphoryl]amino]acetate (Compound 44)

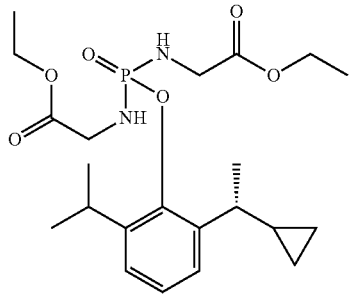 [SMILES: CCOC(=O)CNP(=O)(NCC(=O)OCC)Oc1c(C(C)C)cccc1[C@H](C)C1CC1]

Phosphorous oxychloride (1.65 g, 10.77 mmol), dichloromethane (80 mL) and triethylsilane (4.95 g, 48.95 mmol) were added into the reaction flask in sequence, the mixture was cooled to 0° C. under ice bath under nitrogen atmosphere, and 2-[(1R)-1-cyclopropylethyl]-6-isopropyl-phenol (Compound 16) (4.0 g, 19.58 mmol) was added below 10° C. After addition, the reaction mixture was warmed up to room temperature and stirred for 4 h, then glycine ethyl ester hydrochloride (3.01 g, 21.54 mmol) was added and the mixture was stirred for 15 h. The resulting mixture was filtered and concentrated. The residue was purified by silica gel column chromatography (petroleum ether/ethyl acetate (v/v)=3:1) to afford ethyl2-[[[2-[(1R)-1-cyclopropylethyl]-6-isopropyl-phenoxy]-[(2-ethoxy-2-oxoethyl)amino]phosphoryl]amino]acetate (Compound 44) as a colorless thick liquid (1.50 g, yield: 33.7%, HPLC: 98.60%).

$^1$HNMR (400 MHz, CDCl$_3$): δ 7.26-7.23 (m, 1H), δ 7.144-7.12 (m, 2H), δ 4.23-4.18 (m, 4H), δ 3.88-3.81 (m, 2H), δ 3.74-3.67 (m, 2H), δ 3.47-3.39 (m, 3H), δ 2.74-2.67 (m, 1H), δ 1.29-1.22 (m, 15H), δ 1.01-0.92 (m, 1H), δ 0.58-0.51 (m, 1H), δ 0.40-0.33 (m, 1H), δ 0.28-0.15 (m, 2H).

MS m/z (ESI): 455.4 [M+1].

Example 45

[[2-[(1R)-1-cyclopropylethyl]-6-isopropyl-phenoxy]methoxy-potassiooxyphosphoryl]oxypotassium (Compound 45)

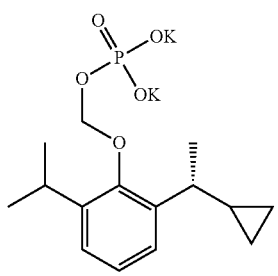

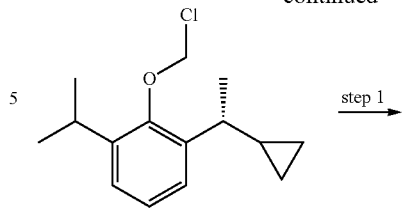

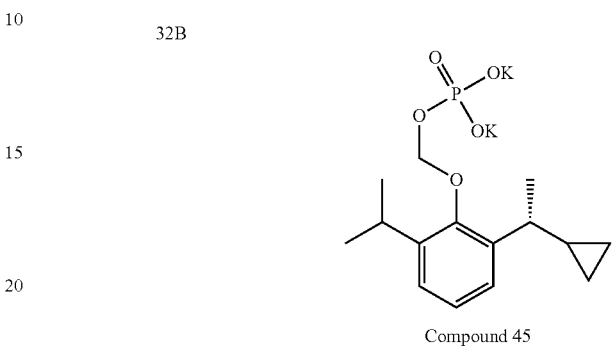

Compound 45

Step 1: [[2-[(1R)-1-cyclopropylethyl]-6-isopropyl-phenoxy]methoxy-potassiooxyphosphoryl]oxypotassium (Compound 45)

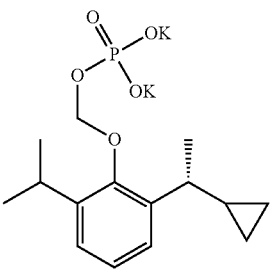

Phosphoric acid (12.41 g, 126.59 mmol), triethylamine (16.01 g, 158.24 mmol) and acetonitrile (100 mL) were added into the reaction flask, the mixture was heated to 60° C. for 0.5 h, 2-(chloromethoxy)-1-[(1R)-1-cyclopropylethyl]-3-isopropyl-benzene (32B) (4.00 g, 15.82 mmol) the mixture and the mixture was stirred for 3 h at 70° C. The mixture was concentrated in vacuo, water (50 mL) was added, the mixture was adjusted with hydrochloric acid (1M) to pH 1, extracted with methyl tert-butyl ether (100 mL×3). The combined organic extracts were concentrated. The residue was dissolved in ethanol (50 mL), 10% (w/w) potassium hydroxide aqueous solution (15.82 mL, 31.65 mmol) was added, and the mixture was stirred at room temperature for 2 h, concentrated, a solution of isopropanol (95%, 20 ml) was added, the mixture was filtered and concentrated to obtain yellow solid. The solid was added to acetonitrile (20 mL), stirred at 50° C., and hot-filtered to afford [[2-[(1R)-1-cyclopropylethyl]-6-isopropyl-phenoxy]methoxy-potassiooxyphosphoryl]oxypotassium (Compound 45) as a beige powder (3.9 g, yield: 69.6%, HPLC: 99.8%).

$^1$HNMR (400 MHz, D$_2$O): δ 7.43-7.41 (m, 1H), δ 7.35-7.29 (m, 2H), δ 5.27-5.21 (m, 2H), δ 3.52-3.46 (m, 1H), δ 2.69-2.61 (m, 1H), δ 1.34 (d, 3H), δ 1.27 (d, 3H), δ 1.24 (d,

3H), δ 1.11-1.02 (m, 1H), δ 0.60-0.58 (m, 1H), δ 0.37-0.33 (m, 2H), δ 0.18-0.16 (m, 1H).

MS m/z (ESI): 313.1 [M−46−1].

Example 46

[[2-[(1R)-1-cyclopropylethyl]-6-isopropyl-phenoxy]-sodiooxy-phosphoryl]oxysodium (Compound 46)

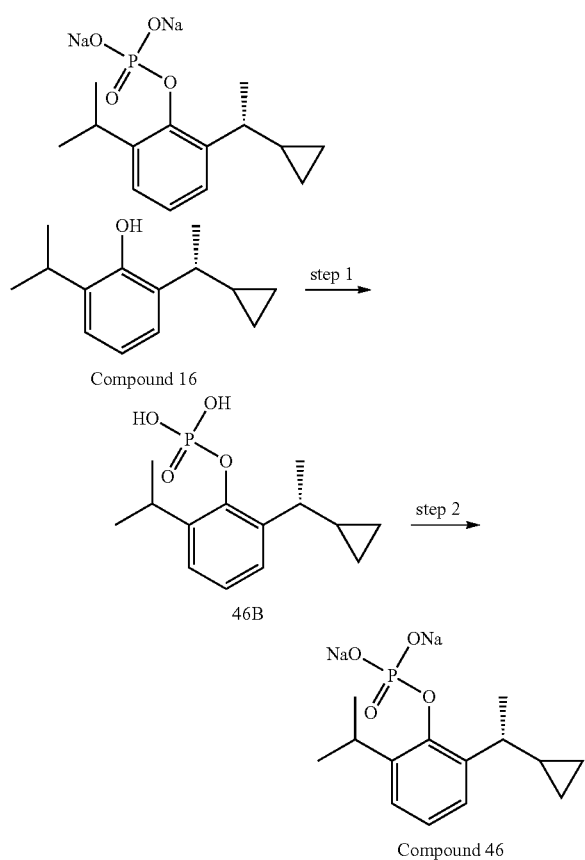

Step 1: [2-[(1R)-1-cyclopropylethyl]-6-isopropyl-phenyl]dihydrogen phosphate (46B)

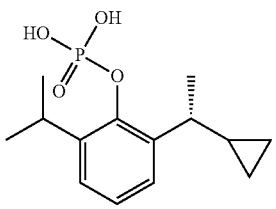 [SMILES: CC(C)c1cccc([C@H](C)C2CC2)c1OP(=O)(O)O]

Phosphorus oxychloride (4.50 g, 29.37 mmol) and dichloromethane (10 mL) was added into the reaction flask under nitrogen atmosphere, the mixture was cooled down to 0° C. under ice bath. A solution of 2-[(1R)-1-cyclopropylethyl]-6-isopropyl-phenol (Compound 16) (5.00 g, 24.47 mmol) and triethylamine (5.45 g, 53.84 mmol) was dissolved in dichloromethane (30 mL), and then the mixture of dichloromethane was slowly dropwise added to the reaction flask below 10° C. After addition, the reaction mixture was recovered to room temperature and stirred for 4 h, filtered to remove solid. Water (20 mL) was added into the filtrate, and then was stirred at room temperature for 3 h, extracted with dichloromethane (50 mL×3), washed with saturated brine (50 mL×3). The combined organic extracts were dried over anhydrous sodium sulfate, filtered and concentrated to obtain [2-[(1R)-1-cyclopropylethyl]-6-isopropyl-phenyl]dihydrogen phosphate (46B) as a redbrown thick liquid (6.2 g, crude product), which was submitted to the next step without further purification.

Step 2: [[2-[(1R)-1-cyclopropylethyl]-6-isopropyl-phenoxy]-sodiooxy-phosphoryl]oxysodium (Compound 46)

[2-[(1R)-1-cyclopropylethyl]-6-isopropyl-phenyl]dihydrogen phosphate (46B) (6.00 g, 21.09 mmol) and ethanol (30 mL) were added into the reaction flask, aqueous sodium hydroxide solution (2 M, 21.09 mL, 42.18 mmol) was added under an ice-water bath. Upon completion of the addition, the mixture was stirred at room temperature for 2 h, concentrated. The residue was dissolved in 95% (w/w) aqueous isopropanol solution (10 mL), filtered, the insoluble substance was removed, and the filtrate was concentrated in vacuo to a yellow solid. The solid was recrystallized with isopropanol (42 mL, 95%, w/w) to afford [[2-[(1R)-1-cyclopropylethyl]-6-isopropyl-phenoxy]-sodiooxy-phosphoryl]oxysodium (Compound 46) as a white powder (3.0 g, yield: 43.3%, HPLC: 96.5%).

¹HNMR (400 MHz, D₂O): δ 7.36 (dd, 1H), δ 7.24 (dd, 1H), δ 7.18 (t, 1H), δ 3.80-3.72 (m, 1H), δ 3.11-3.04 (m, 1H), δ 1.28 (d, 3H), δ 1.24 (d, 3H), δ 1.20 (d, 3H), δ 1.09-0.97 (m, 1H), δ 0.54-0.51 (m, 1H), δ 0.37-0.26 (m, 2H).

MS m/z (ESI): 281.7 [M−46−1].

Example 47

[[2-[(1R)-1-cyclopropylethyl]-6-isopropyl-phenoxy]-potassiooxy-phosphoryl]oxypotassium (Compound 47)

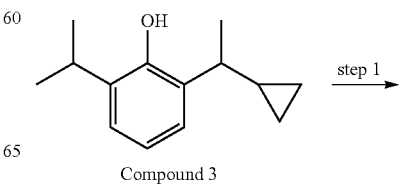

149

-continued

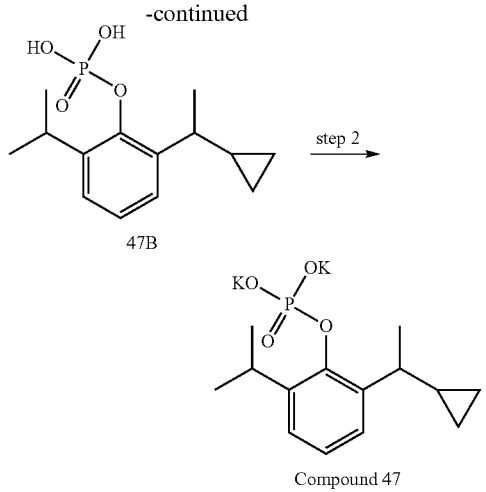

Compound 47

Step 1: [2-(1-cyclopropylethyl)-6-isopropyl-phenyl] dihydrogen phosphate (47B)

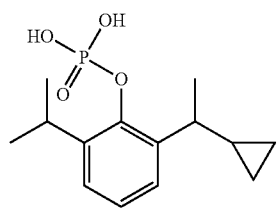 [SMILES: CC(C)c1cccc(C(C)C2CC2)c1OP(=O)(O)O]

Phosphorus oxychloride (11.82 g, 77.09 mmol) and dichloromethane (20 mL) were added into the reaction flask, the mixture was cooled down to 0° C. under nitrogen atmosphere. A solution of 2-(1-cyclopropylethyl)-6-isopropylphenol (Compound 3) (10.50 g, 51.39 mmol) and triethylamine (9.36 g, 92.51 mmol) in dichloromethane (30 mL) was dropwise slowly added to the reaction flask below 10° C. After addition, the reaction mixture was heated to room temperature and stirred for 6 h, filtered and solid was removed. Water (50 mL) was added into the filtrate, the mixture was stirred at room temperature for 5 h, extracted with dichloromethane (150 mL×3), washed with saturated brine (150 mL×3). The combined organic extracts were dried over anhydrous sodium sulfate, filtered and concentrated to afford [2-(1-cyclopropylethyl)-6-isopropyl-phenyl] dihydrogen phosphate (47B) (15.01 g, crude product) as red viscous liquid, which was submitted to the next step without further purification.

Step 2: [[2-[(1R)-1-cyclopropylethyl]-6-isopropyl-phenoxy]-potassiooxy-phosphoryl]oxypotassium (Compound 47)

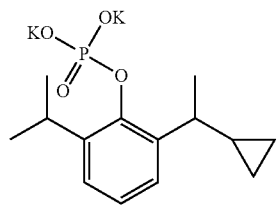

150

[2-(1-cyclopropylethyl)-6-isopropyl-phenyl]dihydrogen phosphate (47B) (5.00 g, 17.59 mmol) and ethanol (20 mL) were added into the reaction flask, a solution of potassium hydroxide (2M, 17.59 mL, 35.18 mmol) was added, and the mixture was stirred at room temperature for 2 h. The resulting mixture was concentrated in vacuo to give a yellow powder, which was then recrystallized with isopropanol solution (95%, w/w, 35 mL) to afford [[2-[(1R)-1-cyclopropylethyl]-6-isopropyl-phenoxy]-potassiooxy-phosphoryl]oxypotassium (Compound 47) as a white powder (2.7 g, yield: 42.6%, HPLC: 97.4%).

$^1$HNMR (400 MHz, D$_2$O): δ 7.35 (dd, 1H), δ 7.25 (dd, 1H), δ 7.17 (t, 1H), δ 3.82-3.72 (m, 1H), δ 3.12-3.04 (m, 1H), δ 1.28 (d, 3H), δ 1.24 (d, 3H), δ 1.20 (d, 3H), δ 1.06-0.97 (m, 1H), δ 0.57-0.50 (m, 1H), δ 0.38-0.26 (m, 2H).

MS m/z (ESI): 360.7 [M−1].

Example 48

[2-(1-cyclopropylethyl)-6-isopropyl-phenyl]diethyl phosphate (Compound 48)

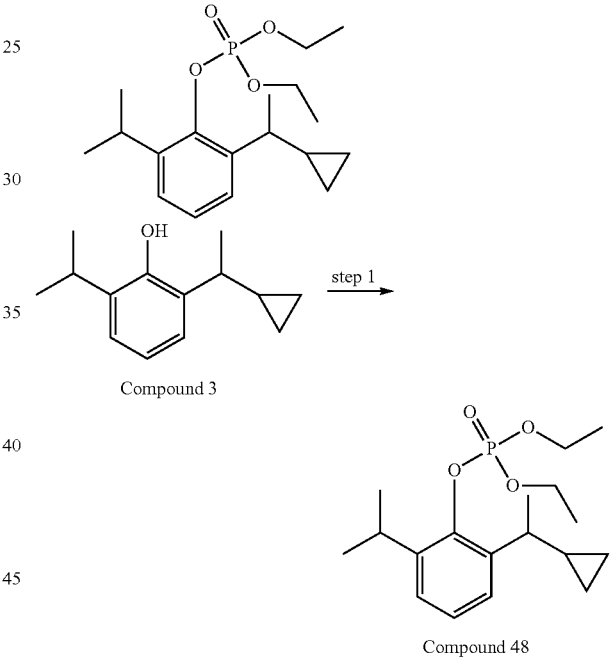

Step 1: [2-(1-cyclopropylethyl)-6-isopropyl-phenyl]diethyl phosphate (Compound 48)

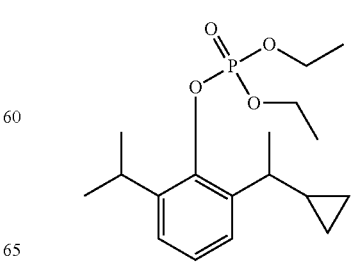

Sodium hydride (0.82 g, 20.56 mmol, 60%), 2-(1-cyclopropylethyl)-6-isopropylphenol (Compound 3) (3.00 g, 14.68 mmol) and tetrahydrofuran (20 mL) were added into the reaction flask, the mixture was stirred for 3 h at 50° C. A solution of diethyl chlorophosphate (2.53 g, 14.68 mmol) in tetrahydrofuran (10 mL) was added to the reaction flask. The reaction mixture was stirred at 50° C. for 18 h, and water (30 mL) was added, the mixture was extracted with ethyl acetate (30 mL×3), washed with saturated brine (30 mL×3). The combined organic extracts were dried over anhydrous sodium sulfate, filtered and concentrated in vacuo. The residue was purified by silica gel column chromatography (petroleum ether/ethyl acetate (v/v)=4:1) to obtain [2-(1-cyclopropylethyl)-6-isopropyl-phenyl]diethyl phosphate (Compound 48) as a light yellow liquid (0.3 g, yield: 6.0%, HPLC: 92.3%).

$^1$HNMR (400 MHz, CDCl$_3$): δ 7.26-7.24 (m, 1H), δ 7.17-7.12 (m, 2H), δ 4.21-4.09 (m, 4H), δ 3.54-3.44 (m, 1H), δ 2.73-2.65 (m, 1H), δ 1.33-1.26 (m, 9H), δ 1.23 (d, 3H), δ 1.22 (d, 3H), δ 1.00-0.91 (m, 1H), δ 0.58-0.49 (m, 1H), δ 0.37-0.34 (m, 1H), δ 0.26-0.17 (m, 2H).

Example 49

[2-[(1R)-1-cyclopropylethyl]-6-isopropyl-phenoxy]methyl isopropyl carbonate (Compound 49)

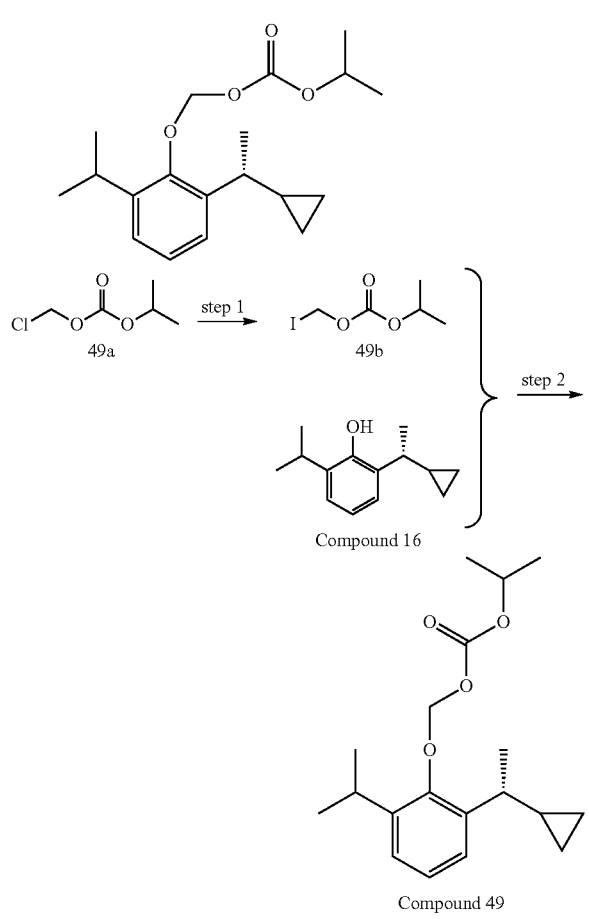

Compound 49

Step 1: Iodomethyl Isopropyl Carbonate (49B)

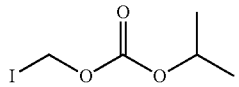

Chloromethyl isopropyl carbonate (49A) (30.0 g, 0.198 mol) was dissolved in acetone (150 mL), sodium iodide (60.0 g, 0.396 mol) was added to the mixture, stirring at 30° C. for 4 h. The mixture was then filtered and concentrated in vacuo, the residue was purified by silica gel column chromatography (petroleum ether) to afford iodomethyl isopropyl carbonate (49B) as a light yellow liquid (40.4 g, yield: 83.7%).

$^1$H NMR (400 MHz, CDCl$_3$): δ 5.93 (s, 1H), 4.97-4.91 (m, 1H), 1.32 (d, 6H).

Step 2: [2-[(1R)-1-cyclopropylethyl]-6-isopropyl-phenoxy]methyl isopropyl carbonate (Compound 49)

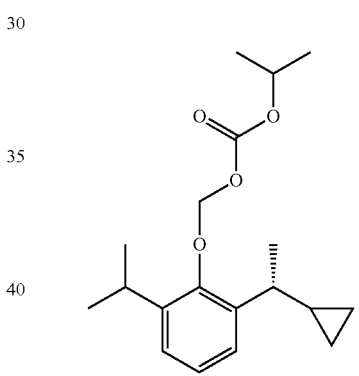

2-[(1R)-1-cyclopropylethyl]-6-isopropyl-phenol (Compound 16) (0.408 g, 2 mmol) was dissolved in dichloromethane (3 mL), tetrabutylammonium bromide (0.13 g, 0.4 mmol) and sodium hydroxide aqueous solution (0.4 g in 3 mL water, 10 mmol) was added successively. The mixture was stirred for 10 minutes, iodomethyl isopropyl carbonate (49B) (0.488 g, 2 mmol) in dichloromethane (1 mL) was added, the mixture was stirred at 30° C. for 4 h. The resulting mixture was stood and separated. The water layer was then extracted with dichloromethane (5 mL). The combined organic extracts were washed with saturated brine (10 mL), dried over anhydrous sodium sulfate, purified by silica gel column chromatography (petroleum ether) to obtain [2-[(1R)-1-cyclopropylethyl]-6-isopropyl-phenoxy]methyl isopropyl carbonate (Compound 49) as a colorless liquid (0.21 g, yield: 32.8%).

$^1$H NMR (400 MHz, CDCl$_3$): δ 7.26-7.07 (m, 3H), 5.73 (s, 2H), 5.01-4.93 (m, 1H), 3.21-3.15 (m, 1H), 2.55-2.48 (m, 1H), 1.36-1.22 (m, 15H), 1.08-1.04 (m, 1H), 0.58-0.56 (m, 1H), 0.49-0.44 (m, 1H), 0.22-0.20 (m, 1H), 0.17-0.16 (m, 1H).

Example 50

1-[(1R)-1-cyclopropylethyl]-3-isopropyl-2-methoxy-benzene (Compound 50)

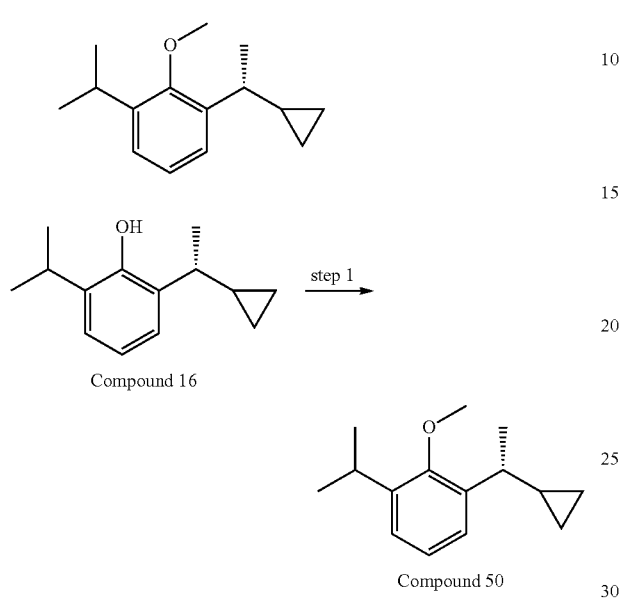

Compound 16

Compound 50

Step 1: 1-[(1R)-1-cyclopropylethyl]-3-isopropyl-2-methoxy-benzene (Compound 50)

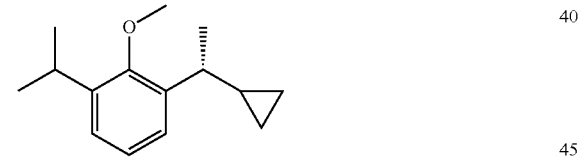

2-[(1R)-1-cyclopropylethyl]-6-isopropyl-phenol (Compound 16) (0.5 g, 2.5 mmol), potassium carbonate (0.69 g, 5 mmol) were dissolved in acetone (5 mL), the mixture was stirred for 5 minutes, then dimethyl sulfate (0.35 mL, 3.75 mmol) was added, the mixture was stirred at 50° C. overnight. The resulting mixture was quenched with saturated aqueous sodium hydroxide solution, the reaction mixture was concentrated to remove acetone, extracted with petroleum ether (10 mL×2). The combined organic extracts were washed with saturated brine (20 mL×2), dried over anhydrous sodium sulfate, filtered and concentrated in vacuo. The residue was purified by silica gel column chromatography (petroleum ether) to afford 1-[(1R)-1-cyclopropylethyl]-3-isopropyl-2-methoxy-benzene (Compound 50) as a colorless liquid (Compound 50) (0.3 g, yield: 55%).

$^1$H NMR (400 MHz, CDCl$_3$): δ 7.24-7.10 (m, 3H), 3.70 (s, 3H), 3.39-3.32 (m, 1H), 2.51-2.45 (m, 1H), 1.32 (d, 3H), 1.27 (s, 6H), 1.03-0.97 (m, 1H), 0.58-0.56 (m, 1H), 0.43-0.36 (m, 1H), 0.26-0.23 (m, 1H), 0.18-0.17 (m, 1H).

Example 51

[2-[(1R)-1-cyclopropylethyl]-6-isopropyl-phenoxy]methylpyridine-3-carboxylate (Compound 51)

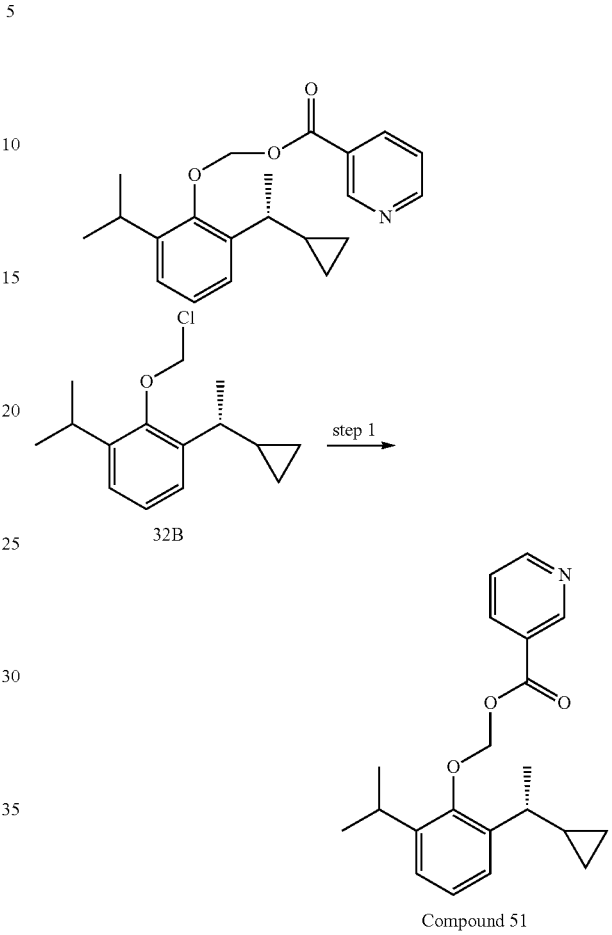

32B

Compound 51

Step 1: [2-[(1R)-1-cyclopropylethyl]-6-isopropyl-phenoxy]methylpyridine-3-carboxylate (Compound 51)

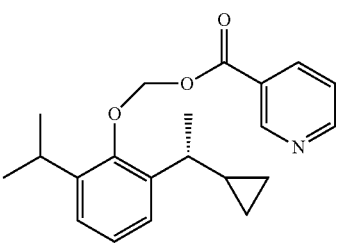 [SMILES: CC(C)c1cccc([C@H](C)C2CC2)c1OCOC(=O)c1cccnc1]

2-(chloromethoxy)-1-[(1R)-1-cyclopropylethyl]-3-isopropyl-benzene (32B) (1 g, 4 mmol) and acetonitrile (20 mL) were added into the reaction flask, diacetoxybenzoic acid (1.08 g, 8.8 mmol) and triethylamine (1.2 mL, 8.8 mmol) were added successively, and the mixture was stirred at 60° C. under nitrogen atmosphere overnight. The reaction mixture was filtered and concentrated, purified by silica gel column chromatography (petroleum ether/ethyl acetate (v/v)=7:1) to afford [2-[(1R)-1-cyclopropylethyl]-6-isopropyl-phenoxy]methylpyridine-3-carboxylate (Compound 51) as a yellow liquid (1.23 g, yield: 90.4%).

$^1$H NMR (400 MHz, CDCl$_3$): δ 9.25 (s, 1H), 8.81 (t, 1H), 8.32 (t, 1H), 7.40 (q, 1H), 7.25-7.13 (m, 3H), 5.80 (s, 2H), 3.38-3.31 (m, 1H), 2.56-2.49 (m, 1H), 1.26-1.20 (m, 9H), 0.93-0.90 (m, 1H), 0.52-0.50 (m, 1H), 0.33-0.30 (m, 1H), 0.13-0.11 (m, 2H).

Example 52

[[2-[(1R)-1-cyclopropylethyl]-6-isopropyl-phenoxy]methyl-sodiooxy-phosphoryl]oxy sodium (Compound 52)

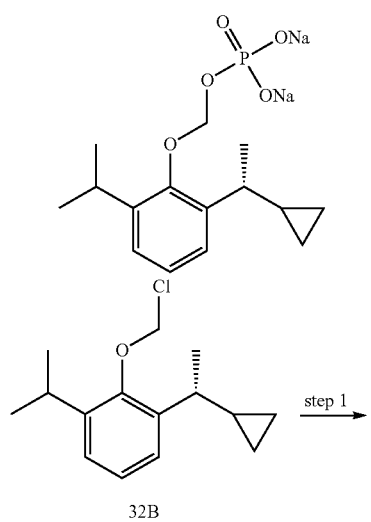

Step 1: [[2-[(1R)-1-cyclopropylethyl]-6-isopropyl-phenoxy]methyl-sodiooxy-phosphoryl]oxysodium (Compound 52)

Phosphoric acid (62.7 g, 0.64 mol), triethylamine (80.9 g, 0.80 mol) and acetonitrile (400 mL) were added into the reaction flask, the mixture was stirred at 65° C. for 30 minutes, and 2-(chloromethoxy)-1-[(1R)-1-cyclopropyl-ethyl]-3-isopropyl-benzene (32B) (20.0 g, 0.08 mol) was added, the mixture was stirred at 75° C. for 3 h. The resulting mixture was concentrated in vacuo, and then the residue was dissolved in water (200 mL), the mixture was adjusted to pH 1 with 10% hydrochloric acid solution, extracted with tert-butylmethylether (200 mL×3), washed with saturated brine (100 mL×1). The combined organic extracts were concentrated and then dissolved in water (100 mL), and was adjusted to pH 10~11 with aqueous sodium hydroxide solution (w/w=20%), washed with tert-butylmethylether (100 mL×3) until the organic layer was colorless. Isopropanol (300 mL) was added into the mixture, and the mixture was concentrated, acetonitrile (70 mL) was added, stirred at 50° C., followed by hot filtration to obtain [[2-[(1R)-1-cyclopropylethyl]-6-isopropyl-phenoxy]methyl-sodiooxy-phosphoryl]oxy sodium (Compound 52) as a white solid (20.0 g, yield: 70%, HPLC: 97.6%).

$^1$H NMR (400 MHz, D$_2$O): δ 7.41-7.38 (m, 1H), 7.31-7.26 (m, 2H), 5.23-5.17 (m, 2H), 3.47-3.44 (m, 1H), 2.63-2.59 (m, 1H), 1.30 (d, 3H), 1.22 (dd, 6H), 1.04-1.01 (m, 1H), 0.57-0.53 (m, 1H), 0.34-0.29 (m, 2H), 0.14-0.12 (m, 1H).

MS m/z (ESI): 313.2 [M−46+1].

Example 53

[2-[(1R)-1-cyclopropylethyl]-6-isopropyl-phenoxy]methyl 2-aminoacetate trifluoroacetate (Compound 53)

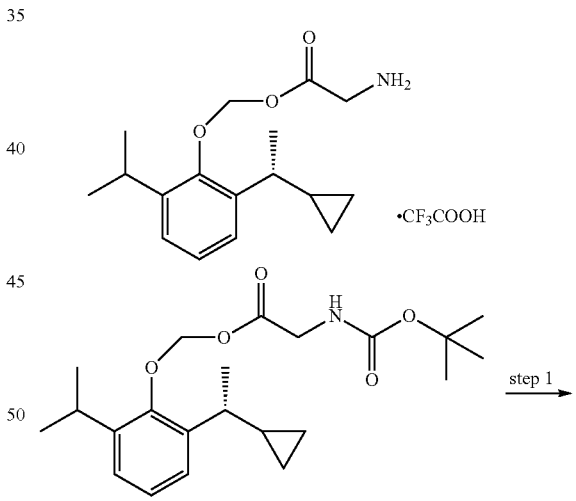

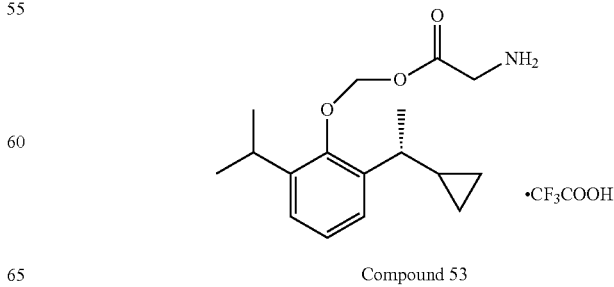

Step 1: [2-[(1R)-1-cyclopropylethyl]-6-isopropyl-phenoxy]methyl2-aminoacetate.trifluoroacetate (Compound 53)

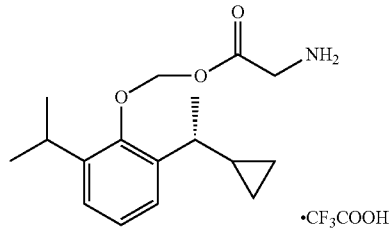

[2-[(1R)-1-cyclopropylethyl]-6-isopropyl-phenoxy] methyl2-(tertbutoxycarbonylamino)acetate (compound 32) (1.0 g, 2.6 mmol) was dissolved in dichloromethane (5 mL), trifluoroacetic acid (2.0 mL, 27 mmol) was added with stirring at room temperature and the mixture was stirred for 1 h at room temperature, the reaction mixture was concentrated in vacuo. The residue was purified by silica gel column chromatography (petroleum ether/ethyl acetate (v/v)=2:1) to obtain [2-[(1R)-1-cyclopropylethyl]-6-isopropyl-phenoxy]methyl2-aminoacetate.trifluoroacetate (Compound 53) as a colorless liquid (0.42 g, yield: 55.3%).

$^1$H NMR (400 MHz, CDCl$_3$): δ 7.90 (s, 2H), 7.20-7.10 (m, 3H), 5.56 (s, 2H), 3.81 (s, 2H), 3.21-3.14 (m, 1H), 2.37-2.34 (m, 1H), 1.26-1.16 (m, 9H), 0.90-0.86 (m, 1H), 0.51-0.49 (m, 1H), 0.31-0.28 (m, 1H), 0.18-0.17 (m, 1H), 0.11-0.09 (m, 1H).

Example 54

[2-[(1R)-1-cyclopropylethyl]-6-isopropyl-phenoxy]methyl3-(tertbutoxycarbonylamino)propanoate (Compound 54)

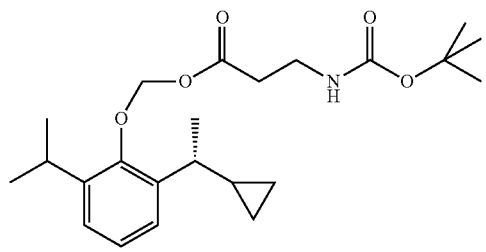

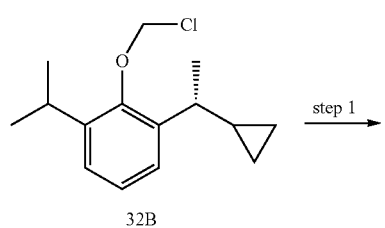

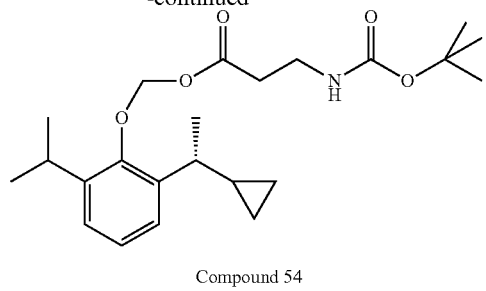

Compound 54

Step 1: [2-[(1R)-1-cyclopropylethyl]-6-isopropyl-phenoxy]methyl3-(tertbutoxycarbonylamino)propanoate (Compound 54)

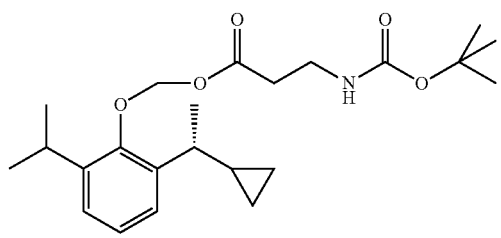 [SMILES: CC(C)c1cccc([C@H](C)C2CC2)c1OCOC(=O)CCNC(=O)OC(C)(C)C]

2-(chloromethoxy)-1-[(1R)-1-cyclopropylethyl]-3-isopropyl-benzene (32B) (0.253 g, 1 mmol), 3-(tert-butoxycarbonylamino) propanoic acid (0.416 g, 2.2 mmol) and triethylamine (0.3 mL, 2.2 mmol) were added into the reaction flask in sequence and were dissolved in acetonitrile (5 mL), the mixture was stirred at 60° C. for 2 h, and concentrated in vacuo. The residue was purified by silica gel column chromatography (petroleum ether/ethyl acetate (v/v)=80:1) to afford [2-[(1R)-1-cyclopropylethyl]-6-isopropyl-phenoxy]methyl3-(tertbutoxycarbonylamino)propanoate (Compound 54) as a colorless liquid (0.307 g, yield: 75.6%).

$^1$H NMR (400 MHz, CDCl$_3$): δ 7.25-7.10 (m, 3H), 5.51 (q, 2H), 5.00 (s, 1H), 3.43-3.37 (m, 2H), 3.30-3.23 (m, 1H), 2.54 (t, 2H), 2.48-2.41 (m, 1H), 1.43 (s, 9H), 1.30-1.20 (m, 9H), 0.94-0.89 (m, 1H), 0.54-0.51 (m, 1H), 0.34-0.31 (m, 1H), 0.22-0.19 (m, 1H), 0.16-0.15 (m, 1H).

Example 55

[2-[(1R)-1-cyclopropylethyl]-6-isopropyl-phenoxy]methyl3-aminopropanoate Trifluoroacetate (Compound 55)

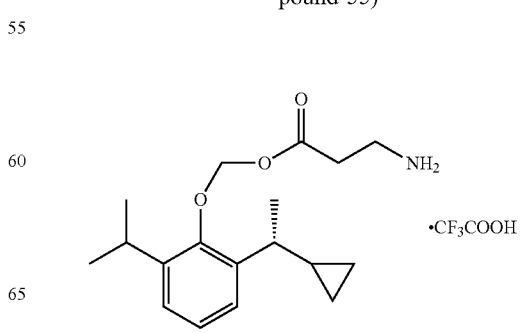

-continued

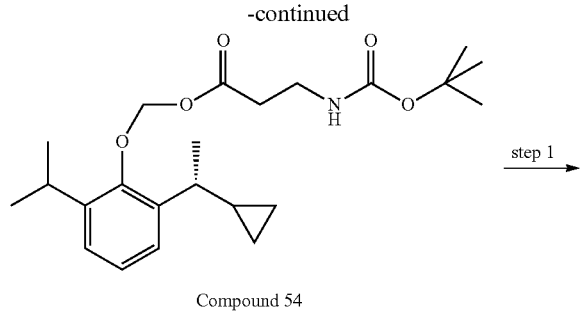

Compound 54

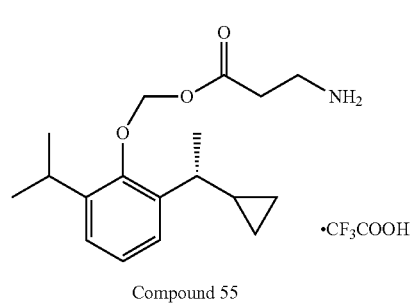

Compound 55

[2-[(1R)-1-cyclopropylethyl]-6-isopropyl-phenoxy] methyl 3-aminopropanoatetrifluoroacetate (Compound 55)

[2-[(1R)-1-cyclopropylethyl]-6-isopropyl-phenoxy]methyl3-(tertbutoxycarbonylamino)propanoate (Compound 54) (1.0 g, 2.6 mmol) was dissolved in dichloromethane (5 mL), trifluoroacetic acid (2.0 mL, 27 mmol) was added with stirring at room temperature, the mixture was stirred for 1 h at room temperature, and was concentrated in vacuo. The residue was purified by silica gel column chromatography (petroleum ether/ethyl acetate (v/v)=2:1) to afford [2-[(1R)-1-cyclopropylethyl]-6-isopropyl-phenoxy]methyl 3-aminopropanoatetrifluoroacetate (Compound 55) as a colorless liquid (0.42 g, yield: 55.3%).

$^1$H NMR (400 MHz, CDCl$_3$): δ 7.91 (s, 2H), 7.21-7.07 (m, 3H), 5.48 (s, 2H), 3.40-3.33 (m, 2H), 3.25-3.20 (m, 1H), 2.50 (t, 2H), 2.44-2.37 (m, 1H), 1.25-1.18 (m, 9H), 0.92-0.88 (m, 1H), 0.51-0.48 (m, 1H), 0.31-0.29 (m, 1H), 0.20-0.16 (m, 1H), 0.13-0.11 (m, 1H).

Example 56

[2-[(1R)-1-cyclopropylethyl]-6-isopropyl-phenoxy] methyl(2S)-2-(tertbutoxycarbonyl amino)propanoate (Compound 56)

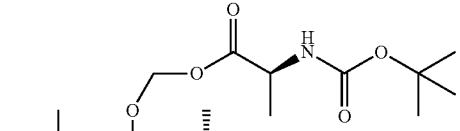

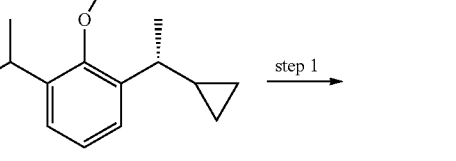

32B

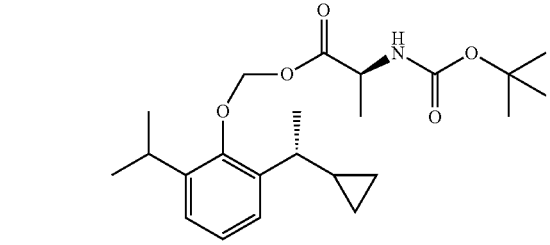

Compound 56

Step 1: [2-[(1R)-1-cyclopropylethyl]-6-isopropyl-phenoxy]methyl(2S)-2-(tert-butoxycarbonylamino)propanoate (Compound 56)

2-(chloromethoxy)-1-[(1R)-1-cyclopropylethyl]-3-isopropyl-benzene (32B) (0.253 g, 1 mmol), 3-(tert-butoxycarbonylamino) propanoic acid (0.416 g, 2.2 mmol), triethylamine (0.3 mL, 2.2 mmol) were dissolved in acetonitrile (5 mL), the mixture was stirred at 60° C. for 2 h, and was concentrated in vacuo. The residue was purified by silica gel column chromatography (petroleum ether/ethyl acetate (v/v)=80:1) to afford [2-[(1R)-1-cyclopropylethyl]-6-isopropyl-phenoxy]methyl(2S)-2-(tert-butoxycarbonyl amino) propanoate (Compound 56) as a colorless liquid (0.37 g, yield: 91.3%).

$^1$H NMR (400 MHz, CDCl$_3$): δ 7.24-7.09 (m, 3H), 5.53 (q, 2H), 5.03 (s, 1H), 4.40-4.30 (m, 1H), 3.33-3.22 (m, 1H), 2.48-2.44 (m, 1H), 1.42 (s, 9H), 1.26 (s, 3H), 1.25-1.19 (m, 9H), 0.92-0.88 (m, 1H), 0.53-0.50 (m, 1H), 0.34-0.31 (m, 1H), 0.25-0.21 (m, 1H), 0.17-0.16 (m, 1H).

Example 57

[2-[(1R)-1-cyclopropylethyl]-6-isopropyl-phenoxy]methyl(2R)-2-(tertbutoxycarbonylamino)-3-methyl-butanoate (Compound 57)

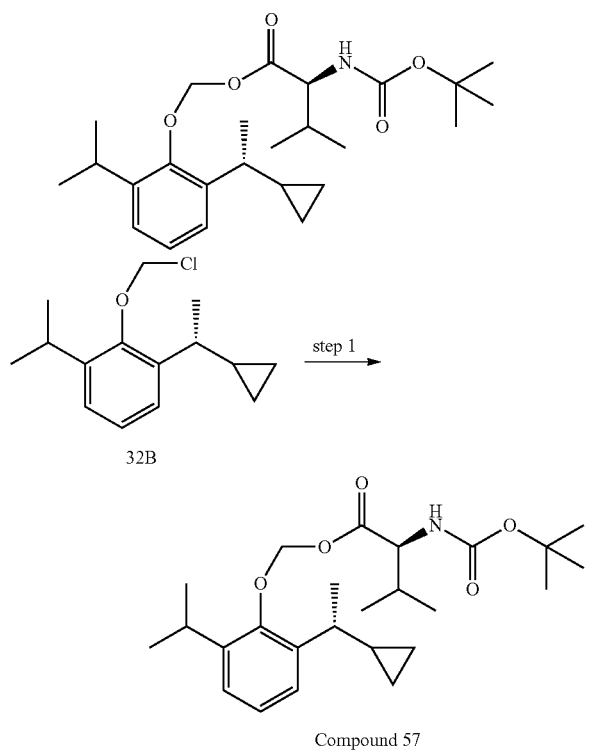

Step 1: [2-[(1R)-1-cyclopropylethyl]-6-isopropyl-phenoxy]methyl(2R)-2-(tert-butoxycarbonylamino)-3-methyl-butanoate (Compound 57)

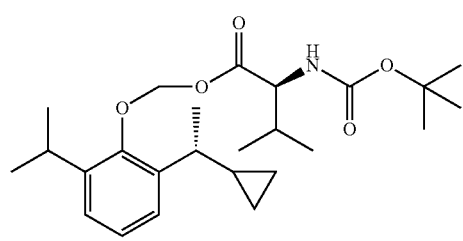 [SMILES: CC(C)c1cccc([C@H](C)C2CC2)c1OCOC(=O)[C@@H](NC(=O)OC(C)(C)C)C(C)C]

2-(chloromethoxy)-1-[(1R)-1-cyclopropylethyl]-3-isopropyl-benzene (32B) (0.253 g, 1 mmol), 3-(tert-butoxycarbonylamino) propanoic acid (0.478 g, 2.2 mmol), triethylamine (0.3 mL, 2.2 mmol) were dissolved in acetonitrile (5 mL), the mixture was stirred at 60° C. for 2 h, and was concentrated in vacuo. The residue was purified by silica gel column chromatography (petroleum ether/ethyl acetate (v/v)=80:1) to obtain [2-[(1R)-1-cyclopropylethyl]-6-isopropyl-phenoxy]methyl(2R)-2-(tert-butoxycarbonylamino)-3-methyl-butanoate (Compound 57) as a colorless liquid (0.28 g, yield: 64.5%).

$^1$H NMR (400 MHz, CDCl$_3$): δ 7.24-7.12 (m, 3H), 5.55 (q, 2H), 5.00 (d, 1H), 4.31-4.20 (m, 1H), 3.34-3.27 (m, 1H), 2.54-2.46 (m, 1H), 1.45 (s, 9H), 1.30-1.20 (m, 9H), 0.90 (d, 3H), 0.90-0.89 (m, 1H), 0.88 (d, 3H), 0.55-0.52 (m, 1H), 0.40-0.36 (m, 1H), 0.24-0.21 (m, 1H), 0.15-0.14 (m, 1H).

Example 58

[2-[(1R)-1-cyclopropylethyl]-6-isopropyl-phenoxy]methyl(2S)-2-amino-3-methyl-butanoate trifluoroacetate (Compound 58)

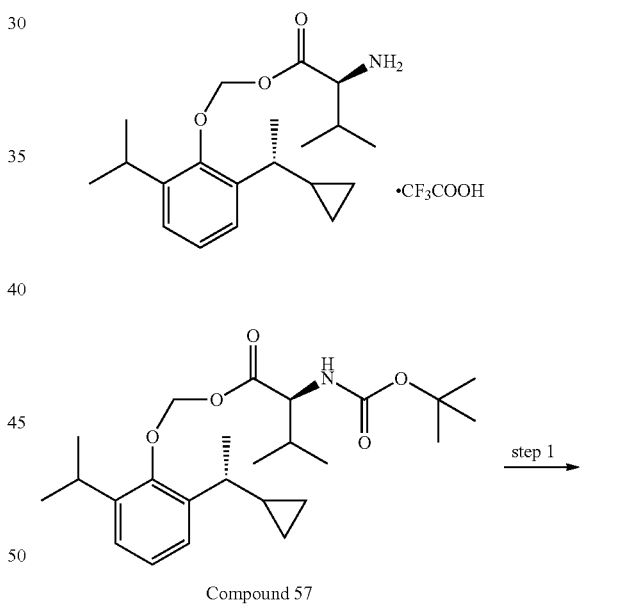

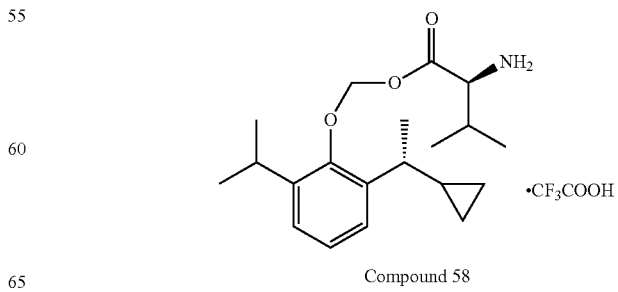

Step 1: [2-[(1R)-1-cyclopropylethyl]-6-isopropyl-phenoxy]methyl(2S)-2-amino-3-methyl-butanoate trifluoroacetate (Compound 58)

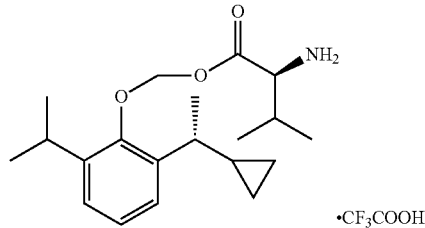 [SMILES: CC(C)c1cccc([C@H](C)C2CC2)c1OCOC(=O)[C@@H](N)C(C)C ; "·CF3COOH"]

·CF₃COOH

[2-[(1R)-1-cyclopropylethyl]-6-isopropyl-phenoxy]methyl(2R)-2-(tert-butoxycarbonylamino)-3-methyl-butanoate (Compound 57) (1.3 g, 3.0 mmol) was dissolved in dichloromethane (5 mL), trifluoroacetic acid (2.0 mL, 27 mmol) was added with stirring at room temperature, and the mixture was stirred at room temperature for 1 h. The resulting mixture was concentrated in vacuo, purified by silica gel column chromatography (petroleum ether/ethyl acetate (v/v)=2:1) to obtain [2-[(1R)-1-cyclopropylethyl]-6-isopropyl-phenoxy]methyl(2S)-2-amino-3-methyl-butanoate trifluoroacetate (Compound 58) as a colorless liquid (0.42 g, yield: 55.3%).

¹H NMR (400 MHz, CDCl₃): δ 7.52 (s, 2H), 7.24-7.11 (m, 3H), 5.58 (q, 2H), 3.88 (d, 1H), 3.28-3.21 (m, 1H), 2.44-2.36 (m, 2H), 1.27-1.05 (m, 15H), 0.97-0.90 (m, 1H), 0.56-0.52 (m, 1H), 0.38-0.34 (m, 1H), 0.31-0.20 (m, 1H), 0.17-0.11 (m, 1H).

Example 59

[2-[(1R)-1-cyclopropylethyl]-6-isopropyl-phenoxy]methyl(2S)-2-(tert-butoxycarbonylamino)-4-methyl-pentanoate (Compound 59)

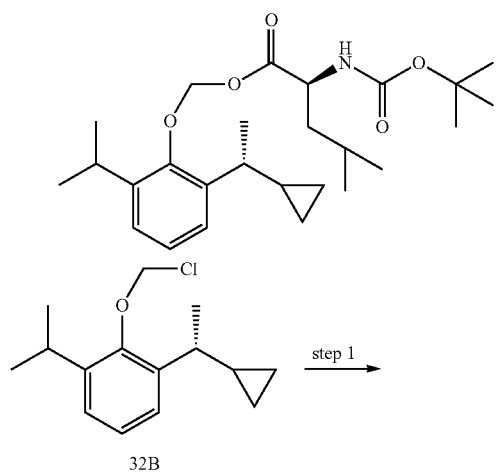

32B

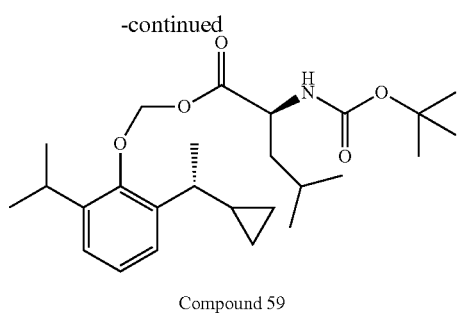

Compound 59

Step 1: [2-[(1R)-1-cyclopropylethyl]-6-isopropyl-phenoxy]methyl(2S)-2-(tertbutoxycarbonylamino)-4-methyl-pentanoate (Compound 59)

2-(chloromethoxy)-1-[(1R)-1-cyclopropylethyl]-3-isopropyl-benzene (32B) (0.253 g, 1 mmol), 3-(tert-butoxycarbonylamino) propanoic acid (0.509 g, 2.2 mmol) and triethylamine (0.3 mL, 2.2 mmol) were dissolved in acetonitrile (5 mL), the mixture was stirred at 60° C. for 2 h, and was concentrated in vacuo. The residue was purified by silica gel column chromatography (petroleum ether/ethyl acetate (v/v)=80:1) to obtain [2-[(1R)-1-cyclopropylethyl]-6-isopropyl-phenoxy]methyl(2S)-2-(tertbutoxycarbonyl amino)-4-methyl-pentanoate (Compound 59) as a colorless liquid (0.20 g, yield: 46.9%).

¹H NMR (400 MHz, CDCl₃): δ 7.24-7.12 (m, 3H), 5.55 (q, 2H), 4.86 (d, 1H), 4.31-4.22 (m, 1H), 3.34-3.27 (m, 1H), 2.51-2.45 (m, 1H), 1.79-1.70 (m, 1H), 1.70-1.60 (m, 1H), 1.60-1.48 (m, 1H), 1.44 (s, 9H), 1.30-1.20 (m, 9H), 0.96-0.90 (m, 7H), 0.55-0.53 (m, 1H), 0.38-0.36 (m, 1H), 0.25-0.22 (m, 1H), 0.17-0.16 (m, 1H).

Example 60

[2-[(1R)-1-cyclopropylethyl]-6-isopropyl-phenoxy]methyl(2S)-2-amino-4-methyl-pentanoate trifluoroacetate (Compound 60)

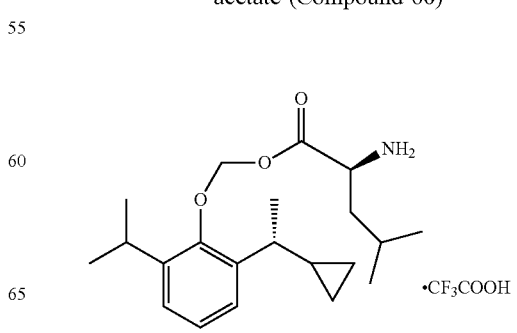

·CF₃COOH

165
-continued

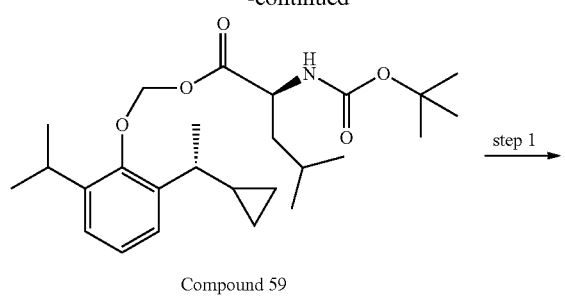

Compound 59

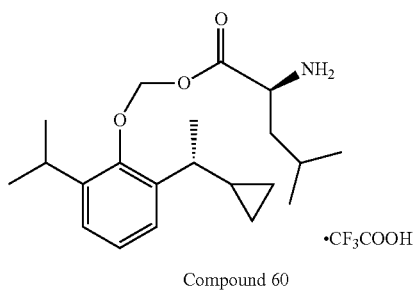

Compound 60

Step 1: [2-[(1R)-1-cyclopropylethyl]-6-isopropyl-phenoxy]methyl(2S)-2-amino-4-methyl-pentanoate trifluoroacetate (Compound 60)

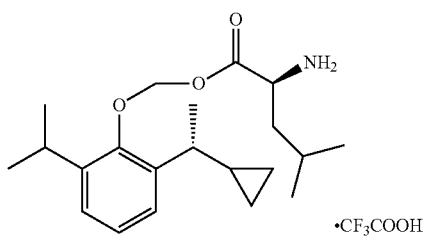 [SMILES: CC(C)C[C@H](N)C(=O)OCOc1c(C(C)C)cccc1[C@H](C)C1CC1 ; "·CF3COOH"]

2-[(1R)-1-cyclopropylethyl]-6-isopropyl-phenoxy]methyl(2S)-2-(tertbutoxycarbonylamino)-4-methyl-pentanoate (Compound 59) (1.7 g, 3.0 mmol) was dissolved in dichloromethane (5 mL), trifluoroacetic acid (2.0 mL, 27 mmol) was added with stirring at room temperature, the mixture reacted for 1 hours at room temperature, and then was concentrated in vacuo. The residue was purified by silica gel column chromatography (petroleum ether/ethyl acetate (v/v)=2:1) to obtain [2-[(1R)-1-cyclopropylethyl]-6-isopropyl-phenoxy]methyl(2S)-2-amino-4-methyl-pentanoate trifluoroacetate (Compound 60) as a colorless liquid (1.04 g, yield: 78.8%).

$^1$H NMR (400 MHz, CDCl$_3$): δ 7.25-7.12 (m, 3H), 5.58 (q, 2H), 3.52-3.48 (m, 1H), 3.32-3.28 (m, 1H), 2.55-2.48 (m, 1H), 1.85-1.80 (m, 1H), 1.56-1.44 (m, 4H), 1.27-1.22 (m, 9H), 0.95-0.88 (m, 7H), 0.56-0.53 (m, 1H), 0.35-0.33 (m, 1H), 0.23-0.19 (m, 1H), 0.17-0.16 (m, 1H).

166

Example 61

[2-[(1R)-1-cyclopropylethyl]-6-isopropyl-phenoxy]methyl(2S)-2-(tert-butoxycarbonylamino)-3-phenyl-propanoate (Compound 61)

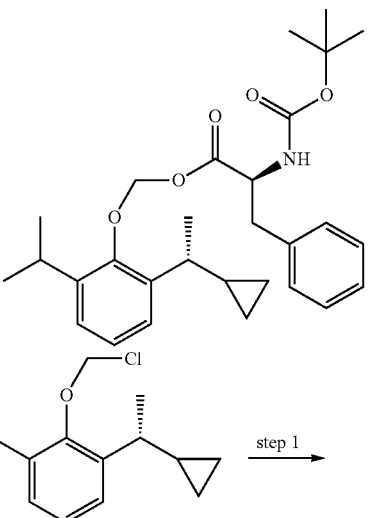

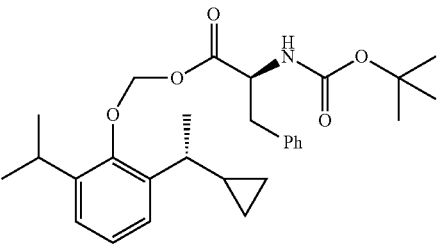

Compound 61

Step 1: [2-[(1R)-1-cyclopropylethyl]-6-isopropyl-phenoxy]methyl(2S)-2-(tertbutoxycarbonylamino)-3-phenyl-propanoate (Compound 61)

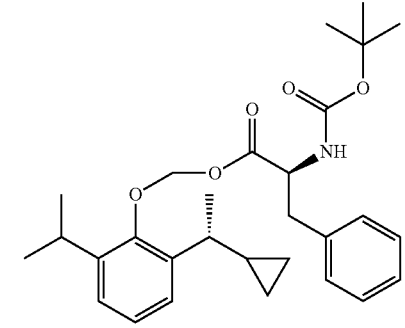 [SMILES: CC(C)c1cccc([C@H](C)C2CC2)c1OCOC(=O)[C@H](Cc1ccccc1)NC(=O)OC(C)(C)C]

2-(chloromethoxy)-1-[(1R)-1-cyclopropylethyl]-3-isopropyl-benzene (32B) (0.253 g, 1 mmol), 3-(tert-butoxycarbonylamino) propanoic acid (0.584 g, 2.2 mmol) and triethylamine (0.3 mL, 2.2 mmol) was dissolved in acetonitrile (5 mL), the mixture was stirred at 60° C. for 2 h, and was concentrated in vacuo. The residue was purified by silica gel column chromatography (petroleum ether/ethyl acetate (v/v)=80:1) to obtain [2-[(1R)-1-cyclopropylethyl]-6-isopropyl-phenoxy]methyl(2S)-2-(tertbutoxycarbonyl amino)-3-phenyl-propanoate (Compound 61) as a colorless liquid (0.374 g, yield: 77.6%).

$^1$H NMR (400 MHz, CDCl$_3$): δ 7.25-7.08 (m, 8H), 5.54 (s, 2H), 4.93 (d, 1H), 4.62 (d, 1H), 3.31-3.25 (m, 1H), 3.17-3.01 (m, 2H), 2.52-2.46 (m, 1H), 1.46 (s, 9H), 11.29-1.21 (m, 9H), 0.98-0.86 (m, 1H), 0.55-0.51 (m, 1H), 0.38-0.34 (m, 1H), 0.23-0.20 (m, 1H), 0.16-0.14 (m, 1H).

Example 62

[2-[(1R)-1-cyclopropylethyl]-6-isopropyl-phenoxy]methyl(2S)-2-amino-3-phenylpropanoate trifluoroacetate (Compound 62)

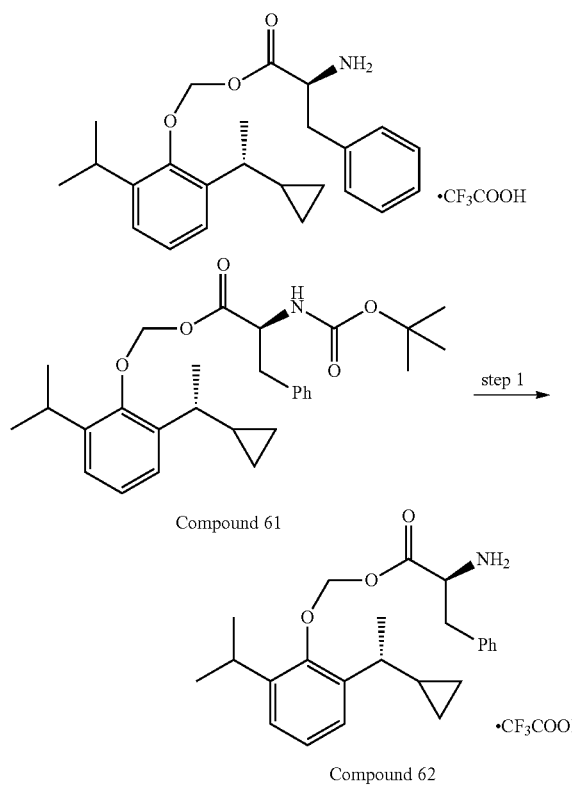

Step 1: [2-[(1R)-1-cyclopropylethyl]-6-isopropyl-phenoxy]methyl(2S)-2-amino-3-phenylpropanoate trifluoroacetate (Compound 62)

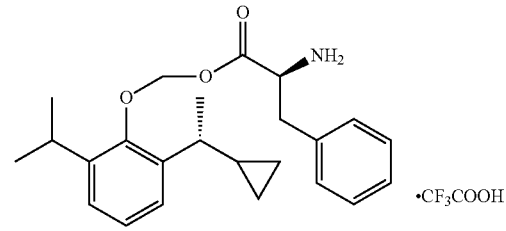

[2-[(1R)-1-cyclopropylethyl]-6-isopropyl-phenoxy]methyl(2S)-2-(tertbutoxycarbonyl amino)-3-phenyl-propanoate (Compound 61) (1.5 g, 3.0 mmol) was dissolved in dichloromethane (5 mL), trifluoroacetic acid (2.0 mL, 27 mmol) was added with stirring at room temperature, and the mixture was stirred at room temperature for 1 h, and was concentrated in vacuo. The residue was purified by silica gel column chromatography (petroleum ether/ethyl acetate (v/v)=2:1) to afford [2-[(1R)-1-cyclopropylethyl]-6-isopropyl-phenoxy]methyl(2S)-2-amino-3-phenylpropanoate trifluoroacetate (Compound 62) as a colorless liquid (1.2 g, yield: 78%).

$^1$H NMR (400 MHz, CDCl$_3$): δ 7.97 (s, 3H), 7.25-7.12 (m, 8H), 5.54 (q, 2H), 4.20 (t, 1H), 3.28-3.17 (m, 3H), 2.48-2.41 (m, 1H), 1.26-1.19 (m, 9H), 0.94-0.90 (m, 1H), 0.54-0.50 (m, 1H), 0.33-0.31 (m, 1H), 0.21-0.17 (m, 1H), 0.13-0.09 (m, 1H).

Example 63

[2-[(1R)-1-cyclopropylethyl]-6-isopropyl-phenoxy]methyl(2S)-2-(tert-butoxycarbonylamino)-3-methyl-pentanoate (Compound 63)

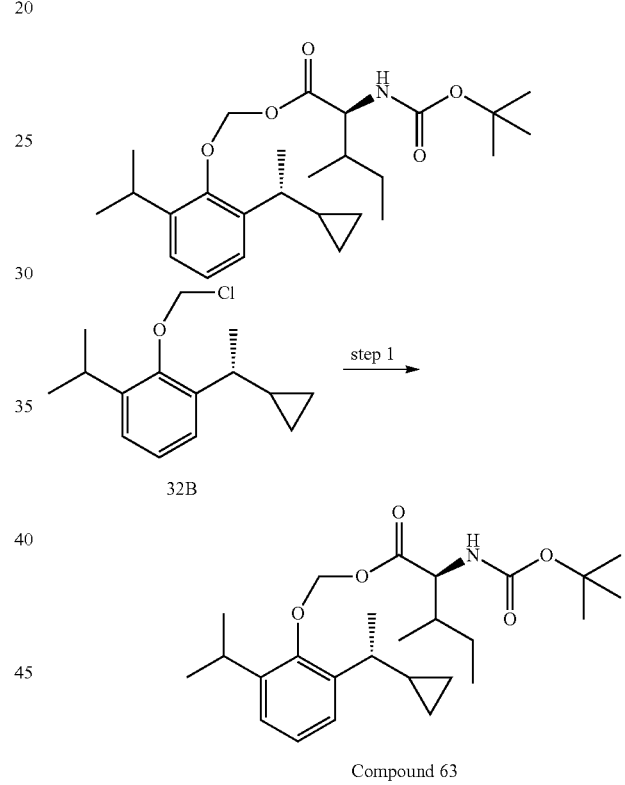

Step 1: [2-[(1R)-1-cyclopropylethyl]-6-isopropyl-phenoxy]methyl(2S)-2-(tertbutoxycarbonylamino)-3-methyl-pentanoate (Compound 63)

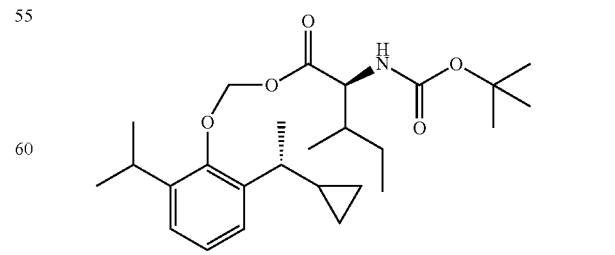

2-(chloromethoxy)-1-[(1R)-1-cyclopropylethyl]-3-isopropyl-benzene (32B) (0.253 g, 1 mmol), 3-(tert-butoxycarbonylamino) propanoic acid (0.509 g, 2.2 mmol) and triethylamine (0.3 mL, 2.2 mmol) were dissolved in acetonitrile (5 mL), the mixture was stirred at 60° C. for 2 h, and was concentrated in vacuo. The residue was purified by silica gel column chromatography (petroleum ether/ethyl acetate (v/v)=80:1) to obtain [2-[(1R)-1-cyclopropylethyl]-6-isopropyl-phenoxy]methyl(2S)-2-(tertbutoxycarbonylamino)-3-methyl-pentanoate (Compound 63) as a colorless liquid (0.347 g, yield: 77.5%).

$^1$H NMR (400 MHz, CDCl$_3$): δ 7.24-7.12 (m, 3H), 5.55 (q, 2H), 5.01 (d, 1H), 4.33-4.29 (m, 1H), 3.35-3.28 (m, 1H), 2.54-2.46 (m, 1H), 1.89 (s, 1H), 1.44 (s, 9H), 1.30-1.25 (m, 9H), 0.95-0.89 (m, 9H), 0.56-0.52 (m, 1H), 0.36-0.33 (m, 1H), 0.26-0.23 (m, 1H), 0.17-0.14 (m, 1H).

Example 64

2-[[2-(1-cyclopropylethyl)-6-isopropyl-phenoxy]methoxy]-4H-benzo[d][1,3,2]dioxaphosphinine 2-oxide (Compound 64)

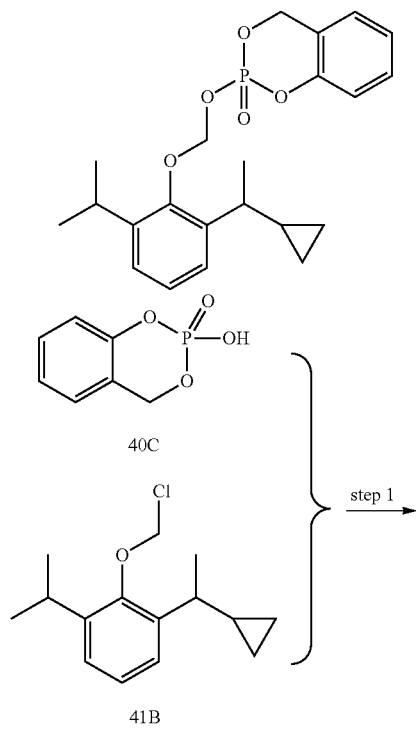

Step 1: 2-[[2-(1-cyclopropylethyl)-6-isopropyl-phenoxy]methoxy]-4H-benzo[d][1,3,2]dioxaphosphinine 2-oxide (Compound 64)

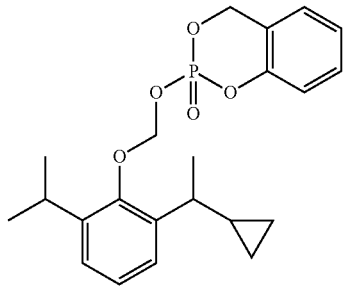 [SMILES: CC(C)c1cccc(C(C)C2CC2)c1OCOP1(=O)OCc2ccccc2O1]

2-hydroxy-4H-benzo[d][1,3,2]dioxaphosphinine 2-oxide (40C) (1.0 g, 5.37 mmol), triethylamine (1.63 mL, 16.12 mmol) and acetonitrile (50 mL) were added into the reaction flask, the mixture was stirred at 50° C. for 30 minutes. 2-(chloromethoxy)-1-(1-cyclopropylethyl)-3-isopropyl-benzene (41B) (1.63 g, 6.45 mmol) was added to the above solution, the mixture was stirred at 70° C. overnight, and was concentrated in vacuo. Water (50 mL) was added into the resulting mixture, the mixture was extracted with ethyl acetate (50 mL×3), washed with saturated brine (50 mL×3), dried over anhydrous, filtered, concentrated. The residue was purified by silica gel column chromatography (petroleum ether/ethyl acetate (v/v)=7:1) to obtain 2-[[2-(1-cyclopropylethyl)-6-isopropyl-phenoxy]methoxy]-4H-benzo[d][1,3,2]dioxaphosphinine 2-oxide (Compound 64) as a light yellow liquid (0.45 g, yield: 20.8%, HPLC: 90.2%).

$^1$HNMR (400 MHz, CDCl$_3$): δ 7.29 (t, 1H), δ 7.20-7.00 (m, 6H), δ 5.65-5.57 (m, 1H), δ 5.53 (dd, 1H), δ 5.34-5.29 (m, 2H), δ 3.27-3.17 (m, 1H), δ 2.46-2.37 (m, 1H), δ 1.17 (dd, 3H), δ 1.16-1.10 (m, 6H), δ 0.95-0.85 (m, 1H), δ 0.55-0.47 (m, 1H), δ 0.32-0.23 (m, 1H), δ 0.12-0.07 (m, 2H).

Example 65

[[2-[(1S)-1-cyclopropylethyl]-6-isopropyl-phenoxy]methyl-sodiooxy-phosphoryl]oxy sodium (Compound 65)

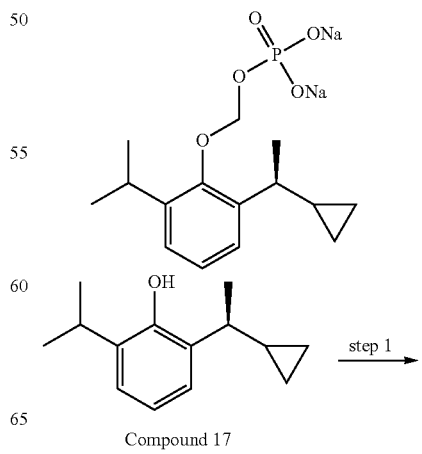

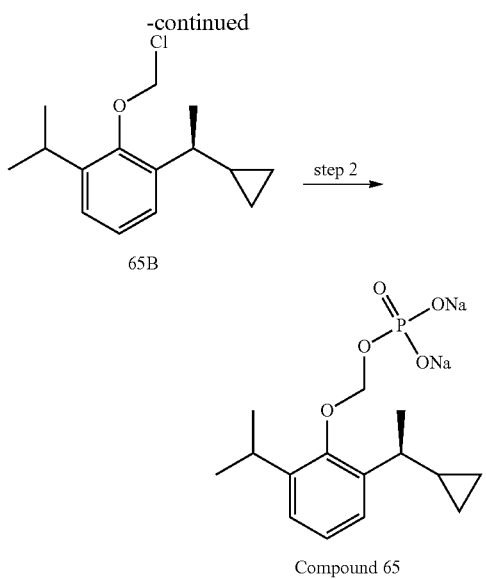

65B

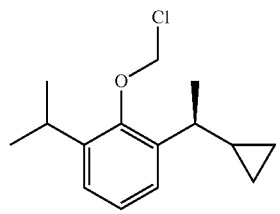 [SMILES: CC(C)c1cccc([C@@H](C)C2CC2)c1OCCl]

Compound 65

Step 1: 2-(chloromethoxy)-1-[(1S)-1-cyclopropylethyl]-3-isopropyl-benzene (65B)

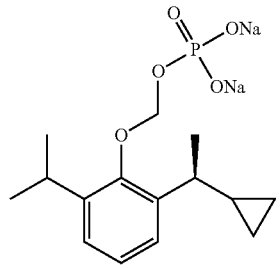

2-[(1S)-1-cyclopropylethyl]-6-isopropyl-phenol (Compound 17) (5.0 g, 0.024 mol), sodium hydroxide (2.0 g, 0.048 mol) and tetrahydrofuran (25 mL) were added into the reaction flask, the mixture was heated to reflux for 30 minutes, then bromochloromethane (63 g, 0.48 mol) was added, the mixture was stirred at 70° C. for 2 h, filtered, concentrated in vacuo. The residue was purified by silica gel column chromatography (petroleum ether) to afford 2-(chloromethoxy)-1-[(1S)-1-cyclopropylethyl]-3-isopropyl-benzene (65B) crude product, which was submitted to the next step without further purification.

$^1$H NMR (400 MHz, CDCl$_3$): δ 7.26-7.24 (m, 1H), 7.21-7.14 (m, 2H), 5.70 (s, 2H), 3.34-3.28 (m, 1H), 2.59-2.52 (m, 1H), 1.28 (d, 3H), 1.23 (dd, 6H), 0.95-0.93 (m, 1H), 0.56-0.54 (m, 1H), 0.35-0.33 (m, 1H), 0.24-0.15 (m, 2H).

Step 2: [[2-[(1S)-1-cyclopropylethyl]-6-isopropylphenoxy]methyl-sodiooxy-phosphoryl]oxysodium (Compound 65)

Phosphoric acid (12.4 g, 0.13 mmol), triethylamine (16 g, 0.16 mol) and acetonitrile (40 mL) were added into the reaction flask, the mixture was heated to 65° C. for 0.5 h. 2-(chloromethoxy)-1-[(1S)-1-cyclopropylethyl]-3-isopropyl-benzene (65B) (4.0 g, 0.016 mol) was added, and the mixture was stirred for 3 h at 75° C. The resulting mixture was concentrated in vacuo, the residue was dissolved in water (20 mL), and then the mixture was adjusted to pH 1 with 10% hydrochloric acid solution, and was extracted with methyl tert-butyl ether (20 mL×3), washed with saturated brine (10 mL×3), the organic layer was combined and concentrated. The residue was dissolved in water (10 mL), and the mixture was adjusted to pH 10~11 with sodium hydroxide solution (w/w=20%), and then was extracted with methyl tert-butyl ether (10 mL×3) until the organic layer colourless. The water phase was concentrated and the residue obtained was dissolved in acetonitrile (15 mL), the mixture was stirred at 50° C., followed by hot filtration to obtain [[2-[(1S)-1-cyclopropylethyl]-6-isopropyl-phenoxy]methyl-sodiooxy-phosphoryl]oxy sodium (Compound 65) as a white solid (4.2 g, yield: 74%, HPLC: 99.90%).

$^1$H NMR (400 MHz, D$_2$O): δ 7.45-7.42 (m, 1H), 7.36-7.30 (m, 2H), 5.27-5.22 (m, 2H), 3.53-3.46 (m, 1H), 2.68-2.62 (m, 1H), 1.34 (d, 3H), 1.27 (dd, 6H), 1.07-1.04 (m, 1H), 0.60-0.58 (m, 1H), 0.37-0.33 (m, 2H), 0.17-0.15 (m, 1H).

MS m/z (ESI): 313.2 [M−46+1].

Example 66

[[2-(1-cyclopropylethyl)-6-isopropyl-phenoxy]methoxy-sodiooxy-phosphoryl]oxysodium (Compound 66)

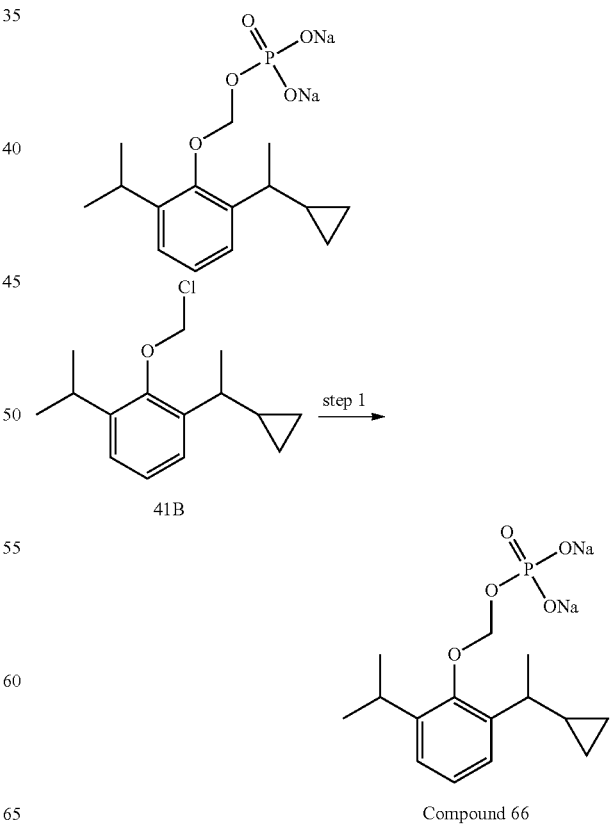

Compound 66

Step 1: [[2-(1-cyclopropylethyl)-6-isopropyl-phenoxy]methoxy-sodiooxy-phosphoryl]oxysodium (Compound 66)

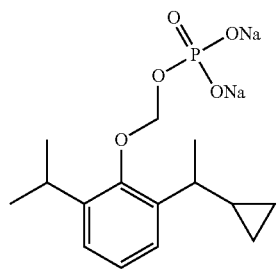

Phosphoric acid (31.6 g, 0.32 mmol), triethylamine (40.5 g, 0.40 mol) and acetonitrile (100 mL) were added into the reaction flask, the mixture was heated to 60° C. for 30 minutes, then 2-(chloromethoxy)-1-(1-cyclopropylethyl)-3-isopropyl-benzene (41B) (10.0 g, 0.04 mol) was added, and the mixture was stirred for 2 h at 75° C. The mixture was concentrated in vacuo, and the residue was dissolved in water (100 mL), the mixture was adjusted to pH 1 with 10% hydrochloric acid solution, and was extracted with methyl tert-butyl ether (100 mL×3). The combined organic extracts were concentrated, dissolved in water (100 mL), and the mixture was adjusted to pH 10~11 with sodium hydroxide solution (w/w=18%), washed with methyl tert-butyl ether (50 mL×4) until the aqueous layer became colourless. The resulting mixture was concentrated to obtain a white viscous residue which was dissolved in acetonitrile (50 mL), the mixture was stirred at 50° C. and filtered before the mixture was cooled, to afford [[2-(1-cyclopropylethyl)-6-isopropyl-phenoxy]methoxy-sodiooxy-phosphoryl]oxysodium (Compound 66) as a white powder (11 g, yield: 72%, HPLC: 95.6%).

$^1$H NMR (400 MHz, D$_2$O): δ 7.40-7.38 (m, 1H), 7.29-7.24 (m, 2H), 5.22-5.17 (m, 2H), 3.49-3.44 (m, 1H), 2.63-2.58 (m, 1H), 1.31 (d, 3H), 1.23 (dd, 6H), 1.04-0.98 (m, 1H), 0.57-0.53 (m, 1H), 0.32-0.25 (m, 2H), 0.13-0.09 (m, 1H).

MS m/z (ESI): 313.2 [M−46+1].

Example 67

[2-(1-cyclopropylethyl)-6-isopropyl-phenyl]acetate (Compound 67)

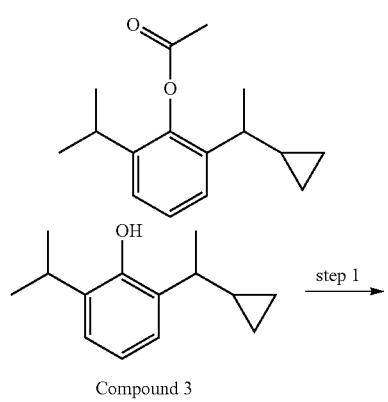

Compound 3

-continued

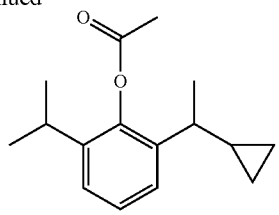

Compound 67

Step 1: [2-(1-cyclopropylethyl)-6-isopropyl-phenyl]acetate (Compound 67)

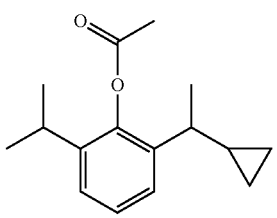 [SMILES: CC(=O)Oc1c(C(C)C)cccc1C(C)C1CC1]

2-(1-cyclopropylethyl)-6-isopropylphenol (Compound 3) (5.00 g, 24.50 mmol), 4-dimethylaminopyridine (1.50 g, 12.20 mmol) and acetic anhydride (50.00 g, 490.20 mmol) were added into the reaction flask, the mixture was stirred at 30° C. for 15 h. The resulting mixture was adjusted to pH 7 with 1M aqueous sodium hydroxide solution, and was extracted with ethyl acetate (100 mL×3), washed with brine (100 mL×3), dried over anhydrous sodium sulfate, filtered and the filtrate was concentrated in vacuo. The residue was purified by silica gel column chromatography (petroleum ether/ethyl acetate (v/v)=100:1) to obtain [2-(1-cyclopropylethyl)-6-isopropyl-phenyl]acetate (Compound 67) as a light yellow liquid (2.5 g, yield: 41.6%, HPLC: 96.6%).

$^1$HNMR (400 MHz, CDCl$_3$): δ 7.25 (dd, 1H), δ 7.21 (t, 1H), δ 7.21 (dd, 1H), δ 2.94-2.83 (m, 1H), δ 2.38 (s, 3H), δ 2.05-2.00 (m, 1H), δ 1.23 (d, 3H), δ 1.20 (d, 3H), δ 1.18 (d, 3H), δ 1.05-0.91 (m, 1H), δ 0.57-0.50 (m, 1H), δ 0.46-0.37 (m, 1H), δ 0.21-0.06 (m, 2H).

Example 68

2-[2-(1-cyclopropylethyl)-6-isopropyl-phenoxy]ethanol (Compound 68)

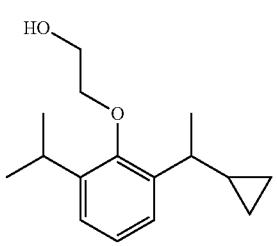

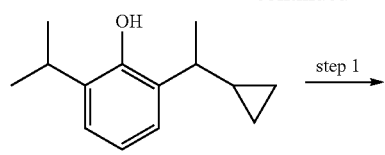

Compound 3

→ step 1

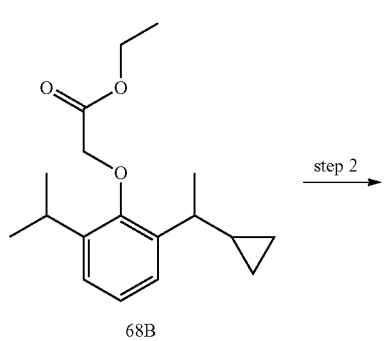

68B

→ step 2

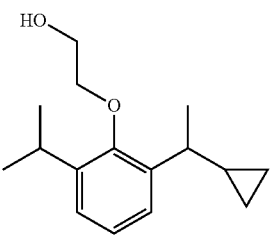

Compound 68

Step 1: ethyl 2-[2-(1-cyclopropylethyl)-6-isopropyl-phenoxy]acetate (68B)

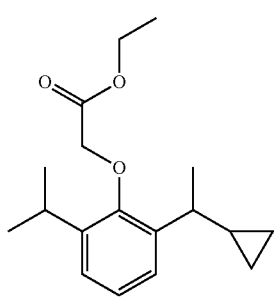 [SMILES: CCOC(=O)COc1c(C(C)C)cccc1C(C)C1CC1]

2-(1-cyclopropylethyl)-6-isopropylphenol (Compound 3) (10.00 g, 49.02 mmol), potassium carbonate (13.8 g, 100.00 mmol) and acetonitrile (50 mL) were added into the reaction flask, the mixture was stirred at 40° C. for 1 h. Ethyl bromoacetate (9.2 g, 55.00 mmol) was added into the mixture, the mixture was stirred at 40° C. for 14 h, filtered and concentrated in vacuo. The residue was purified by silica gel column chromatography (petroleum ether) to afford ethyl 2-[2-(1-cyclopropylethyl)-6-isopropyl-phenoxy]acetate (68B) as a colorless liquid (7.0 g, yield: 48.3%).

Step 2: 2-[2-(1-cyclopropylethyl)-6-isopropyl-phenoxy]ethanol (Compound 68)

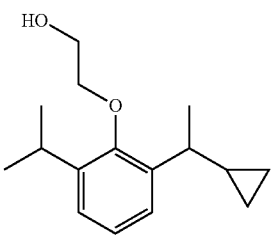 [SMILES: CC(C)c1cccc(C(C)C2CC2)c1OCCO]

Ethyl 2-[2-(1-cyclopropylethyl)-6-isopropyl-phenoxy]acetate (68B) (5.00 g, 17.20 mmol) and ethanol (50 mL) were added into the reaction flask, sodium borohydride (1.90 g, 51.6 mmol) was added in an ice-water bath. After addition, the reaction mixture was heated to 40° C. and stirred for 3 h, the reaction was quenched with 1M hydrochloric acid solution at 0° C. in an ice-water bath. The reaction mixture was concentrated in vacuo to remove ethanol, and the residue was extracted with ethyl acetate (50 mL×3), washed with saturated brine (50 mL×3), dried over anhydrous sodium sulfate, filtered and concentrated in vacuo. The residue was purified by silica gel column chromatography (petroleum ether/ethyl acetate (v/v)=2:1)) to obtain 2-[2-(1-cyclopropylethyl)-6-isopropyl-phenoxy]ethanol (Compound 68) as a white solid (2.0 g, yield: 47.6%, HPLC: 99.3%).

$^1$HNMR (400 MHz, CDCl$_3$): δ 7.24-7.20 (m, 1H), δ 7.15-7.10 (m, 2H), δ 3.94-3.87 (m, 2H), δ 3.84-3.79 (m, 2H), δ 3.40-3.22 (m, 1H), δ 2.35-2.45 (m, 1H), δ 1.28 (d, 3H), δ 1.23 (d, 6H), δ 1.02-0.94 (m, 1H), δ 0.57-0.53 (m, 1H), δ 0.38-0.35 (m, 1H), δ 0.25-0.06 (m, 2H).

MS m/z (ESI): 247.1 (M−1).

Example 69

[2-[(1R)-1-cyclopropylethyl]-6-isopropyl-phenyl]N-isopropylcarbamate (Compound 69)

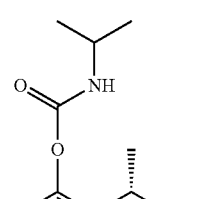

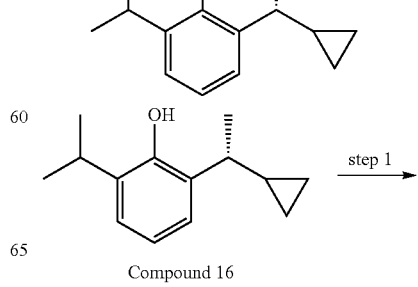

Compound 16

→ step 1

-continued

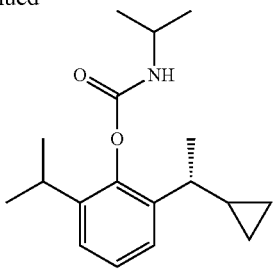

Compound 69

Step 1: [2-[(1R)-1-cyclopropylethyl]-6-isopropyl-phenyl]N-isopropylcarbamate (Compound 69)

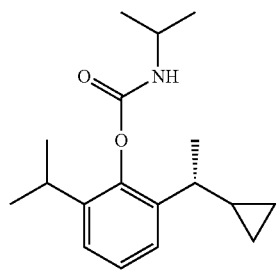 [SMILES: CC(C)NC(=O)Oc1c(C(C)C)cccc1[C@H](C)C1CC1]

2-[(1R)-1-cyclopropylethyl]-6-isopropyl-phenol (Compound 16) (0.80 g, 3.92 mmol), dry tetrahydrofuran (30 mL) and triethylamine (1.11 g, 10.96 mmol) were added into the reaction flask in sequence. Isopropyl isocyante (0.50 g, 5.87 mmol) was added under the nitrogen atmosphere, the mixture was heated to 70° C. and stirred for 15 h. The resulting mixture was concentrated in vacuo, the residue was extracted with ethyl acetate (30 mL×3), washed with saturated brine (30 mL×3), the organic phase was dried over anhydrous sodium sulfate, filtered and concentrated in vacuo. The residue was purified by silica gel column chromatography (petroleum ether/ethyl acetate (v/v)=20:1)) to obtain [2-[(1R)-1-cyclopropylethyl]-6-isopropyl-phenyl]N-isopropylcarbamate (Compound 69) as a white solid (0.9 g, yield: 79.6%, HPLC: 97.6%).

¹HNMR (400 MHz, CDCl₃): δ 7.26-7.13 (m, 3H), δ 4.81 (d, 1H), δ 3.91-3.85 (m, 1H), δ 3.06-2.99 (m, 1H), δ 2.19-2.11 (m, 1H), δ 1.26-1.20 (m, 15H), δ 1.00-0.96 (m, 1H), δ 0.56-0.52 (m, 1H), δ 0.39-0.34 (m, 1H), δ 0.19-0.12 (m, 2H).

MS m/z (ESI): 290.2 (M+1).

Example 70 tert-butyl [2-(1-cyclopropylethyl)-6-isopropyl-phenyl]carbonate (Compound 70)

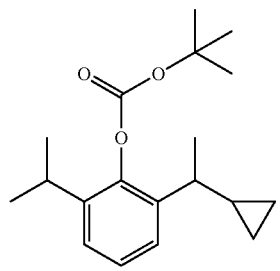

-continued

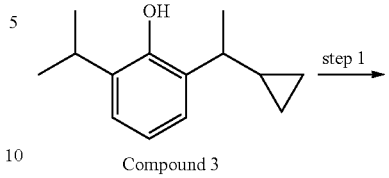

Compound 3

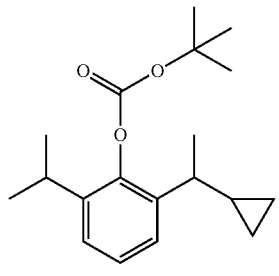

Compound 70

Step 1: tert-butyl [2-(1-cyclopropylethyl)-6-isopropyl-phenyl]carbonate (Compound 70)

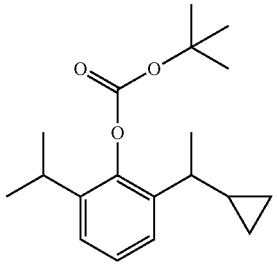 [SMILES: CC(C)c1cccc(C(C)C2CC2)c1OC(=O)OC(C)(C)C]

2-(1-cyclopropylethyl)-6-isopropylphenol (Compound 3) (1.00 g, 4.89 mmol), dichloromethane (30 mL) and 4-dimethylaminopyridine (0.12 g, 0.79 mmol) were added into the reaction flask in sequence, di-tert-butyl dicarbonate (2.14 g, 9.79 mmol) was added after a thorough mixing, and the mixture was stirred at room temperature overnight. The resulting mixture was extracted with dichloromethane (30 mL×3), washed with hydrochloric acid solution (1M, 30 mL×3) and saturated brine (30 mL×2), dried over anhydrous sodium sulfate, filtered and concentrated in vacuo. The residue was purified by silica gel column chromatography (petroleum ether) to afford tert-butyl [2-(1-cyclopropylethyl)-6-isopropyl-phenyl]carbonate (Compound 70) as a colorless liquid (1.2 g, yield: 80.0%, HPLC: 97.1%).

¹HNMR (400 MHz, CDCl₃): δ 7.25 (dd, 1H), δ 7.20 (t, 1H), δ 7.15 (dd, 1H), δ 3.06-2.99 (m, 1H), δ 2.17-2.09 (m, 1H), δ 1.52 (s, 9H), δ 1.25 (d, 3H), δ 1.21 (dd, 6H), δ 1.04-0.96 (m, 1H), δ 0.57-0.53 (m, 1H), δ 0.39-0.35 (m, 1H), δ 0.22-0.11 (m, 2H).

Example 71

[2-[(1R)-1-cyclopropylethyl]-6-isopropyl-phenoxy]methyl(2S)-2-amino-3-methylpentanoate trifluoroacetate (Compound 71)

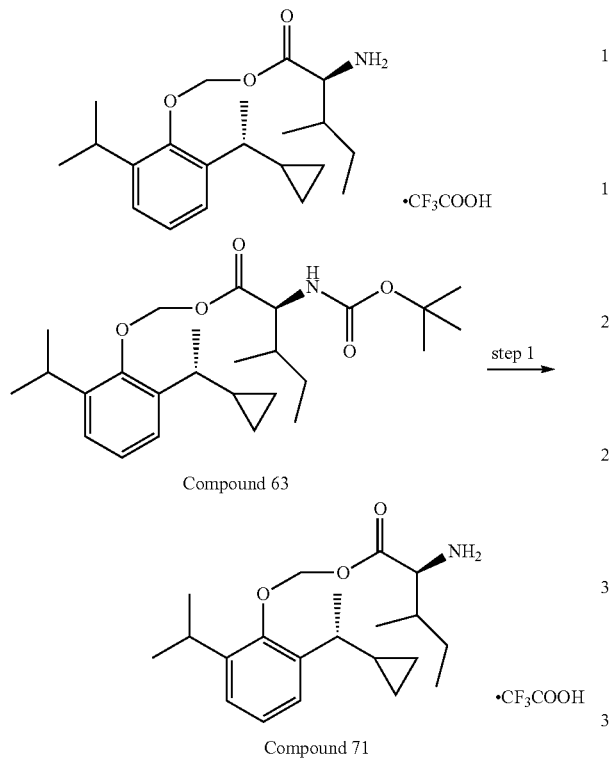

Step 1: [2-[(1R)-1-cyclopropylethyl]-6-isopropyl-phenoxy]methyl(2S)-2-amino-3-methylpentanoate trifluoroacetate (Compound 71)

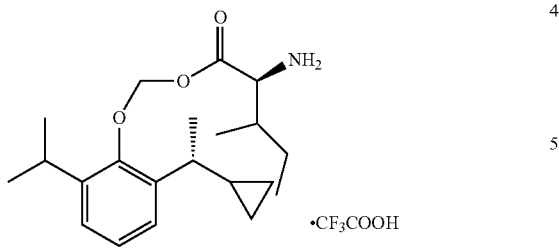

[2-[(1R)-1-cyclopropylethyl]-6-isopropyl-phenoxy]methyl(2S)-2-(tert-butoxycarbonyl amino)-3-methyl-pentanoate (Compound 63) (1.7 g, 3.0 mmol) was dissolved in dichloromethane (5 mL), trifluoroacetic acid (2.0 m L, 27 mmol) was added with a stirring at room temperature, and the mixture was stirred for 1 hours at room temperature. The resulting mixture was concentrated in vacuo, purified by silica gel column chromatography (petroleum ether/ethyl acetate (v/v)=2:1)) to obtain [2-[(1R)-1-cyclopropylethyl]-6-isopropyl-phenoxy]methyl(2S)-2-amino-3-methylpentanoate trifluoroacetate (Compound 71) as a yellow liquid (0.78 g, yield: 62%).

$^1$H NMR (400 MHz, CDCl$_3$): δ 7.25-7.12 (m, 3H), 5.55 (dd, 2H), 3.38 (d, 1H), 3.36-3.29 (m, 1H), 2.56-2.49 (m, 1H), 1.83-1.76 (m, 1H), 1.60 (s, 2H), 1.52-1.42 (m, 1H), 1.28-1.21 (m, 10H), 0.98-0.88 (m, 7H), 0.59-0.53 (m, 1H), 0.39-0.33 (m, 1H), 0.25-0.13 (m, 2H).

Example 72 sodium (2,6-bis(1-cyclopropylethyl)phenoxy)methyl phosphate (Compound 72)

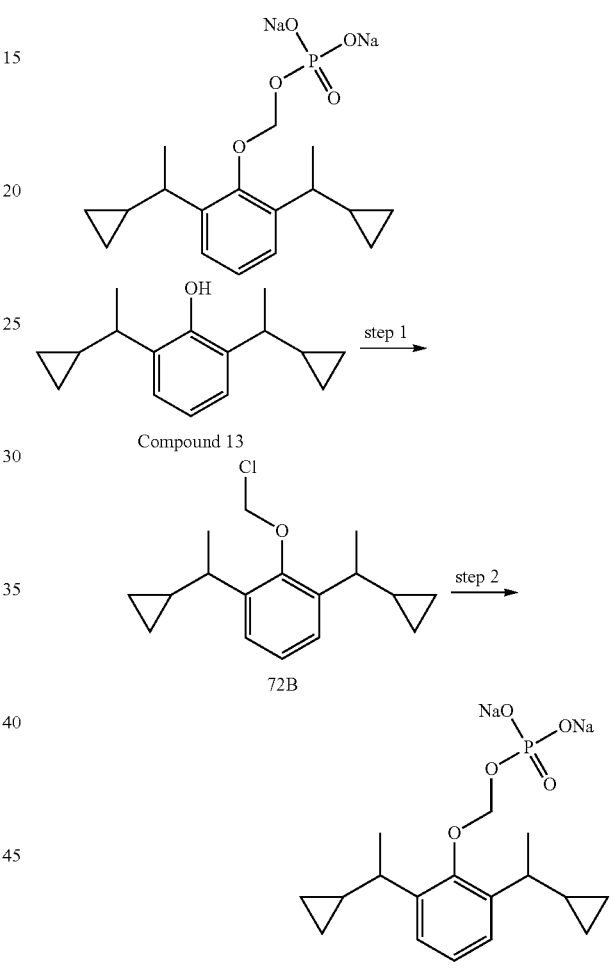

Step 1: 2-(chloromethoxy)-1,3-bis(1-cyclopropylethyl)benzene (72B)

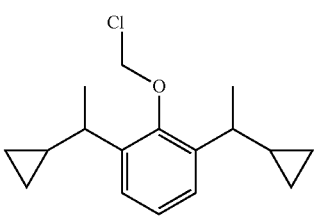 [SMILES: CC(c1cccc(C(C)C2CC2)c1OCCl)C1CC1]

2,6-bis(1-cyclopropylethyl)phenol (Compound 13) (2.0 g, 0.0086 mol), sodium hydroxide (0.69 g, 0.017 mol) and tetrahydrofuran (10 mL) were added into the reaction flask, the mixture was refluxed for 30 minutes, then bromochloromethane (28 g, 0.21 mol) was added, followed by a stirring at 70° C. for another 2 h. The resulting mixture was filtered, concentrated in vacuo, the residue was purified by silica gel column chromatography (petroleum ether) to obtain 2-(chloromethoxy)-1,3-bis(1-cyclopropylethyl)benzene (72B) crude product (1.5 g, yield: 61.9%) as a colorless liquid, which was submitted to the next step without further purification.

Step 2: sodium (2,6-bis(1-cyclopropylethyl)phenoxy)methyl phosphate (Compound 72)

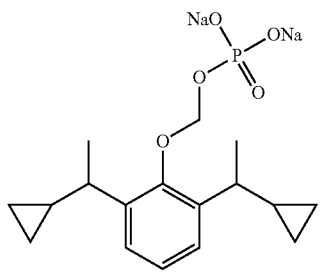

Acetonitrile (15 mL), phosphoric acid (4.22 g, 0.043 mol) and triethylamine (5.44 g, 0.54 mol) were added into the reaction flask, the mixture was heated to 65° C. for 30 minutes, then 2-(chloromethoxy)-1,3-bis(1-cyclopropylethyl)benzene (72B) (1.5 g, 0.0054 mol) was added, followed by a stirring for 3 h at 75° C. The mixture was concentrated in vacuo, the residue was dissolved in water (20 mL), and was adjusted pH to 1 with 10% hydrochloric acid solution, extracted with methyl tert-butyl ether (20 mL×3), washed with saturated brine (20 mL×2). The combined organic layer was concentrated, and the residue was dissolved in water (20 mL), and was adjusted to pH 9~10 with sodium hydroxide solution (w/w=20%), extracted with methyl tert-butyl ether (30 mL×2). The water phase was concentrated and the residue was dissolved in isopropanol (30 mL), the mixture was filtered and concentrated in vacuo, the residue was dissolved in acetonitrile, stirred and filtered to afford sodium (2,6-bis(1-cyclopropylethyl)phenoxy)methyl phosphate (Compound 72) as a white solid (0.9 g, yield: 49%, HPLC: 97%).

¹H NMR (400 MHz, D₂O): δ 7.45 (dd, 2H), 7.34 (t, 1H), 5.21-5.15 (m, 2H), 2.70-2.62 (m, 2H), 1.34 (dd, 6H), 1.37-1.31 (m, 2H), 0.62-0.55 (m, 2H), 0.32-0.30 (m, 4H), 0.20-0.13 (m, 2H).

Example 73

[[2-(1-cyclopropylethyl)-6-sec-butyl-phenoxy]methyl-sodiooxy-phosphoryl]oxy-sodium (Compound 73)

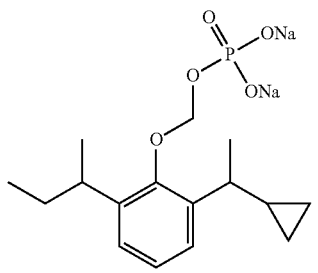

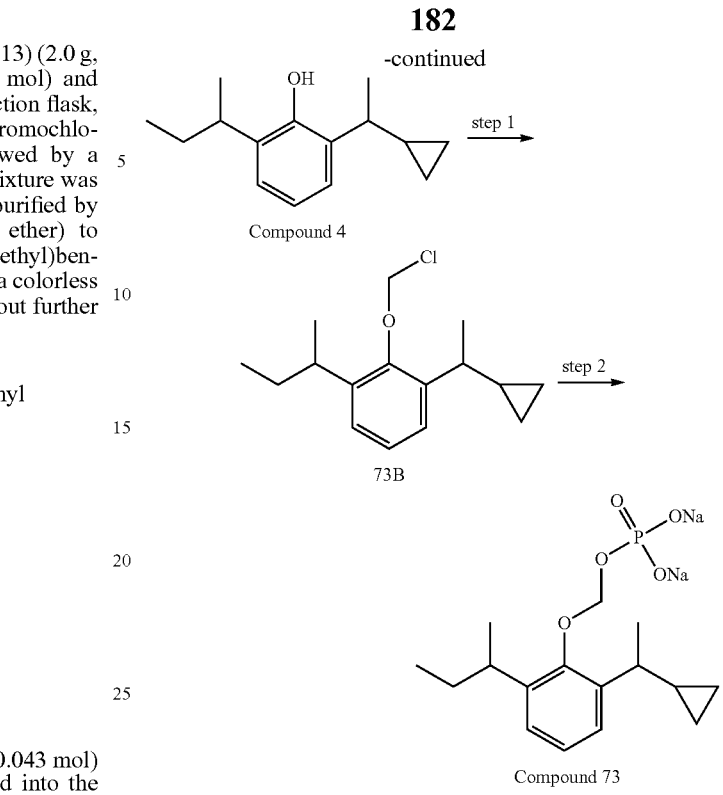

Step 1: 2-(chloromethoxy)-1-(1-cyclopropylethyl)-3-sec-butyl-benzene (73B)

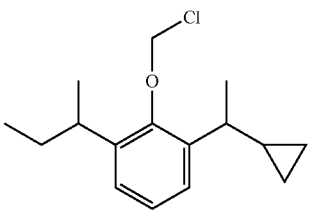 [SMILES: CCC(C)c1cccc(C(C)C2CC2)c1OCCl]

2-sec-butyl-6-(1-cyclopropylethyl)phenol (Compound 4) (2.34 g, 10.7 mmol) was dissolved in tetrahydrofuran (50 mL), sodium hydroxide (0.86 g, 21.4 mol) was added, and the mixture was heated to reflux for 30 minutes at 70° C., bromochloromethane (20.9 mL, 322 mmol) was added, followed by a stirring at 70° C. for another 2 h. The resulting mixture was concentrated to remove tetrahydrofuran and bromochloromethane, petroleum ether (50 mL) was added, and the mixture was washed with water (10 m L×2). The organic phase was dried over anhydrous sodium sulfate, concentrated in vacuo, purified by silica gel column chromatography (petroleum ether) to obtain 2-(chloromethoxy)-1-(1-cyclopropylethyl)-3-sec-butyl-benzene (73B) (2.37 g, yield: 83%, HPLC: 73.37%) crude product, which was submitted to the next step without further purification.

¹H NMR (400 MHz, CDCl₃): δ7.22-7.27 (m, 1H), 7.16-7.20 (m, 1H), 7.08-7.11 (m, 1H), 5.66-5.70 (m, 2H), 3.00-3.06 (m, 1H), 2.54-2.59 (m, 1H), 1.50-1.60 (m, 2H), 1.20-1.32 (m, 6H), 0.89-0.98 (m, 1H), 0.72-0.86 (m, 3H), 0.49-0.60 (m, 1H), 0.13-0.30 (m, 3H).

MS m/z (ESI): 263.2[M-Cl+CH₃O+1].

Step 2: [[2-(1-cyclopropylethyl)-6-sec-butyl-phenoxy]methyl-sodiooxy-phosphoryl]oxy-sodium (Compound 73)

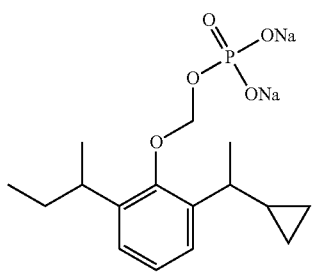

Phosphoric acid (85%, 5.10 g, 71.1 mmol) and triethylamine (9.00 g, 9 mmol) was dissolved in acetonitrile (50 mL), the mixture was heated to 60° C. for 30 minutes, a solution of 2-(chloromethoxy)-1-(1-cyclopropylethyl)-3-sec-butyl-benzene (73B) in acetonitrile (10 mL, 8.9 mmol) was added dropwise. Upon completion of addition, the reaction mixture was stirred for another 2 h at 60° C. The mixture was concentrated in vacuo, the obtained viscous solid was dissolved in water (50 mL), the mixture was adjusted pH to 1 with 10% hydrochloric acid solution, extracted with methyl tert-butyl ether (30 mL×3). Water (30 mL) was added into the combined organic layer, and adjusted pH to 11 with sodium hydroxide solution (w/w=20%), the obtained aqueous phase was washed with methyl tert-butyl ether (10 mL×3), and then was concentrated in vacuo to obtain [[2-(1-cyclopropylethyl)-6-sec-butyl-phenoxy]methyl-sodiooxy-phosphoryl]oxy-sodium (Compound 73) (4.00 g, yield: 100%, HPLC: 95.60%) as a white solid.

$^1$H NMR (400 MHz, D$_2$O) 7.37-7.42 (m, 1H), 7.25-7.31 (m, 2H), 5.20-5.22 (m, 2H), 3.16-3.23 (m, 1H), 2.64-2.70 (m, 1H), 1.54-1.68 (m, 2H), 1.33 (dd, 3H), 1.23 (dd, 3H), 0.99-1.10 (m, 1H), 0.78-0.85 (m, 3H), 0.53-0.59 (m, 1H), 0.27-0.37 (m, 2H), 0.11-0.17 (m, 1H).

Example 74

[[2-[(1R)-1-cyclobutylethyl]-6-isopropyl-phenoxy]methoxy-sodiooxyphosphoryl]oxy sodium (Compound 74)

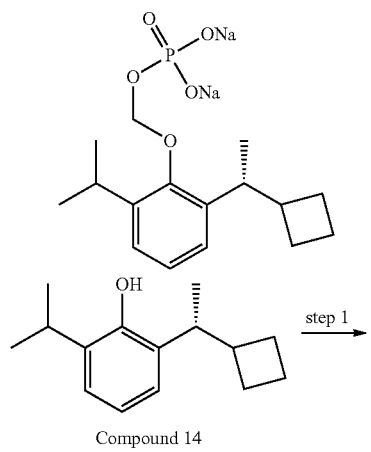

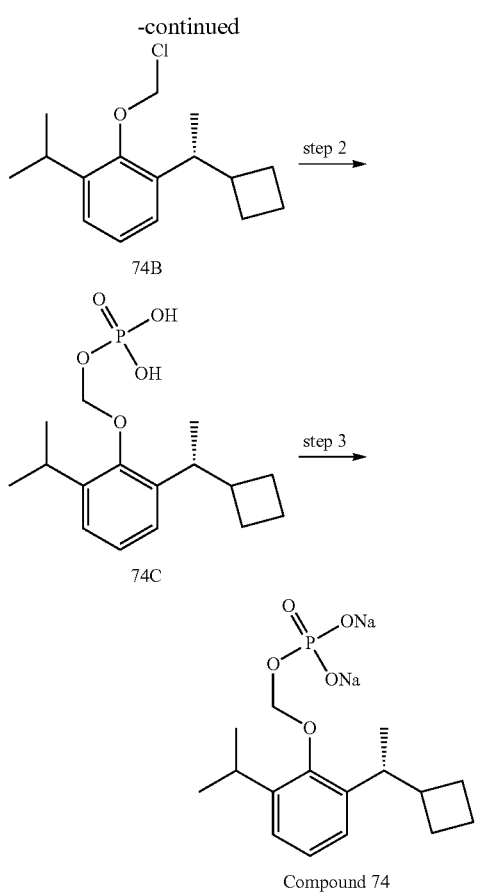

Step 1: 2-(chloromethoxy)-1-[(1R)-1-cyclobutylethyl]-3-isopropyl-benzene (74B)

2-[(1R)-1-cyclobutylethyl]-6-isopropyl-phenol (Compound 14) (2.00 g, 9.16 mmol), tetrahydrofuran (20 mL) and sodium hydroxide (0.73 g, 18.32 mmol) were added into the reaction flask in sequence, the mixture was heated to 50° C. for 30 minutes in nitrogen atmosphere, then bromochloromethane (35.56 g, 274.31 mmol) was added, and the mixture was stirred at 70° C. for 2 h. The resulting mixture was filtered, concentrated in vacuo, and the residue was purified by silica gel column chromatography (petroleum ether) to obtain 2-(chloromethoxy)-1-[(1R)-1-cyclobutylethyl]-3-isopropyl-benzene (74B) crude product as colorless oil (1.9 g, yield: 77.9%), which was submitted to the next step without further purification.

Step 2: [2-[(1R)-1-cyclobutylethyl]-6-isopropyl-phenoxy]methyl dihydrogen phosphate (74C)

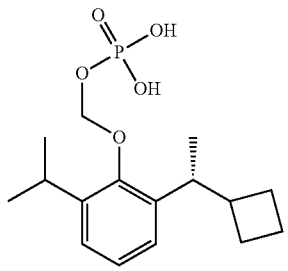 [SMILES: CC(C)c1cccc([C@H](C)C2CCC2)c1OCOP(=O)(O)O]

Phosphoric acid (5.29 g, 53.97 mmol), triethylamine (6.83 g, 67.46 mmol) and acetonitrile (30 mL) were added into the reaction flask, the mixture was heated to 60° C. for 30 minutes, and then 2-(chloromethoxy)-1-[(1R)-1-cyclobutylethyl]-3-isopropyl-benzene (74B) (1.80 g, 6.75 mmol) was added, followed by a stirring for 20 h at 70° C. The mixture was concentrated in vacuo, the residue was dissolved in water (50 mL), and pH was adjusted to 1 with hydrochloric acid solution (1M), the mixture was extracted with methyl tert-butyl ether (100 mL×3). The combined organic layer was dried by anhydrous sodium sulfate, filtered and the filtrate was concentrated, the residue was purified by silica gel column chromatography (ethanol/dichloromethane (v/v)=1:1) to afford [2-[(1R)-1-cyclobutylethyl]-6-isopropyl-phenoxy]methyl dihydrogen phosphate (74C) as a dark brown liquid (1.60 g, yield: 72%, HPLC: 99.3%).

$^1$HNMR (400 MHz, CDCl$_3$): δ 7.10-7.08 (m, 2H), δ 7.00-6.97 (m, 1H), δ 5.45 (s, 2H), δ 3.72 (s, 2H), δ 3.35-3.29 (m, 1H), δ 3.12-3.06 (m, 1H), δ 2.59-2.55 (m, 1H), δ 2.42-2.38 (m, 1H), δ 2.10-2.04 (m, 1H), δ 1.74-1.52 (m, 5H), δ 1.25-1.14 (m, 6H), δ 1.09-1.06 (m, 3H).

MS m/z (ESI): 327.3 [M−1].

Step 3: [[2-[(1R)-1-cyclobutylethyl]-6-isopropyl-phenoxy]methoxy-sodiooxyphosphoryl]oxysodium (Compound 74)

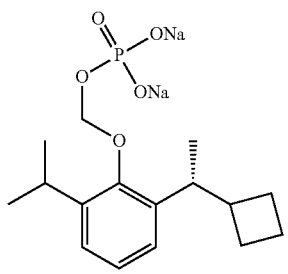

[2-[(1R)-1-cyclobutylethyl]-6-isopropyl-phenoxy]methyl dihydrogen phosphate (74C) (1.60 g, 4.87 mmol) and ethanol (10 mL) were added into the reaction flask, pH of the mixture was adjusted to 10 with 10% sodium hydroxide solution (w/w), the mixture was stirred at room temperature for 2 h. The resulting mixture was concentrated, dissolved in 95% isopropanol aqueous solution (w/w, 10 mL), filtered to remove the insoluble substance, the filtrate was concentrated in vacuo to obtain gray-green viscous liquid. Acetonitrile (5 mL) was added into the above liquid, followed by a stirring at 50° C., the mixture was filtered to obtain [[2-[(1R)-1-cyclobutylethyl]-6-isopropyl-phenoxy]methoxy-sodiooxy-phosphoryl]oxysodium (Compound 74) as a gray-green powder (1.00 g, yield: 53%, HPLC: 96.4%).

$^1$HNMR (400 MHz, D$_2$O): δ 7.25 (dd, 1H), δ 7.20 (t, 1H), δ 7.15 (dd, 1H), δ 5.30-5.25 (m, 2H), δ 3.35-3.46 (m, 1H), δ 3.24-3.16 (m, 1H), δ 2.52-2.42 (m, 1H), δ 2.15-2.08 (m, 1H), δ 1.86-1.63 (m, 4H), δ 1.55-1.46 (m, 1H), δ 1.24 (d, 3H), δ 1.18 (d, 3H), δ 1.18 (d, 3H).

MS m/z (ESI): 327.3 [M−46−1].

Example 75 sodium (2,6-bis((R)-1-cyclopropylethyl)phenoxy)methyl phosphate (Compound 75)

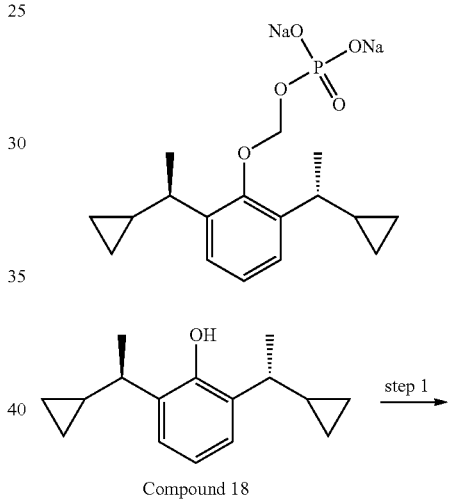

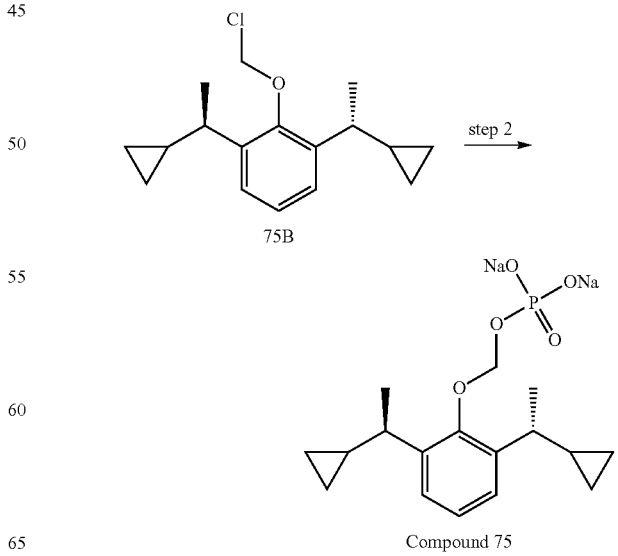

Step 1: 2-(chloromethoxy)-1,3-bis((R)-1-cyclopropylethyl)benzene (75B)

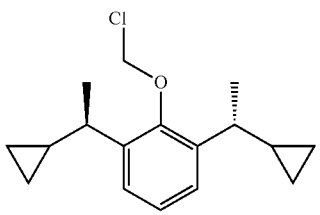 [SMILES: C[C@@H](c1cccc([C@H](C)C2CC2)c1OCCl)C1CC1]

2,6-bis[(1R)-1-cyclopropylethyl]phenol (Compound 18) (1 g, 0.0043 mol), tetrahydrofuran (5 mL) and sodium hydroxide (0.30 g, 0.009 mmol) were added into the reaction flask, the mixture was heated to 50° C. for 30 minutes, then bromochloromethane (35.56 g, 274.31 mmol) was added, and followed by a stirring at 70° C. for 2 h, the mixture was filtered, concentrated in vacuo. The residue was purified by silica gel column chromatography (petroleum ether) to obtain 2-(chloromethoxy)-1,3-bis((R)-1-cyclopropylethyl)benzene (75B) crude product (0.8 g, yield: 70%) as a colorless liquid, which was submitted to the next step without further purification.

$^1$H NMR (400 MHz, CDCl$_3$): δ 7.29-7.16 (m, 2H), 7.22-7.18 (m, 1H), 5.67-5.62 (m, 2H), 2.54-2.50 (m, 2H), 1.27 (d, 6H), 0.99-0.93 (m, 2H), 0.58-0.53 (m, 2H), 0.38-0.34 (m, 2H), 0.27-0.22 (m, 2H), 0.18-0.13 (m, 2H).

Step 2: sodium (2,6-bis((R)-1-cyclopropylethyl)phenoxy)methyl phosphate (Compound 75)

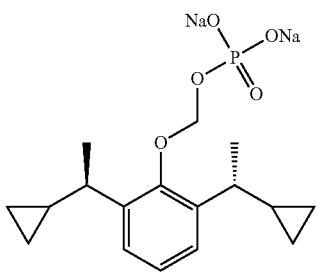

Acetonitrile (10 mL), phosphoric acid (2.25 g, 0.0229 mol) and triethylamine (2.90 g, 0.0287 mol) were added into the reaction flask, the mixture was heated to 65° C. for 30 minutes, then 2-(chloromethoxy)-1,3-bis((R)-1-cyclopropylethyl)benzene (75B) (0.8 g, 0.0028 mol) was added, followed by a stirring for 3 h at 75° C. The mixture was concentrated in vacuo, the residue was dissolved in water (20 mL), pH of the mixture was adjusted to 1 with a solution of hydrochloric acid (10%), the mixture was extracted with methyl tert-butyl ether (20 mL×3), washed with brine (20 mL×2). The combined organic layer was concentrated, and the residue was dissolved in water (20 mL), adjusted pH to 9~10 with sodium hydroxide solution (w/w=20%), the mixture was extracted with methyl tert-butyl ether (30 mL×2). The combined inorganic layer was concentrated, the residue was added into isopropanol (30 mL), filtered, and concentrated. The residue was added into acetonitrile, stirred, filtered to obtain sodium (2,6-bis((R)-1-cyclopropylethyl)phenoxy)methyl phosphate (Compound 75) as a white solid (0.6 g, yield: 54.4%, HPLC: 97.3%).

$^1$H NMR (400 MHz, D$_2$O): δ 7.45 (d, 2H), 7.32 (t, 1H), 5.21-5.15 (m, 2H), 2.66-2.62 (m, 2H), 1.31 (d, 6H), 1.12-1.09 (m, 2H), 0.63-0.58 (m, 2H), 0.32-0.30 (m, 4H), 0.19-0.15 (m, 2H).

Example 76 sodium (2-((R)-1-cyclopropylethyl)-6-((S)-1-cyclopropylethyl)phenoxy)methyl phosphate (Compound 76)

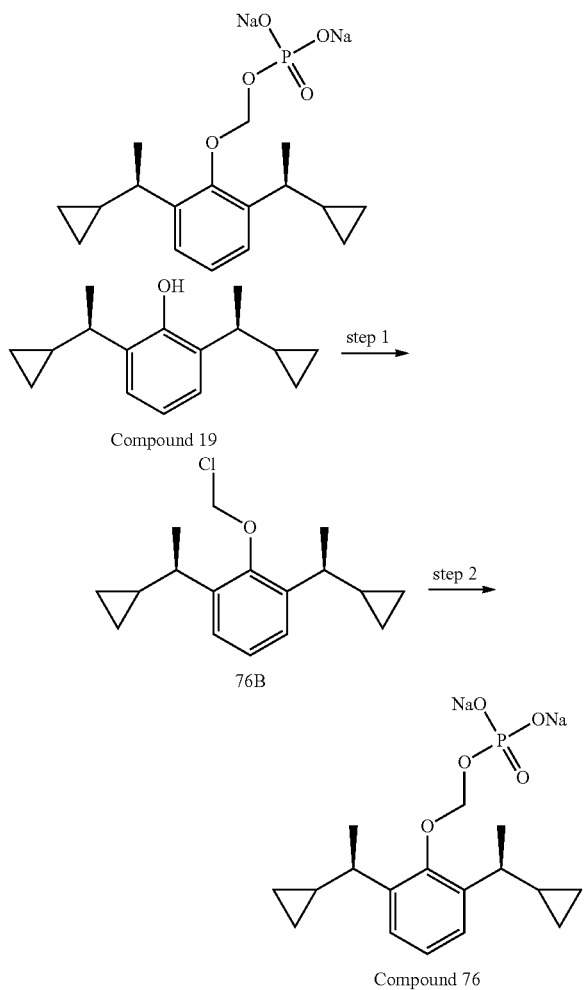

Step 1: 2-(chloromethoxy)-1-((R)-1-cyclopropylethyl)-3-((S)-1-cyclopropylethyl)benzene (76B)

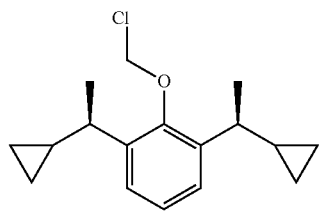 [SMILES: C[C@H](c1cccc([C@H](C)C2CC2)c1OCCl)C1CC1]

2-[(1S)-1-cyclopropylethyl]-6-[(1R)-1-cyclopropylethyl] phenol (Compound 19) (2 g, 0.00868 mol), tetrahydrofuran (10 mL) and sodium hydroxide (0.69 g, 0.0174 mmol) were added into the reaction flask, the mixture was heated to reflux for 30 minutes, and bromochloromethane (28 g, 0.217 mmol) was added, followed by a stirring at 70° C. for 2 h. The resulting mixture was filtered, concentrated in vacuo, the residue was purified by silica gel column chromatography (petroleum ether) to obtain 2-(chloromethoxy)-1-((R)-1-cyclopropylethyl)-3-((S)-1-cyclopropylethyl)benzene (76B) crude product as a colorless liquid (1.8 g, yield: 74.3%), which was submitted to the next step without further purification.

$^1$H NMR (400 MHz, CDCl$_3$): δ 7.25 (t, 2H), 7.20 (d, 1H), 5.63 (s, 2H), 2.56-2.49 (m, 2H), 1.27 (dd, 6H), 0.92-0.87 (m, 2H), 0.53-0.50 (m, 2H), 0.32-0.28 (m, 2H), 0.20-0.15 (m, 4H).

Step 2: sodium(2-((R)-1-cyclopropylethyl)-6-((S)-1-cyclopropylethyl)phenoxy)methyl phosphate (Compound 76)

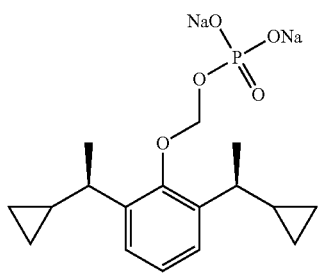

Acetonitrile (20 mL), phosphoric acid (5.06 g, 0.0516 mol) and triethylamine (6.53 g, 0.0545 mol) were added into the reaction flask, the mixture was heated to 65° C. for 30 minutes, then 2-(chloromethoxy)-1-((R)-1-cyclopropylethyl)-3-((S)-1-cyclopropylethyl)benzene (76B) (1.8 g, 0.0064 mol) was added, followed by a stirring for 3 h at 75° C. The mixture was concentrated in vacuo, the residue was dissolved in water (20 mL), adjusted pH to 1 with 10% hydrochloric acid solution, the mixture was extracted with methyl tert-butyl ether (30 mL×3), washed with saturated brine (30 mL×2). The combined organic layer was concentrated, dissolved in water (30 mL), adjusted pH to 9~10 with sodium hydroxide solution (w/w=20%), the mixture was extracted with methyl tert-butyl ether (40 mL×2). The combined inorganic layer was concentrated, the residue was added into isopropanol (40 mL), the mixture was filtered, concentrated, then acetonitrile was added, the mixture was slurried and filtered to obtain sodium(2-((R)-1-cyclopropylethyl)-6-((S)-1-cyclopropylethyl)phenoxy)methyl phosphate (Compound 76) as a white solid (1.5 g, yield: 60.46%, HPLC: 96.5%).

$^1$H NMR (400 MHz, D$_2$O): δ 7.44 (d, 2H), 7.33 (t, 1H), 5.17 (d, 2H), 2.71-2.64 (m, 2H), 1.35 (dd, 6H), 1.05-1.01 (m, 2H), 0.58-0.54 (m, 2H), 0.18-0.15 (m, 4H), 0.14-0.11 (m, 2H).

Example 77 sodium (2,6-bis((S)-1-cyclopropylethyl)phenoxy) methyl phosphate (Compound 77)

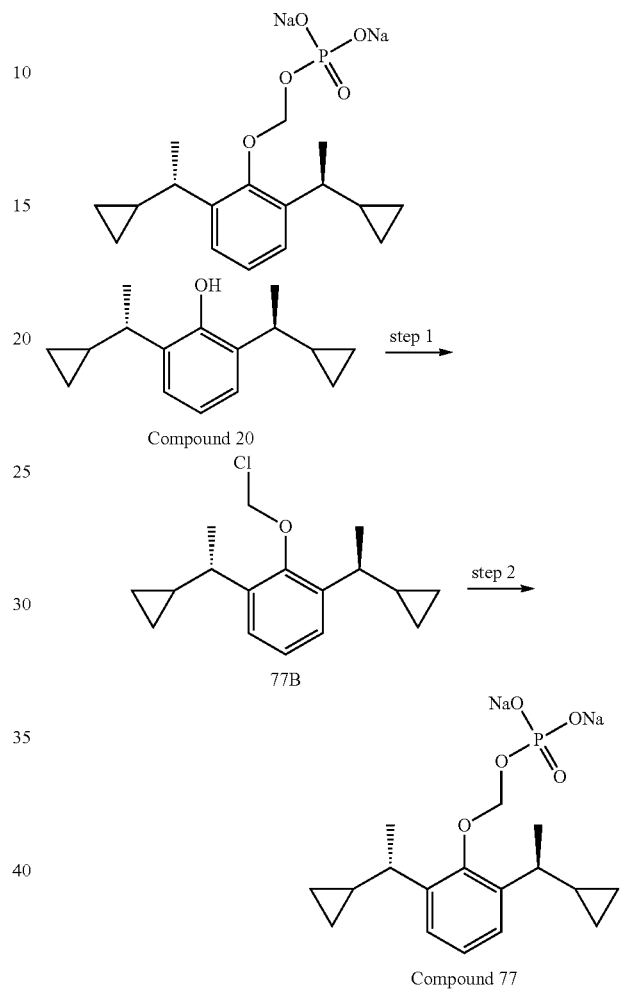

Step 1: 2-(chloromethoxy)-1,3-bis((S)-1-cyclopropylethyl)benzene (77B)

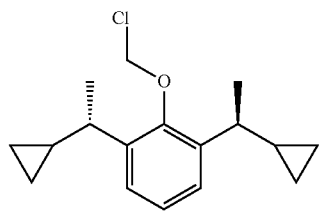 [SMILES: C[C@H](c1cccc([C@@H](C)C2CC2)c1OCCl)C1CC1]

2,6-bis[(1S)-1-cyclopropylethyl]phenol (Compound 20) (1 g, 0.0043 mol), tetrahydrofuran (5 mL) and sodium hydroxide (0.30 g, 0.009 mmol) were added into the reaction flask, the mixture was refluxed for 30 minutes, then bromochloromethane (14 g, 0.11 mol) was added, followed by a stirring at 70° C. for 2 h. The resulting mixture was filtered, concentrated in vacuo, the residue was purified by silica gel column chromatography (petroleum ether) to obtain 2-(chloromethoxy)-1,3-bis((S)-1-cyclopropylethyl)benzene (77B) crude product as a colorless liquid (0.8 g, yield: 70%), which was used in the next step without further purification.

¹H NMR (400 MHz, CDCl₃): δ 7.31-7.20 (m, 3H), 5.66 (dd, 2H), 2.58-2.50 (m, 2H), 1.30 (d, 6H), 0.98-0.94 (m, 2H), 0.58-0.55 (m, 2H), 0.39-0.35 (m, 2H), 0.28-0.23 (m, 2H), 0.20-0.14 (m, 2H).

Step 2: sodium (2,6-bis((S)-1-cyclopropylethyl)phenoxy)methyl phosphate (Compound 77)

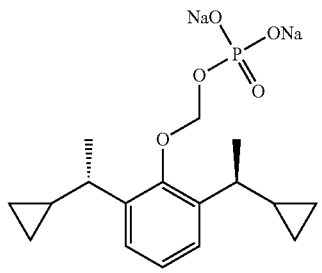

Acetonitrile (10 mL), phosphoric acid (2.25 g, 0.0229 mol) and triethylamine (2.90 g, 0.0287 mol) were added into the reaction flask, the mixture was heated to 65° C. for 30 minutes, then 2-(chloromethoxy)-1,3-bis((S)-1-cyclopropylethyl)benzene (77B) (0.8 g, 0.0028 mol) was added, followed by a stirring for 3 h at 75° C. The mixture was concentrated in vacuo, the residue was dissolved in water (20 mL), adjusted pH to 1 with 10% hydrochloric acid solution, the mixture was extracted with methyl tert-butyl ether (20 mL×3), washed with brine (20 mL×2). The combined organic layer was concentrated, the residue was dissolved in water (20 mL), adjusted pH 9~10 with sodium hydroxide solution (w/w=20%), the mixture was extracted with methyl tert-butyl ether (30 mL×2). The combined inorganic layer was concentrated, isopropanol (30 mL) was added, the mixture was filtered, concentrated, acetonitrile was added, followed by a stirring and filtration to afford sodium (2,6-bis((S)-1-cyclopropylethyl)phenoxy)methyl phosphate (Compound 77) as a white solid (0.6 g, yield: 54.4%, HPLC: 98.57%).

¹H NMR (400 MHz, D₂O): δ 7.45 (d, 2H), 7.34 (t, 1H), 5.21-5.15 (m, 2H), 2.68-2.60 (m, 2H), 1.32 (d, 6H), 1.10-1.06 (m, 2H), 0.61-0.57 (m, 2H), 0.37-0.34 (m, 4H), 0.20-0.16 (m, 2H).

Example 78

[[2-[(1R)-1-cyclopropylethyl]-6-[(1R)-1-methylpropyl]phenoxy]methoxy-sodiooxyphosphoryl]oxysodium (Compound 78)

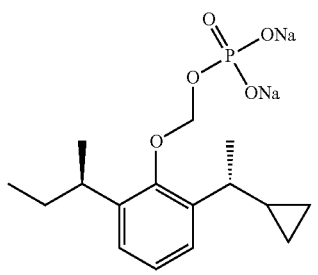

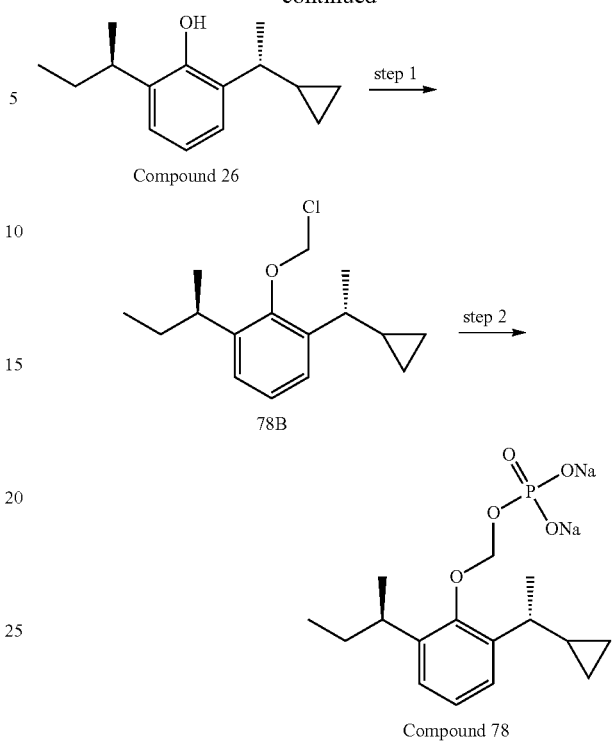

Step 1: 2-(chloromethoxy)-1-[(1R)-1-cyclopropylethyl]-3-[(1R)-1-methylpropyl]benzene (78B)

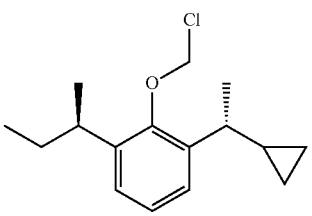 [SMILES: CC[C@@H](C)c1cccc([C@H](C)C2CC2)c1OCCl]

2-[(1R)-1-cyclopropylethyl]-6-[(1R)-1-methylpropyl]phenol (Compound 26) (0.50 g, 2.29 mmol), tetrahydrofuran (10 mL) and sodium hydroxide (0.18 g, 4.58 mmol) were added into the reaction flask, the mixture was refluxed 30 minutes, then bromochloromethane (8.89 g, 68.70 mol) was added, followed by a stirring at 70° C. for 3 h. The resulting mixture was filtered, concentrated in vacuo, the residue was purified by silica gel column chromatography (hexane) to obtain 2-(chloromethoxy)-1-[(1R)-1-cyclopropylethyl]-3-[(1R)-1-methylpropyl]benzene (78B) crude product (0.55 g) as a colorless liquid, which was submitted to the next step without further purification.

¹H NMR (400 MHz, CDCl₃): δ 7.26 (dd, 1H), δ 7.18 (t, 1H), 7.10 (dd, 1H), 5.70-5.67 (m, 2H), 3.05-3.00 (m, 1H), 2.59-2.55 (m, 1H), 1.60-1.54 (m, 2H), 1.25 (d, 3H), 1.21 (d, 3H), 0.96-0.82 (m, 1H), 0.85 (t, 3H), 0.60-0.53 (m, 1H), 0.39-0.36 (m, 1H), 0.26-0.15 (m, 2H).

Step 2: [[2-[(1R)-1-cyclopropylethyl]-6-[(1R)-1-methylpropyl]phenoxy]methoxy-sodiooxyphosphoryl]oxysodium (Compound 78)

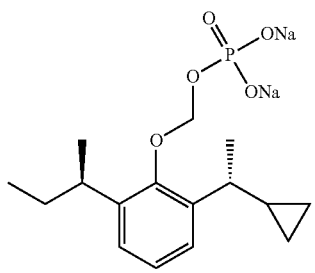

Phosphoric acid (1.62 g, 16.49 mmol), triethylamine (2.09 g, 20.61 mmol) and acetonitrile (10 mL) were added into the reaction flask, the mixture was heated to 55° C. for 30 minutes, then 2-(chloromethoxy)-1-[(1R)-1-cyclopropylethyl]-3-[(1R)-1-methylpropyl]benzene (78B) (0.55 g, 2.06 mmol) was added, followed by a stirring for 2 h at 70° C. The mixture was concentrated in vacuo, the residue was dissolved in water (20 mL), and then was adjusted pH to 1 with 10% hydrochloric acid solution, the mixture was extracted with methyl tert-butyl ether (20 mL×3). The combined organic layer was concentrated, the residue was dissolved in water (10 mL), adjusted pH to 10~11 with sodium hydroxide solution (w/w=20%), extracted with methyl tert-butyl ether (10 mL×3) until the organic layer was colourless. The combined inorganic layer was concentrated, the residue was added into acetonitrile (3 mL), followed by a stirring at 50° C., and the mixture was filtered to obtain [[2-[(1R)-1-cyclopropylethyl]-6-[(1R)-1-methylpropyl]phenoxy]methoxy-sodiooxyphosphoryl]oxysodium (Compound 78) as a white solid (0.50 g, yield: 71%, HPLC: 98.1%).

$^1$H NMR (400 MHz, D2O): δ 7.44 (dd, 1H), 7.34-7.27 (m, 2H), 5.25-5.21 (m, 2H), 3.23-3.18 (m, 1H), 2.72-2.64 (m, 1H), 1.72-1.59 (m, 2H), 1.32 (d, 3H), 1.23 (d, 3H), 1.11-1.07 (m, 1H), 0.86 (t, 3H), 0.61-0.58 (m, 1H), 0.41-0.33 (m, 2H), 0.19-0.16 (m, 1H).

MS m/z (ESI): 327.1 [M−46+1].

Example 79

[[2-[(1R)-1-cyclopropylethyl]-6-[(1S)-1-methylpropyl]phenoxy]methoxy-sodiooxy-phosphoryl]oxysodium (Compound 79)

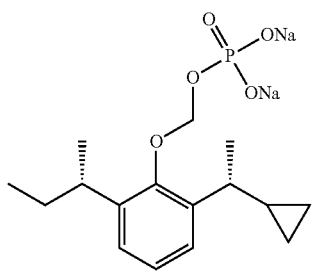

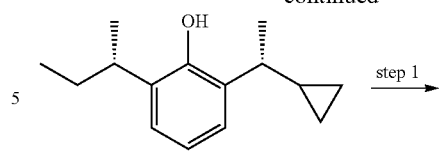

Compound 25

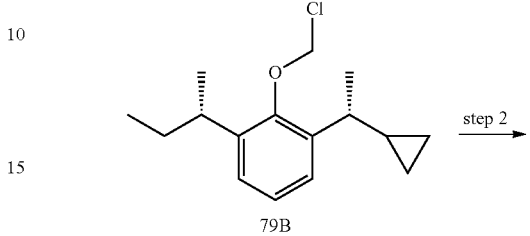

79B

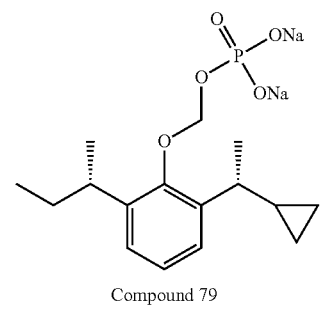

Compound 79

Step 1: 2-(chloromethoxy)-1-[(1R)-1-cyclopropylethyl]-3-[(1 S)-1-methylpropyl]benzene (79B)

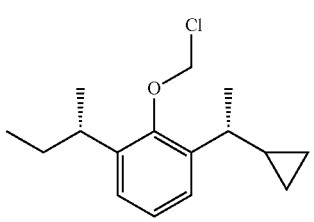 [SMILES: CC[C@H](C)c1cccc([C@H](C)C2CC2)c1OCCl]

2-[(1R)-1-cyclopropylethyl]-6-[(1S)-1-methylpropyl]phenol (Compound 25) (0.50 g, 2.29 mmol), tetrahydrofuran (10 mL) and sodium hydroxide (0.18 g, 4.58 mmol) were added into the reaction flask, the mixture was heated to reflux for 30 minutes, then bromochloromethane (8.89 g, 68.70 mol) was added, followed by a stirring at 70° C. for 3 h. The resulting mixture was filtered, concentrated in vacuo, and the residue was purified by silica gel column chromatography (hexane) to afford 2-(chloromethoxy)-1-[(1R)-1-cyclopropylethyl]-3-[(1S)-1-methylpropyl]benzene (79B) (crude product), which was submitted to the next step without further purification.

$^1$H NMR (400 MHz, CDCl$_3$): δ 7.23 (dd, 1H), δ 7.18 (t, 1H), 7.10 (dd, 1H), 5.69-5.66 (m, 2H), 3.08-2.99 (m, 1H), 2.60-2.53 (m, 1H), 1.61-1.49 (m, 2H), 1.31 (d, 3H), 1.23 (d, 3H), 0.95-0.79 (m, 1H), 0.80 (t, 3H), 0.56-0.49 (m, 1H), 0.32-0.11 (m, 3H).

Step 2: [[2-[(1R)-1-cyclopropylethyl]-6-[(1S)-1-methylpropyl]phenoxy]methoxy-sodiooxyphosphoryl]oxysodium (Compound 79)

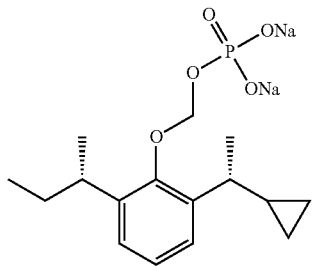

Phosphoric acid (1.62 g, 16.49 mmol), triethylamine (2.09 g, 20.61 mmol) and acetonitrile (10 mL) were added into the reaction flask, the mixture was heated to 55° C. for 30 minutes, then 2-(chloromethoxy)-1-[(1R)-1-cyclopropylethyl]-3-[(1S)-1-methylpropyl]benzene (79B) (0.55 g, 2.06 mmol) was added, followed by a stirring for 2 h at 70° C. The mixture was concentrated in vacuo, the residue was dissolved in water (20 mL), and then was adjusted pH to 1 with 10% hydrochloric acid solution, the mixture was extracted with methyl tert-butyl ether (20 mL×3). The combined organic layer was concentrated, the residue was dissolved in water (10 mL), adjusted pH to 10~11 with sodium hydroxide solution (w/w=20%), the mixture was extracted with methyl tert-butyl ether (10 mL×3) until the organic layer was colourless. The combined aqueous layer was concentrated, the residue was added into acetonitrile (3 mL), the mixture was slurried at 50° C., filtered to obtain [[2-[(1R)-1-cyclopropylethyl]-6-[(1S)-1-methylpropyl]phenoxy]methoxy-sodiooxyphosphoryl]oxysodium (Compound 79) as a white solid (0.41 g, yield: 53.95%, HPLC: 99.5%).

$^1$H NMR (400 MHz, D2O): δ 7.42 (dd, 1H), 7.34-7.28 (m, 2H), 5.24-5.21 (m, 2H), 3.27-3.18 (m, 1H), 2.74-2.66 (m, 1H), 1.70-1.51 (m, 2H), 1.36 (d, 3H), 1.27 (d, 3H), 1.10-1.01 (m, 1H), 0.82 (t, 3H), 0.61-0.53 (m, 1H), 0.34-0.29 (m, 2H), 0.17-0.11 (m, 1H).

MS m/z (ESI): 327.1 [M−46+1].

BIOLOGICAL TEST EXAMPLES

1. Righting Reflex Experiment on Mice

SPF-grade ICR mice (SCXY(Sichuan)-2008-24, Chengdu Dashuo Bioscience & Tech Co. Ltd.), each weighing 18 to 22 g, half male and half female, were used. A well-established mouse anesthesia model was used to study the general anesthetic effect of the test compounds (Ratnakumari Lingamaneni, et al., (2001) Anesthesiology, 2001, 94, 1050-7). Indicators such as median effective dose ($ED_{50}$), median lethal dose ($LD_{50}$), therapeutic index (TI, i.e. $LD_{50}/ED_{50}$), safety index (SI, i.e. $LD_5/ED_{95}$), anesthesia induction time, anesthesia maintenance time, and maximum tolerated dose (MTD) were used to evaluate the effect and safety of anesthesia. A desired concentration of the compound to be tested was formulated with a solvent of 10% DMSO, 15% solutol HS15 and 75% saline, for further use. After adapting to the laboratory environment, laboratory animals were fasted for 12 hours. On the next day, administration was carried out at 10 mg/kg body weight. Upon intravenous injection, the time of loss of the righting reflex was recorded. The period from finishing of drug administration until loss of the righting reflex was recorded as the anesthesia induction time, and the period from loss of the righting reflex until recovery of the righting reflex was recorded as the anesthesia maintenance time. The anesthesia induction time and the anesthesia maintenance time were used to indicate how strong an anesthetic effect was. Meanwhile, the dose required to cause a 7-min anesthesia ($HD_7$) was measured and used to evaluate relative efficacy.

The experimental results are shown in Tables 1 and 2.

TABLE 1

Data from righting reflex experiment on mice

| Compound No. | $ED_{50}$ (mg/kg) | $LD_{50}$ (mg/kg) | TI | SI | Anesthesia induction time (s) | Anesthesia maintenance time (s) | MTD (mg/kg) |
| --- | --- | --- | --- | --- | --- | --- | --- |
| Propofol | 11.7 | 31.3 | 2.7 | 1.5 | <15.0 s | 652.5 | 20.0 |
| 3 | 3.7 | 22.7 | 6.1 | 1.7 | <15.0 s | 660.4 | 10.0 |
| 4 | 4.5 | 38.1 | 8.4 | 2.6 | <15.0 s | 901.7 | 25.0 |
| 5 | 14.5 | 80.0 | 5.5 | 4.0 | <15.0 s | 1669.5 | 60.0 |
| 6 | 10.5 | 40.0 | 3.8 | 2.7 | <15.0 s | 554.9 | 30.0 |
| 7 | 7.1 | 40.0 | 5.7 | 2.7 | <15.0 s | 958.0 | 30.0 |
| 8 | 7.3 | 67.0 | 9.1 | 7.0 | <15.0 s | 394.8 | 40.0 |
| 11 | 30.1 | 100.0 | 3.3 | 2.5 | <15.0 s | 1494.7 | 80.0 |
| 13 | 3.6 | 20.0 | 5.5 | 3.0 | <15.0 s | 554.4 | 10.0 |
| 14 | 6.6 | 38.2 | 5.8 | 3.7 | <15.0 s | 2235.6 | 35.0 |
| 15 | 46.1 | 107.3 | 2.3 | 1.1 | <15.0 s | 485.8 | 70.0 |
| 16 | 1.5 | 9.9 | 6.7 | 4.1 | <15.0 s | 631.9 | 6.0 |
| 18 | 5.8 | 43.6 | 7.5 | 3.5 | <15.0 s | 1031.6 | 20.0 |
| 19 | 1.5 | 6.3 | 4.1 | 3.8 | <15.0 s | 754.4 | 5.0 |
| 20 | 15.7 | 150.0 | 9.6 | 4.4 | <15.0 s | 1207.7 | 90.0 |
| 25 | 2.0 | 14.3 | 7.1 | 4.6 | <15.0 s | 1048.0 | 10.0 |
| 26 | 1.3 | 8.3 | 6.4 | 2.4 | <15.0 s | 690.0 | 4.0 |
| 28 | 5.3 | 36.8 | 6.9 | 3.0 | <15.0 s | 885.9 | 15.0 |
| 29 | 10.1 | 65.4 | 6.4 | 3.7 | <15.0 s | 1149.5 | 40.0 |

Conclusions: compared to propofol, the compounds of the present invention showed higher therapeutic index and safety index, and a broader therapeutic window. Most of the compounds of the present invention have an $ED_{50}$ value less than that of propofol, indicating that these testing compounds have a lower minimum effective dose and higher activity than propofol. The compounds of the present invention showed a low free concentration in the aqueous phase of corresponding formulations, and are expected to have an effect of avoiding pain on injection.

TABLE 2

Comparison of $HD_7$ between the testing compounds and propofol.

| Compound No. | $HD_7$ (mg/kg) |
| --- | --- |
| Propofol | 14.0 |
| 3 | 6.0 |
| 4 | 4.0 |
| 13 | 7.0 |
| 16 | 3.5 |
| 18 | 2.5 |
| 25 | 4.0 |
| 26 | 2.5 |
| 28 | 8.0 |

Conclusions: the compounds of the present invention require a significantly lower dose than propofol to produce the same anesthetic effect.

2. Pharmacokinetic Experiment on Rats 3 male SD rats, each weighing 180 to 240 g, were fasted overnight with water access. A 1 mL/kg solution of the compound was formulated with 10% DMA, 20% solutol HS-15 (30%, w/v) and 70% physiological saline. Blood was sampled before administration and 2 min, 4 min, 8 min, 12 min, 15 min, 30 min, 1 h, 1.5 h and 2 h after administration. Blood samples were centrifuged at 5500 rpm for 10 min, and plasma was collected and stored at −40° C. 10 μl rat plasma from each time point was added to a 200 μl acetonitrile solution containing an internal standard and mixed, followed by 1-min vortexing and 18-min centrifugation at 3700 rpm. Then 70 μl supernatant was mixed with 70 μl water, and 10 μl of the mixture was analyzed by LC-MS/MS. Major pharmacokinetic parameters were subjected to a non-compartment analysis with the software WinNonlin 6.3. The experimental results are shown in Table 3.

TABLE 3

Results of pharmacokinetic experiment on rats

Intravenous Injection into Rats (1 mg/kg)

| Compound No. | $AUC_{0 \to t}$ (ng * h/mL) | $t_{1/2}$ (h) | CL (mL/kg/min) |
|---|---|---|---|
| Propofol | 81.9 | 0.7 | 204.0 |
| 8 | 132.0 | 0.8 | 119.0 |
| 13 | 187.0 | 0.2 | 87.5 |
| 16 | 168.0 | 0.5 | 105.0 |
| 25 | 78.1 | 0.4 | 208.0 |
| 26 | 124.0 | 0.5 | 134.0 |
| 28 | 143.0 | 0.3 | 115.0 |
| 29 | 114.0 | 0.4 | 145.0 |

Conclusions: the pharmacokinetic analysis demonstrates that the tested compounds showed good pharmacokinetic properties upon intravenous administration.

3. Pharmacokinetic Experiment on Rats, Righting Reflex Experiment on Mice, and Efficacy Experiment on Rats, with Prodrugs A. Pharmacokinetic Analysis with Prodrugs 3 male SD rats, each weighing 180 to 240 g, were fasted overnight with water access. After a single intravenous administration of a prodrug at 10 mg/kg to rats, the plasma concentrations of the prodrug and the active form were each measured by LC-MS/MS, and the pharmacokinetic parameters were analyzed. The experimental results are shown in Table 4.

TABLE 4

Data from pharmacokinetic experiment on rats with prodrugs.

Intravenous Injection into Rats (10 mg/kg)

| Compound No. | Types | $AUC_{0 \to t}$ (ng * h/mL) | $t_{1/2}$ (h) | CL (mL/kg/min) |
|---|---|---|---|---|
| Propofol | — | 81.9 | 0.7 | 204.0 |
| 46 | prodrug | 22437.0 | 0.9 | 6.1 |
|  | active form released upon hydrolysis | 39.7 | 0.7 | NA |
| 52 | prodrug | 15946.0 | 0.4 | 10.5 |
|  | active form released upon hydrolysis | 606.0 | 0.5 | NA |

Conclusions: the compounds of the present invention can be metabolized in vivo into the active form of the drug, and showed good pharmacokinetic properties.

B. Righting Reflex Experiment on Mice with Prodrugs.

SPF-grade ICR mice (SCXY(Sichuan)-2008-24, Chengdu Dashuo Bioscience & Tech Co. Ltd.), each weighing 18 to 22 g, half male and half female, were used. A well-established mouse anesthesia model was used to study the general anesthetic effect of the test compounds (Ratnakumari Lingamaneni, et al., (2001) Anesthesiology, 2001, 94, 1050-7). A desired concentration of the compound to be tested was formulated with physiological saline, for further use. After adapting to the laboratory environment, the SPF-grade ICR mice were fasted for 12 hours. On the next day, administration was carried out at 10 mg/kg body weight. Upon intravenous injection, the time of loss of the righting reflex was recorded. The period from finishing of drug administration until loss of the righting reflex was recorded as the anesthesia induction time, and the period from loss of the righting reflex until recovery of the righting reflex was recorded as the anesthesia maintenance time. The anesthesia induction time and the anesthesia maintenance time were used to indicate how strong an anesthetic effect was. Indicators such as median effective dose ($ED_{50}$), median lethal dose ($LD_{50}$), therapeutic index (TI, i.e. $LD_{50}/ED_{50}$), safety index (SI, i.e. $LD_5/ED_{95}$), anesthesia induction time, anesthesia maintenance time, and maximum tolerated dose (MTD) were used to evaluate the effect and safety of anesthesia.

The experimental results are shown in Table 5.

TABLE 5

Data from righting reflex experiment on mice with prodrugs

| Compound No. | $ED_{50}$ (mg/kg) | $LD_{50}$ (mg/kg) | TI | SI | Anesthesia induction time (s) | Anesthesia maintenance time (s) | MTD (mg/kg) |
|---|---|---|---|---|---|---|---|
| Propofol | 11.7 | 31.3 | 2.7 | 1.5 | <15.0 | 652.5 | 20.0 |
| 35 | 39.3 | 200.0 | 5.1 | 4.9 | <15.0 | 1915.5 | 200.0 |
| 38 | 26.1 | 80.0 | 3.1 | 1.3 | 141.0 | 478.9 | 50.0 |
| 45 | 18.6 | 72.6 | 3.9 | 1.7 | 50.0 | 1716.0 | 50.0 |
| 46 | 72.6 | 225.0 | 3.1 | 2.4 | 167.0 | 2204.6 | 200.0 |
| 51 | 28.3 | 80.0 | 2.8 | 1.2 | 159.0 | 1159.9 | 40.0 |
| 52 | 20.4 | 86.2 | 4.2 | 3.3 | 73.0 | 1830.2 | 60.0 |
| 57 | 36.7 | 120.0 | 3.3 | 1.3 | 135.8 | 1931.2 | 80.0 |
| 60 | 13.8 | 79.6 | 5.8 | 3.1 | 6.0 | 1473.0 | 50.0 |
| 61 | 6.1 | 87.4 | 14.4 | 3.7 | 17.5 | 1109.2 | 40.0 |
| 62 | 7.7 | 45.6 | 5.9 | 1.6 | <15.0 | 696.9 | 30.0 |
| 65 | 82.7 | 369.8 | 4.5 | 2.9 | 82.5 | 3278.0 | 200.0 |
| 74 | 48.3 | 192.0 | 4.0 | 2.5 | 96.5 | 2378.3 | 120.0 |
| 75 | 11.7 | 42.4 | 3.6 | 2.3 | 129.2 | 2070.4 | 30.0 |
| 76 | 35.8 | 142.8 | 4.0 | 2.5 | 111.8 | 1992.8 | 80.0 |
| 77 | 94.7 | 274.3 | 2.9 | 1.7 | 175.4 | 1859.1 | 160.0 |
| 78 | 15.9 | 63.7 | 4.0 | 2.9 | 65.2 | 2634.6 | 40.0 |
| 79 | 24.3 | 91.8 | 3.8 | 2.1 | 72.5 | 2252.1 | 60.0 |

Conclusions: in the experiment, all the prodrug compounds of the present invention can be dissolved in physiological saline for administration, thereby preventing bacterial infection that could be easily caused when lipid emulsion is potentially required. The experimental results demonstrate that the prodrugs showed improved solubility in water, can be metabolized in vivo into the active form, and showed a strong anesthetic effect on mice. Some prodrug compounds showed a high therapeutic index (TI) value and considerably improved safety. Particularly, Compounds 61 and 62 showed a smaller $ED_{50}$ value and higher efficacy than propofol.

C. Efficacy Experiment on Rats with Prodrugs.

This experiment selected SD rats, each weighing 180 to 200 g. The rats were randomized, with 10 animals per group, half male and half female. After having been fasted for 16 h, the rats were dosed via their tail veins at 5 ml/kg body weight, with administration duration of 10 s. The time of administration, time of loss of the righting reflex, time of recovery of the righting reflex, and time of walking were recorded. Adverse effects shown by the rats after administration were also recorded.

Evaluation Standards:

Time of loss of the righting reflex: the righting reflex is lost; a rat made lying on its back can maintain the lying for a period of 60 s;

Time of recovery of the righting reflex: the righting reflex ability is restored; a rat made lying on its back rights in less than 2 s;

Time of walking: spontaneous forwarding moving occurs, and muscle tension of the limbs recovers.

Using GraphPad Prism 5, $ED_{50}$ and $LD_{50}$ values were calculated from a non-linear fitting of number of anesthetic or dead animals resulting from various doses. The results are shown in Table 6.

TABLE 6

Results of efficacy evaluation for rats

| Compound No. | $ED_{50}$ (mg/kg) | $LD_{50}$ (mg/kg) | TI | SI | Anesthesia induction time (s) | Anesthesia maintenance time (s) | MTD (mg/kg) |
|---|---|---|---|---|---|---|---|
| Propofol | 5.7 | 19.1 | 3.4 | 1.5 | 0.0 | 652.0 | 12.5 |
| 52 | 12.5-15.0 | 61.4 | 4.1-4.9 | — | 92.8 | 1946.3 | 30.0 |
| 61 | 6.5 | 60.8 | 9.4 | 6.3 | 0.0 | 1474.9 | 40.0 |

Conclusions: the experimental results demonstrate that the compounds of the present invention showed better safety than propofol. Particularly, Compound 61 showed a smaller $ED_{50}$ and higher efficacy than propofol.

4. Receptor Patch Clamp Experiment 1.3 µM muscimol, a $GABA_A$ receptor agonist, was added to a stable cell strain $CHO/GABA_A$ and then washed off, which was repeated 3 times at an interval of 45 s, so as to obtain a stable baseline current. Then various concentrations of Compound 16 and propofol as a control were each added to a stable cell strain $CHO/GABA_A$, and incubated for 45 s to ensure that the test compounds reach equilibrium with the acceptor. Various concentrations of test compounds and muscimol were added together to $CHO/GABA_A$, and the current mediated by $GABA_A$ receptors was measured. Two measurements were performed for each concentration to obtain an average response current. The enhancement of the current mediated by $GABA_A$ receptors was calculated by the following equation:

Enhancement (%)=100*(Test Compound−Control)/Control

The Control group is the peak current amplitude induced by muscimol, and the Test Compound group is the peak current amplitude co-induced by the test compounds and muscimol. The enhancement (%) was calculated for each concentration, and $EC_{50}$ was calculated by normalization.

By perfusion of $1\times10^{-7}$ M, $3\times10^{-7}$ M, $1\times10^{-6}$ M, $3\times10^{-6}$ M, $1\times10^{-5}$ M Compound 16 and propofol to a $CHO/GABA_A$ cell strain, the effect of the compounds on cell potentials was analyzed using the automated whole-cell patch-clamp technique. The experimental results are shown in Table 7.

TABLE 7

Receptor patch-clamp experimental results.

| Compounds | Propofol | Compound 16 |
|---|---|---|
| $EC_{50}$ (µM) | 5.3 | 1.1 |

Conclusions: both test Compound 16 and propofol showed an activating effect on the ion channels of $GABA_A$ receptors, with Compound 16 showing a lower $ED_{50}$, indicating that Compound 16 has stronger activity than Propofol.

5. Haemodynamic Effects in Beagle Dogs

The effects of the test compounds and the analogous control propofol on the cardiovascular system functions of Beagle dogs were investigated.

Figure 2:
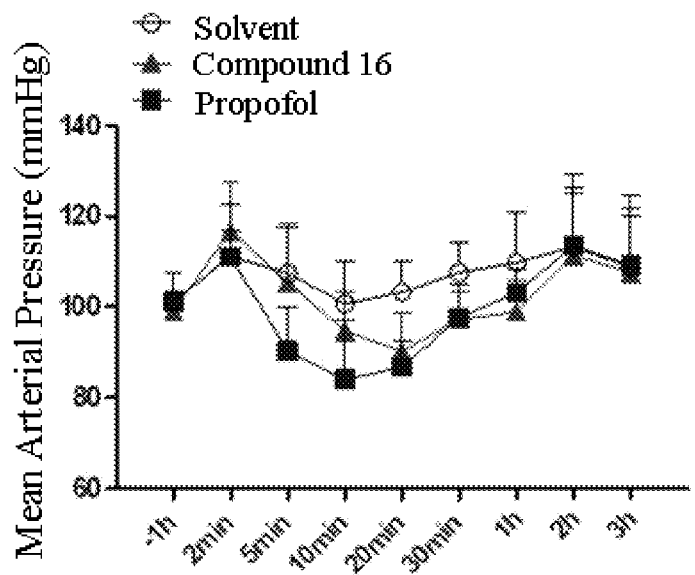
FIG. 2 is a schematic representation of the effects of intravenous administration of a emulsion for injection of test Compound 16 and propofol on the mean arterial pressure (mmHg) of conscious Beagle dogs ($\overline{X}\pm SD$, n=4)

In this experiment, 4 Beagle dogs in total were used, half male and half female, which were each sequentially given an emulsion for injection of test Compound 16 (2 mg/kg), propofol as an analogous control (10 mg/kg), and a solvent control. A cross-dosing design was applied to the emulsion for injection of test Compound 16 and the analogous control propofol. Data of various indicators such as electrocardiogram, blood pressure and body temperature of the animals were continuously collected from about 3.5 hours before administration until 6 hours after administration. At the assay time points of: before administration, and 2 min (±1 min), 5 min (±1 min), 10 min (±2 min), 20 min (±5 min), 30 min (±5 min), 1 h (±15 min), 2 h (±15 min) and 3 h (±30 min) after administration, data of the above indicators were compared and evaluated between the administered emulsion for injection of test Compound 16, the analogous control propofol, and the solvent control. The plasma concentrations of test Compound 16 and propofol were analyzed by LC-MS/MS. The experimental results are shown in FIGS. 1 and 2.

Conclusions: the experimental results demonstrate that propofol and Compound 16 required doses of 10 mg/kg and 2 mg/kg, respectively, to produce the same anesthetic effect. Compound 16 showed an effect on the heart rate and blood pressure of Beagle dogs smaller than that of propofol, and is expected to have better safety than propofol.

6. Aqueous Phase Concentration of Free API in the Lipid Formulation of the Tested Compounds Soybean oil, a medium chain triglyceride, and egg yolk lecithin were weighed out, placed in a 61° C. water bath, and heated under stirring. The beaker containing the oil phase was sealed with a sealing film, and about 1 h later, the oil phase turned clear, the egg yolk lecithin was completely dispersed in the oil phase. Propofol or Compound 16 was added to the oil phase, which was further stirred for about 1 min. Glycerol was weighed out, and deionized water was added, followed by heating in a 65° C. water bath under stirring. The pH was adjusted, followed by further heating in a 65° C. water bath under stirring, and the temperature was maintained. Under shearing, the oil phase was added dropwise to the aqueous phase, followed by further shearing and emulsifying for 5 min, to afford an initial emulsion. The initial emulsion was homogenized 5 times at homogenizing pressure of 800 bar, then dispensed, and sterilized at 115° C. for 32 min.

Figure 3:
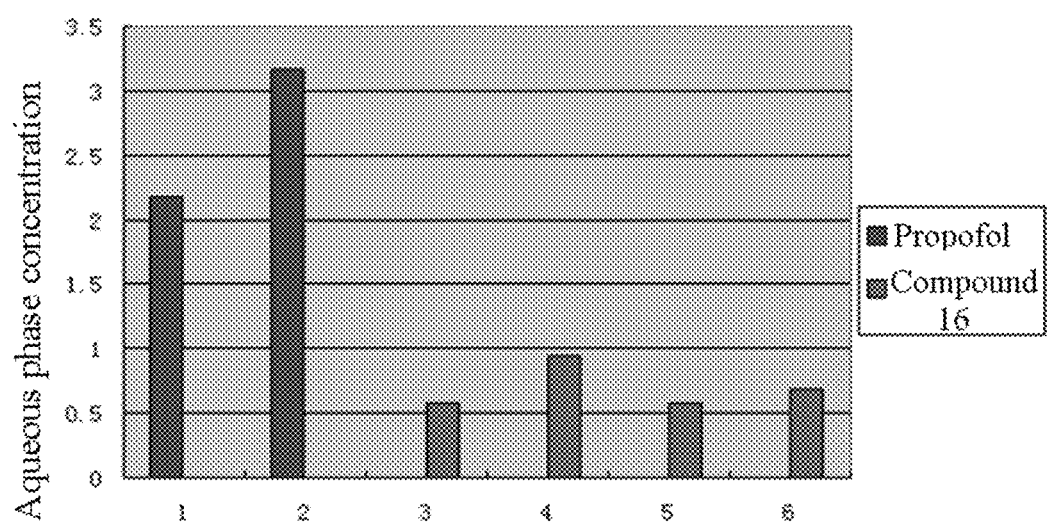
FIG. 3 shows the measurement results for the concentration of free API in aqueous phase.

The sample was placed in a Millipore Ultra-4 ultrafiltration tube (Molecular Weight Cut-Off: 3000) and centrifuged at 25° C. for 15 min. The aqueous phase at the lower part was removed and measured for concentration, wherein propofol was measured twice, Compound 16 was measured 4 times, and the data were averaged. The results are shown in FIG. 3 and Table 8.

TABLE 8

Experimental results of aqueous phase concentration of free API of the compounds.

| Compound | Aqueous phase concentration of free API |
|---|---|
| Lipid emulsion of propofol (10 mg/mL) | 2.7 ug/mL |
| Lipid emulsion of Compound 16 (10 mg/mL) | 0.7 ug/mL |

Conclusions: Compound 16 had an aqueous phase concentration 4 to 5 times lower than that of propofol in the same formulation, and is expected to avoid pain on injection.

The invention claimed is:
1. A compound of general formula (A),

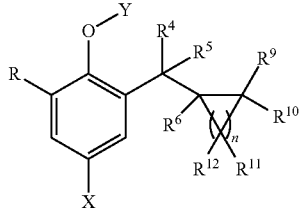

wherein
R is selected from F, Cl, Br, I, —OR$^7$ or

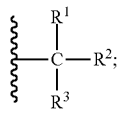

R$^1$, R$^2$ and R$^3$ are each independently selected from H, F, Cl, Br, I, hydroxyl, C$_{1-6}$ alkyl, C$_{1-6}$ alkoxy, a 3- to 5-membered carbocyclic group, or a 3- to 5-membered heterocyclic group, wherein the alkyl, alkoxy, carbocyclic group or heterocyclic group is optionally further substituted with 0 to 5 substituents selected from F, Cl, Br, I, hydroxyl, C$_{1-6}$ alkyl, C$_{1-6}$ alkoxy, a 3- to 5-membered carbocyclic group or a 3- to 5-membered heterocyclic group, the heterocyclic group has 1 to 2 heteroatoms selected from N, O or S, and R$^1$, R$^2$ and R$^3$ are not all H;
alternatively, any pair of R$^1$ and R$^2$, R$^2$ and R$^3$, or R$^1$ and R$^3$ forms a 3- to 5-membered ring, the 3- to 5-membered ring has 0 to 2 heteroatoms selected from N, O or S, and the formed 3- to 5-membered ring is optionally further substituted with 0 to 4 R$^8$s;

R$^4$ and R$^5$ are each independently selected from H, F, Cl, Br, I, hydroxyl, cyano, C$_{1-6}$ alkyl, C$_{1-6}$ alkoxy, a 3- to 5-membered carbocyclic group or a 3- to 5-membered heterocyclic group, wherein the alkyl, alkoxy, carbocyclic group or heterocyclic group is optionally further substituted with 0 to 5 substituents selected from hydroxyl, C$_{1-6}$ alkyl, C$_{1-6}$ alkoxy, a 3- to 5-membered carbocyclic group or a 3- to 5-membered heterocyclic group, the heterocyclic group has 1 to 2 heteroatoms selected from N, O or S, and R$^4$ and R$^5$ are not both H;
alternatively, R$^4$ and R$^5$ may form a 3- to 5-membered ring, the 3- to 5-membered ring may have 0 to 2 heteroatoms selected from N, O or S, and the formed 3- to 5-membered may optionally be further substituted with 0 to 4 R$^8$s;
R$^6$ is selected from H or hydroxyl;
R$^7$ is selected from H, C$_{1-4}$ alkyl or a 3- to 5-membered carbocyclic group, wherein the alkyl or carbocyclic group is optionally further substituted with 0 to 5 substituents selected from F, Cl, Br, I, hydroxyl, C$_{1-4}$ alkyl, C$_{1-4}$ alkoxy or a 3- to 5-membered carbocyclic group;
R$^8$ is selected from F, Cl, Br, hydroxyl, C$_{1-4}$ alkyl, C$_{1-4}$ alkoxy, a 3- to 5-membered carbocyclic group or a 3- to 5-membered heterocyclic group, and the heterocyclic group has 1 to 2 heteroatoms selected from N, O or S;
R$^9$, R$^{10}$, R$^{11}$ and R$^{12}$ are each independently selected from H, F, Cl, Br, I, hydroxyl, C$_{1-6}$ alkyl or C$_{1-6}$ alkoxy;
X is selected from H, F or carboxyl;
Y is selected from H, COR$^{13}$, PEG, COOR$^{13}$, CONR$^{13}$R$^{14}$, COSR$^{13}$,

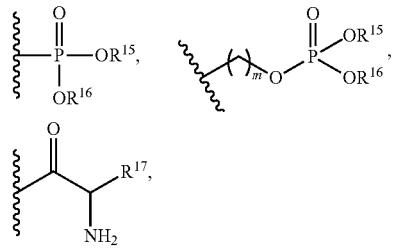

C$_{1-20}$ alkyl, —(CH$_2$CH$_2$O)$_q$—H, —(CR$^{ya}$R$^{yb}$)$_{m1}$COOR$^{y1}$,
—(CR$^{ya}$R$^{yb}$)$_{m1}$—(W$_1$)$_p$—C(=O)(W$_4$R$^{y3}$) or
—(CR$^{ya}$R$^{yb}$)$_{m1}$—(W$_1$)$_p$—P(=O)(W$_2$R$^{y4}$)(W$_3$R$^{y5}$) or

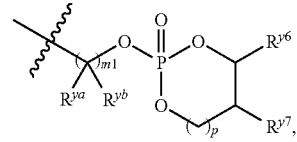

wherein the alkyl is optionally further substituted with 0 to 4 substituents selected from H, F, Cl, Br, I, hydroxyl, amino, cyano, carboxyl, C$_{1-6}$ alkyl, C$_{1-6}$ alkoxy, a C$_{3-8}$ carbocyclic group or a 4- to 8-membered heterocyclic group, and the heterocyclic group has 1 to 2 heteroatoms selected from N, O or S;
R$^{13}$ and R$^{14}$ are each independently selected from H, C$_{1-6}$ alkyl, a 3- to 8-membered carbocyclic or heterocyclic group, wherein the alkyl, carbocyclic group or heterocyclic group may optionally be further substituted with 0 to 5 substituents selected from F, Cl, Br, I, hydroxyl, $C_{1-6}$ alkyl, $C_{1-6}$ alkoxy, a 3- to 8-membered carbocyclic group or a 3- to 8-membered heterocyclic group, and the heterocyclic group has 1 to 2 heteroatoms selected from N, O or S;

$R^{15}$ and $R^{16}$ are each independently selected from H, an alkali metal ion, an alkali earth metal ion, a protonated amine or a protonated amino acid, wherein the alkali metal ion is selected from $Na^+$, $K^+$ or $Li^+$, the alkali earth metal ion is selected from $Be^{2+}$, $Mg^{2+}$ or $Ca^{2+}$, the amine is selected from trometamol, triethanolamine, ethanolamine, triethylamine or N-methylglucosamine, and the amino acid is selected from arginine or lysine;

alternatively, $R^{15}$ and $R^{16}$ may form a 3- to 8-membered ring, the 3- to 8-membered ring may have 0 to 2 heteroatoms selected from N, O or S, and the formed 3- to 8-membered ring may optionally be further substituted with 0 to 4 $R^8$s;

$R^{17}$ is the side-chain group of an amino acid, wherein the amino acid is selected from lysine, arginine, histidine, proline, 2,3-diaminopropionic acid, 2,4-diaminopropionic acid, alanine, valine, leucine, isoleucine, phenylalanine, tryptophan, methionine, glycine, serine, threonine, cysteine, tyrosine, asparagine, glutamine, aspartic acid, aspartate, or glutamic acid;

$W_1$, $W_2$ and $W_3$ are each independently selected from $NR^{y8}$, O or S;

$W_4$ is selected from $CR^{y9}R^{y10}$, $NR^{y8}$, O, S, or is absent;

$R^{y1}$ is each independently selected from H, $C_{1-6}$ alkyl, a $C_{3-8}$ carbocyclic group or a 4- to 8-membered heterocyclic group, wherein the alkyl, carbocyclic group or heterocyclic group may optionally be further substituted with 0 to 5 substituents selected from H, F, Cl, Br, I, hydroxyl, amino, cyano, carboxyl, $C_{1-6}$ alkyl, $C_{1-6}$ alkoxy, a $C_{3-8}$ carbocyclic group or a 4- to 8-membered heterocyclic group, and the heterocyclic group has 1 to 2 heteroatoms selected from N, O or S;

$R^{y3}$ is selected from H, amino, $C_{1-6}$ alkyl, a $C_{3-8}$ carbocyclic group or a 4- to 8-membered heterocyclic group, $-(CR^{ya}R^{yb})_{m1}-NR^{yc}R^{yd}$ or $-(CR^{ya}R^{yb})_{m1}-NR^{yc}C(=O)OR^{yd}$, wherein the amino group, alkyl, carbocyclic group or heterocyclic group may optionally be further substituted with 0 to 5 substituents selected from H, F, Cl, Br, I, hydroxyl, amino, cyano, carboxyl, $C_{1-6}$ alkyl, $C_{1-6}$ alkoxy, $-(CH_2)_{m1}-OC(=O)-C_{1-6}$ alkyl, $-(CH_2)_{m1}-C(=O)O-C_{1-6}$ alkyl, $-(CH_2)_{m1}-C(=O)O(CH_2)_{m1}-(C_{3-6}$ carbocyclic group), $-(CH_2)_{m1}-C(=O)-C_{1-6}$ alkyl, $-(CH_2)_{m1}-(C_{3-8}$ carbocyclic group) or $-(CH_2)_{m1}-$(4- to 8-membered heterocyclic group), and the heterocyclic group has 1 to 2 heteroatoms selected from N, O or S;

$R^{y4}$ and $R^{y5}$ are each independently selected from H, an alkali metal ion, an alkali earth metal ion, a protonated amine or a protonated amino acid, $C_{1-6}$ alkyl, $-(CR^{ya}R^{yb})_{m1}-$(3-to 8-membered ring), $-(CR^{ya}R^{yb})_{m1}-OC(=O)C_{1-6}$ alkyl, $-(CR^{ya}R^{yb})_{m1}-OC(=O)-$(3-to 8-membered ring), $-(CR^{ya}R^{yb})_{m1}-C(=O)OC_{1-6}$ alkyl or $-(CR^{ya}R^{yb})_{m1}-OC(=O)OC_{1-6}$ alkyl;

$R^{y6}$ and $R^{y7}$ are each independently selected from H, F, Cl, Br, I, hydroxyl, amino, cyano, carboxyl, $C_{1-6}$ alkyl or $C_{1-6}$ alkoxy;

alternatively, $R^{y6}$ and $R^{y7}$ may form a 5- to 8-membered ring together with the atoms to which they are attached, the 5- to 8-membered ring may have 0 to 4 heteroatoms selected from N, O or S, and the 5- to 8-membered ring may optionally be further substituted with 0 to 4 substituents selected from H, F, Cl, Br, I, $C_{1-6}$ alkyl or $C_{1-6}$ alkoxy;

$R^{y8}$s are each independently selected from H or $C_{1-6}$ alkyl;

$R^{y9}$ and $R^{y10}$ are each independently selected from H, $C_{1-6}$ alkyl, a $C_{3-8}$ carbocyclic group or a 4- to 8-membered heterocyclic group, wherein the alkyl, carbocyclic group and heterocyclic group are each optionally further substituted with 0 to 4 substituents selected from H, hydroxyl, amino, mercapto, carboxyl, guanidino, carbamoyl, $C_{1-6}$ alkyl, $C_{1-6}$ alkoxy, a 3- to 8-membered carbocycle or a 3- to 8-membered heterocycle;

$R^{ya}$, $R^{yb}$, $R^{yc}$ and $R^{yd}$ are each independently selected from H or $C_{1-6}$ alkyl;

n is selected from 1, 2 or 3;
m is selected from 1 or 2;
q is selected from 1 to 200;
m1 is selected from 0, 1, 2 or 3;
p is selected from 0, 1 or 2;

or a stereoisomer, a solvate, a metabolite, a prodrug, a pharmaceutically acceptable salt, or a cocrystal thereof, provided that the compound of general formula (A) is not

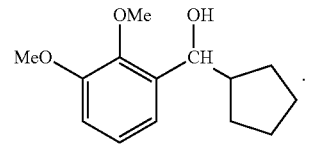

2. The compound according to claim 1, selected from compounds of general formula (I):

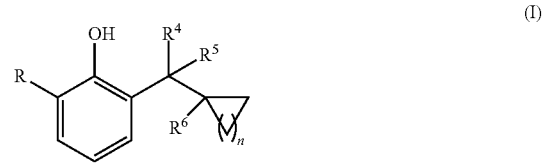

or a stereoisomer, a solvate, a metabolite, a prodrug, a pharmaceutically acceptable salt, or a cocrystal thereof.

3. The compound according to claim 2, wherein
R is selected from F, Br, $-OR^7$ or

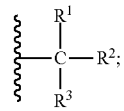

$R^1$, $R^2$ and $R^3$ are each independently selected from H, F, Cl, Br, hydroxyl, $C_{1-5}$ alkyl, $C_{1-5}$ alkoxy or a 3- to 5-membered carbocyclic group, wherein the alkyl, alkoxy or carbocyclic group is optionally further substituted with 0 to 3 substituents selected from F, Cl, Br, hydroxyl, $C_{1-4}$ alkyl, $C_{1-4}$ alkoxy or a 3- to 5-membered carbocyclic group, and $R^1$, $R^2$ and $R^3$ are not all H;

alternatively, any pair of $R^1$ and $R^2$, $R^2$ and $R^3$, or $R^1$ and $R^3$ may form a 3- to 5-membered carbocycle, and the carbocycle may optionally be further substituted with 0 to 4 $R^8$s;

$R^4$ and $R^5$ are each independently selected from H, F, Cl, Br, hydroxyl, cyano, $C_{1-4}$ alkyl or $C_{1-4}$ alkoxy or a 3- to 5-membered carbocyclic group, wherein the alkyl, alkoxy or carbocyclic group is optionally further substituted with 0 to 3 substituents selected from hydroxyl, $C_{1-4}$ alkyl or $C_{1-4}$ alkoxy, and $R^4$ and $R^5$ are not both H;

alternatively, $R^4$ and $R^5$ may form a 3- to 5-membered carbocyclic group, and the carbocyclic group may optionally be further substituted with 0 to 4 $R^8$s;

$R^6$ is selected from H or hydroxyl;

$R^7$ is selected from H, $C_{1-4}$ alkyl or a 3- or 4-membered carbocyclic group, wherein the alkyl or carbocyclic group may be further substituted with 0 to 3 substituents selected from F, hydroxyl or $C_{1-3}$ alkyl;

$R^8$ is selected from F, Cl, Br, hydroxyl, $C_{1-4}$ alkyl or $C_{1-4}$ alkoxy;

n is selected from 1 or 2;

or a stereoisomer, a solvate, a metabolite, a prodrug, a pharmaceutically acceptable salt, or a cocrystal thereof.

4. The compound according to claim 3, wherein R is selected from Br or

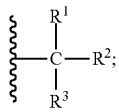

$R^1$, $R^2$ and $R^3$ are each independently selected from H, F, Cl, Br, hydroxyl, $C_{1-4}$ alkyl, $C_{1-4}$ alkoxy or a 3- to 5-membered carbocyclic group, wherein the alkyl, alkoxy or carbocyclic group is optionally further substituted with 0 to 3 substituents selected from F, Cl, Br, hydroxyl, $C_{1-4}$ alkyl, $C_{1-4}$ alkoxy or a 3- to 5-membered carbocyclic group, and $R^1$, $R^2$ and $R^3$ are not all H;

alternatively, any pair of $R^1$ and $R^2$, $R^2$ and $R^3$, or $R^1$ and $R^3$ may form a 3- to 5-membered carbocyclic group, and the carbocyclic group may optionally be further substituted with 0 to 4 $R^8$s;

or a stereoisomer, a solvate, a metabolite, a prodrug, a pharmaceutically acceptable salt, or a cocrystal thereof.

5. The compound according to claim 4, selected from compounds of general formula (II):

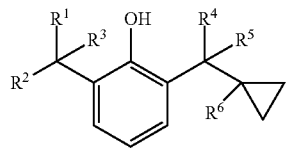
(II)

or a stereoisomer, a solvate, a metabolite, a prodrug, a pharmaceutically acceptable salt, or a cocrystal thereof.

6. The compound according to claim 5, wherein:

$R^1$, $R^2$ and $R^3$ are each independently selected from H, F, Cl, Br, hydroxyl, $C_{1-4}$ alkyl, $C_{1-4}$ alkoxy or a 3- to 5-membered carbocyclic group, wherein the alkyl, alkoxy or carbocyclic group is optionally further substituted with 0 to 3 substituents selected from F or hydroxyl, and $R^1$, $R^2$ and $R^3$ are not all H;

alternatively, any pair of $R^1$ and $R^2$, $R^2$ and $R^3$, or $R^1$ and $R^3$ may form a 3-membered carbocyclic group, and the carbocyclic group may optionally be further substituted with 0 to 4 substituents selected from F or hydroxyl;

$R^4$ and $R^5$ are each independently selected from H, F, Cl, Br, hydroxyl, cyano, $C_{1-4}$ alkyl, $C_{1-4}$ alkoxy or a 3- to 5-membered carbocyclic group, wherein the alkyl, alkoxy or carbocyclic group is optionally further substituted with 0 to 3 hydroxyl groups, and $R^4$ and $R^5$ are not both H;

or a stereoisomer, a solvate, a metabolite, a prodrug, a pharmaceutically acceptable salt, or a cocrystal thereof.

7. The compound according to claim 6, wherein:

$R^1$, $R^2$ and $R^3$ are each independently selected from H, hydroxyl, $C_{1-4}$ alkyl or a 3- to 5-membered carbocyclic group, wherein the alkyl or carbocyclic group is optionally further substituted with 0 to 3 substituents selected from F or hydroxyl, and $R^1$, $R^2$ and $R^3$ are not all H;

alternatively, any pair of $R^1$ and $R^2$, $R^2$ and $R^3$, or $R^1$ and $R^3$ may form a 3-membered carbocyclic group, and the carbocyclic group may optionally be further substituted with 0 to 4 substituents selected from F or hydroxyl;

$R^4$ and $R^5$ are each independently selected from H, hydroxyl, cyano, $C_{1-4}$ alkyl or a 3- to 5-membered carbocyclic group, wherein the alkyl or carbocyclic group is optionally further substituted with 0 to 3 hydroxyl groups, and $R^4$ and $R^5$ are not both H;

or a stereoisomer, a solvate, a metabolite, a prodrug, a pharmaceutically acceptable salt, or a cocrystal thereof.

8. The compound according to claim 7, wherein:

$R^1$, $R^2$ and $R^3$ are each independently selected from H, hydroxyl, methyl, ethyl or cyclopropyl, and $R^1$, $R^2$ and $R^3$ are not all H;

alternatively, any pair of $R^1$ and $R^2$, $R^2$ and $R^3$, or $R^1$ and $R^3$ may form cyclopropyl;

$R^4$ and $R^5$ are each independently selected from H, hydroxyl, cyano, methyl, ethyl or cyclopropyl, and $R^4$ and $R^5$ are not both H;

or a stereoisomer, a solvate, a metabolite, a prodrug, a pharmaceutically acceptable salt, or a cocrystal thereof.

9. The compound according to claim 1, selected from

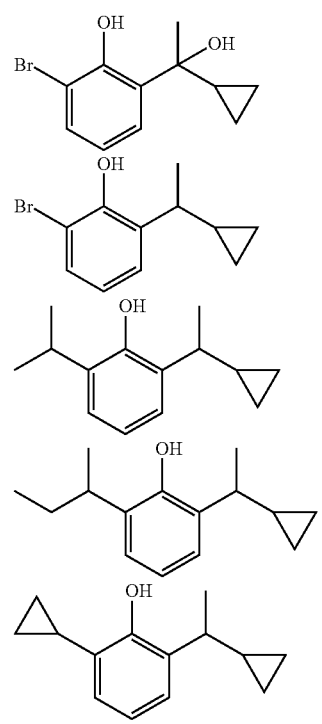

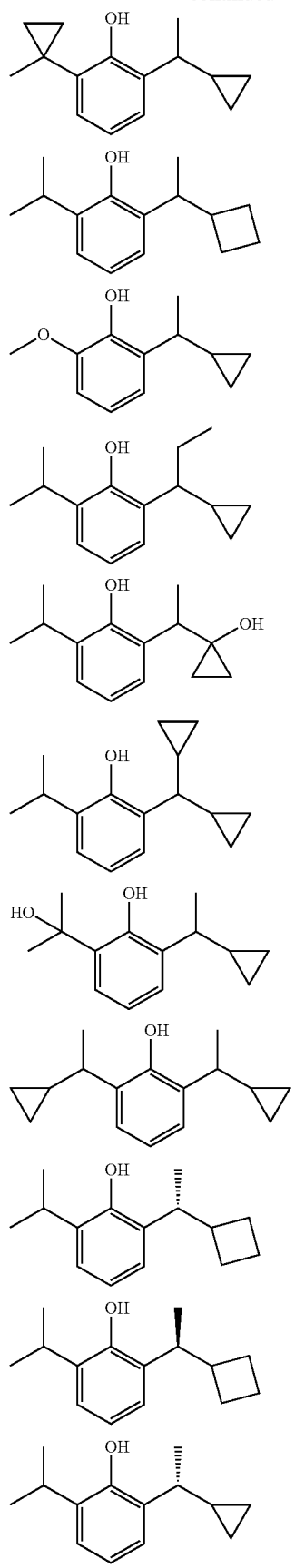
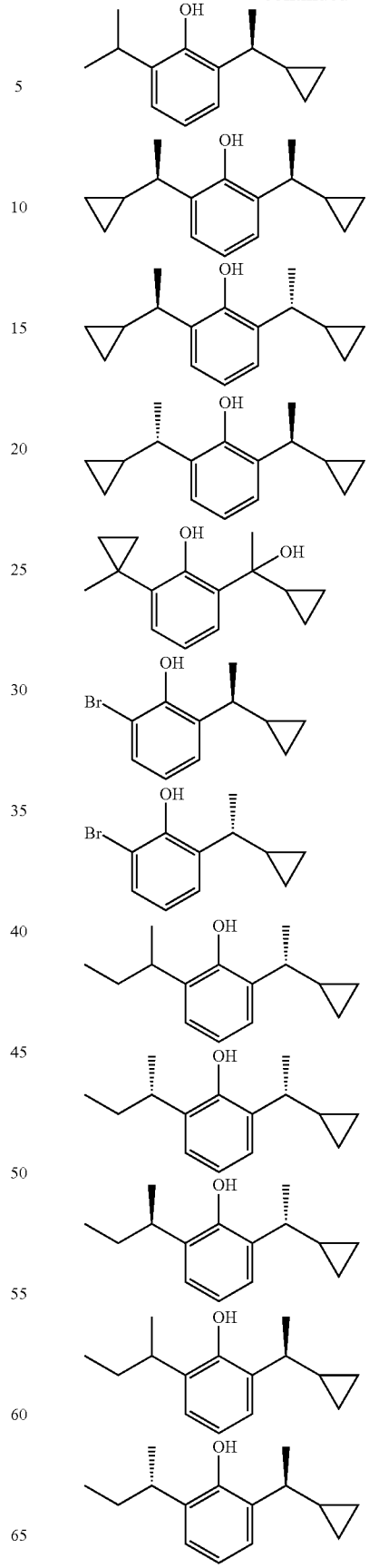

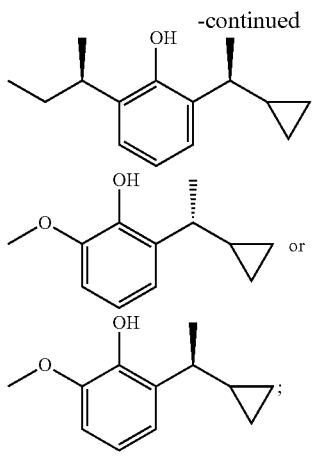

or a stereoisomer, a solvate, a metabolite, a prodrug, a pharmaceutically acceptable salt, or a cocrystal thereof.

10. The compound according to claim 1, wherein:
$R^9$, $R^{10}$, $R^{11}$ and $R^{12}$ are H;
Y is selected from H, PEG,

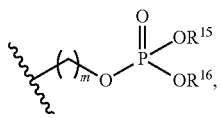

$C_{1-20}$ alkyl, $-(CH_2CH_2O)_q-H$, $-(CR^{ya}R^{yb})_{m1}COOR^{y1}$, $-(CR^{ya}R^{yb})_{m1}-(W_1)_p-C(=O)(W_4R^{y3})$ or $-(CR^{ya}R^{yb})_{m1}-(W_1)_p-P(=O)(W_2R^{y4})(W_3R^{y5})$ or

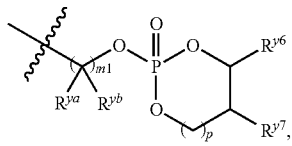

wherein the alkyl is optionally further substituted with 0 to 4 substituents selected from H, F, Cl, Br, I, hydroxyl, amino, cyano, carboxyl, $C_{1-6}$ alkyl, $C_{1-6}$ alkoxy, a $C_{3-8}$ carbocyclic group or a 4- to 8-membered heterocyclic group;
$R^{13}$ and $R^{14}$ are each independently selected from H or $C_{1-6}$ alkyl;
$R^{15}$ and $R^{16}$ are each independently selected from H or an alkali metal ion, and the alkali metal ion is selected from $Na^+$, $K^+$ or $Li^+$;
or a stereoisomer, a solvate, a metabolite, a prodrug, a pharmaceutically acceptable salt, or a cocrystal thereof.

11. The compound according to claim 10, wherein:
R is selected from Br, $OR^7$, or

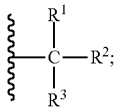

$R^1$, $R^2$ and $R^3$ are each independently selected from H, F, Cl, Br, hydroxyl, $C_{1-4}$ alkyl, $C_{1-4}$ alkoxy or a 3- to 5-membered carbocyclic group, wherein the alkyl, alkoxy or carbocyclic group is optionally further substituted with 0 to 3 substituents selected from F, Cl, Br, hydroxyl, $C_{1-4}$ alkyl, $C_{1-4}$ alkoxy or a 3- to 5-membered carbocyclic group, and $R^1$, $R^2$ and $R^3$ are not all H;
alternatively, any pair of $R^1$ and $R^2$, $R^2$ and $R^3$, or $R^1$ and $R^3$ may form a 3- to 5-membered carbocyclic group, and the carbocyclic group may optionally be further substituted with 0 to 4 $R^8$s;
$R^4$ and $R^5$ are each independently selected from H, F, Cl, Br, hydroxyl, cyano, $C_{1-4}$ alkyl or $C_{1-4}$ alkoxy or a 3- to 5-membered carbocyclic group, wherein the alkyl, alkoxy or carbocyclic group is optionally further substituted with 0 to 3 substituents selected from hydroxyl, $C_{1-4}$ alkyl or $C_{1-4}$ alkoxy, and $R^4$ and $R^5$ are not both H;
alternatively, $R^4$ and $R^5$ may form a 3- to 5-membered carbocyclic group, and the carbocyclic group may optionally be further substituted with 0 to 4 $R^8$s;
$R^6$ is selected from H or hydroxyl;
$R^7$ is selected from H or $C_{1-4}$ alkyl;
$R^8$ is selected from F, Cl, Br, hydroxyl, $C_{1-4}$ alkyl or $C_{1-4}$ alkoxy;
X is H;
$R^{y1}$ is each independently selected from H, $C_{1-6}$ alkyl, a $C_{3-6}$ carbocyclic group or a 4- to 6-membered heterocyclic group, wherein the alkyl, carbocyclic group or heterocyclic group may optionally be further substituted with 0 to 5 substituents selected from H, F, Cl, Br, I, hydroxyl, amino, cyano, carboxyl, $C_{1-6}$ alkyl, $C_{1-6}$ alkoxy, a $C_{3-8}$ carbocyclic group or a 4- to 8-membered heterocyclic group, and the heterocyclic group has 1 to 2 heteroatoms selected from N, O or S;
$R^{y3}$ is selected from H, amino, $C_{1-6}$ alkyl, a $C_{3-6}$ carbocyclic group or a 4- to 6-membered heterocyclic group, $-(CR^{ya}R^{yb})_{m1}-NR^{yc}R^{yd}$ or $-(CR^{ya}R^{yb})_{m1}-NR^{yc}C(=O)OR^{yd}$, wherein the amino group, alkyl, carbocyclic group or heterocyclic group may optionally be further substituted with 0 to 5 substituents selected from H, F, Cl, Br, I, hydroxyl, amino, cyano, carboxyl, $C_{1-6}$ alkyl, $C_{1-6}$ alkoxy, $-(CH_2)_{m1}-OC(=O)-C_{1-6}$ alkyl, $-(CH_2)_{m1}-C(=O)O-C_{1-6}$ alkyl, $-(CH_2)_{m1}-C(=O)O(CH_2)_{m1}-(C_{3-6}$ carbocyclic group), $-(CH_2)_{m1}-C(=O)-C_{1-6}$ alkyl, $-(CH_2)_{m1}-(C_{3-6}$ carbocyclic group) or a $-(CH_2)_{m1}-$(4- to 6-membered heterocyclic group), and the heterocyclic group has 1 to 2 heteroatoms selected from N, O or S;
$R^{y4}$ and $R^{y5}$ are each independently selected from H, an alkali metal ion, an alkali earth metal ion, a protonated amine or a protonated amino acid, $C_{1-6}$ alkyl, $-(CR^{ya}R^{yb})_{m1}$-(3-to 6-membered ring), $-(CR^{ya}R^{yb})_{m1}-OC(=O)C_{1-6}$ alkyl, $-(CR^{ya}R^{yb})_{m1}-OC(=O)$-(3-to 6-membered ring), $-(CR^{ya}R^{yb})_{m1}-C(=O)OC_{1-6}$ alkyl or $-(CR^{ya}R^{yb})_{m1}-OC(=O)OC_{1-6}$ alkyl;
$R^{y9}$ and $R^{10}$ are each independently selected from H, $C_{1-6}$ alkyl, a $C_{3-6}$ carbocyclic group or a 4- to 6-membered heterocyclic group, wherein the alkyl, carbocyclic group and heterocyclic group are each optionally further substituted with 0 to 4 substituents selected from H, hydroxyl, amino, mercapto, carboxyl, guanidino, carbamoyl, $C_{1-6}$ alkyl, $C_{1-6}$ alkoxy, a 3- to 8-membered carbocycle or a 3- to 8-membered heterocycle;
or a stereoisomer, a solvate, a metabolite, a prodrug, a pharmaceutically acceptable salt, or a cocrystal thereof.

12. The compound according to claim 11, wherein:
Y is selected from $C_{1-10}$ alkyl, $-(CH_2CH_2O)_q-H$, $-(CR^{ya}R^{yb})_{m1}-(W_1)_p-C(=O)(W_4R^{y3})$ or $-(CR^{ya}R^{yb})_{m1}-(W_1)_p-P(=O)(W_2R^{y4})(W_3R^{y5})$ or

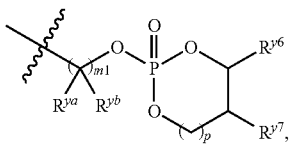

wherein the alkyl is optionally further substituted with 0 to 4 substituents selected from H, F, Cl, Br, I, hydroxyl, amino, cyano, carboxyl, $C_{1-6}$ alkyl or a $C_{3-6}$ carbocyclic group;

or a stereoisomer, a solvate, a metabolite, a prodrug, a pharmaceutically acceptable salt, or a cocrystal thereof.

13. The compound according to claim 12, wherein:
$R^1$, $R^2$ and $R^3$ are each independently selected from H, hydroxyl, methyl, ethyl or cyclopropyl, and $R^1$, $R^2$ and $R^3$ are not all H;
alternatively, any pair of $R^1$ and $R^2$, $R^2$ and $R^3$, or $R^1$ and $R^3$ may form cyclopropyl;
$R^4$ and $R^5$ are each independently selected from H, hydroxyl, cyano, methyl, ethyl or cyclopropyl, and $R^4$ and $R^5$ are not both H;
$R^7$ is selected from H, methyl or ethyl;
Y is selected from $C_{1-4}$ alkyl, —$(CR^{ya}R^{yb})_{m1}$—$(W_1)_p$—$C(=O)(W_4R^{y3})$ or —$(CR^{ya}R^{yb})_{m1}$—$(W_1)_p$—$P(=O)(W_2R^{y4})(W_3R^{y5})$ or

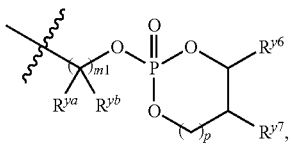

wherein the alkyl is optionally further substituted with 0 to 4 substituents selected from H, F, Cl, Br, I, hydroxyl, amino, cyano, carboxyl, $C_{1-4}$ alkyl or a $C_{3-6}$ carbocyclic group;
$R^{y3}$ is selected from H, amino, $C_{1-6}$ alkyl, a $C_{3-6}$ carbocyclic group or a 4- to 6-membered heterocyclic group, —$(CR^{ya}R^{yb})_{m1}$—$NR^{yc}R^{yd}$ or —$(CR^{ya}R^{yb})_{m1}$—$NR^{yc}C(=O)OR^{yd}$, wherein the amino group, alkyl, carbocyclic group or heterocyclic group may optionally be further substituted with 0 to 5 substituents selected from —$(CH_2)_{m1}$—$OC(=O)$—$C_{1-4}$ alkyl, —$(CH_2)_{m1}$—$C(=O)O$—$C_{1-4}$ alkyl, —$(CH_2)_{m1}$—$C(=O)O(CH_2)_{m1}$—$(C_{3-6}$ carbocyclic group), —$(CH_2)_{m1}$—$C(=O)$—$C_{1-4}$ alkyl, —$(CH_2)_{m1}$—$(C_{3-6}$ carbocyclic group) or —$(CH_2)_{m1}$-(4- to 6-membered heterocyclic group), and the heterocyclic group has 1 to 2 heteroatoms selected from N, O or S;
$R^{y4}$ and $R^{y5}$ are each independently selected from H, an alkali metal ion, $C_{1-4}$ alkyl, —$(CR^{ya}R^{yb})_{m1}$-(3- to 6-membered ring), —$(CR^{ya}R^{yb})_{m1}$—$OC(=O)$—$C_{1-4}$alkyl, —$(CR^{ya}R^{yb})_{m1}$—$OC(=O)$-(3- to 6-membered ring), —$(CR^{ya}R^{yb})_{m1}$—$C(=O)O$—$C_{1-4}$alkyl or —$(CR^{ya}R^{yb})_{m1}$—$OC(=O)O$—$C_{1-4}$alkyl;
$R^{y6}$ and $R^{y7}$ are each independently selected from H, $C_{1-4}$ alkyl or $C_{1-4}$ alkoxy;
alternatively, $R^{y6}$ and $R^{y7}$ may form a 5- to 6-membered ring together with the atoms to which they are attached, and the 5- to 6-membered ring may have 0 to 4 heteroatoms selected from N, O, or S;
$R^{y8}$s are each independently selected from H or $C_{1-4}$ alkyl;
$R^{y9}$ and $R^{y10}$ are each independently selected from H, $C_{1-6}$ alkyl or a 4- to 6-membered heterocyclic group, wherein the alkyl and heterocyclic group are optionally further substituted with 0 to 4 substituents selected from H, hydroxyl, amino, mercapto, carboxyl, guanidino, carbamoyl, $C_{1-6}$ alkyl, $C_{1-6}$ alkoxy, a 3- to 6-membered carbocycle or a 4- to 6-membered heterocycle;
$R^{ya}$, $R^{yb}$, $R^{yc}$ and $R^{yd}$ are each independently selected from H or $C_{1-4}$ alkyl;
q is selected from 1 to 10;
or a stereoisomer, a solvate, a metabolite, a prodrug, a pharmaceutically acceptable salt, or a cocrystal thereof.

14. The compound according to claim 13, wherein:
Y is selected from $C_{1-4}$ alkyl, —$(CR^{ya}R^{yb})_{m1}$—$(W_1)_p$—$C(=O)(W_4R^{y3})$ or —$(CR^{ya}R^{yb})_{m1}$—$(W_1)_p$—$P(=O)(W_2R^{y4})(W_3R^{y5})$ or

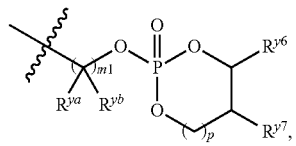

wherein the alkyl is optionally further substituted with 0 to 4 substituents selected from H, hydroxyl, amino, $C_{1-4}$ alkyl or a $C_{5-6}$ carbocyclic group;
$R^{y3}$ is selected from amino, $C_{1-4}$ alkyl, —$(CR^{ya}R^{yb})_{m1}NR^{yc}R^{yd}$, —$(CR^{ya}R^{yb})_{m1}NR^{yc}C(=O)OR^{yd}$, a $C_{3-6}$ carbocyclic group or a 3- to 6-membered heterocyclic group, wherein the amino group, alkyl, carbocyclic group or heterocyclic group is optionally further substituted with 0 to 4 substituents selected from —$OC(=O)$—$C_{1-4}$ alkyl, —$C(=O)O$—$C_{1-4}$ alkyl or —$C(=O)OCH_2$—$(C_{5-6}$ carbocyclic group), and the heterocyclic group has at least 1 to 2 heteroatoms selected from N, O or S;
$R^{y4}$ and $R^{y5}$ are each independently selected from H, an alkali metal ion, $C_{1-4}$ alkyl, —$(CR^{ya}R^{yb})_{m1}$-(5- to 6-membered ring), —$(CR^{ya}R^{yb})_{m1}$—$OC(=O)C_{1-4}$ alkyl, —$(CR^{ya}R^{yb})_{m1}$—$C(=O)OC_{1-4}$ alkyl or —$(CR^{ya}R^{yb})_{m1}$—$OC(=O)OC_{1-4}$ alkyl;
$R^{y6}$ and $R^{y7}$ are each independently H or $C_{1-4}$ alkyl;
alternatively, $R^{y6}$ and $R^{y7}$ may form a 5- to 6-membered ring together with the atoms to which they are attached, and the 5- to 6-membered ring may have 0 to 4 heteroatoms selected from N, O, or S;
$R^{y8}$ is selected from H or $C_{1-4}$ alkyl;
$R^{y9}$ is selected from H or $C_{1-4}$ alkyl;
$R^{y10}$ is selected from H or $C_{1-4}$ alkyl, wherein the alkyl is optionally further substituted with 0 to 4 substituents selected from H, hydroxyl, amino, mercapto, carboxyl, guanidino, carbamoyl, $C_{1-4}$ alkyl, or a 5- to 6-membered carbocycle;
or a stereoisomer, a solvate, a metabolite, a prodrug, a pharmaceutically acceptable salt, or a cocrystal thereof.

15. The compound according to claim 14, wherein:
$W_1$, $W_2$, $W_3$ are each independently selected from NH or O;
$W_4$ are each independently selected from $CHR^{y10}$ or O, or is absent;
$R^{y3}$ is selected from amino, $C_{1-4}$ alkyl, —$(CH_2)_{m1}NR^{yc}R^{yd}$, —$(CH_2)_{m1}NR^{yc}C(=O)OR^{yd}$, a $C_{5-6}$ carbocyclic group or a 5- to 6-membered heterocyclic group, wherein the amino group, alkyl, carbocyclic group or heterocyclic group is optionally further substituted with 0 to 4 substituents selected from —$OC(=O)$—$C_{1-4}$ alkyl, —$C(=O)O$—$C_{1-4}$ alkyl or —C(=O)OCH$_2$—(C$_{5-6}$ carbocyclic group), and the heterocyclic group at least has 1 to 2 heteroatoms selected from N, O or S;

R$^{y4}$ and R$^{y5}$ are each independently selected from H, an alkali metal ion, C$_{1-4}$ alkyl, —(CH$_2$)$_{m1}$-(5- to 6-membered ring), —(CH$_2$)$_{m1}$—OC(=O)C$_{1-4}$ alkyl, —(CH$_2$)$_{m1}$—C(=O)OC$_{1-4}$ alkyl or —(CH$_2$)$_{m1}$—OC(=O)OC$_{1-4}$ alkyl;

R$^{y10}$ is selected from H or C$_{1-4}$ alkyl, wherein the alkyl is optionally further substituted with 0 to 4 substituents selected from H, C$_{1-4}$ alkyl, or a 5- to 6-membered carbocycle;

R$^{ya}$, R$^{yb}$, R$^{yc}$ and R$^{yd}$ are each independently selected from H or C$_{1-4}$ alkyl;

or a stereoisomer, a solvate, a metabolite, a prodrug, a pharmaceutically acceptable salt, or a cocrystal thereof.

16. The compound according to claim 15, wherein:

the

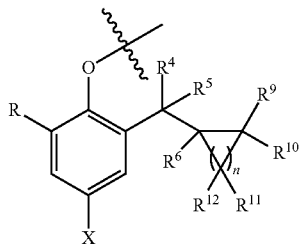

is selected from the structures below:

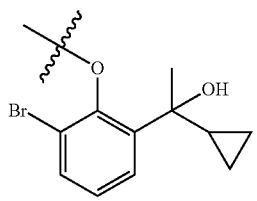

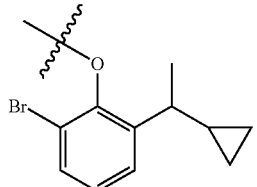

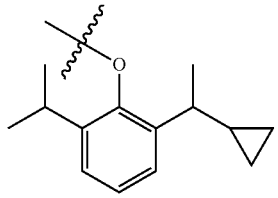

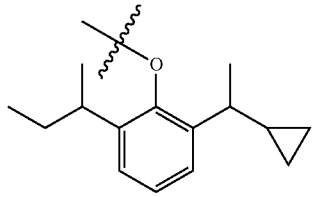

-continued

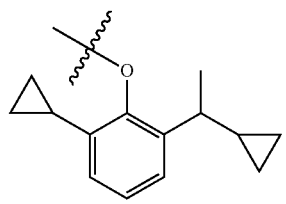

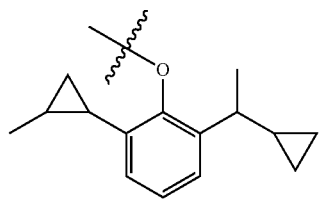

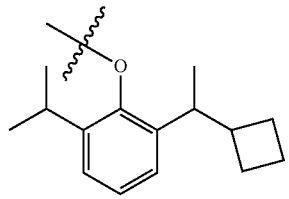

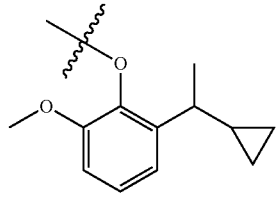

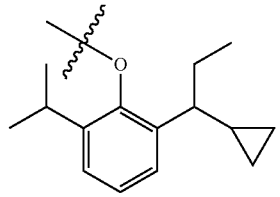

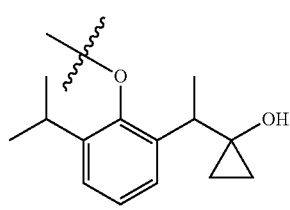

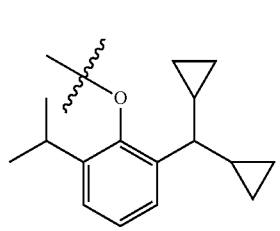

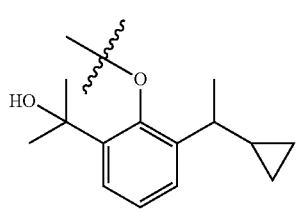

215
-continued
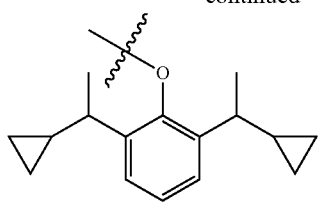
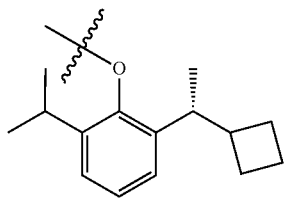
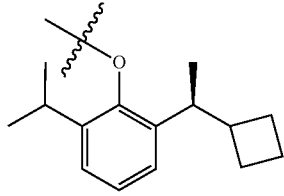
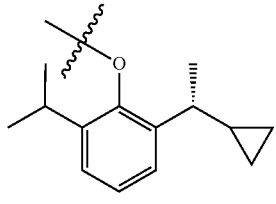
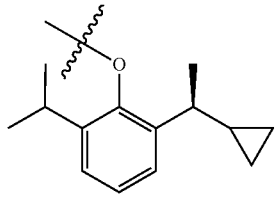
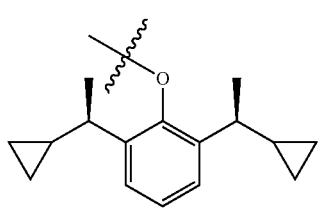
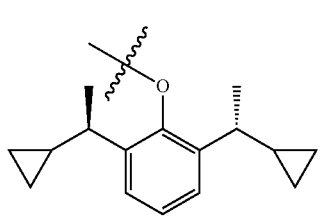
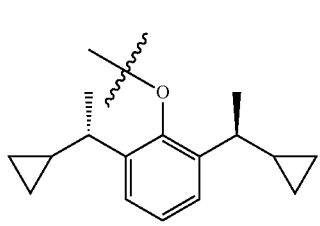
216
-continued
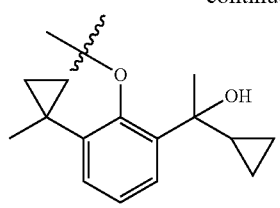
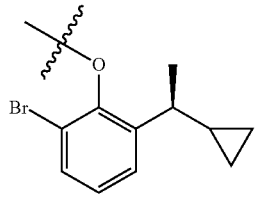
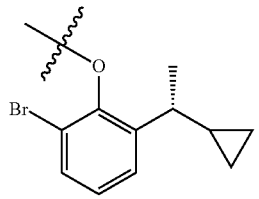
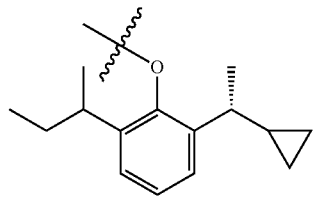
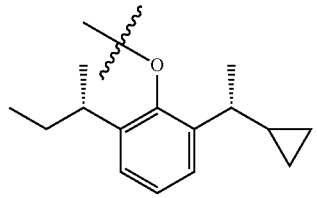
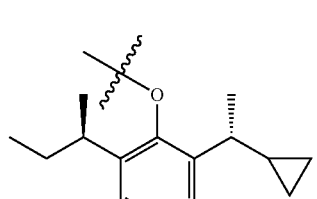
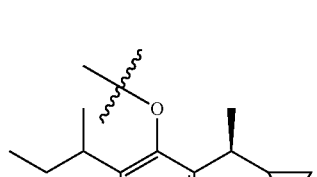
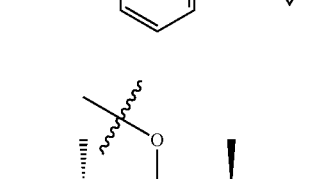

-continued

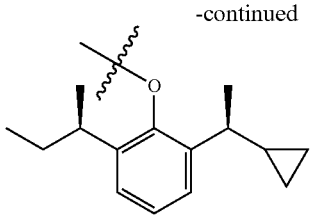

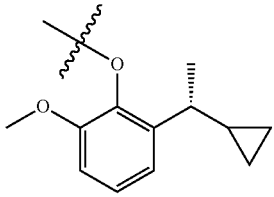

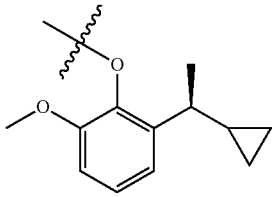

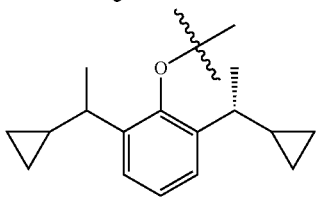

or

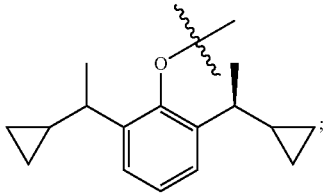

Y is selected from methyl, hydroxyethyl, —CH$_2$OC(=O)(R$^{y3}$), —C(=O)(R$^{y3}$), —CH$_2$OC(=O)(W$_4$R$^{y3}$), —C(=O)(W$_4$R$^{y3}$), —CH(CH$_3$)OC(=O)(W$_4$R$^{y3}$), —CH$_2$OP(=O)(W$_2$R$^{y4}$)(W$_3$R$^{y5}$), —P(=O)(W$_2$R$^{y4}$)(W$_3$R$^{y5}$) or

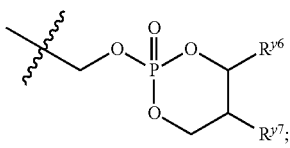

W$_2$ and W$_3$ are each independently selected from NH or O;
W$_4$ is selected from CHR$^{y10}$ or O;
R$^{y3}$ is selected from amino, aminomethylene, isopropyl, t-butyl, (t-butoxycarbonyl)amino, (t-butoxycarbonyl)aminomethylene, pyrrolylalkyl, phenyl or pyridinyl, wherein the amino group, pyrrolylalkyl, phenyl and pyridinyl are optionally further substituted with 0 to 4 substituents selected from t-butoxycarbonyl, acetoxy, or benzyloxycarbonyl;
R$^{y4}$ and R$^{y5}$ are each independently selected from H, Na$^+$, K$^+$, ethyl, benzyl, —CH$_2$OC(=O)C(CH$_3$)$_3$, —CH(CH$_3$)OC(=O)CH(CH$_3$)$_2$, —CH$_2$OC(=O)CH$_2$CH$_3$, —CH$_2$C(=O)OCH$_2$CH$_3$ or —CH$_2$OC(=O)OCH(CH$_3$)$_2$;

R$^{y6}$ and R$^{y7}$ form phenyl together with the atoms to which they are attached;
R$^{y10}$ is selected from H, methyl, isopropyl, sec-butyl, 2-methylpropyl or benzyl;
or a stereoisomer, a solvate, a metabolite, a prodrug, a pharmaceutically acceptable salt, or a cocrystal thereof.

17. The compound according to claim 16, wherein: the

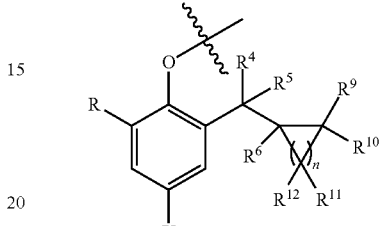

is selected from the structures below:

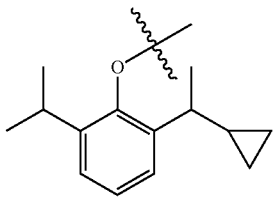

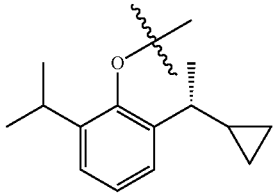

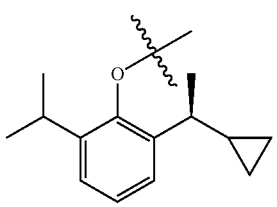

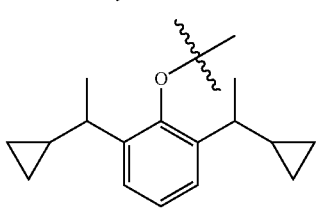

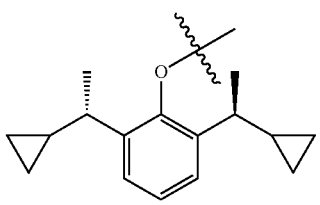

-continued
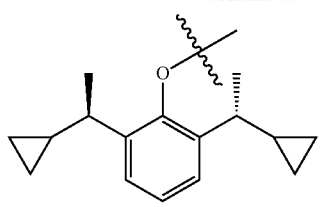
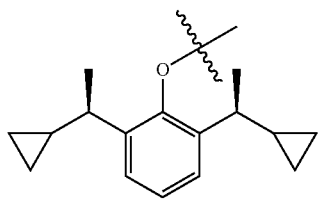
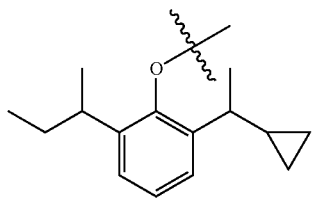
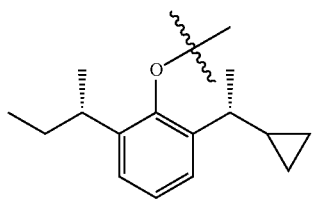
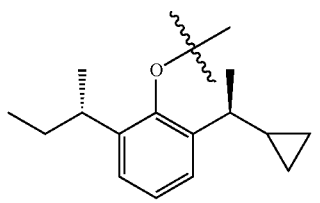
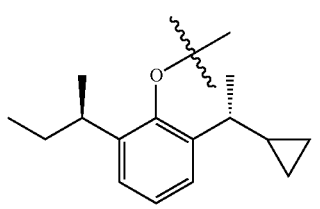
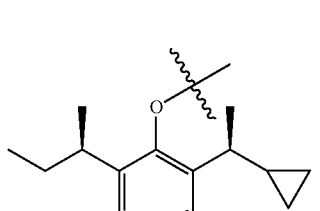
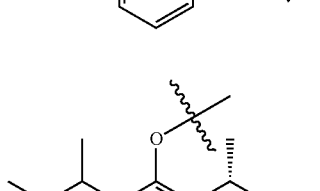
-continued
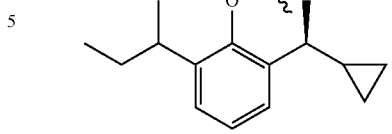
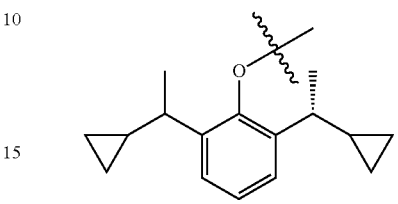
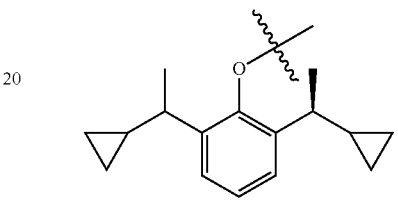
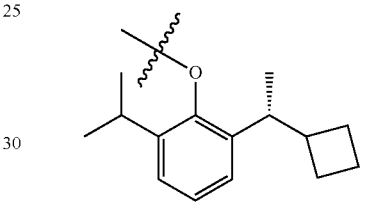
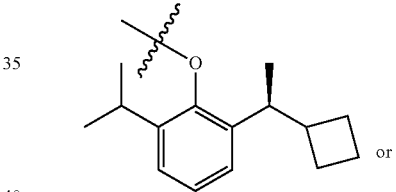
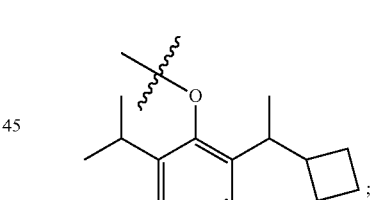 or
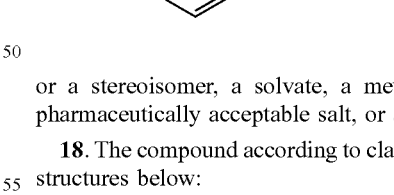 ;
or a stereoisomer, a solvate, a metabolite, a prodrug, a pharmaceutically acceptable salt, or a cocrystal thereof.
18. The compound according to claim 1, selected from the structures below:
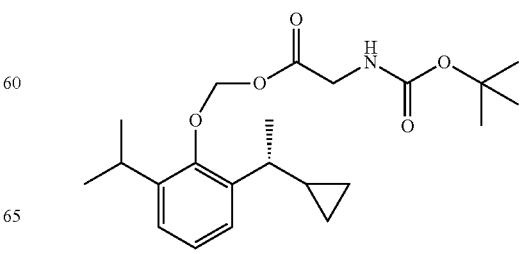

221
-continued
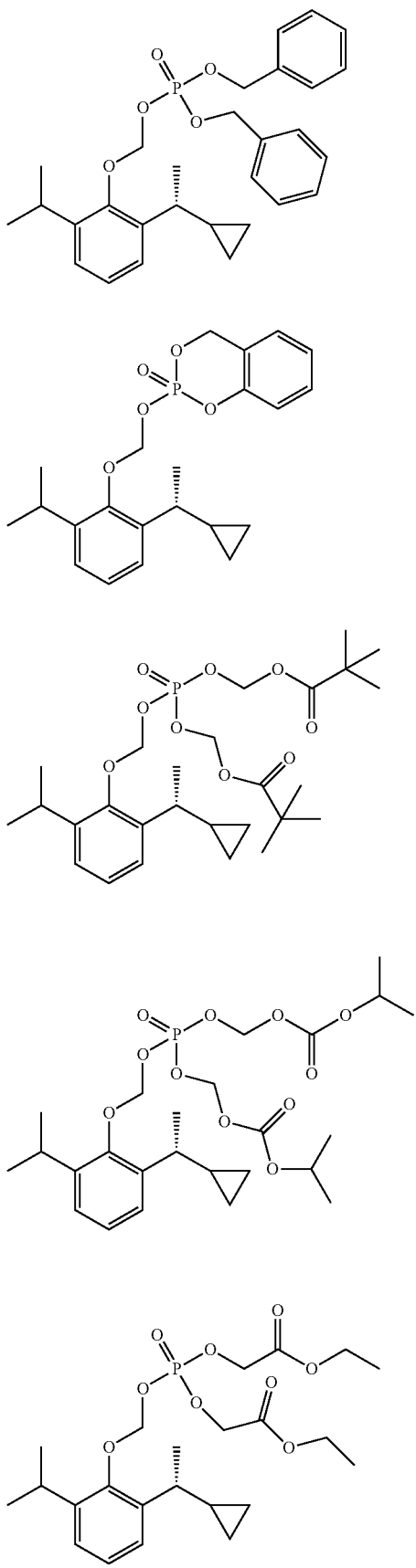
222
-continued
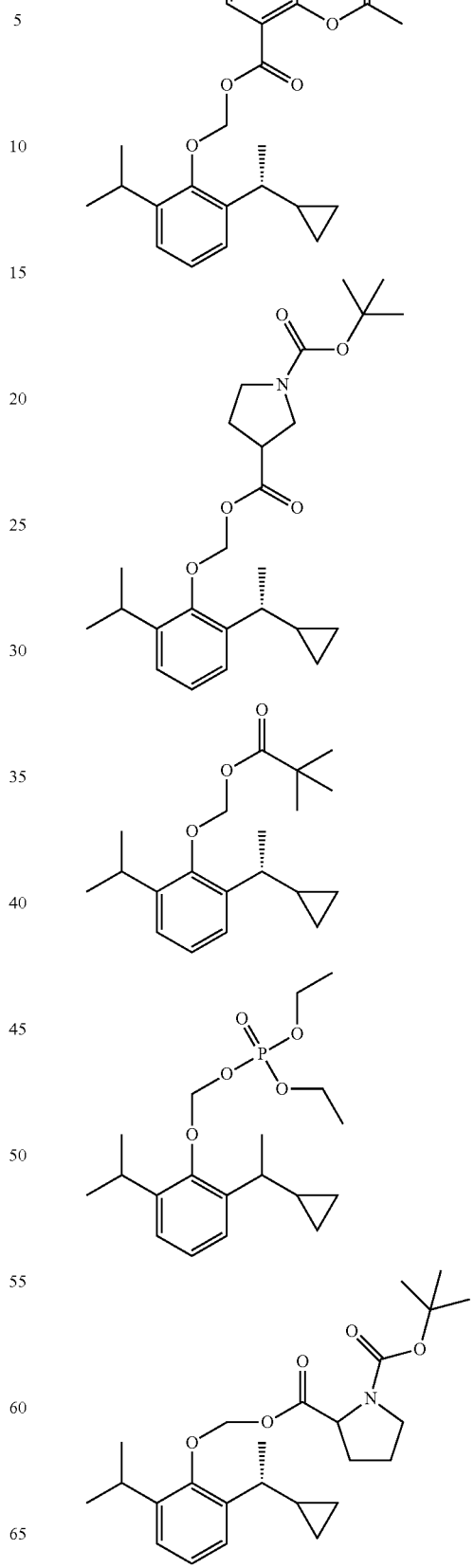

223
-continued
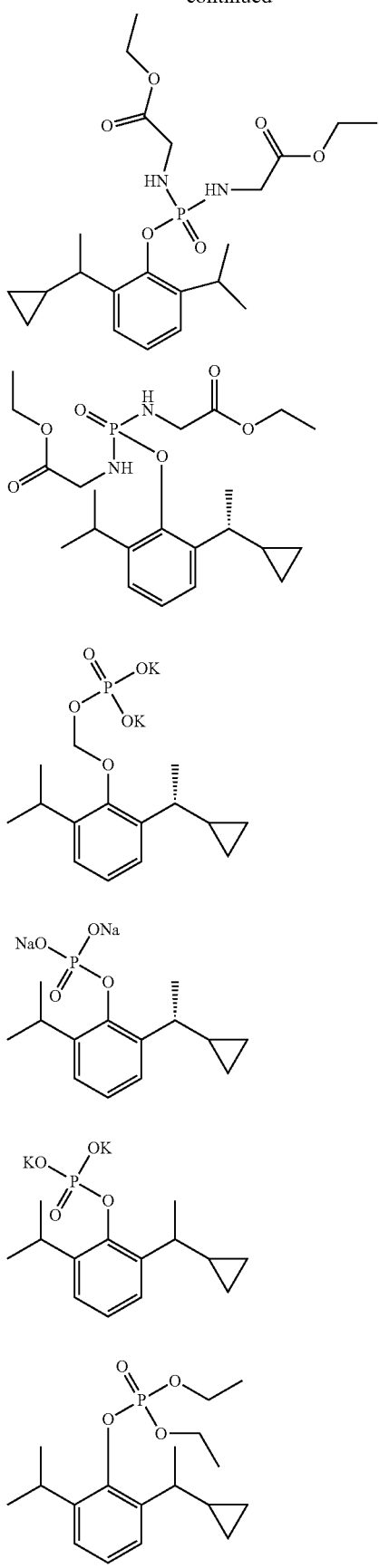
224
-continued
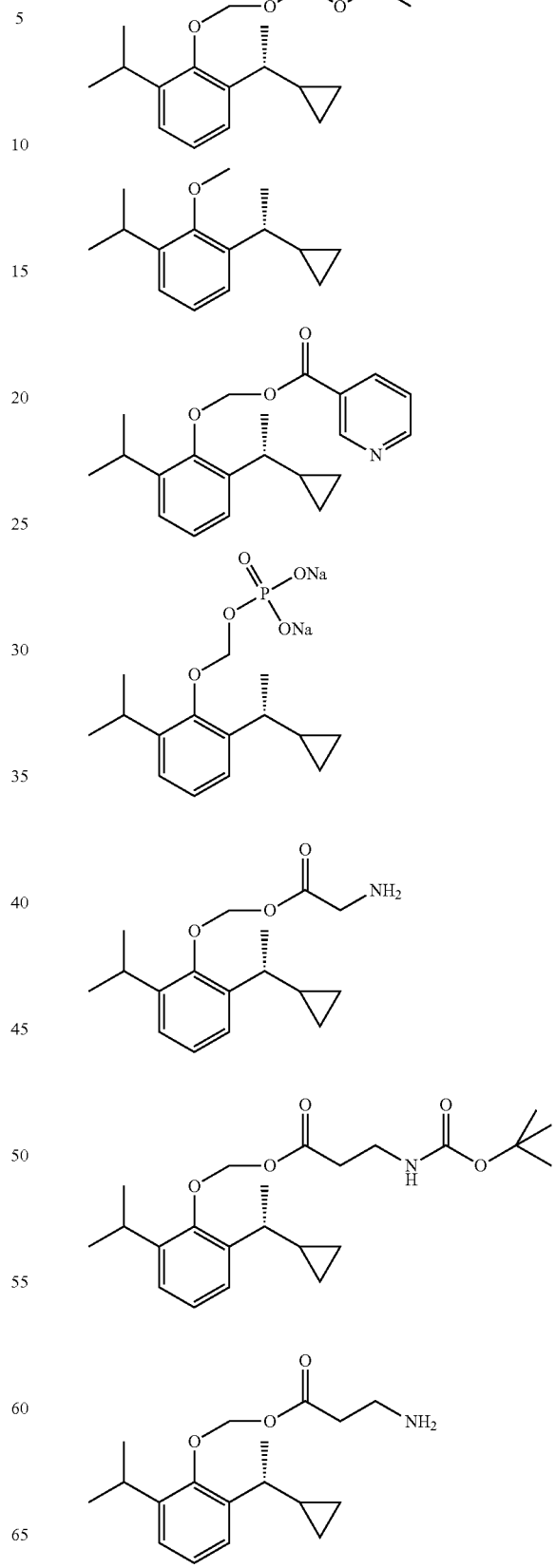

225
-continued
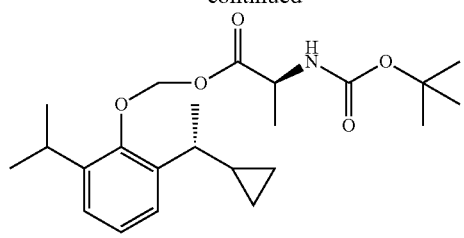
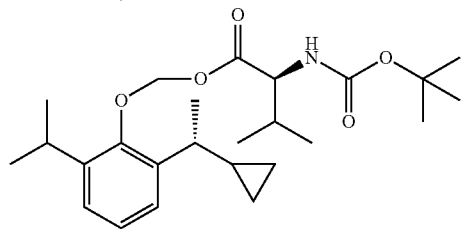
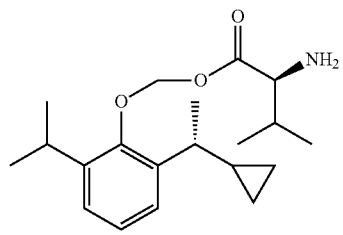
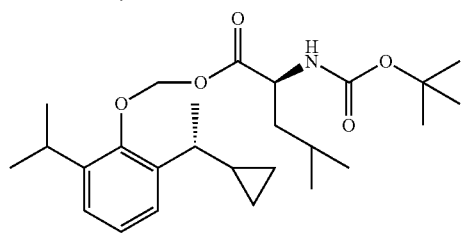
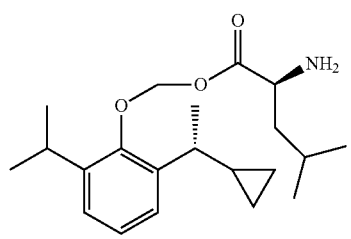
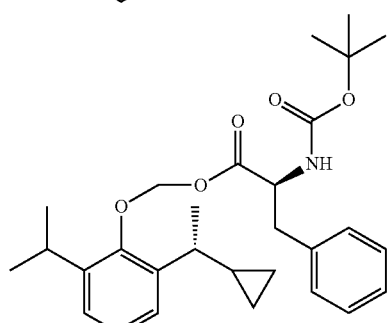
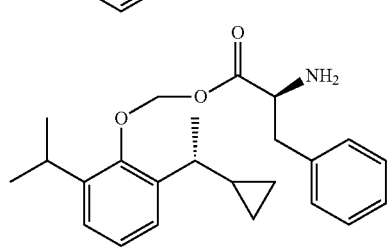
226
-continued
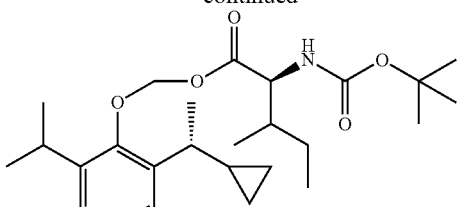
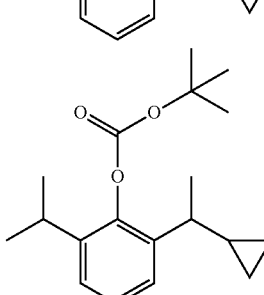
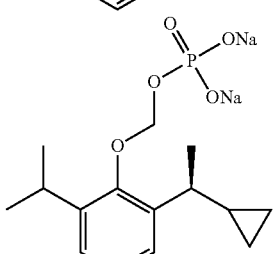
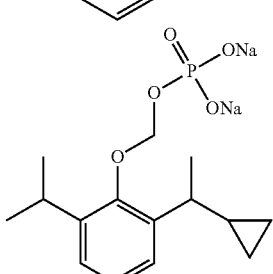
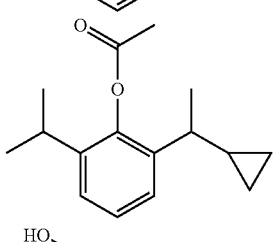
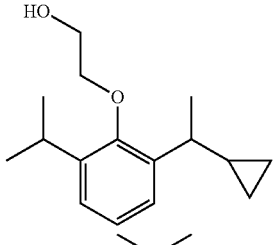
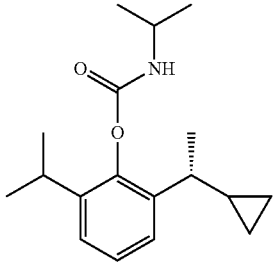

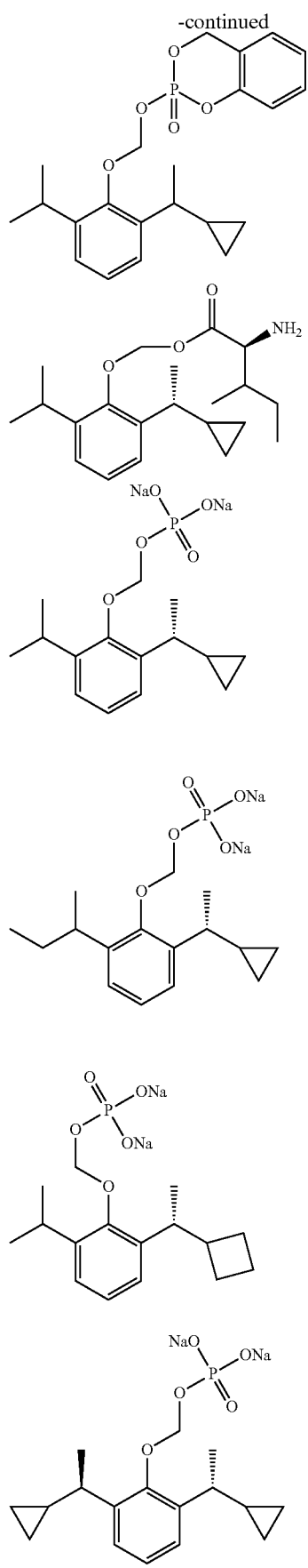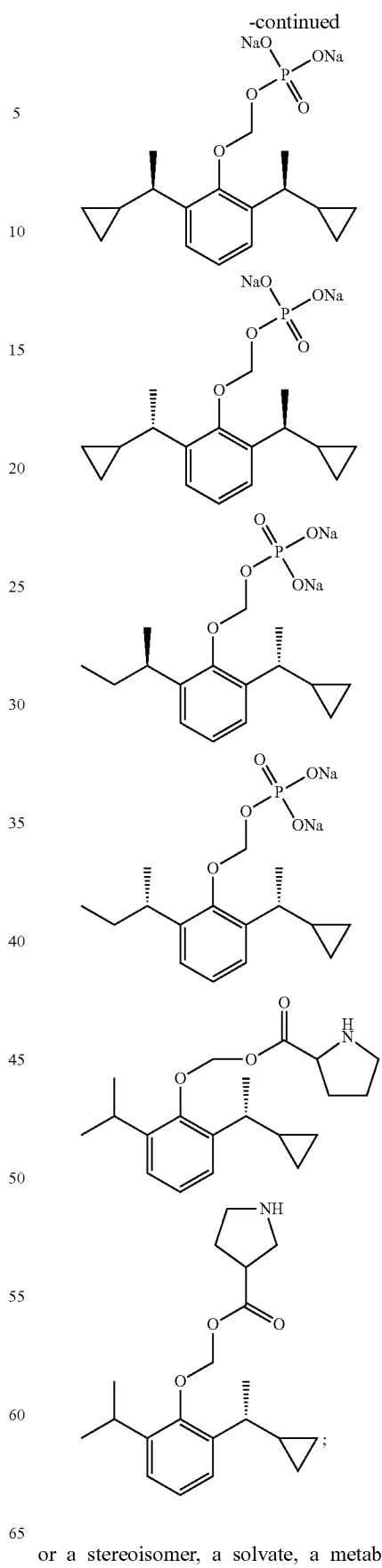
or a stereoisomer, a solvate, a metabolite, a prodrug, a pharmaceutically acceptable salt, or a cocrystal thereof.

19. The compound according to claim 1, or a stereoisomer, a solvate, a metabolite, a prodrug, a pharmaceutically acceptable salt, or a cocrystal thereof,
wherein the salt includes an ammonium salt, a potassium salt, a sodium salt, a calcium salt, a magnesium salt, a tetramethylammonium salt, a tetraethylammonium salt, a tetrapropylammonium salt, a tetrabutylammonium salt, a tetra(isopentyl)ammonium salt, an ethanolamine salt, a diethanolamine salt, a triethanolamine salt, trimethylamine salt, N-methylglucosamine salt, hydrochloride sulfate, phosphate, acetate, trifluoroacetate, fumarate, hemifumarate, maleate, malate, citrate, succinate, benzenesulfonate, or p-toluenesulfonate.

20. A method for preparing a compound according to claim 1, comprising:

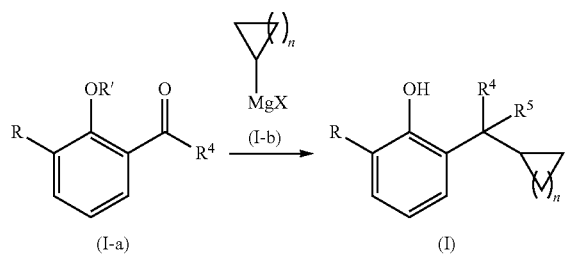

conducting a Grignard reaction between a compound of general formula (I-a) and a compound of general formula (I-b) to afford a compound of general formula (I); or
conducting a Grignard reaction between a compound of general formula (I-a) and a compound of general formula (I-b), and further removing R' from the product of the Grignard reaction to afford a compound of general formula (I);
or
conducting a Grignard reaction between a compound of general formula (I-a) and a compound of general formula (I-b), and removing hydroxyl from the product of the Grignard reaction by a reducing agent, to afford a compound of general formula (I);
or
conducting a Grignard reaction between a compound of general formula (I-a) and a compound of general formula (I-b), removing R' from the product of the Grignard reaction, and further removing hydroxyl therefrom by a reducing agent, to afford a compound of general formula (I);
wherein R' is selected from H, methyl, ethyl, benzyl, p-methoxybenzyl, triphenylmethyl, trimethylsilyl, or t-butyl(dimethyl)silyl; R, $R^4$, $R^5$ and n have the same definitions as those for the compound of general formula (I); X is selected from F, Cl, Br or I;
or,

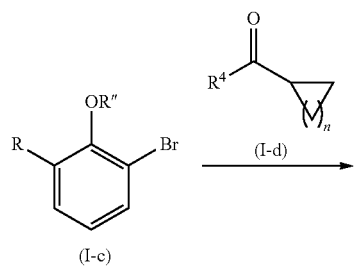

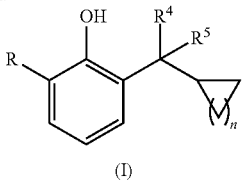

allowing a compound of general formula (I-c) to either undergo a Grignard reaction, or react with a compound of general formula (I-d) under the action of an organolithium reagent, and then removing R" to afford a compound of general formula (I); or
allowing a compound of general formula (I-c) to either undergo a Grignard reaction, or react with a compound of general formula (I-d) under the action of an organolithium reagent, then removing R", and further removing hydroxyl therefrom by a reducing agent, to afford a compound of general formula (I); or
allowing a compound of general formula (I-c) to either undergo a Grignard reaction, or react with a compound of general formula (I-d) under the action of an organolithium reagent, further alkylating the product thereof, and then removing R" therefrom to afford a compound of general formula (I);
wherein R" is selected from, methyl, ethyl, benzyl, p-methoxybenzyl, triphenylmethyl, trimethylsilyl, or t-butyl(dimethyl)silyl; R, $R^4$, $R^5$ and n have the same definitions as those for the compound of general formula (I).

21. A method for preparing a compound according to claim 10, comprising:

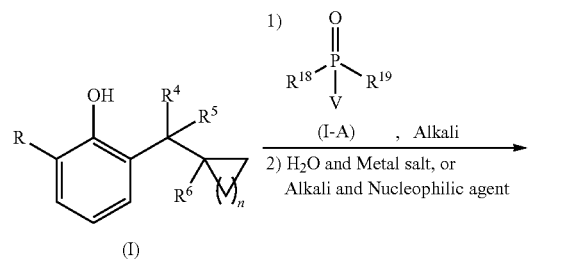

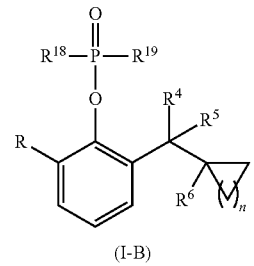

wherein
allowing a compound of general formula (I) and a compound of general formula (I-A) to undergo nucleophilic substitution under the action of an alkali to directly afford a compound of general formula (I-B); or
allowing a compound of general formula (I) and a compound of general formula (I-A) to undergo nucleophilic substitution under the action of an alkali to afford an intermediate for a compound of general formula (I-B), and subjecting the intermediate to hydrolysis and then to an exchange reaction with a metal salt to afford a compound of general formula (I-B); or allowing a compound of general formula (I) and a compound of general formula (I-A) to undergo nucleophilic substitution under the action of an alkali to afford an intermediate for a compound of general formula (I-B), and allowing the intermediate to further react with a nucleophilic reagent under the action of an alkali to afford a compound of general formula (I-B);

or,

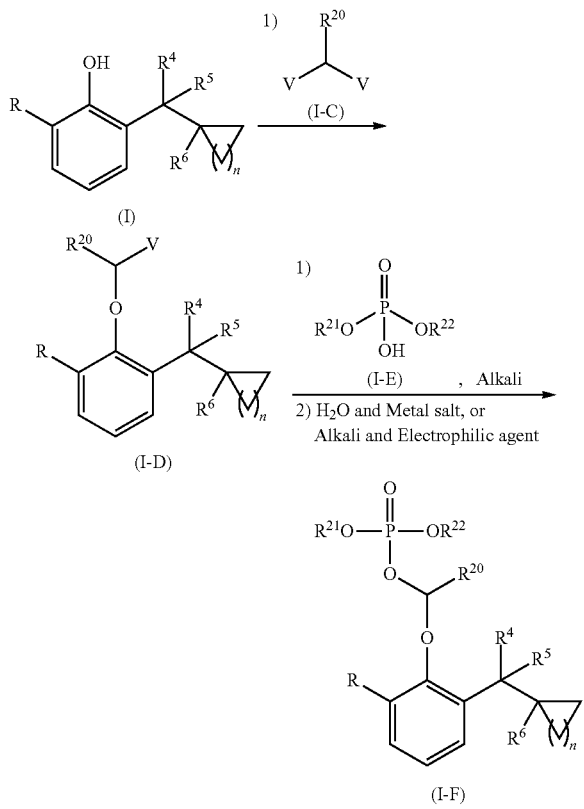

allowing a compound of general formula (I) and a compound of general formula (I-C) to undergo nucleophilic substitution to afford a compound of general formula (I-D); and then allowing the compound of general formula (I-D) and a compound of general formula (I-E) to undergo nucleophilic substitution under the action of an alkali to directly afford a compound of general formula (I-F); or allowing the compound of general formula (I-D) and a compound of general formula (I-E) to undergo nucleophilic substitution under the action of an alkali to afford an intermediate for a compound of general formula (I-F), and subjecting the intermediate to hydrolysis and then to an exchange reaction with a metal salt to afford a compound of general formula (I-F); or allowing the compound of general formula (I-D) and a compound of general formula (I-E) to undergo nucleophilic substitution under the action of an alkali to afford an intermediate for a compound of general formula (I-F), and allowing the intermediate to further react with an electrophilic reagent under the action of an alkali to afford a compound of general formula (I-F);

wherein, $R^{18}$ or $R^{19}$ is each independently selected from F, Cl, Br, I, $C_{1-10}$ alkyl or $C_{1-10}$ alkoxy, $R^{20}$, $R^{21}$ and $R^{22}$ are each independently selected from H, F, Cl, Br, I or $C_{1-10}$ alkyl;

V is selected from F, Cl, Br, I;

n, R, $R^4$, $R^5$ and $R^6$ have the same definitions as those in general formula (I).

22. A pharmaceutical composition, comprising:
a compound according to claim 1, or a stereoisomer, a solvate, a metabolite, a pharmaceutically acceptable salt, a cocrystal, or a prodrug thereof; and
one or more pharmaceutically acceptable vehicles and/or excipients.

23. A method for inducing and maintaining anesthesia in an animal or a human, facilitating sedation and hypnosis of an animal or a human, or treating and/or preventing anxiety, depression, insomnia, nausea, vomiting, migraine, schizophrenia, convulsion, and epilepsy comprising:
administering a compound according to claim 1, or a stereoisomer, a solvate, a metabolite, a pharmaceutically acceptable salt, a cocrystal, or a prodrug thereof.

* * * * *

(12) EX PARTE REEXAMINATION CERTIFICATE (11577th)
United States Patent
Qin et al.

(10) Number: US 9,517,988 C1
(45) Certificate Issued: Sep. 18, 2019

(54) PHENOL DERIVATIVE AND PREPARATION METHOD AND USE IN MEDICINE THEREOF

(71) Applicant: Sichuan Haisco Pharmaceutical Co., Ltd., Chengdu (CN)

(72) Inventors: Linlin Qin, Chengdu (CN); Fangqiong Li, Chengdu (CN); Shixu Yi, Chengdu (CN); Huadong Luo, Chengdu (CN); Xinfeng Luo, Chengdu (CN); Songlin Wan, Chengdu (CN); Lei Ren, Chengdu (CN); Guoliang Liu, Chengdu (CN); Yonggang Wei, Chengdu (CN); Jianyu Liu, Chengdu (CN); Peng Cho Tang, Chengdu (CN)

(73) Assignee: SICHUAN HAISCO PHARMACEUTICAL CO., LTD., Wenjiang District, Chengdu, Sichuan Province (CN)

Reexamination Request:
No. 90/014,265, Feb. 18, 2019

Reexamination Certificate for:
Patent No.: 9,517,988
Issued: Dec. 13, 2016
Appl. No.: 14/936,310
Filed: Nov. 9, 2015

Related U.S. Application Data

(63) Continuation of application No. PCT/CN2014/076907, filed on May 6, 2014.

(30) Foreign Application Priority Data

May 9, 2013 (CN) .......................... 2013 1 0169462

(51) Int. Cl.
| | |
|---|---|
| C07C 271/44 | (2006.01) |
| C07C 229/08 | (2006.01) |
| C07F 9/09 | (2006.01) |
| C07C 69/96 | (2006.01) |
| C07C 43/21 | (2006.01) |
| C07C 271/22 | (2006.01) |
| C07C 68/00 | (2006.01) |
| C07C 39/42 | (2006.01) |
| C07C 43/00 | (2006.01) |
| C07C 39/00 | (2006.01) |
| C07D 213/00 | (2006.01) |
| C07F 9/00 | (2006.01) |
| C07C 39/17 | (2006.01) |
| C07C 41/18 | (2006.01) |
| C07C 67/10 | (2006.01) |
| C07C 69/07 | (2006.01) |
| C07C 69/78 | (2006.01) |
| C07F 9/6574 | (2006.01) |
| C07F 9/12 | (2006.01) |
| C07F 9/24 | (2006.01) |
| C07D 213/80 | (2006.01) |
| C07C 37/62 | (2006.01) |
| C07C 229/36 | (2006.01) |
| C07C 37/00 | (2006.01) |
| C07F 9/06 | (2006.01) |
| C07D 213/803 | (2006.01) |
| C07C 269/00 | (2006.01) |
| C07C 227/04 | (2006.01) |
| C07D 207/16 | (2006.01) |
| C07C 69/82 | (2006.01) |
| C07C 69/157 | (2006.01) |
| C07C 69/24 | (2006.01) |
| C07C 43/23 | (2006.01) |

(52) U.S. Cl.
CPC .............. *C07C 39/17* (2013.01); *C07C 37/00* (2013.01); *C07C 37/001* (2013.01); *C07C 37/62* (2013.01); *C07C 39/42* (2013.01); *C07C 41/18* (2013.01); *C07C 43/21* (2013.01); *C07C 43/23* (2013.01); *C07C 67/10* (2013.01); *C07C 68/00* (2013.01); *C07C 69/07* (2013.01); *C07C 69/157* (2013.01); *C07C 69/24* (2013.01); *C07C 69/78* (2013.01); *C07C 69/82* (2013.01); *C07C 69/96* (2013.01); *C07C 227/04* (2013.01); *C07C 229/08* (2013.01); *C07C 229/36* (2013.01); *C07C 269/00* (2013.01); *C07C 271/22* (2013.01); *C07C 271/44* (2013.01); *C07D 207/16* (2013.01); *C07D 213/80* (2013.01); *C07D 213/803* (2013.01); *C07F 9/06* (2013.01); *C07F 9/091* (2013.01); *C07F 9/094* (2013.01); *C07F 9/12* (2013.01); *C07F 9/242* (2013.01); *C07F 9/2458* (2013.01); *C07C 2601/02* (2017.05); *C07C 2601/04* (2017.05)

(58) Field of Classification Search
None
See application file for complete search history.

(56) References Cited

To view the complete listing of prior art documents cited during the proceeding for Reexamination Control Number 90/014,265, please refer to the USPTO's public Patent Application Information Retrieval (PAIR) system under the Display References tab.

*Primary Examiner* — Dwayne C. Jones

(57) ABSTRACT

The present invention relates to a phenol derivative and the preparation method and use in medicine thereof, and particular to a phenol derivative represented by general formula (A) or a stereoisomer, a solvate, a metabolite, a prodrug, a pharmaceutically acceptable salt or a cocrystal thereof, a preparation method thereof, a pharmaceutical composition comprising the same, and use of the compound or composition of the present invention in the field of the central nervous system; wherein the definitions of substituents in general formula (A) are the same as those in the Description.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2-23, dependent on an amended claim, are determined to be patentable.

1. A compound of general formula (A),

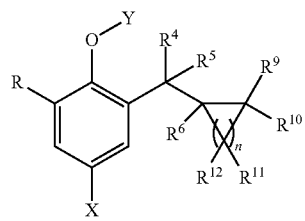

wherein
R is selected from F, Cl, Br, I, —OR$^7$ or

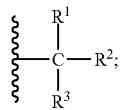

R$^1$, R$^2$ and R$^3$ are each independently selected from H, F, Cl, Br, I, hydroxyl, C$_{1-6}$ alkyl, C$_{1-6}$ alkoxy, a 3- to 5-membered carbocyclic group, or a 3- to 5-membered heterocyclic group, wherein the alkyl, alkoxy, carbocyclic group or heterocyclic group is optionally further substituted with 0 to 5 substituents selected from F, Cl, Br, I, hydroxyl, C$_{1-6}$ alkyl, C$_{1-6}$ alkoxy, a 3- to 5-membered carbocyclic group or a 3- to 5-membered heterocyclic group, the heterocyclic group has 1 to 2 heteroatoms selected from N, O or S, and R$^1$, R$^2$ and R$^3$ are not all H;

alternatively, any pair of R$^1$ and R$^2$, R$^2$ and R$^3$, or R$^1$ and R$^3$ forms a 3- to 5-membered ring, the 3- to 5-membered ring has 0 to 2 heteroatoms selected from N, O or S, and the formed 3- to 5-membered ring is optionally further substituted with 0 to 4 R$^8$s;

R$^4$ and R$^5$ are each independently selected from H, F, Cl, Br, I, hydroxyl, cyano, C$_{1-6}$ alkyl, C$_{1-6}$ alkoxy, a 3- to 5-membered carbocyclic group or a 3- to 5-membered heterocyclic group, wherein the alkyl, alkoxy, carbocyclic group or heterocyclic group is optionally further substituted with 0 to 5 substituents selected from hydroxyl, C$_{1-6}$ alkyl, C$_{1-6}$ alkoxy, a 3- to 5-membered carbocyclic group or a 3- to 5-membered heterocyclic group, the heterocyclic group has 1 to 2 heteroatoms selected from N, O or S, and R$^4$ and R$^5$ are not both H;

alternatively, R$^4$ and R$^5$ may form a 3- to 5-membered ring, the 3- to 5-membered ring may have 0 to 2 heteroatoms selected from N, O or S, and the formed 3- to 5-membered may optionally be further substituted with 0 to 4 R$^8$s;

R$^6$ is selected from H or hydroxyl;

R$^7$ is selected from H, C$_{1-4}$ alkyl or a 3- to 5-membered carbocyclic group, wherein the alkyl or carbocyclic group is optionally further substituted with 0 to 5 substituents selected from F, Cl, Br, I, hydroxyl, C$_{1-4}$ alkyl, C$_{1-4}$ alkoxy or a 3- to 5-membered carbocyclic group;

R$^8$ is selected from F, Cl, Br, hydroxyl, C$_{1-4}$ alkyl, C$_{1-4}$ alkoxy, a 3- to 5-membered carbocyclic group or a 3- to 5-membered heterocyclic group, and the heterocyclic group has 1 to 2 heteroatoms selected from N, O or S;

R$^9$, R$^{10}$, R$^{11}$ and R$^{12}$ are each independently selected from H, F, Cl, Br, I, hydroxyl, C$_{1-6}$ alkyl or C$_{1-6}$ alkoxy;

X is selected from H, F or carboxyl;

Y is selected from H, COR$^{13}$, PEG, COOR$^{13}$, CONR$^{13}$R$^{14}$, COSR$^{13}$,

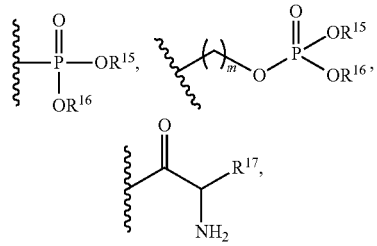

C$_{1-20}$ alkyl, —(CH$_2$CH$_2$O)$_q$—H, —(CR$^{ya}$R$^{yb}$)$_{m1}$COORY$^{y1}$, —(CR$^{ya}$R$^{yb}$)$_{m1}$—(W$_1$)$_p$—(=O)(W$_4$R$^{y3}$) or —(CR$^{ya}$R$^{yb}$)$_{m1}$—(W$_1$)$_p$—P(=O)(W$_2$R$^{y4}$)(W$_3$R$^{y5}$) or

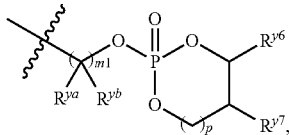

wherein the alkyl is optionally further substituted with 0 to 4 substituents selected from H, F, Cl, Br, I, hydroxyl, amino, cyano, carboxyl, C$_{1-6}$ alkyl, C$_{1-6}$ alkoxy, a C$_{3-8}$ carbocyclic group or a 4- to 8-membered heterocyclic group, and the heterocyclic group has 1 to 2 heteroatoms selected from N, O or S;

R$^{13}$ and R$^{14}$ are each independently selected from H, C$_{1-6}$ alkyl, a 3- to 8-membered carbocyclic or heterocyclic group, wherein the alkyl, carbocyclic group or heterocyclic group may optionally be further substituted with 0 to 5 substituents selected from F, Cl, Br, I, hydroxyl, C$_{1-6}$ alkyl, C$_{1-6}$ alkoxy, a 3- to 8-membered carbocyclic group or a 3- to 8-membered heterocyclic group, and the heterocyclic group has 1 to 2 heteroatoms selected from N, O or S;

R$^{15}$ and R$^{16}$ are each independently selected from H, an alkali metal ion, an alkali earth metal ion, a protonated amine or a protonated amino acid, wherein the alkali metal ion is selected from Na$^+$, K$^+$ or Li$^+$, the alkali earth metal ion is selected from Be$^{2+}$, Mg$^{2+}$ or Ca$^{2+}$, the amine is selected from trometamol, triethanolamine, ethanolamine, triethylamine or N-methylglucosamine, and the amino acid is selected from arginine or lysine;

alternatively, $R^{15}$ and $R^{16}$ may form a 3- to 8-membered ring, the 3- to 8-membered ring may have 0 to 2 heteroatoms selected from N, O or S, and the formed 3- to 8-membered ring may optionally be further substituted with 0 to 4 $R^8$s;

$R^{17}$ is the side-chain group of an amino acid, wherein the amino acid is selected from lysine, arginine, histidine, proline, 2,3-diaminopropionic acid, 2,4-diaminopropionic acid, alanine, valine, leucine, isoleucine, phenylalanine, tryptophan, methionine, glycine, serine, threonine, cysteine, tyrosine, asparagine, glutamine, aspartic acid, aspartate, or glutamic acid;

$W_1$, $W_2$ and $W_3$ are each independently selected from $NR^{y8}$, O or S;

$W_4$ is selected from $CR^{y9}R^{y10}$, $NR^{y8}$, O, S, or is absent;

$R^{y1}$ is each independently selected from H, $C_{1-6}$ alkyl, a $C_{3-8}$ carbocyclic group or a 4- to 8-membered heterocyclic group, wherein the alkyl, carbocyclic group or heterocyclic group may optionally be further substituted with 0 to 5 substituents selected from H, F, Cl, Br, I, hydroxyl, amino, cyano, carboxyl, $C_{1-6}$ alkyl, $C_{1-6}$ alkoxy, a $C_{3-8}$ carbocyclic group or a 4- to 8-membered heterocyclic group, and the heterocyclic group has 1 to 2 heteroatoms selected from N, O or S;

$R^{y3}$ is selected from H, amino, $C_{1-6}$ alkyl, a $C_{3-8}$ carbocyclic group or a 4- to 8-membered heterocyclic group, $-(CR^{ya}R^{yb})_{m1}-NR^{yc}R^{yd}$ or $-(CR^{ya}R^{yb})_{m1}-NR^{yc}C(=O)OR^{yd}$, wherein the amino group, alkyl, carbocyclic group or heterocyclic group may optionally be further substituted with 0 to 5 substituents selected from H, F, Cl, Br, I, hydroxyl, amino, cyano, carboxyl, $C_{1-6}$ alkyl, $C_{1-6}$ alkoxy, $-(CH_2)_{m1}-OC(=O)-C_{1-6}$ alkyl, $-(CH_2)_{m1}-C(=O)O-C_{1-6}$ alkyl, $-(CH_2)_{m1}-C(=O)O(CH_2)_{m1}-(C_{3-6}$ carbocyclic group), $-(CH_2)_{m1}-C(=O)-C_{1-6}$ alkyl, $-(CH_2)_{m1}-(C_{3-8}$ carbocyclic group) or $-(CH_2)_{m1}$-(4- to 8—membered heterocyclic group), and the heterocyclic group has 1 to 2 heteroatoms selected from N, O or S;

$R^{y4}$ and $R^{y5}$ are each independently selected from H, an alkali metal ion, an alkali earth metal ion, a protonated amine or a protonated amino acid, $C_{1-6}$ alkyl, $-(CR^{ya}R^{yb})_{m1}$-(3- to 8-membered ring), $-(CR^{ya}R^{yb})_{m1}-OC(=O)C_{1-6}$ alkyl, $-(CR^{ya}R^{yb})_{m1}-OC(=O)$-(3- to 8-membered ring), $-(CR^{ya}R^{yb})_{m1}-C(=O)OC_{1-6}$ alkyl or $-(CR^{ya}R^{yb})_{m1}-OC(=O)OC_{1-6}$ alkyl;

$R^{y6}$ and $R^{y7}$ are each independently selected from H, F, Cl, Br, I, hydroxyl, amino, cyano, carboxyl, $C_{1-6}$ alkyl or $C_{1-6}$ alkoxy;

alternatively, $R^{y6}$ and $R^{y7}$ may form a 5- to 8-membered ring together with the atoms to which they are attached, the 5- to 8-membered ring may have 0 to 4 heteroatoms selected from N, O or S, and the 5- to 8-membered ring may optionally be further substituted with 0 to 4 substituents selected from H, F, Cl, Br, I, $C_{1-6}$ alkyl or $C_{1-6}$ alkoxy;

$R^{y8}$s are each independently selected from H or $C_{1-6}$ alkyl;

$R^{y9}$ and $R^{y10}$ are each independently selected from H, $C_{1-6}$ alkyl, a $C_{3-8}$ carbocyclic group or a 4- to 8-membered heterocyclic group, wherein the alkyl, carbocyclic group and heterocyclic group are each optionally further substituted with 0 to 4 substituents selected from H, hydroxyl, amino, mercapto, carboxyl, guanidino, carbamoyl, $C_{1-6}$ alkyl, $C_{1-6}$ alkoxy, a 3- to 8-membered carbocycle or a 3- to 8-membered heterocycle;

$R^{ya}$, $R^{yb}$, $R^{yc}$ and $R^{yd}$ are each independently selected from H or $C_{1-6}$ alkyl;

n is selected from 1, 2 or 3;
m is selected from 1 or 2;
q is selected from 1 to 200;
m1 is selected from 0, 1, 2 or 3;
p is selected from 0, 1 or 2;

or a stereoisomer, a solvate, a metabolite, a prodrug, a pharmaceutically acceptable salt, or a cocrystal thereof, provided that the compound of general formula (A) is not

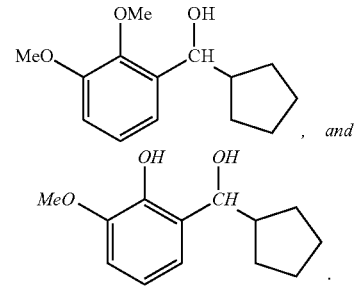

, and

* * * * *